United States Patent
Menet et al.

(10) Patent No.: US 10,568,879 B2
(45) Date of Patent: Feb. 25, 2020

(54) DIHYDROPYRIDOISOQUINOLINONES AND PHARMACEUTICAL COMPOSITIONS THEREOF FOR THE TREATMENT OF INFLAMMATORY DISORDERS

(71) Applicant: GALAPAGOS NV, Mechelen (BE)

(72) Inventors: Christel Jeanne Marie Menet, Brussels (BE); Julien Georges Pierre-Olivier Doyon, Beerse (BE); Pieter Isabelle Roger Claes, Mechelen (BE); Brigitte Allart, Mechelen (BE); Maxim Maria Paul De Wachter, Mechelen (BE); Giovanni Alessandro Tricarico, Mechelen (BE)

(73) Assignee: GALAPAGOS NV, Mechelen (BE)

( * ) Notice: Subject to any disclaimer, the term of this patent is extended or adjusted under 35 U.S.C. 154(b) by 41 days.

(21) Appl. No.: 15/568,275

(22) PCT Filed: Apr. 19, 2016

(86) PCT No.: PCT/EP2016/058607
§ 371 (c)(1),
(2) Date: Oct. 20, 2017

(87) PCT Pub. No.: WO2016/169911
PCT Pub. Date: Oct. 27, 2016

(65) Prior Publication Data
US 2019/0062325 A1 Feb. 28, 2019

(30) Foreign Application Priority Data
Apr. 23, 2015 (GB) .................................. 1506894.3

(51) Int. Cl.
A61K 31/4745 (2006.01)
C07D 519/00 (2006.01)
C07D 471/04 (2006.01)
A61P 19/02 (2006.01)
A61P 1/00 (2006.01)
A61P 29/00 (2006.01)
A61K 31/496 (2006.01)

(52) U.S. Cl.
CPC ........ *A61K 31/4745* (2013.01); *A61K 31/496* (2013.01); *A61P 1/00* (2018.01); *A61P 19/02* (2018.01); *A61P 29/00* (2018.01); *C07D 471/04* (2013.01); *C07D 519/00* (2013.01)

(58) Field of Classification Search
CPC .......................... A61K 31/4745; C07D 471/16
USPC ........................................... 514/210.16, 294
See application file for complete search history.

(56) References Cited

U.S. PATENT DOCUMENTS

| 8,927,543 B2 | 1/2015 | Labeguere et al. |
| 9,255,095 B2 | 2/2016 | Labéguère et al. |
| 9,708,312 B2 | 7/2017 | Labéguère et al. |
| 2013/0165437 A1* | 6/2013 | Labegu Re .......... A61K 31/519 514/233.2 |

FOREIGN PATENT DOCUMENTS

WO  WO 2007/027661 A2  3/2007
WO  WO 2012/037782 A1  3/2012
(Continued)

OTHER PUBLICATIONS

Meredith et al, Emetine and Related Compounds, Part V. (Year: 1963).*

(Continued)

*Primary Examiner* — Craig D Ricci
*Assistant Examiner* — Janet L. Coppins
(74) *Attorney, Agent, or Firm* — Arent Fox LLP

(57) ABSTRACT

A compound according to Formula I:

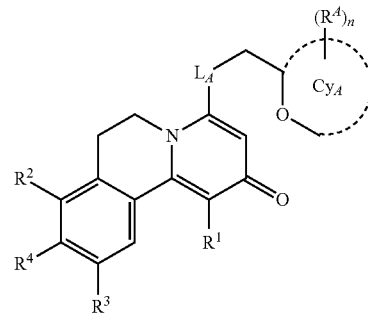

wherein $R^1$, $L_A$, $Cy_A$, $R^A$, $R^2$, $R^3$, and $R^4$ are as described herein.

The present invention relates to novel compounds according to Formula I that antagonize GPR84, a G-protein-coupled receptor that is involved in inflammatory conditions, and methods for the production of these novel compounds, pharmaceutical compositions comprising these compounds, and methods for the prevention and/or treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions by administering a compound of the invention.

10 Claims, No Drawings

(56) References Cited

FOREIGN PATENT DOCUMENTS

| WO | WO 2014/095798 A1 | 6/2014 |
|----|-------------------|--------|
| WO | WO 2015/197550 A1 | 12/2015 |

OTHER PUBLICATIONS

Meredith et al, Emetine and Related Compounds, Part V., pp. 2672-2677. (Year: 1963).*
Anderson, A. Chemistry & Biology (2003), vol. 10, pp. 787-797. (Year: 2003).*
Thiel, Karl, Nature Biotechnology (2004), vol. 22(5), pp. 513-519. (Year: 2004).*
Proschak et al, J. Med Chem (2017), vol. 60, pp. 5235-5266. (Year: 2017).*
Abdel-Aziz H et al., GPR84 and TREM-1 signaling contribute to the pathogenesis of reflux esophagitis, Molecular Medicine, 2015; vol. 21, No. 1, pp. 1011-1024.
Berry MPR et al., An Interferon-Inducible Neutrophil-Driven Blood Transcriptional Signature in Human Tuberculosis, Nature, 2010; vol. 466, No. 7309, pp. 973-977 (15 pages total).
Bouchard C et al., G protein-coupled receptor 84, a microglia-associated protein expressed in neuroinflammatory conditions, Glia, 2007; vol. 55, No. 8, pp. 790-800.
Brand DD et al., Collagen-induced arthritis, Nature protocols, 2007; vol. 2, No. 5, pp. 1269-1275.
Dietrich PA et al., GPR84 sustains aberrant Beta-catenin signaling in leukemic stem cells for maintenance of MLL leukemogenesis, Blood, 2014; vol. 124, No. 22, pp. 3284-3294.
Du Bois RM, Strategies for treating idiopathic pulmonary fibrosis, Nature Reviews Drug Discovery, 2010; vol. 9, No. 2, pp. 129-140.
Gamo K et al., G-Protein-Coupled Receptor Screen Reveals a Role for Chemokine Receptor CCR5 in Suppressing Microglial Neurotoxicity, The Journal of Neuroscience, 2008; vol. 28, No. 46, pp. 11980-11988.
Kadl A et al., Identification of a Novel Macrophage Phenotype That Develops in Response to Atherogenic Phospholipids via Nrf2, Circulation Research, 2010; vol. 107, No. 6, pp. 737-746.
Khachigian LM, Collagen antibody-induced arthritis, Nature Protocols, 2006; vol. 1, No. 5, pp. 2512-2516.
Lin H-S et al., Anti-rheumatic activities of histone deacetylase (HDAC) inhibitors in vivo in collagen-induced arthritis in rodents, British Journal of Pharmacology, 2007; vol. 150, No. 7, pp. 862-872.
Nagasaki H et al., Inflammatory changes in adipose tissue enhance expression of GPR84, a medium-chain fatty acid receptor: TNFa enhances GPR84 expression in adipocytes, FEBS Letters, 2012; vol. 586, No. 4, pp. 368-372.
Nicol LSC et al., The Role of G-Protein Receptor 84 in Experimental Neuropathic Pain, The Journal of Neuroscience, 2015; vol. 35, No. 23, pp. 8959-8969.
Roman S, Disruption of the GPR84 GPCR gene reduces inflammatory and abolishes neuropathic pain, Jun. 2010, http://fens2010.neurosciences.asso.fr/abstracts/R6/A162_28.htl, 1 page.
Salvemini D et al., Amelioration of joint disease in a rat model of collagen-induced arthritis by M40403, a superoxide dismutase mimetic, Arthritis and rheumatism, 2001; vol. 44, No. 12, pp. 2909-2921.
Sina C et al., G Protein-Coupled Receptor 43 Is Essential for Neutrophil Recruitment during Intestinal Inflammation, The Journal of Immunology, 2009; vol. 183, No. 11, pp. 7514-7522.
Suzuki M et al., Medium-chain fatty acid-sensing receptor, GPR84, is a proinflammatory receptor, The Journal of Biological Chemistry, 2013; vol. 288, No. 15, pp. 10684-10691.
Venkataraman C et al., The G-protein coupled receptor, GPR84 regulates IL-4 production by T lymphocytes in response to CD3 crosslinking, Immunology Letters, 2005; vol. 101, No. 2, pp. 144-153.
Wang J et al., Medium-chain Fatty Acids as Ligands for Orphan G Protein-coupled Receptor GPR84, Journal of Biological Chemistry, 2006; vol. 281, No. 45, pp. 34457-34464.
Wirtz S et al., Chemically induced mouse models of intestinal inflammation, Nature Protocols, 2007; vol. 2, No. 3, pp. 541-546.
Wittenberger T et al., An expressed sequence tag (EST) data mining strategy succeeding in the discovery of new G-protein coupled receptors, Journal of Molecular Biology, 2001; vol. 307, No. 3, pp. 799-813.
Yousefi S et al., Cloning and expression analysis of a novel G-protein-coupled receptor selectively expressed on granulocytes, Journal of Leukocyte Biology, 2001; vol. 69, No. 6, pp. 1045-1052.
International Search Report issued in International Patent Application No. PCT/EP2016/058607, dated Jul. 8, 2016 (3 pages).

* cited by examiner

DIHYDROPYRIDOISOQUINOLINONES AND PHARMACEUTICAL COMPOSITIONS THEREOF FOR THE TREATMENT OF INFLAMMATORY DISORDERS

CROSS REFERENCE TO RELATED APPLICATIONS

This application is a 35 U.S.C. 371 National Phase of PCT Application No. PCT/EP2016/058607, filed Apr. 19, 2016, which claims benefit to GB Application No. 1506894.3, filed Apr 23, 2015, the disclosure of which is hereby incorporated by reference it its entirety.

FIELD OF THE INVENTION

The present invention relates to novel compounds that antagonize GPR84, a G-protein-coupled receptor that is involved in inflammatory conditions.

The present invention also provides methods for the production of these novel compounds, pharmaceutical compositions comprising these compounds, and methods for the prevention and/or treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions by administering a compound of the invention.

BACKGROUND OF THE INVENTION

GPR84 was recently isolated and characterized from human B cells (Wittenberger et al. 2001) as the result of an expressed sequence tag data mining strategy, and also using a degenerate primer reverse transcriptase-polymerase chain reaction (RT-PCR) approach aimed to identify novel chemokine receptors expressed in neutrophils (Yousefi et al. 2001).

GPR84 (also known as EX33) remained an orphan GPCR until the identification of medium-chain Free Fatty Acids (FFAs) with carbon chain lengths of 9-14 as ligands for this receptor (Wang et al. 2006). GPR84 was described to be activated by capric acid (C10:0), undecanoic acid (C11:0) and lauric acid (C12:0) with potencies of 5 μM, 9 μM and 11 μM, respectively. Three small molecules were also described to have some GPR84 agonist activity: 3,3'-diindolylmethane (DIM) (Wang et al. 2006), embelin (Hakak et al. 2007) and 6-n-octylaminouracil (6-OAU) (Suzuki et al. 2013).

GPR84 has been shown to be expressed in immune cells at least but not limited to polymorphonuclear leukocytes (PMN), neutrophils, monocytes, T cells and B cells. (Hakak et al. 2007; Venkataraman & Kuo 2005; Wang et al. 2006; Yousefi et al. 2001). Higher levels of GPR84 were measured in neutrophils and eosinophils than in T-cells and B-cells. GPR84 expression was demonstrated in tissues that may play a role in the propagation of the inflammatory response such as lung, spleen, bone marrow.

For example, in a recent review, Du Bois reported the current status of therapies for lung interstitial diseases, such as idiopathic pulmonary fibrosis (IPF). There are almost 300 distinct injurious or inflammatory causes of interstitial lung disease that can result in diffuse lung scarring, and the initial stages of the IPF pathology are very likely to involve inflammation (Bois 2010), and combination therapies involving anti-inflammatory treatment could be advantageously used.

The expression of GPR84 was highly up-regulated in monocytes/macrophages upon LPS stimulation (Wang et al. 2006).

GPR84 knock-out (KO) mice are viable and indistinguishable from wild-type littermate controls (Venkataraman & Kuo 2005). The proliferation of T and B cells in response to various mitogens is reported to be normal in GPR84-deficient mice (Venkataraman & Kuo 2005). T helper 2 ($TH_2$) differentiated T cells from GPR84 KO secreted higher levels of IL4, IL5, IL13, the 3 major $TH_2$ cytokines, compared to wild-type littermate controls. In contrast, the production of the Th1 cytokine, INFγ, was similar in Th1 differentiated T cells from GPR84 KO and wild-type littermate (Venkataraman & Kuo 2005).

In addition, capric acid, undecanoic acid and lauric acid dose dependently increased the secretion of interleukin-12 p40 subunit (IL-12 p40) from RAW264.7 murine macrophage-like cells stimulated with LPS. The pro-inflammatory cytokine IL-12 plays a pivotal role in promoting cell-mediated immunity to eradicate pathogens by inducing and maintaining T helper 1 (Th1) responses and inhibiting T helper 2 ($TH_2$) responses. Medium-chain FFAs, through their direct actions on GPR84, may affect Th1/$TH_2$ balance.

Berry et al. identified a whole-blood 393-gene transcriptional signature for active tuberculosis (TB) (Berry et al. 2010). GPR84 was part of this whole-blood 393-gene transcriptional signature for active TB indicating a potential role for GPR84 in infectious diseases.

GPR84 expression was also described in microglia, the primary immune effector cells of the central nervous system (CNS) from myeloid-monocytic origin (Bouchard et al. 2007). As observed in peripheral immune cells, GPR84 expression in microglia was highly inducible under inflammatory conditions such as TNFa and IL1 treatment but also notably endotoxemia and experimental autoimmune encephalomyelitis (EAE), suggesting a role in neuro-inflammatory processes. Those results suggest that GPR84 would be up-regulated in CNS not only during endotoxemia and multiple sclerosis, but also in all neurological conditions in which TNFα or IL1b pro-inflammatory cytokines are produced, including brain injury, infection, Alzheimer's disease (AD), Parkinson's disease (PD).

GPR84 expression was also observed in adipocytes and shown to be enhanced by inflammatory stimuli (Nagasaki et al. 2012). The results suggest that GPR84 emerges in adipocytes in response to TNFα from infiltrating macrophages and exacerbates the vicious cycle between adiposity and diabetes/obesity, and therefore the inhibition of GPR84 activity might be beneficial for the treatment of endocrine and/or metabolic diseases.

GPR84 expression is also upregulated in microglia surrounding the neurons, after nerve injury. (Gamo et al, 2008). Furthermore in GPR84 knock-out mice, hypersensitivity to mechanical stimuli were significantly reduced or completely absent in mouse models of inflammatory and neuropathic pain (Nicol et al. 2015; Roman 2010). Molecules which block the activation of GPR84 may therefore have the potential to deliver broad-spectrum analgesia.

GPR84 expression is increased in human leukemic stem cells (LSC) from acute myeloid leukemia (AML) patients compared to hematopoietic stem cells from healthy donors. GPR84 simultaneously augments β-catenin signaling and an oncogenic transcription program essential for establishment of MLL leukemia (Dietrich et al, 2014). Suppression of GPR84 significantly inhibited cell growth in pre-LSCs, reduced LSC frequency and impaired reconstitution of stem cell-derived MLL leukemia, which represents a particularly aggressive and drug-resistant subtype of AML. Targeting the oncogenic GPR84/β-catenin signaling axis may represent a novel therapeutic strategy for AML and possibly other leukemias.

GPR84 expression is increased by 49.9 times in M1 type macrophages isolated from aortic artherosclerotic lesions of LDLR−/− mice fed a high western diet (Kadl et al. 2010). Therefore, molecules targeting GPR84 may have a potential benefit in treatment of artherosclerosis.

In experimental oesophagitis, GPR84 is upregulated in the oesophageal tissue, mainly in the epithelial cells, and is significantly decreased in rats treated with either omeprazole (proton pump inhibitor) or STW5, an herbal preparation shown to ameliorate oesophagitis without affecting refluxate pH (Abdel-Aziz et al. 2015). This finding is supported by Western blot and immunohistochemistry in rat tissue and HET-1A cells, a human oesophageal squamous cell line. GPR84 was also found to be significantly upregulated in oesophageal biopsies from patients with grade B reflux esophagitis. Molecules that block the GPR84 receptor activity may therefore represent a new therapeutic paradigm for the treatment of oesophagitis.

Therefore, the identification and development of novel compounds, processes for their preparation and their use in the preparation of a medicament would be highly desirable for patients suffering from inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

SUMMARY OF THE INVENTION

The present invention relates to novel dihydropyridoisoquinolinone compounds that antagonize GPR84, and that are potentially useful for the treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

The present invention also provides methods for the production of these compounds, pharmaceutical compositions comprising these compounds and methods for treating inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Accordingly, in a first aspect of the invention, a compound of the invention is disclosed having a Formula I:

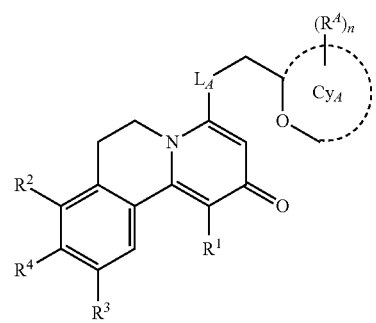

wherein
$L_A$ is O, or NH;
$Cy_A$ is monocyclic 4-6 membered heterocycloalkyl, comprising one or two O atoms;
each $R^4$ is independently selected from halo, and $C_{1-3}$ alkyl;
the subscript n is 0, 1 or 2;
$R^1$ is H or $C_{1-3}$ alkyl;
$R^2$ is H, —OH, or $C_{1-3}$ alkoxy;
$R^3$ is H or $C_{1-3}$ alkoxy;
$R^4$ is
 —CN,
 —OH,
 —O—S(=O)$_2$—C$_{1-4}$ alkyl optionally substituted with one or more independently selected halo, or
 -L$_1$-W$_1$-G$_1$;
$L_1$ is a direct bond, —O—, —S—, —SO$_2$—, —C(=O)NR$^{5a}$—, —NR$^{5b}$C(=O)—, or —NR$^{5c}$—;
$R^{5a}$, $R^{5b}$ and $R^{5c}$ are independently H or $C_{1-4}$ alkyl;
$W_1$ is a direct bond or $C_{1-2}$ alkylene optionally substituted with one or more independently selected halo;
$G_1$ is
 $C_{3-6}$ cycloalkyl optionally substituted with one or more independently selected halo,
 5-6 membered heteroaryl comprising one to four heteroatoms independently selected from N, O, and S, which heteroaryl is optionally substituted with one or more independently selected $C_{1-4}$ alkyl,
 5-7 membered heterocycloalkenyl comprising one double bond, and one to three heteroatoms independently selected from N, O, and S, which heterocycloalkenyl is optionally substituted with one or more independently selected $R^6$,
 monocyclic or spiro bicyclic 4-8 membered heterocycloalkyl comprising one to three heteroatoms independently selected from N, O, and S, which heterocycloalkyl is optionally substituted with one or more independently selected $R^6$,
 monocyclic 4-6 membered heterocycloalkyl comprising one to three heteroatoms independently selected from N, O, and S, fused to one or two phenyls,
 $C_{1-4}$ alkyl optionally substituted with one or more independently selected halo, —NR$^{7a}$R$^{7b}$, or $C_{1-4}$ alkoxy, which alkoxy is optionally substituted with one or more independently selected halo,
 phenyl optionally substituted with one or more independently selected halo or $C_{1-4}$ alkoxy, which alkoxy is optionally substituted with one or more independently selected halo;

$R^6$ is
  halo,
  =O,
  —CN,
  —OH,
  —C(=O)—$C_{1-4}$ alkoxy optionally substituted with one or more independently selected halo,
  —C(=O)—$C_{3-4}$ cycloalkyl,
  —S(=O)$_2$—$C_{1-4}$ alkyl,
  $C_{1-4}$ alkyl optionally substituted by one or more independently selected $C_{1-3}$ alkoxy, halo, or —OH,
  $C_{1-4}$ alkoxy,
  phenyl optionally substituted by one or more independently selected halo,
  —C(=O)-monocyclic 4-6 membered heterocycloalkyl comprising one to three heteroatoms independently selected from N, O, and S,
  —C(=O)NR$^{8a}$R$^{8b}$, or
  5-7 membered heteroaryl comprising one to four heteroatoms independently selected from N, O, and S, which heteroaryl is optionally substituted with one or more independently selected $C_{1-4}$ alkyl;
$R^{7a}$ and $R^{7b}$ are independently H or $C_{1-4}$ alkyl, and
$R^{8a}$ and $R^{8b}$ are independently H or $C_{1-3}$ alkyl.

In a particular aspect, the compounds of the invention may exhibit a good exposure and solubility, which in turn may result in lower dosage regimen.

In a further more particular aspect, the compounds of the invention may exhibit a substantial chemical stability at acidic pH, more particularly between pH 1.0 and 6.0, and specifically at pH 1.2 and/or 5.0, which in turn may result in stable solution dosage forms, low stomach acid-catalyzed degradation and low inter-subject oral bioavailability variability.

In yet a further aspect more particular aspect, the compounds of the invention may exhibit a substantial light stability, which in turn may result in photostable dosage forms.

In a further aspect, the present invention provides pharmaceutical compositions comprising a compound of the invention, and a pharmaceutical carrier, excipient or diluent. Moreover, a compound of the present invention useful in the pharmaceutical compositions and treatment methods disclosed herein, is pharmaceutically acceptable as prepared and used. In this aspect of the invention, the pharmaceutical composition may additionally comprise further active ingredients suitable for use in combination with a compound of the invention.

In another aspect of the invention, this invention provides novel compounds of the invention for use in therapy.

In a further aspect of the invention, this invention provides a method of treating a mammal susceptible to or afflicted with a condition from among those listed herein, and particularly, such condition as may be associated with aberrant activity of GPR84 and/or aberrant GPR84 expression and/or aberrant GPR84 distribution, for example inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, which method comprises administering a therapeutically effective amount of a compound of the invention, or one or more of the pharmaceutical compositions herein described.

In a further aspect, the present invention provides a compound of the invention for use in the treatment or prevention of a condition selected from those listed herein, particularly such conditions as may be associated with aberrant activity of GPR84 and/or aberrant GPR84 expression and/or aberrant GPR84 distribution expression such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

In additional aspects, this invention provides methods for synthesizing a compound of the invention, with representative synthetic protocols and pathways disclosed herein.

Accordingly, it is a principal object of this invention to provide a compound of the invention, which can modify the activity of GPR84 and thus prevent or treat any conditions that may be causally related thereto.

It is further an object of this invention to provide a compound of the invention that can treat or alleviate conditions or diseases or symptoms of same, such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, that may be causally related to the activity and/or expression and/or distribution of GPR84.

A still further object of this invention is to provide pharmaceutical compositions that may be used in the treatment or prevention of a variety of disease states, including the diseases associated with aberrant activity of GPR84 and/or aberrant GPR84 expression and/or aberrant GPR84 distribution such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—CH$_3$), ethyl (—CH$_2$CH$_3$), n-propyl (—CH$_2$—CH$_2$CH$_3$), isopropyl (—CH(CH$_3$)$_2$), n-butyl (—CH$_2$—CH$_2$—CH$_2$CH$_3$), tert-butyl (—CH$_2$—C(CH$_3$)$_3$), sec-butyl (—CH$_2$—CH(CH$_3$)$_2$), n-pentyl (—CH$_2$—CH$_2$—CH$_2$—CH$_2$CH$_3$), n-hexyl (—CH$_2$—CH$_2$—CH$_2$—CH$_2$—CH$_2$CH$_3$), and 1,2-dimethylbutyl (—CHCH$_3$)—C(CH$_3$)H$_2$—CH$_2$CH$_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkoxy' refers to the group O-alkyl, where the alkyl group has the number of carbon atoms specified. In particular the term refers to the group —O—C$_{1-6}$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocycloalkyl, aryl, e.g., heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, isobenzoxazolyl, benzisoxazolyl, benzothiazolyl, benzoisothiazolyl, isobenzofuranyl, indolyl, isoindolyl, indolizinyl, purinyl (e.g., adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

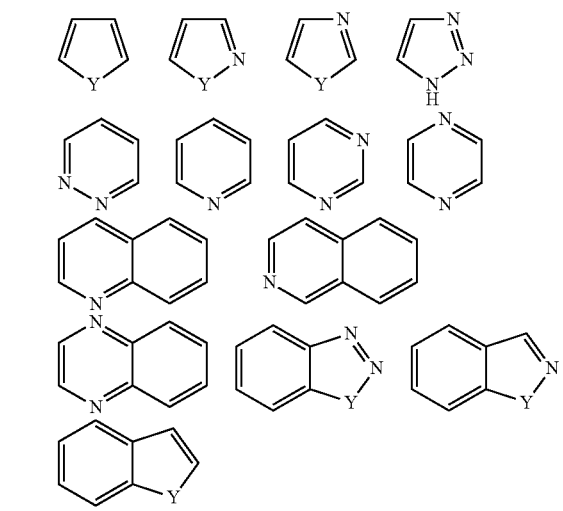

wherein each Y is selected from >C=O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g., 1-pyrrolidinyl, 2-pyrrolidinyl and 3-pyrrolidinyl), tetrahydrofuranyl (e.g., 1-tetrahydrofuranyl, 2-tetrahydrofuranyl and 3-tetrahydrofuranyl), tetrahydrothiophenyl (e.g., 1-tetrahydrothiophenyl, 2-tetrahydrothiophenyl and 3-tetrahydrothiophenyl), piperidinyl (e.g., 1-piperidinyl, 2-piperidinyl, 3-piperidinyl and 4-piperidinyl), tetrahydropyranyl (e.g., 4-tetrahydropyranyl), tetrahydrothiopyranyl (e.g., 4-tetrahydrothiopyranyl), morpholinyl, thiomorpholinyl, dioxanyl, or piperazinyl.

Particular examples of monocyclic rings are shown in the following illustrative examples:

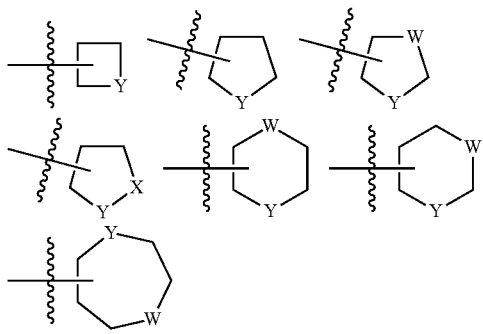

wherein each W and Y is independently selected from —CH$_2$—, —NH—, —O— and —S—.

Particular examples of fused bicyclic rings are shown in the following illustrative examples:

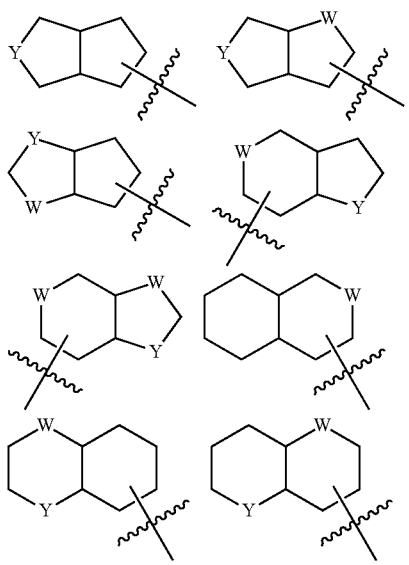

wherein each W and Y is independently selected from —CH$_2$—, —NH—, —O— and —S—.

Particular examples of bridged bicyclic rings are shown in the following illustrative examples:

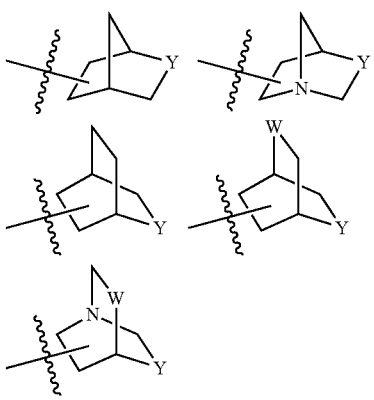

wherein each W and Y is independently selected from —CH$_2$—, —NH—, —O— and —S—.

Particular examples of spirocyclic rings are shown in the following illustrative examples:

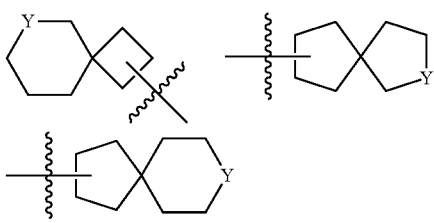

wherein each Y is selected from —CH$_2$—, —NH—, —O— and —S—.

As used herein, the term 'heterocycloalkenyl' means a 'heterocycloalkyl', which comprises at least one double bond. Particular examples of heterocycloalkenyl groups are shown in the following illustrative examples:

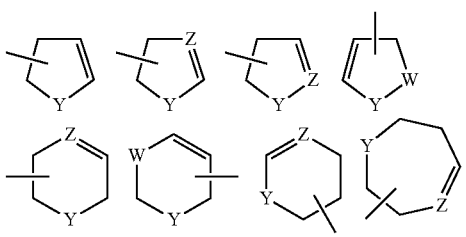

wherein each W and Y is independently selected from —CH$_2$—, —NH—, —O— and —S—; and each Z is selected from =N— and =CH—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —S-alkyl where the alkyl group has the number of carbon atoms specified. In particular the term refers to the group —S—C$_{1-6}$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g., in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein the term 'inflammatory condition(s)' refers to the group of conditions including inflammatory bowel diseases (IBD) (e.g., Crohn's disease, ulcerative colitis), rheumatoid arthritis, vasculitis, lung diseases (e.g., chronic obstructive pulmonary disease (COPD) and lung interstitial diseases (e.g., idiopathic pulmonary fibrosis (IPF))), psoriasis, gout, allergic airway disease (e.g., asthma, rhinitis), and endotoxin-driven disease states (e.g., complications after bypass surgery or chronic endotoxin states contributing to e.g., chronic cardiac failure). Particularly the term refers to rheumatoid arthritis, allergic airway disease (e.g., asthma) and inflammatory bowel diseases. In a further particular aspect, the term refers to uveitis, periodontitis, oesophagitis, neutrophilic dermatoses (e.g., pyoderma gangrenosum, Sweet's syndrome), severe asthma, and skin and/or colon inflammation caused by oncology treatments aimed at activating the immune response.

As used herein the term 'pain' refers to diseases or disorders characterized by unpleasant feeling often caused by intense or damaging stimuli, and include but is not limited to nociceptive pain, inflammatory pain (associated with tissue damage and inflammatory cell infiltration) and neuropathic or dysfunctional pain (caused by damage to or abnormal function of the nervous system), and/or pain associated or caused by the conditions mentioned herein. Pain can be acute or chronic.

As used herein the term 'neuroinflammatory conditions' refers to diseases or disorders characterized by abrupt neurologic deficits associated with inflammation, demyelination, and axonal damage, and includes but is not limited to conditions such as Guillain-Barré syndrome (GBS), multiple sclerosis, axonal degeneration, and autoimmune encephalomyelitis.

As used herein the term 'neurodegenerative conditions' refers to diseases or disorders characterized by progressive loss of structure or function of neurons, including death of neurons, and includes but is not limited to conditions such as dementia, degenerative dementia, senile dementia, vascular dementia, dementia associated with intracranial space occupying lesions, mild cognitive impairment associated with ageing, age associated memory impairment, and/or peripheral neuropathies. In particular, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, Amyotrophic lateral sclerosis (ALS), motor neurone disease (MND), Spinocerebellar ataxia (SCA), and/or Spinal muscular atrophy (SMA). More particularly, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, and/or Amyotrophic lateral sclerosis (ALS).

As used herein, the term 'infectious diseases' refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, or enterobacteria species.

As used herein the term 'autoimmune disease(s)' refers to the group of diseases including obstructive airways disease (including conditions such as COPD (chronic obstructive pulmonary disease)), psoriasis, asthma (e.g., intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, vasculitis, inflammatory bowel disease (e.g., Crohn's disease and ulcerative colitis), atherosclerosis and amyotrophic lateral sclerosis. Particularly the term refers to COPD, asthma, psoriasis, systemic lupus erythematosus, type I diabetes mellitus, vasculitis and inflammatory bowel disease.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity.

As used herein the term "cardiovascular diseases" refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. Particularly, the term refers to atherosclerosis.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein, the term 'diseases involving impairment of immune cell functions' includes conditions with symptoms such as recurrent and drawn out viral and bacterial infections, and slow recovery. Other invisible symptoms may be the inability to kill off parasites, yeasts and bacterial pathogens in the intestines or throughout the body.

'Compound(s) of the invention', and equivalent expressions, are meant to embrace compounds of the Formula(e) as herein described, which expression includes the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-6}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, (Bundgaard 1985)). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, and substituted or unsubstituted $C_{6-10}$ aryl, esters of the compounds of the invention.

As used herein, the term 'isotopic variant' refers to a compound that contains unnatural proportions of isotopes at one or more of the atoms that constitute such compound For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. 3H, and carbon-14, i.e. 14C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Compounds

The present invention relates to novel compounds that antagonize GPR84 and that may be useful for the treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

The present invention also provides methods for the production of the compounds of the invention, pharmaceutical compositions comprising the compounds of the invention and methods for treating inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, by administering a compound of the invention. A compound of the invention is an antagonist of GPR84.

Accordingly, in a first aspect of the invention, a compound of the invention is disclosed having a Formula I:

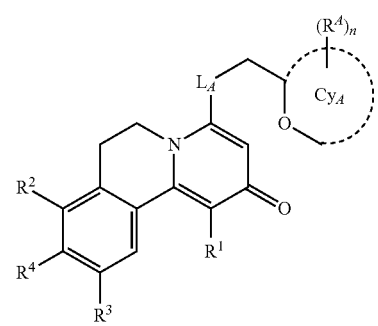

I wherein $L_A$ is O, or NH;

$Cy_A$ is monocyclic 4-6 membered heterocycloalkyl, comprising one or two O atoms;

each $R^A$ is independently selected from halo, and $C_{1-3}$ alkyl;

the subscript n is 0, 1 or 2;

$R^1$ is H or $C_{1-3}$ alkyl;

$R^2$ is H, —OH, or $C_{1-3}$ alkoxy;

$R^3$ is H or $C_{1-3}$ alkoxy;

$R^4$ is
- —CN,
- —OH,
- —O—S(=O)$_2$—C$_{1-4}$ alkyl optionally substituted with one or more independently selected halo, or
- -L$_1$-W$_1$-G$_1$;

$L_1$ is a direct bond, —O—, —S—, —SO$_2$—, —C(=O)NR$^{5a}$—, —NR$^{5b}$C(=O)—, or —NR$^{5c}$—;

$R^{5a}$, $R^{5b}$, and $R^{5c}$ re independently H or $C_{1-4}$ alkyl;

$W_1$ is a direct bond or $C_{1-2}$ alkylene optionally substituted with one or more independently selected halo;

$G_1$ is
- $C_{3-6}$ cycloalkyl optionally substituted with one or more independently selected halo,
- 5-6 membered heteroaryl comprising one to four heteroatoms independently selected from N, O, and S, which heteroaryl is optionally substituted with one or more independently selected $C_{1-4}$ alkyl,
- 5-7 membered heterocycloalkenyl comprising one double bond, and one to three heteroatoms independently selected from N, O, and S, which heterocycloalkenyl is optionally substituted with one or more independently selected $R^6$,
- monocyclic or spiro bicyclic 4-8 membered heterocycloalkyl comprising one to three heteroatoms independently selected from N, O, and S, which heterocycloalkyl is optionally substituted with one or more independently selected $R^6$,
- monocyclic 4-6 membered heterocycloalkyl comprising one to three heteroatoms independently selected from N, O, and S, fused to one or two phenyls,
- $C_{1-4}$ alkyl optionally substituted with one or more independently selected halo, —NR$^{7a}$R$^{7b}$, or $C_{1-4}$ alkoxy, which alkoxy is optionally substituted with one or more independently selected halo, or
- phenyl optionally substituted with one or more independently selected halo or $C_{1-4}$ alkyl, which alkoxy is optionally substituted with one or more independently selected halo;

$R^6$ is
- halo,
- =O,
- —CN,
- —OH,
- —C(=O)—C$_{1-4}$ alkoxy optionally substituted with one or more independently selected halo,
- —C(=O)—C$_{3-4}$ cycloalkyl,
- —S(=O)$_2$—C$_{1-4}$ alkyl,
- $C_{1-4}$ alkyl optionally substituted by one or more independently selected $C_{1-3}$ alkoxy, halo, or —OH,
- —C$_{1-4}$ alkoxy,
- phenyl optionally substituted by one or more independently selected halo,
- —C(=O)-monocyclic 4-6 membered heterocycloalkyl comprising one to three heteroatoms independently selected from N, O, and S,
- —C(=O)NR$^{8a}$R$^{8b}$, or
- 5-7 membered heteroaryl comprising one to four heteroatoms independently selected from N, O, and S, which heteroaryl is optionally substituted with one or more independently selected $C_{1-4}$ alkyl;

$R^{7a}$ and $R^{7b}$ are independently H or $C_{1-4}$ alkyl; and $R^{8a}$ and $R^{8b}$ are independently H or $C_{1-3}$ alkyl.

In one embodiment a compound of the invention is according to Formula I, wherein $Cy_A$ is and $R^A$ and the subscript n are as described above.

In one embodiment a compound of the invention is according to Formula I, wherein the subscript n is 1 or 2.

In one embodiment a compound of the invention is according to Formula I, wherein each $R^A$ is independently selected from halo, and $C_{1-3}$ alkyl. In a particular embodiment, each $R^A$ is independently selected from F, Cl, —CH$_3$, and —CH$_2$CH$_3$. In a more particular embodiment, each $R^A$ is independently selected from F, and —CH$_3$.

In one embodiment a compound of the invention is according to Formula I, wherein the subscript n is 0.

In one embodiment a compound of the invention is according to Formula IIa, or IIb:

IIa

IIb wherein $L_A$, $R^1$, $R^2$, $R^3$, and $R^4$ are as defined above.

In one embodiment a compound of the invention is according to Formula IIc or IId:

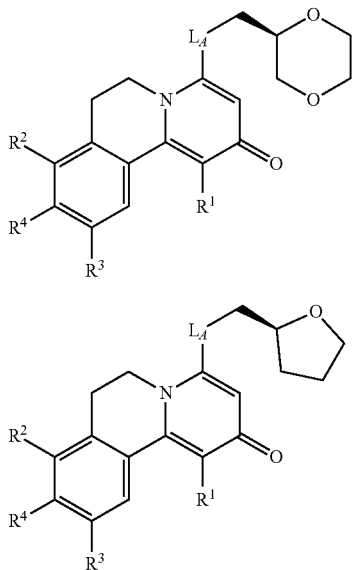

IIc

IId wherein $L_A$, $R^1$, $R^2$, $R^3$, and $R^4$ are as defined above.

In one embodiment, the compound of the invention is according to any one of Formulae I-IId, wherein $R^2$ is H.

In one embodiment, the compound of the invention is according to any one of Formulae I-IId, wherein $R^2$ is —OH.

In one embodiment, the compound of the invention is according to any one of Formulae I-IId, wherein $R^2$ is $C_{1-3}$ alkoxy. In a particular embodiment, $R^2$ is —OCH$_3$, or —OCH$_2$CH$_3$. In a more particular embodiment, $R^2$ is —OCH$_3$.

In one embodiment, the compound of the invention is according to any one of Formulae I-IId, wherein $R^3$ is H.

In one embodiment, the compound of the invention is according to any one of Formulae I-IId, wherein $R^3$ is $C_{1-3}$ alkoxy. In a particular embodiment, $R^3$ is —OCH$_3$, or —OCH$_2$CH$_3$. In a more particular embodiment, $R^3$ is —OCH$_3$.

In one embodiment, the compound of the invention is according to any one of Formulae I-IId, wherein $R^2$ is $C_{1-3}$ alkoxy and $R^3$ is H. In a particular embodiment, $R^2$ is —OCH$_3$, or —OCH$_2$CH$_3$, and $R^3$ is H. In a particular embodiment, $R^2$ is —OCH$_3$ and $R^3$ is H.

In one embodiment, the compound of the invention is according to any one of Formulae I-IId, wherein $R^2$ is H and $R^3$ is $C_{1-3}$ alkoxy. In a particular embodiment, $R^2$ is H, and $R^3$ is —OCH$_3$, or —OCH$_2$CH$_3$. In a particular embodiment, $R^2$ is H and $R^3$ is —OCH$_3$.

In one embodiment, the compound of the invention is according to any one of Formulae I-IId, wherein $R^1$ is H.

In one embodiment, the compound of the invention is according to any one of Formulae I-IId, wherein $R^1$ is $C_{1-3}$ alkyl. In a particular embodiment, $R^1$ is —CH$_3$, or —CH$_2$CH$_3$. In a more particular embodiment, $R^4$ is —CH$_3$.

In one embodiment, the compound of the invention is according to any one of Formulae I-IId, wherein $R^4$ is —OSO$_2$C$_{1-4}$ alkyl. In a particular embodiment, $R^4$ is —OSO$_2$CH$_3$, or —OSO$_2$CH$_2$CH$_3$. In a more particular embodiment, $R^4$ is —OSO$_2$CH$_3$.

In one embodiment, the compound of the invention is according to any one of Formulae I-IId, wherein $R^4$ is —OSO$_2$C$_{1-4}$ alkyl substituted with one or more halo. In a particular embodiment, $R^4$ is —OSO$_2$CH$_3$, or —OSO$_2$CH$_2$CH$_3$, each of which is substituted with one or more halo. In another particular embodiment, $R^4$ is —OSO$_2$CH$_3$, or —OSO$_2$CH$_2$CH$_3$, each of which is substituted with one or more F. In a most particular embodiment, $R^4$ is —OSO$_2$CF$_3$.

In one embodiment, the compound of the invention is according to Formula IIIa, or IIIb:

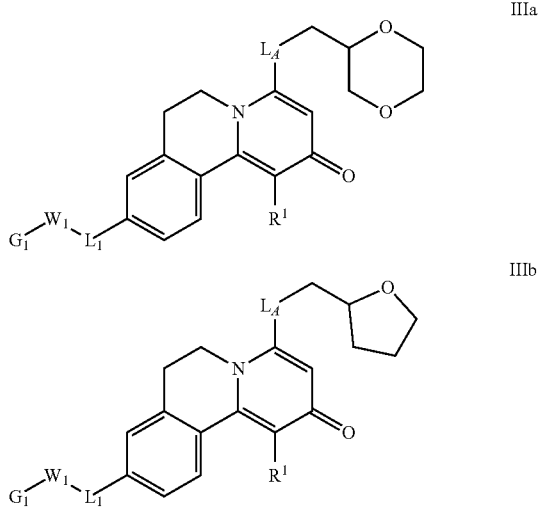

IIIa

IIIb wherein $L_A$, $R^1$, $L_1$, $W_1$ and $G_1$ are as previously defined.

In one embodiment, the compound of the invention is according to Formula IIIc, or IIId:

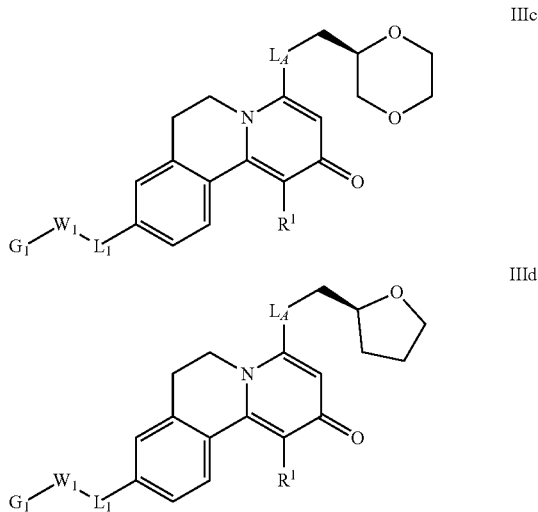

IIIc

IIId wherein $L_A$, $R^1$, $L_1$, $W_1$ and $G_1$ are as previously defined.

In one embodiment, the compound of the invention is according to any one of Formulae I-IIId, wherein $L_1$ is a direct bond.

In one embodiment, the compound of the invention is according to any one of Formulae I-IIId, wherein $L_1$ is —O—.

In one embodiment, the compound of the invention is according to any one of Formulae I-IIId, wherein $L_1$ is —S—.

In one embodiment, the compound of the invention is according to any one of Formulae I-IIId, wherein $L_1$ is —SO$_2$—.

In one embodiment, the compound of the invention is according to any one of Formulae I-IIId, wherein $L_1$ is —C(=O)NR$^{5a}$—, wherein R$^{5a}$ is H or C$_{1-4}$ alkyl. In a particular embodiment, R$^{5a}$ is H. In another particular embodiment, R$^{5a}$ is —CH$_3$, or —CH$_2$CH$_3$. In a more particular embodiment, R$^{5a}$ is —CH$_3$.

In one embodiment, the compound of the invention is according to any one of Formulae I-IIId, wherein $L_1$ is —NR$^{5b}$C(=O)—, wherein R$^{5b}$ is H or C$_{1-4}$ alkyl. In a particular embodiment, R$^{5b}$ is H. In another particular embodiment, R$^{5b}$ is —CH$_3$, or —CH$_2$CH$_3$. In a more particular embodiment, R$^{5b}$ is —CH$_3$.

In one embodiment, the compound of the invention is according to any one of Formulae I-IIId, wherein $L_1$ is —NR$^{5c}$—, wherein R$^{5c}$ is H or C$_{1-4}$ alkyl. In a particular embodiment, R$^{5c}$ is H. In another particular embodiment, R$^{5c}$ is —CH$_3$, or —CH$_2$CH$_3$. In a more particular embodiment, R$^{5c}$ is —CH$_3$.

In one embodiment, the compound of the invention is according to any one of Formulae I-IIId, wherein $L_A$ is NH.

In one embodiment, the compound of the invention is according to any one of Formulae I-IIId, wherein $L_A$ is O.

In one embodiment, the compound of the invention is according to Formula IVa:

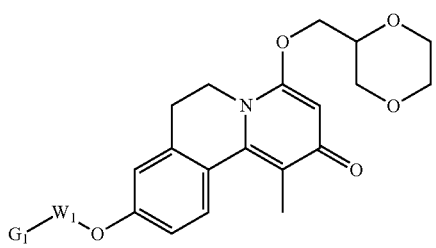

IVa wherein $W_1$ and $G_1$ are as defined above.

In one embodiment, the compound of the invention is according to Formula IVb:

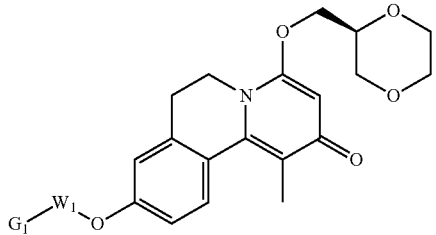

IVb wherein $W_1$ and $G_1$ are as defined above.

In one embodiment, the compound of the invention is according to any one of Formulae I-IVb, wherein $W_1$ is a direct bond.

In one embodiment, the compound of the invention is according to any one of Formulae I-IVb, wherein $W_1$ is C$_{1-2}$ alkylene. In a particular embodiment, $W_1$ is —CH$_2$—, or —CH$_2$—CH$_2$—. In a particular embodiment, $W_1$ is —CH$_2$—.

In one embodiment, the compound of the invention is according to any one of Formulae I-IVb, wherein $G_1$ is C$_{3-6}$ cycloalkyl. In a particular embodiment, $G_1$ is cyclopropyl, cyclobutyl, cyclopentyl or cyclohexyl. In a particular embodiment, $G_1$ is cyclopropyl, cyclobutyl, or cyclopentyl. In a more particular embodiment, $G_1$ is cyclopropyl.

In another embodiment, the compound of the invention is according to any one of Formulae I-IVb, wherein $G_1$ is C$_{3-6}$ cycloalkyl substituted with one or more halo. In a particular embodiment, $G_1$ is cyclopropyl, cyclobutyl, cyclopentyl or cyclohexyl, each of which is substituted with one or more halo. In a particular embodiment, $G_1$ is cyclopropyl, cyclobutyl, or cyclopentyl, each of which is substituted with one or more halo. In a particular embodiment, $G_1$ is cyclopropyl, cyclobutyl, cyclopentyl or cyclohexyl, each of which is substituted with one or more F. In another particular embodiment, $G_1$ is C$_{3-6}$ cycloalkyl substituted with one or more F. In a particular embodiment, $G_1$ is cyclopropyl, cyclobutyl, or cyclopentyl, each of which is substituted with one or more F. In a most particular embodiment, $G_1$ is cyclopropyl substituted with one or two F.

In one embodiment, the compound of the invention is according to any one of Formulae I-IVb, wherein $G_1$ is 5-6 membered heteroaryl comprising one to four heteroatoms independently selected from N, O, and S. in a particular embodiment, $G_1$ is pyrazolyl, oxadiazolyl, or pyridinyl. In a more particular embodiment, $G_1$ is pyridinyl.

In one embodiment, the compound of the invention is according to any one of Formulae I-IVb, wherein $G_1$ is 5-6 membered heteroaryl comprising one to four heteroatoms independently selected from N, O, and S, which heteroaryl is optionally substituted with one or more independently selected C$_{1-4}$ alkyl. In a particular embodiment, $G_1$ is pyrazolyl, oxadiazolyl, or pyridinyl, each of which is optionally substituted with one or more independently selected C$_{1-4}$ alkyl. In another particular embodiment, $G_1$ is 5-6 membered heteroaryl comprising one to four heteroatoms independently selected from N, O, and S, which heteroaryl is optionally substituted with one or more independently selected —CH$_3$, or —CH$_2$CH$_3$. In a more particular embodiment, $G_1$ is pyrazolyl, oxadiazolyl, or pyridinyl, each of which is optionally substituted with one or more independently selected —CH$_3$, or —CH$_2$CH$_3$. In a most particular embodiment, $G_1$ is pyrazolyl, oxadiazolyl, or pyridinyl, each of which is optionally substituted with one —CH$_3$, or —CH$_2$CH$_3$.

In one embodiment, the compound of the invention is according to any one of Formulae I-IVb, wherein $G_1$ is 5-6 membered heteroaryl comprising one to four heteroatoms independently selected from N, O, and S, which heteroaryl is substituted with one or more independently selected C$_{1-4}$ alkyl. In a particular embodiment, $G_1$ is pyrazolyl, oxadiazolyl, or pyridinyl, each of which is substituted with one or more independently selected C$_{1-4}$ alkyl. In another particular embodiment, $G_1$ is 5-6 membered heteroaryl comprising one to four heteroatoms independently selected from N, O, and S, which heteroaryl is substituted with one or more independently selected —CH$_3$, or —CH$_2$CH$_3$. In a more particular embodiment, $G_1$ is pyrazolyl, oxadiazolyl, or pyridinyl, each of which is substituted with one or more independently selected —CH$_3$, or —CH$_2$CH$_3$. In a most particular embodiment, $G_1$ is pyrazolyl, oxadiazolyl, or pyridinyl, each of which is substituted with one —CH$_3$, or —CH$_2$CH$_3$.

In one embodiment, the compound of the invention is according to any one of Formulae I-IVb, wherein $G_1$ is 5-7 membered heterocycloalkenyl comprising one double bond, and one to three heteroatoms independently selected from N, O, and S. In a particular embodiment, $G_1$ is 1,2,3,6-tetrahydro-pyridinyl, or 3,6-dihydro-2H-pyran.

In one embodiment, the compound of the invention is according to any one of Formulae I-IVb, wherein $G_1$ is 5-7 membered heterocycloalkenyl comprising one double bond, and one to three heteroatoms independently selected from N, O, and S, which heterocycloalkenyl is substituted with one or more independently selected $R^6$. In another embodiment, $G_1$ is 1,2,3,6-tetrahydro-pyridinyl, or 3,6-dihydro-2H-pyran, each of which is substituted with one or more independently selected $R^6$. In a particular embodiment, $G_1$ is 5-7 membered heterocycloalkenyl comprising one double bond, and one, to three heteroatoms independently selected from N, O, and S, which heterocycloalkenyl is substituted with one, two, or three independently selected $R^6$. In another particular embodiment, $G_1$ is 1,2,3,6-tetrahydro-pyridinyl, or 3,6-dihydro-2H-pyran, each of which is substituted with one, two, or three independently selected $R^6$. In a more particular embodiment, $G_1$ is 5-7 membered heterocycloalkenyl comprising one double bond, and one to three heteroatoms independently selected from N, O, and S, which heterocycloalkenyl is substituted with one $R^6$. In another more particular embodiment, $G_1$ is 1,2,3,6-tetrahydro-pyridinyl, or 3,6-dihydro-2H-pyran, each of which is substituted with one $R^6$.

In one embodiment, the compound of the invention is according to any one of Formulae I-IVb, wherein $G_1$ is monocyclic or spiro bicyclic 4-8 membered heterocycloalkyl comprising one to three heteroatoms independently selected from N, O, and S. In a particular embodiment, $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl.

In one embodiment, the compound of the invention is according to any one of Formulae I-IVb, wherein $G_1$ is monocyclic or spiro bicyclic 4-8 membered heterocycloalkyl comprising one to three heteroatoms independently selected from N, O, and S, which heterocycloalkyl is substituted with one or more independently selected $R^6$. In another embodiment, $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one or more independently selected $R^6$. In a particular embodiment, $G_1$ is monocyclic or spiro bicyclic 4-8 membered heterocycloalkyl comprising one to three heteroatoms independently selected from N, O, and S, which heterocycloalkyl is substituted with one, two, or three independently selected $R^6$. In another particular embodiment, $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one, two, or three independently selected $R^6$. In a more particular embodiment, $G_1$ is monocyclic or spiro bicyclic 4-8 membered heterocycloalkyl comprising one to three heteroatoms independently selected from N, O, and S, which heterocycloalkyl is substituted with one $R^6$. In another more particular embodiment, $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one $R^6$.

In one embodiment, the compound of the invention is according to any one of Formulae I-IVb, wherein $G_1$ is monocyclic 4-6 membered heterocycloalkyl comprising one to three heteroatoms independently selected from N, O, and S, fused to one or two phenyls. In a particular embodiment, $G_1$ is pyrrolyl fused to two phenyls.

In one embodiment, the compound of the invention is according to any one of Formulae I-IVb, wherein $R^6$ is halo, =O, —CN, or —OH. In a particular embodiment, $R^6$ is F, =O, —CN, or —OH. In a more particular embodiment, $R^6$ is F, or —OH. In a most particular embodiment, $R^6$ is F.

In one embodiment, the compound of the invention is according to any one of Formulae I-IVb, wherein $R^6$ is —C(=O)—$C_{1-4}$ alkoxy. In a particular embodiment, $R^6$ is —C(=O)OMe, —C(=O)OEt, —C(=O)OiPr, or —C(=O)OtBu. In a more particular embodiment, $R^6$ is —C(=O)OtBu.

In one embodiment, the compound of the invention is according to any one of Formulae I-IVb, wherein $R^6$ is —C(=O)—$C_{1-4}$ alkoxy substituted with one or more independently selected halo. In a particular embodiment, $R^6$ is —C(=O)OMe, —C(=O)OEt, —C(=O)OiPr, or —C(=O)OtBu, each of which is substituted with one or more independently selected halo. In another particular embodiment, $R^6$ is —C(=O)—$C_{1-4}$ alkoxy substituted with one or more F. In a more particular embodiment, $R^6$ is —C(=O)OCH$_2$CF$_3$.

In one embodiment, the compound of the invention is according to any one of Formulae I-IVb, wherein $R^6$ is —C(=O)—$C_{3-4}$ cycloalkyl. In a particular embodiment, $R^6$ is —C(=O)cyclopropyl.

In one embodiment, the compound of the invention is according to any one of Formulae I-IVb, wherein $R^6$ is —S(=O)$_2$—$C_{1-4}$ alkyl. In a particular embodiment, $R^6$ is —S(=O)$_2$-Me.

In one embodiment, the compound of the invention is according to any one of Formulae I-IVb, wherein $R^6$ is $C_{1-4}$ alkyl. In a particular embodiment, $R^6$ is —CH$_3$, or —CH$_2$CH$_3$. In a more particular embodiment, $R^6$ is —CH$_3$.

In one embodiment, the compound of the invention is according to any one of Formulae I-IVb, wherein $R^6$ is $C_{1-4}$ alkyl substituted by one or more independently selected $C_{1-3}$ alkoxy, halo, or —OH. In a particular embodiment, $R^6$ is —CH$_3$, —CH$_2$CH$_3$, or —CH(CH$_3$)$_2$, each of which is substituted by one or more independently selected $C_{1-3}$ alkoxy, halo, or —OH. In another particular embodiment, $R^6$ is $C_{1-4}$ alkyl substituted by one or more independently selected —OCH$_3$, —OCH$_2$CH$_3$, F, or —OH. In a more particular embodiment, $R^6$ is —C(CH$_3$)$_2$OH.

In one embodiment, the compound of the invention is according to any one of Formulae I-IVb, wherein $R^6$ is $C_{1-4}$ alkoxy. In a particular embodiment, $R^6$ is —OCH$_3$, or —OCH$_2$CH$_3$. In a more particular embodiment, $R^6$ is —OCH$_3$.

In one embodiment, the compound of the invention is according to any one of Formulae I-IVb, wherein $R^6$ is phenyl.

In one embodiment, the compound of the invention is according to any one of Formulae I-IVb, wherein $R^6$ is phenyl substituted with one or more independently selected halo. In a particular embodiment, $R^6$ is phenyl substituted with one halo. In a more particular embodiment, $R^6$ is phenyl substituted with one or more independently selected F, or Cl. In a more particular embodiment, $R^6$ is phenyl substituted with one F or Cl. In a most particular embodiment, $R^6$ is phenyl substituted with one F.

In one embodiment, the compound of the invention is according to any one of Formulae I-IVb, wherein $R^6$ is —C(=O)-monocyclic 4-6 membered heterocycloalkyl comprising one to three heteroatoms independently selected from N, O, and S. In a particular embodiment, $R^6$ is —C(=O)-azetidinyl, —C(=O)-pyrrolyl, —C(=O)-piperidinyl, —C(=O)-piperazinyl, —C(=O)-morpholinyl, or —C(=O)-thiomorpholinyl. In a more particular embodiment, $R^6$ is —C(=O)-piperidinyl.

In one embodiment, the compound of the invention is according to any one of Formulae I-IVb, wherein $R^6$ is —C(=O)$NR^{8a}R^{8b}$, and wherein $R^{8a}$ and $R^{8b}$ are independently H or $C_{1-3}$ alkyl. In a particular embodiment, $R^{8a}$ is H and $R^{8b}$ is H or $C_{1-3}$ alkyl. In a more particular embodiment, $R^{8a}$ and $R^{8b}$ are independently H, —$CH_3$, —$CH_2CH_3$ or —$CH(CH_3)_2$. In another more particular embodiment, $R^{8a}$ is H and $R^{8b}$ is H, —$CH_3$, —$CH_2CH_3$ or —$CH(CH_3)_2$. In a most particular embodiment, $R^{8a}$ and $R^{8b}$ are —$CH_3$.

In one embodiment, the compound of the invention is according to any one of Formulae I-IVb, wherein $R^6$ is 5-7 membered heteroaryl comprising one to four heteroatoms independently selected from N, O, and S. In a particular embodiment, $R^6$ is pyrazolyl.

In one embodiment, the compound of the invention is according to any one of Formulae I-IVb, wherein $R^6$ is 5-7 membered heteroaryl comprising one to four heteroatoms independently selected from N, O, and S, substituted with one or more independently selected $C_{1-4}$ alkyl. In a particular embodiment, $R^6$ is pyrazolyl, substituted with one or more $C_{1-4}$ alkyl. In another particular embodiment, $R^6$ is 5-7 membered heteroaryl comprising one to four heteroatoms independently selected from N, O, and S, substituted with one or more independently selected —$CH_3$, —$CH_2CH_3$, or —$CH(CH_3)_2$. In a more particular embodiment, $R^6$ is pyrazolyl, substituted with one or more independently selected —$CH_3$, —$CH_2CH_3$, or —$CH(CH_3)_2$ In one embodiment, the compound of the invention is according to any one of Formulae I-IVb, wherein $G_1$ is $C_{1-4}$ alkyl. In a particular embodiment, $G_1$ is —$CH_3$, or —$CH_2CH_3$. In a more particular embodiment, $G_1$ is —$CH_3$.

In one embodiment, the compound of the invention is according to any one of Formulae I-IVb, wherein $G_1$ is $C_{1-4}$ alkyl, substituted with one or more independently selected halo, —$NR^{7a}R^{7b}$, or $C_{1-4}$ alkoxy, which alkoxy is optionally substituted with one or more independently selected halo, and wherein $R^{7a}$ and $R^{7b}$ are independently H or $C_{1-4}$ alkyl. In a particular embodiment, $G_1$ is —$CH_3$, or —$CH_2CH_3$, each of which substituted with one or more independently selected halo, —$NR^{7a}R^{7b}$, or $C_{1-4}$ alkoxy, which alkoxy is optionally substituted with one or more independently selected halo, and wherein $R^{7a}$ and $R^{7b}$ are independently H or $C_{1-4}$ alkyl. In another particular embodiment, $G_1$ is $C_{1-4}$ alkyl, substituted with one or more independently selected F, —$NHCH_3$, —$NHCH_2CH_3$, —$N(CH_3)_2$, —$OCH_3$, —$OCH_2CH_3$, —$OCF_3$, or —$OCH_2CF_3$. In a more particular embodiment, $G_1$ is $C_{1-4}$ alkyl, substituted with one —$NHCH_3$, —$NHCH_2CH_3$, —$N(CH_3)_2$, —$OCH_3$, —$OCH_2CH_3$, —$OCF_3$, or —$OCH_2CF_3$. In a most particular embodiment, $G_1$ is —$CF_3$, —$CHF_2$, —$CH_2$—$CHF_2$, —$CH_2$—$CF_3$, —$CH_2$—$CH_2$—$N(CH_3)_2$, or —$CH_2$—$CH_2$—$OCF_3$. In a further most particular embodiment, $G_1$ is —$CF_3$, In one embodiment, the compound of the invention is according to any one of Formulae I-IVb, wherein $G_1$ is phenyl.

In one embodiment, the compound of the invention is according to any one of Formulae I-IVb, wherein $G_1$ is phenyl substituted with one or more independently selected halo or $C_{1-4}$ alkoxy, which alkoxy is optionally substituted with one or more independently selected halo. In a particular embodiment, $G_1$ is phenyl substituted with one or more independently selected F, Cl, —$OCH_3$, —$OCH_2CH_3$, —$OCF_3$, or —$OCH_2CF_3$. In a more particular embodiment, $G_1$ is phenyl substituted with one F, Cl, —$OCH_3$, —$OCH_2CH_3$, —$OCF_3$, or —$OCH_2CF_3$. In a most particular embodiment, $G_1$ is phenyl substituted with one F, or —$OCH_3$.

In one embodiment, the compound of the invention is according to Formula Va:

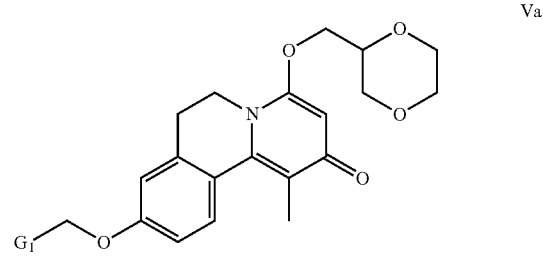

wherein $G_1$ is as defined above.

In one embodiment, the compound of the invention is according to Formula Vb:

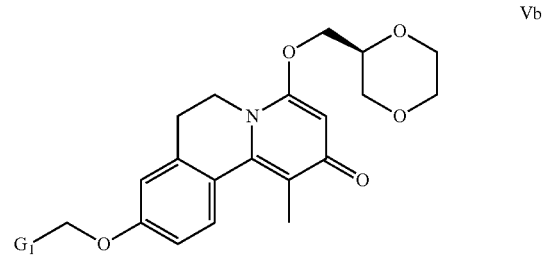

wherein $G_1$ is as defined above.

In one embodiment, the compound of the invention is according to Formula Va, or Vb, wherein $G_1$ is $C_{3-6}$ cycloalkyl. In a particular embodiment, $G_1$ is cyclopropyl, cyclobutyl, cyclopentyl or cyclohexyl. In a particular embodiment, $G_1$ is cyclopropyl, cyclobutyl, or cyclopentyl. In a more particular embodiment, $G_1$ is cyclopropyl.

In one embodiment, the compound of the invention is according to Formula Va, or Vb, wherein $G_1$ is $C_{3-6}$ cycloalkyl substituted with one or more halo. In a particular embodiment, $G_1$ is cyclopropyl, cyclobutyl, cyclopentyl or cyclohexyl, each of which is substituted with one or more halo. In a particular embodiment, $G_1$ is cyclopropyl, cyclobutyl, or cyclopentyl, each of which is substituted with one or more halo. In another particular embodiment, $G_1$ is $C_{3-6}$ cycloalkyl substituted with one or more F. In a more particular embodiment, $G_1$ is cyclopropyl, cyclobutyl, cyclopentyl or cyclohexyl, each of which is substituted with one or more F. In a more particular embodiment, $G_1$ is cyclopropyl, cyclobutyl, or cyclopentyl, each of which is substituted with one or more F. In a most particular embodiment, $G_1$ is cyclopropyl substituted with one or more F.

In one embodiment, the compound of the invention is according to Formula Va, or Vb, wherein $G_1$ is $C_{1-4}$ alkyl, substituted with one or more independently selected halo, —$NR^{7a}R^{7b}$, or $C_{1-4}$ alkoxy, which alkoxy is optionally substituted with one or more independently selected halo, and wherein $R^{7a}$ and $R^{7b}$ are independently H or $C_{1-4}$ alkyl. In a particular embodiment, $G_1$ is —$CH_3$, or —$CH_2CH_3$, each of which substituted with one or more independently selected halo, —NR$^{7a}$R$^{7b}$, or C$_{1-4}$ alkoxy, which alkoxy is optionally substituted with one or more independently selected halo, and wherein R$^{7a}$ and R$^{7b}$ are independently H or C$_{1-4}$ alkyl. In another particular embodiment, G$_1$ is C$_{1-4}$ alkyl, substituted with one or more independently selected F, —NHCH$_3$, —NHCH$_2$CH$_3$, —N(CH$_3$)$_2$, —OCH$_3$, —OCH$_2$CH$_3$, —OCF$_3$, or —OCH$_2$CF$_3$. In a more particular embodiment, G$_1$ is C$_{1-4}$ alkyl, substituted with one —NHCH$_3$, —NHCH$_2$CH$_3$, —N(CH$_3$)$_2$, —OCH$_3$, —OCH$_2$CH$_3$, —OCF$_3$, or —OCH$_2$CF$_3$. In a most particular embodiment, G$_1$ is —CF$_3$, —CHF$_2$, —CH$_2$—CHF$_2$, —CH$_2$—CF$_3$, —CH$_2$—CH$_2$—N(CH$_3$)$_2$, or —CH$_2$—CH$_2$—OCF$_3$. In a further most particular embodiment, G$_1$ is —CF$_3$, In one embodiment, the compound of the invention is according to Formula VIa:

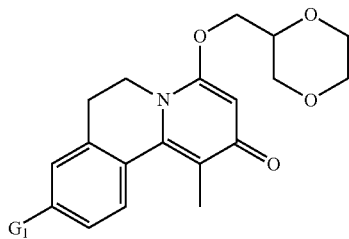

VIa wherein G$_1$ is as defined above.

In one embodiment, the compound of the invention is according to Formula VIb:

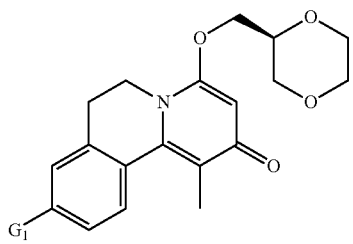

VIb wherein G$_1$ is as defined above.

In one embodiment, the compound of the invention is according to Formula VIa, or VIb, wherein G$_1$ is 5-7 membered heterocycloalkenyl comprising one double bond, and one to three heteroatoms independently selected from N, O, and S. In a particular embodiment, G$_1$ is 1,2,3,6-tetrahydro-pyridinyl, or 3,6-dihydro-2H-pyran.

In one embodiment, the compound of the invention is according to Formula VIa, or VIb, wherein G$_1$ is 5-7 membered heterocycloalkenyl comprising one double bond, and one to three heteroatoms independently selected from N, O, and S, which heterocycloalkenyl is substituted with one or more independently selected R$^6$. In another embodiment, G$_1$ is 1,2,3,6-tetrahydro-pyridinyl, or 3,6-dihydro-2H-pyran, each of which is substituted with one or more independently selected R$^6$. In a particular embodiment, G$_1$ is 5-7 membered heterocycloalkenyl comprising one double bond, and one, to three heteroatoms independently selected from N, O, and S, which heterocycloalkenyl is substituted with one, two, or three independently selected R$^6$. In another particular embodiment, G$_1$ is 1,2,3,6-tetrahydro-pyridinyl, or 3,6-dihydro-2H-pyran, each of which is substituted with one, two, or three independently selected R$^6$. In a more particular embodiment, G$_1$ is 5-7 membered heterocycloalkenyl comprising one double bond, and one to three heteroatoms independently selected from N, O, and S, which heterocycloalkenyl is substituted with one R$^6$. In another more particular embodiment, G$_1$ is 1,2,3,6-tetrahydro-pyridinyl, or 3,6-dihydro-2H-pyran, each of which is substituted with one R$^6$.

In one embodiment, the compound of the invention is according to Formula VIa, or VIb, wherein G$_1$ is monocyclic or spiro bicyclic 4-8 membered heterocycloalkyl comprising one to three heteroatoms independently selected from N, O, and S. In a particular embodiment, G$_1$ is azetidinyl, tetrahydrofuranyl, tetrahydropyranyl, dioxanyl, piperidinyl, piperazinyl, morpholinyl, or 2-oxa-6-aza-spiro[3.3]heptanyl.

In one embodiment, the compound of the invention is according to Formula VIa, or VIb, wherein G$_1$ is monocyclic or spiro bicyclic 4-8 membered heterocycloalkyl comprising one to three heteroatoms independently selected from N, O, and S, which heterocycloalkyl is substituted with one or more independently selected R$^6$. In another embodiment, G$_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one or more independently selected R$^6$. In a particular embodiment, G$_1$ is monocyclic or spiro bicyclic 4-8 membered heterocycloalkyl comprising one to three heteroatoms independently selected from N, O, and S, which heterocycloalkyl is substituted with one, two, or three independently selected R$^6$. In another particular embodiment, G$_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one, two, or three independently selected R$^6$. In a more particular embodiment, G$_1$ is monocyclic or spiro bicyclic 4-8 membered heterocycloalkyl comprising one to three heteroatoms independently selected from N, O, and S, which heterocycloalkyl is substituted with one R$^6$. In another more particular embodiment, G$_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one R$^6$.

In one embodiment, the compound of the invention is according to Formula VIa, or VIb, wherein R$^6$ is halo, or —OH. In a particular embodiment, R$^6$ is F or —OH.

In one embodiment, the compound of the invention is according to Formula VIa, or VIb, wherein R$^6$ is —C(=O)—C$_{1-4}$ alkoxy. In a particular embodiment, R$^6$ is —C(=O)OMe, —C(=O)OEt, —C(=O)OiPr, or —C(=O)OtBu. In a more particular embodiment, R$^6$ is —C(=O)OtBu.

In one embodiment, the compound of the invention is according to Formula VIa, or VIb, wherein R$^6$ is —C(=O)—C$_{1-4}$ alkoxy substituted with one or more independently selected halo. In a particular embodiment, R$^6$ is —C(=O)OMe, —C(=O)OEt, —C(=O)OiPr, or —C(=O)OtBu, each of which is substituted with one or more independently selected halo. In another particular embodiment, R$^6$ is —C(=O)—C$_{1-4}$ alkoxy substituted with one or more F. In a more particular embodiment, R$^6$ is —C(=O)OCH$_2$CF$_3$.

In one embodiment, the compound of the invention is according to Formula VIa, or VIb, wherein R$^6$ is —C(=O)—C$_{3-4}$ cycloalkyl. In a particular embodiment, R$^6$ is —C(=O)cyclopropyl.

In one embodiment, the compound of the invention is according to Formula VIa, or VIb, wherein $R^6$ is —S(=O)$_2$—C$_{1-4}$ alkyl. In a particular embodiment, $R^6$ is —S(=O)$_2$-Me.

In one embodiment, the compound of the invention is according to Formula VIa, or VIb, wherein $R^6$ is C$_{1-4}$ alkyl. In a particular embodiment, $R^6$ is —CH$_3$, or —CH$_2$CH$_3$. In a more particular embodiment, $R^6$ is —CH$_3$.

In one embodiment, the compound of the invention is according to Formula VIa, or VIb, wherein $R^6$ is C$_{1-4}$ alkyl substituted by one or more independently selected C$_{1-3}$ alkoxy, halo, or —OH. In a particular embodiment, $R^6$ is —CH$_3$, —CH$_2$CH$_3$, or —CH(CH$_3$)$_2$, each of which is substituted by one or more independently selected C$_{1-3}$ alkoxy, halo, or —OH. In another particular embodiment, $R^6$ is C$_{1-4}$ alkyl substituted by one or more independently selected —OCH$_3$, —OCH$_2$CH$_3$, F, or —OH. In a more particular embodiment, $R^6$ is —C(CH$_3$)$_2$OH.

In one embodiment, the compound of the invention is according to Formula VIa, or VIb, wherein $R^6$ is C$_{1-4}$ alkoxy. In a particular embodiment, $R^6$ is —OCH$_3$, or —OCH$_2$CH$_3$. In a more particular embodiment, $R^6$ is —OCH$_3$.

In one embodiment, the compound of the invention is according to Formula VIa, or VIb, wherein $R^6$ is phenyl.

In one embodiment, the compound of the invention is according to Formula VIa, or VIb, wherein $R^6$ is phenyl substituted with one or more independently selected halo. In a particular embodiment, $R^6$ is phenyl substituted with one halo. In a more particular embodiment, $R^6$ is phenyl substituted with one or more independently selected F, or Cl. In a more particular embodiment, $R^6$ is phenyl substituted with one F or Cl. In a most particular embodiment, $R^6$ is phenyl substituted with one F.

In one embodiment, the compound of the invention is according to Formula VIa, or VIb, wherein $R^6$ is —C(=O)-monocyclic 4-6 membered heterocycloalkyl comprising one to three heteroatoms independently selected from N, O, and S. In a particular embodiment, $R^6$ is —C(=O)-azetidinyl, —C(=O)-pyrrolyl, —C(=O)-piperidinyl, —C(=O)-piperazinyl, —C(=O)-morpholinyl, or —C(=O)-thiomorpholinyl. In a more particular embodiment, $R^6$ is —C(=O)-piperidinyl.

In one embodiment, the compound of the invention is according to Formula VIa, or VIb, wherein $R^6$ is —C(=O)NR$^{8a}$R$^{8b}$, and wherein R$^{8a}$ and R$^{8b}$ are independently H or C$_{1-3}$ alkyl. In a particular embodiment, R$^{8a}$ is H and R$^{8b}$ is H or C$_{1-3}$ alkyl. In a more particular embodiment, R$^{8a}$ and R$^{8b}$ are independently H, —CH$_3$, —CH$_2$CH$_3$ or —CH(CH$_3$)$_2$. In another more particular embodiment, R$^{8a}$ is H and R$^{8b}$ is H, —CH$_3$, —CH$_2$CH$_3$ or —CH(CH$_3$)$_2$. In a most particular embodiment, R$^{8a}$ and R$^{8b}$ are —CH$_3$.

In one embodiment, the compound of the invention is according to Formula VIa, or VIb, wherein $R^6$ is 5-7 membered heteroaryl comprising one to four heteroatoms independently selected from N, O, and S. In a particular embodiment, $R^6$ is pyrazolyl.

In one embodiment, the compound of the invention is selected from:

4-[[(2S)-1,4-dioxan-2-yl]methoxy]-9,10-dimethoxy-1-methyl-6,7-dihydrobenzo[a]quinolizin-2-one,
9,10-dimethoxy-1-methyl-4-(tetrahydrofuran-2-ylmethyl-amino)-6,7-dihydrobenzo[a]quinolizin-2-one,
1-ethyl-9-hydroxy-4-(tetrahydrofuran-2-ylmethylamino)-6,7-dihydrobenzo[a]quinolizin-2-one,
9,10-Dimethoxy-4-[(tetrahydro-furan-2-ylmethyl)-amino]-6,7-dihydro-pyrido[2,1-a]isoquinolin-2-one,
4-[([1,4]Dioxan-2-ylmethyl)-amino]-9,10-dimethoxy-6,7-dihydro-pyrido[2,1-a]isoquinolin-2-one,
4-[[(2R)-1,4-dioxan-2-yl]methylamino]-9,10-dimethoxy-1-methyl-6,7-dihydrobenzo[a]quinolizin-2-one,
9-(2,2-Difluoro-cyclopropylmethoxy)-1-methyl-4-[(tetra-hydro-furan-2-ylmethyl)-amino]-6,7-dihydro-pyrido[2,1-a]isoquinolin-2-one,
1-methyl-4-(tetrahydrofuran-2-ylmethylamino)-9-(2,2,2-trifluoroethoxy)-6,7-dihydrobenzo[a]quinolizin-2-one,
-Methyl-4-[(tetrahydro-furan-2-ylmethyl)-amino]-9-(tetra-hydro-furan-2-yloxy)-6,7-dihydro-pyrido[2,1-a]isoquino-lin-2-one,
8,9-dimethoxy-1-methyl-4-(tetrahydrofuran-2-ylmethyl-amino)-6,7-dihydrobenzo[a]quinolizin-2-one,
4-[[(2S)-1,4-dioxan-2-yl]methoxy]-8,9-dimethoxy-1-methyl-6,7-dihydrobenzo[a]quinolizin-2-one,
9-(2,2-difluoroethoxy)-1-methyl-4-(tetrahydropyran-2-ylm-ethylamino)-6,7-dihydrobenzo[a]quinolizin-2-one,
1-methyl-4-(tetrahydropyran-2-ylmethylamino)-9-(2,2,2-trifluoroethoxy)-6,7-dihydrobenzo[a]quinolizin-2-one,
8,9-dimethoxy-1-methyl-4-(tetrahydropyran-2-ylmethyl-amino)-6,7-dihydrobenzo[a]quinolizin-2-one,
4-(1,4-dioxan-2-ylmethylamino)-8,9-dimethoxy-1-methyl-6,7-dihydrobenzo[a]quinolizin-2-one,
4-[[(2S)-1,4-dioxan-2-yl]methoxy]-1-methyl-9-(2,2,2-trif-luoroethoxy)-6,7-dihydrobenzo[a]quinolizin-2-one,
4-(1,4-dioxan-2-ylmethylamino)-8,9-dimethoxy-6,7-dihyd-robenzo[a]quinolizin-2-one,
8,9-dimethoxy-4-(tetrahydrofuran-2-ylmethylamino)-6,7-dihydrobenzo[a]quinolizin-2-one,
4-(1,4-dioxan-2-ylmethylamino)-9-hydroxy-8-methoxy-6,7-dihydrobenzo[a]quinolizin-2-one,
4-(1,4-dioxan-2-ylmethylamino)-8-hydroxy-9-methoxy-6,7-dihydrobenzo[a]quinolizin-2-one,
9-(2,2-Difluoro-ethoxy)-4-[([1,4]dioxan-2-ylmethyl)-amino]-8-methoxy-1-methyl-6,7-dihydro-pyrido[2,1-a]isoquinolin-2-one,
9-(2,2-Difluoro-ethoxy)-8-methoxy-1-methyl-4-[(tetra-hydro-furan-2-ylmethyl)-amino]-6,7-dihydro-pyrido[2,1-a]isoquinolin-2-one,
4-[[(2S)-1,4-dioxan-2-yl]methoxy]-1-methyl-2-oxo-6,7-di-hydrobenzo[a]quinolizine-9-carbonitrile,
9-(2,2-difluoroethoxy)-1-ethyl-4-(tetrahydrofuran-2-ylm-ethylamino)-6,7-dihydrobenzo[a]quinolizin-2-one,
1-ethyl-4-(tetrahydrofuran-2-ylmethylamino)-9-(2,2,2-trif-luoroethoxy)-6,7-dihydrobenzo[a]quinolizin-2-one,
8,9-dimethoxy-1-methyl-4-(tetrahydrofuran-2-ylmethoxy)-6,7-dihydrobenzo[a]quinolizin-2-one,
8,9-dimethoxy-1-methyl-4-(tetrahydropyran-2-ylmethoxy)-6,7-dihydrobenzo[a]quinolizin-2-one,
4-[[(2S)-1,4-dioxan-2-yl]methoxy]-1-methyl-9-(tetrahydro-pyran-4-ylmethoxy)-6,7-dihydrobenzo[a]quinolizin-2-one,
4-[[(2S)-1,4-dioxan-2-yl]methoxy]-1-methyl-9-(2-pyridyl-methoxy)-6,7-dihydrobenzo[a]quinolizin-2-one,
4-[[(2S)-1,4-dioxan-2-yl]methoxy]-1-methyl-9-[[3-(trifluo-romethoxy)phenyl]methoxy]-6,7-dihydrobenzo[a]quino-lizin-2-one,
9-benzyloxy-4-[[(2S)-1,4-dioxan-2-yl]methoxy]-1-methyl-6,7-dihydrobenzo[a]quinolizin-2-one,
9-benzyloxy-4-[[(2R)-1,4-dioxan-2-yl]methylamino]-1-methyl-6,7-dihydrobenzo[a]quinolizin-2-one,
9-(2,2-difluoroethoxy)-4-[[(2R)-1,4-dioxan-2-yl]methyl-amino]-1-methyl-6,7-dihydrobenzo[a]quinolizin-2-one,
4-[[(2R)-1,4-dioxan-2-yl]methylamino]-1-methyl-9-(2,2,2-trifluoroethoxy)-6,7-dihydrobenzo[a]quinolizin-2-one,

[4-[[(2S)-1,4-dioxan-2-yl]methoxy]-1-methyl-2-oxo-6,7-dihydrobenzo[a]quinolizin-9-yl]trifluoromethanesulfonate,
4-[[(2S)-1,4-dioxan-2-yl]methoxy]-1-methyl-9-[(1-methylpyrazol-4-yl)methoxy]-6,7-dihydrobenzo[a]quinolizin-2-one,
9-(3,6-dihydro-2H-pyran-4-yl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-9-(1-ethylpyrazol-4-yl)-1-methyl-6,7-dihydrobenzo[a]quinolizin-2-one,
4-[[(2S)-1,4-dioxan-2-yl]methoxy]-1-methyl-9-tetrahydropyran-4-yl-6,7-dihydrobenzo[a]quinolizin-2-one,
1-methyl-4-[[(2S)-tetrahydrofuran-2-yl]methylamino]-9-(2,2,2-trifluoroethoxy)-6,7-dihydrobenzo[a]quinolizin-2-one,
1-methyl-9-[(3-methyl-1,2,4-oxadiazol-5-yl)methoxy]-4-(tetrahydrofuran-2-ylmethoxy)-6,7-dihydrobenzo[a]quinolizin-2-one,
1-methyl-9-[(3-methyl-1,2,4-oxadiazol-5-yl)methoxy]-4-(tetrahydropyran-2-ylmethoxy)-6,7-dihydrobenzo[a]quinolizin-2-one,
1-methyl-9-(2-pyridylmethoxy)-4-(tetrahydrofuran-2-ylmethoxy)-6,7-dihydrobenzo[a]quinolizin-2-one,
1-methyl-9-(2-pyridylmethoxy)-4-(tetrahydropyran-2-ylmethoxy)-6,7-dihydrobenzo[a]quinolizin-2-one,
1-methyl-4-(tetrahydrofuran-2-ylmethoxy)-9-(tetrahydropyran-3-ylmethoxy)-6,7-dihydrobenzo[a]quinolizin-2-one,
1-methyl-4-(tetrahydropyran-2-ylmethoxy)-9-(tetrahydropyran-3-ylmethoxy)-6,7-dihydrobenzo[a]quinolizin-2-one,
4-[[(2S)-1,4-dioxan-2-yl]methoxy]-1-methyl-9-(tetrahydropyran-3-ylmethoxy)-6,7-dihydrobenzo[a]quinolizin-2-one,
1-methyl-9-[(6-methyl-3-pyridyl)methoxy]-4-(tetrahydrofuran-2-ylmethoxy)-6,7-dihydrobenzo[a]quinolizin-2-one,
1-methyl-9-[(6-methyl-3-pyridyl)methoxy]-4-(tetrahydropyran-2-ylmethoxy)-6,7-dihydrobenzo[a]quinolizin-2-one,
4-[[(2S)-1,4-dioxan-2-yl]methoxy]-1-methyl-9-[(6-methyl-3-pyridyl)methoxy]-6,7-dihydrobenzo[a]quinolizin-2-one,
9-(2-dimethylaminoethyloxy)-1-methyl-4-(tetrahydrofuran-2-ylmethoxy)-6,7-dihydrobenzo[a]quinolizin-2-one,
9-(2-dimethylaminoethyloxy)-1-methyl-4-(tetrahydropyran-2-ylmethoxy)-6,7-dihydrobenzo[a]quinolizin-2-one,
9-(2-dimethylaminoethyloxy)-4-[[(2S)-1,4-dioxan-2-yl]methoxy]-1-methyl-6,7-dihydrobenzo[a]quinolizin-2-one,
[4-[[(2S)-1,4-dioxan-2-yl]methoxy]-1-methyl-2-oxo-6,7-dihydrobenzo[a]quinolizin-9-yl] methanesulfonate,
1-methyl-9-(2-pyridylmethoxy)-4-[[(2S)-tetrahydrofuran-2-yl]methoxy]-6,7-dihydrobenzo[a]quinolizin-2-one,
4-[[(2S)-1,4-dioxan-2-yl]methoxy]-1-methyl-9-[(3-methyl-1,2,4-oxadiazol-5-yl)methoxy]-6,7-dihydrobenzo[a]quinolizin-2-one,
9-(difluoromethoxy)-4-[[(2S)-1,4-dioxan-2-yl]methoxy]-1-methyl-6,7-dihydrobenzo[a]quinolizin-2-one,
tert-butyl 4-[4-[[(2S)-1,4-dioxan-2-yl]methoxy]-1-methyl-2-oxo-6,7-dihydrobenzo[a]quinolizin-9-yl]piperazine-1-carboxylate,
9-(2,2-difluoroethoxy)-4-[[(2S)-1,4-dioxan-2-yl]methoxy]-1-methyl-6,7-dihydrobenzo[a]quinolizin-2-one,
4,9-bis[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-morpholino-6,7-dihydrobenzo[a]quinolizin-2-one,
4-[[(2S)-1,4-dioxan-2-yl]methoxy]-1-methyl-9-phenylsulfanyl-6,7-dihydrobenzo[a]quinolizin-2-one,
9-(4,4-difluoro-1-piperidyl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-piperazin-1-yl-6,7-dihydrobenzo[a]quinolizin-2-one,
9-(benzenesulfonyl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-(4-methylsulfonylpiperazin-1-yl)-6,7-dihydrobenzo[a]quinolizin-2-one,
9-[4-(cyclopropanecarbonyl)piperazin-1-yl]-4-[[(2S)-1,4-dioxan-2-yl]methoxy]-1-methyl-6,7-dihydrobenzo[a]quinolizin-2-one,
N-[4-[[(2S)-1,4-dioxan-2-yl]methoxy]-1-methyl-2-oxo-6,7-dihydrobenzo[a]quinolizin-9-yl]cyclopropanecarboxamide,
tert-butyl 3-[4-[[(2S)-1,4-dioxan-2-yl]methoxy]-1-methyl-2-oxo-6,7-dihydrobenzo[a]quinolizin-9-yl]azetidine-1-carboxylate,
4-[[(2S)-1,4-dioxan-2-yl]methoxy]-1-methyl-9-[2-(trifluoromethoxy)ethoxy]-6,7-dihydrobenzo[a]quinolizin-2-one,
N-[4-[[(2S)-1,4-dioxan-2-yl]methoxy]-1-methyl-2-oxo-6,7-dihydrobenzo[a]quinolizin-9-yl]-N-methyl-cyclopropanecarboxamide,
tert-butyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate,
tert-butyl 4-[4-[[(2S)-1,4-dioxan-2-yl]methoxy]-1-methyl-2-oxo-6,7-dihydrobenzo[a]quinolizin-9-yl]piperidine-1-carboxylate,
methyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate,
ethyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate,
isopropyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate,
2,2,2-trifluoroethyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate,
methyl 4-[4-[[(2S)-1,4-dioxan-2-yl]methoxy]-1-methyl-2-oxo-6,7-dihydrobenzo[a]quinolizin-9-yl]piperidine 1-carboxylate,
ethyl 4-[4-[[(2S)-1,4-dioxan-2-yl]methoxy]-1-methyl-2-oxo-6,7-dihydrobenzo[a]quinolizin-9-yl]piperidine 1-carboxylate,
isopropyl 4-[4-[[(2S)-1,4-dioxan-2-yl]methoxy]-1-methyl-2-oxo-6,7-dihydrobenzo[a]quinolizin-9-yl]piperidine-1-carboxylate,
2,2,2-trifluoroethyl 4-[4-[[(2S)-1,4-dioxan-2-yl]methoxy]-1-methyl-2-oxo-6,7-dihydrobenzo[a]quinolizin-9-yl]piperidine-1-carboxylate,
N-cyclopropyl-4-[[(2S)-1,4-dioxan-2-yl]methoxy]-1-methyl-2-oxo-6,7-dihydrobenzo[a]quinolizine-9-carboxamide,
4-[[(2S)-1,4-dioxan-2-yl]methoxy]-9-hydroxy-1-methyl-6,7-dihydrobenzo[a]quinolizin-2-one,
9-(3,3-difluoroazetidin-1-yl)-4-[[(2S)-1,4-dioxan-2-yl]methoxy]-1-methyl-6,7-dihydrobenzo[a]quinolizin-2-one, 4-[[(2S)-1,4-dioxan-2-yl]methoxy]-1-methyl-9-(6-oxa-2-azaspiro[3.3]heptan-2-yl)-6,7-dihydrobenzo[a]quinolizin-2-one,
N-cyclopropyl-4-[[(2S)-1,4-dioxan-2-yl]methoxy]-N,1-dimethyl-2-oxo-6,7-dihydrobenzo[a]quinolizine-9-carboxamide,
4-[[(2S)-1,4-dioxan-2-yl]methoxy]-9-methoxy-1-methyl-6,7-dihydrobenzo[a]quinolizin-2-one,
4-(1,4-dioxan-2-ylmethoxy)-1-methyl-9-(2,2,2-trifluoroethoxy)-6,7-dihydrobenzo[a]quinolizin-2-one,
4-[[(2S)-1,4-dioxan-2-yl]methoxy]-9-(3-fluoroazetidin-1-yl)-1-methyl-6,7-dihydrobenzo[a]quinolizin-2-one,
4-[[(2S)-1,4-dioxan-2-yl]methoxy]-9-[3-(1-hydroxy-1-methyl-ethyl)azetidin-1-yl]-1-methyl-6,7-dihydrobenzo[a]quinolizin-2-one,
9-(azetidin-1-yl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-(3-methylsulfonylazetidin-1-yl)-6,7-dihydrobenzo[a]quinolizin-2-one,
4-[[(2S)-1,4-dioxan-2-yl]methoxy]-1-methyl-9-(3-pyrazol-1-ylazetidin-1-yl)-6,7-dihydrobenzo[a]quinolizin-2-one,
9-(3,3-dimethylazetidin-1-yl)-4-[[(2S)-1,4-dioxan-2-yl]methoxy]-1-methyl-6,7-dihydrobenzo[a]quinolizin-2-one,
methyl 1-[4-[[(2S)-1,4-dioxan-2-yl]methoxy]-1-methyl-2-oxo-6,7-dihydrobenzo[a]quinolizin-9-yl]azetidine-3-carboxylate,
4-[[(2S)-1,4-dioxan-2-yl]methoxy]-1-methyl-9-(3-pyridyl)-6,7-dihydrobenzo[a]quinolizin-2-one,
4-[[(2S)-1,4-dioxan-2-yl]methoxy]-9-(3-fluorophenyl)-1-methyl-6,7-dihydrobenzo[a]quinolizin-2-one,
4-[[(2S)-1,4-dioxan-2-yl]methoxy]-1-methyl-9-(4-pyridyl)-6,7-dihydrobenzo[a]quinolizin-2-one,
4-[[(2S)-1,4-dioxan-2-yl]methoxy]-1-methyl-9-(2-pyridyl)-6,7-dihydrobenzo[a]quinolizin-2-one,
4-[[(2S)-1,4-dioxan-2-yl]methoxy]-1-methyl-9-(3-methyl-2-pyridyl)-6,7-dihydrobenzo[a]quinolizin-2-one,
4-[[(2S)-1,4-dioxan-2-yl]methoxy]-1-methyl-9-(4-methyl-2-pyridyl)-6,7-dihydrobenzo[a]quinolizin-2-one,
tert-butyl 3-[[4-[[(2S)-1,4-dioxan-2-yl]methoxy]-1-methyl-2-oxo-6,7-dihydrobenzo[a]quinolizin-9-yl]oxy]azetidine-1-carboxylate,
3-deuterio-9-(1-deuterio-2,2-difluoro-vinyloxy)-4-[[(2S)-1,4-dioxan-2-yl]methoxy]-1-methyl-6,7-dihydrobenzo[a]quinolizin-2-one,
9-(1,1-dideuterio-2,2,2-trifluoro-ethoxy)-4-[[(2S)-1,4-dioxan-2-yl]methoxy]-1-methyl-6,7-dihydrobenzo[a]quinolizin-2-one,
9-benzyloxy-1-methyl-4-(oxetan-2-ylmethoxy)-6,7-dihydrobenzo[a]quinolizin-2-one,
9-benzyloxy-1-methyl-4-[[(2S)-tetrahydrofuran-2-yl]methoxy]-6,7-dihydrobenzo[a]quinolizin-2-one,
9-benzyloxy-1-methyl-4-(tetrahydropyran-2-ylmethoxy)-6,7-dihydrobenzo[a]quinolizin-2-one,
4-[[(2S)-1,4-dioxan-2-yl]methoxy]-9-(3-methoxyazetidin-1-yl)-1-methyl-6,7-dihydrobenzo[a]quinolizin-2-one,
4-[[(2S)-1,4-dioxan-2-yl]methoxy]-9-(4-methoxy-1-piperidyl)-1-methyl-6,7-dihydrobenzo[a]quinolizin-2-one,
4-[[(2S)-1,4-dioxan-2-yl]methoxy]-1-methyl-9-[4-(piperidine-1-carbonyl)-1-piperidyl]-6,7-dihydrobenzo[a]quinolizin-2-one,
4-[[(2S)-1,4-dioxan-2-yl]methoxy]-1-methyl-9-(4-phenyl-1-piperidyl)-6,7-dihydrobenzo[a]quinolizin-2-one,
methyl 1-[4-[[(2S)-1,4-dioxan-2-yl]methoxy]-1-methyl-2-oxo-6,7-dihydrobenzo[a]quinolizin-9-yl]piperidine-4-carboxylate,
4-[[(2S)-1,4-dioxan-2-yl]methoxy]-9-[4-(ethoxymethyl)-1-piperidyl]-1-methyl-6,7-dihydrobenzo[a]quinolizin-2-one,
4-[[(2S)-1,4-dioxan-2-yl]methoxy]-1-methyl-9-(1-piperidyl)-6,7-dihydrobenzo[a]quinolizin-2-one,
4-[[(2S)-1,4-dioxan-2-yl]methoxy]-1-methyl-9-(3-methyl-1-piperidyl)-6,7-dihydrobenzo[a]quinolizin-2-one,
4-[[(2S)-1,4-dioxan-2-yl]methoxy]-9-[4-(4-fluorophenyl)-1-piperidyl]-1-methyl-6,7-dihydrobenzo[a]quinolizin-2-one,
9-[1-(cyclopropanecarbonyl)azetidin-3-yl]oxy-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-[1-(2,2,2-trifluoroacetyl)azetidin-3-yl]oxy-6,7-dihydrobenzo[a]quinolizin-2-one,
ethyl 3-[[4-[[(2S)-1,4-dioxan-2-yl]methoxy]-1-methyl-2-oxo-6,7-dihydrobenzo[a]quinolizin-9-yl]oxy]azetidine-1-carboxylate,
4-[[(2S)-1,4-dioxan-2-yl]methoxy]-1-methyl-9-[4-(3-pyridyloxy)-1-piperidyl]-6,7-dihydrobenzo[a]quinolizin-2-one,
1-[4-[[(2S)-1,4-dioxan-2-yl]methoxy]-1-methyl-2-oxo-6,7-dihydrobenzo[a]quinolizin-9-yl]piperidine-4-carbonitrile,
9-(3,3-difluoro-1-piperidyl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-9-isopropyl-1-methyl-6,7-dihydrobenzo[a]quinolizin-2-one,
3-deuterio-4-[[(2S)-1,4-dioxan-2-yl]methoxy]-1-methyl-9-(2,2,2-trifluoroethoxy)-6,7-dihydrobenzo[a]quinolizin-2-one,
3-deuterio-4-[[(2S)-1,4-dioxan-2-yl]methoxy]-1-methyl-9-(1,1,2,2-tetradeuterio-2-fluoro-ethoxy)-6,7-dihydrobenzo[a]quinolizin-2-one,
tert-butyl 3-[[4-[[(2S)-1,4-dioxan-2-yl]methoxy]-1-methyl-2-oxo-6,7-dihydrobenzo[a]quinolizin-9-yl]oxy]pyrrolidine-1-carboxylate,
tert-butyl 4-[[4-[[(2S)-1,4-dioxan-2-yl]methoxy]-1-methyl-2-oxo-6,7-dihydrobenzo[a]quinolizin-9-yl]oxy]piperidine-1-carboxylate,
4-[[(2S)-1,4-dioxan-2-yl]methoxy]-1-methyl-9-[methyl(3,3,3-trifluoropropyl)amino]-6,7-dihydrobenzo[a]quinolizin-2-one,
4-[[(2S)-1,4-dioxan-2-yl]methoxy]-1-methyl-9-pyrrolidin-1-yl-6,7-dihydrobenzo[a]quinolizin-2-one,
9-(3,3-difluoropyrrolidin-1-yl)-4-[[(2S)-1,4-dioxan-2-yl]methoxy]-1-methyl-6,7-dihydrobenzo[a]quinolizin-2-one,
4-[[(2S)-1,4-dioxan-2-yl]methoxy]-1-methyl-9-[3-(trifluoromethyl)azetidin-1-yl]-6,7-dihydrobenzo[a]quinolizin-2-one,
4-[[(2S)-1,4-dioxan-2-yl]methoxy]-1-methyl-9-[4-(trifluoromethyl)-3,6-dihydro-2H-pyridin-1-yl]-6,7-dihydrobenzo[a]quinolizin-2-one,
4-[[(2S)-1,4-dioxan-2-yl]methoxy]-1-methyl-9-[(2R)-2-methylpyrrolidin-1-yl]-6,7-dihydrobenzo[a]quinolizin-2-one,
4-[[(2S)-1,4-dioxan-2-yl]methoxy]-9-(3-fluoro-1-piperidyl)-1-methyl-6,7-dihydrobenzo[a]quinolizin-2-one,
9-carbazol-9-yl-4-[[(2S)-1,4-dioxan-2-yl]methoxy]-1-methyl-6,7-dihydrobenzo[a]quinolizin-2-one,
9-(3,5-dimethyl-1-piperidyl)-4-[[(2S)-1,4-dioxan-2-yl]methoxy]-1-methyl-6,7-dihydrobenzo[a]quinolizin-2-one, 9-(3,3-dimethylpyrrolidin-1-yl)-4-[[(2S)-1,4-dioxan-2-yl]
  methoxy]-1-methyl-6,7-dihydrobenzo[a]quinolizin-2-
  one,
9-(4,4-dimethyl-1-piperidyl)-4-[[(2S)-1,4-dioxan-2-yl]
  methoxy]-1-methyl-6,7-dihydrobenzo[a]quinolizin-2-
  one,
4-[[(2S)-1,4-dioxan-2-yl]methoxy]-1-methyl-9-[4-(trifluo-
  romethyl)-1-piperidyl]-6,7-dihydrobenzo[a]quinolizin-2-
  one,
4-[[(2S)-1,4-dioxan-2-yl]methoxy]-1-methyl-9-(4-methyl-
  1-piperidyl)-6,7-dihydrobenzo[a]quinolizin-2-one,
4-[[(2S)-1,4-dioxan-2-yl]methoxy]-1-methyl-9-(2,2,2-trif-
  luoroethylamino)-6,7-dihydrobenzo[a]quinolizin-2-one,
4-[[(2S)-1,4-dioxan-2-yl]methoxy]-1-methyl-9-(2-methyl-
  1-piperidyl)-6,7-dihydrobenzo[a]quinolizin-2-one,
9-[1-(cyclopropanecarbonyl)pyrrolidin-3-yl]oxy-4-[[(2S)-1,
  4-dioxan-2-yl]methoxy]-1-methyl-6,7-dihydrobenzo[a]
  quinolizin-2-one,
ethyl 3-[[4-[[(2S)-1,4-dioxan-2-yl]methoxy]-1-methyl-2-
  oxo-6,7-dihydrobenzo[a]quinolizin-9-yl]oxy]pyrrolidine-
  1-carboxylate,
9-[1-(cyclopropanecarbonyl)azetidin-3-yl]-4-[[(2S)-1,4-di-
  oxan-2-yl]methoxy]-1-methyl-6,7-dihydrobenzo[a]qui-
  nolizin-2-one,
ethyl 3-[4-[[(2S)-1,4-dioxan-2-yl]methoxy]-1-methyl-2-
  oxo-6,7-dihydrobenzo[a]quinolizin-9-yl]azetidine-1-car-
  boxylate,
3-[4-[[(2S)-1,4-dioxan-2-yl]methoxy]-1-methyl-2-oxo-6,7-
  dihydrobenzo[a]quinolizin-9-yl]-N,N-dimethyl-azeti-
  dine-1-carboxamide,
3-[4-[[(2S)-1,4-dioxan-2-yl]methoxy]-1-methyl-2-oxo-6,7-
  dihydrobenzo[a]quinolizin-9-yl]-N-isopropyl-azetidine-
  1-carboxamide,
3-[[4-[[(2S)-1,4-dioxan-2-yl]methoxy]-1-methyl-2-oxo-6,7-
  dihydrobenzo[a]quinolizin-9-yl]oxy]-N,N-dimethyl-aze-
  tidine-1-carboxamide,
3-[4-[[(2S)-1,4-dioxan-2-yl]methoxy]-1-methyl-2-oxo-6,7-
  dihydrobenzo[a]quinolizin-9-yl]-N-isopropyl-azetidine-
  1-carboxamide,
9-benzyloxy-4-[(4,4-dimethyloxetan-2-yl)methoxy]-1-
  methyl-6,7-dihydrobenzo[a]quinolizin-2-one,
9-benzyloxy-1-methyl-4-[(2-methyltetrahydrofuran-2-yl)
  methoxy]-6,7-dihydrobenzo[a]quinolizin-2-one,
9-benzyloxy-4-[(5,5-dimethyltetrahydrofuran-2-yl)
  methoxy]-1-methyl-6,7-dihydrobenzo[a]quinolizin-2-
  one,
4-[[(2S)-1,4-dioxan-2-yl]methoxy]-1-methyl-9-(2,2,3,3,3-
  pentafluoropropoxy)-6,7-dihydrobenzo[a]quinolizin-2-
  one,
4-[[(2S)-1,4-dioxan-2-yl]methoxy]-1-methyl-6,7-dihyd-
  robenzo[a]quinolizin-2-one,
4-[[(2S)-1,4-dioxan-2-yl]methoxy]-1-methyl-9-(2-oxopyr-
  rolidin-1-yl)-6,7-dihydrobenzo[a]quinolizin-2-one, and
3-deuterio-4-[[(2S)-1,4-dioxan-2-yl]methoxy]-1-methyl-9-
  (1,1,2,2-tetradeuterio-2-fluoro-ethoxy)-6,7-dihydrobenzo
  [a]quinolizin-2-one.

In one embodiment, the compound of the invention is 4-[[(2S)-1,4-dioxan-2-yl]methoxy]-1-methyl-9-(2,2,2-trifluoroethoxy)-6,7-dihydrobenzo[a]quinolizin-2-one.

In another embodiment, the compound of the invention is not 4-[[(2S)-1,4-dioxan-2-yl]methoxy]-1-methyl-9-(2,2,2-trifluoroethoxy)-6,7-dihydrobenzo[a]quinolizin-2-one.

In one embodiment, the compound of the invention is 4-[[(2S)-1,4-dioxan-2-yl]methoxy]-9-(2-fluoroethoxy)-1-methyl-6,7-dihydrobenzo[a]quinolizin-2-one.

In one embodiment a compound of the invention is not an isotopic variant.

In one aspect a compound of the invention is present as the free base.

In one aspect a compound of the invention is a pharmaceutically acceptable salt.

In one aspect a compound of the invention is present as the free base or a pharmaceutically acceptable salt.

In one aspect a compound of the invention is a solvate.

In one aspect a compound of the invention is a solvate of a pharmaceutically acceptable salt of the compound.

In certain aspects, the present invention provides prodrugs and derivatives of a compound of the invention according to the formulae above. Prodrugs are derivatives of a compound of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_{1-8}$ alkyl, $C_{2-8}$ alkenyl, aryl, $C_{7-12}$ substituted aryl, and $C_{7-12}$ arylalkyl esters of the compounds of the invention.

While specified groups for each embodiment have generally been listed above separately, a compound of the invention includes one in which several or each embodiment in the above Formulae, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

Clauses

1) A compound according to Formula I:

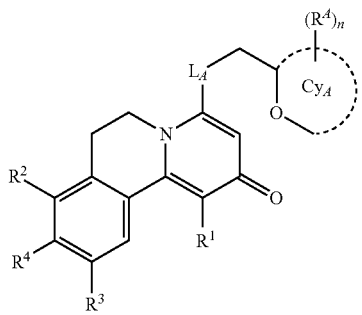

wherein
$L_A$ is O, or NH;
$Cy_A$ is monocyclic 4-6 membered heterocycloalkyl, comprising one or two O atoms;
each $R^A$ is independently selected from halo, and $C_{1-3}$ alkyl;
the subscript n is 0, 1 or 2;
$R^1$ is H or $C_{1-3}$ alkyl;
$R^2$ is H, —OH, or $C_{1-3}$ alkoxy;
$R^3$ is H or $C_{1-3}$ alkoxy;
$R^4$ is
—CN,
—OH,
—O—S(=O)$_2$—C$_{1-4}$ alkyl optionally substituted with one or more independently selected halo, or
-L$_1$-W$_1$-G$_1$;
$L_1$ is a direct bond, —O—, —S—, —SO$_2$—, —C(=O)NR$^{5a}$—, —NR$^{5b}$C(=O)—, or —NR$^{5c}$—;
$R^{5a}$, $R^{5b}$, and $R^{5c}$ are independently H or C$_{1-4}$ alkyl;
$W_1$ is a direct bond or C$_{1-2}$ alkylene optionally substituted with one or more independently selected halo;
$G_1$ is
C$_{3-6}$ cycloalkyl optionally substituted with one or more independently selected halo,
5-6 membered heteroaryl comprising one to four heteroatoms independently selected from N, O, and S, which heteroaryl is optionally substituted with one or more independently selected C$_{1-4}$ alkyl,
5-7 membered heterocycloalkenyl comprising one double bond, and one to three heteroatoms independently selected from N, O, and S, which heterocycloalkenyl is optionally substituted with one or more independently selected $R^6$,
monocyclic or spiro bicyclic 4-8 membered heterocycloalkyl comprising one to three heteroatoms independently selected from N, O, and S, which heterocycloalkyl is optionally substituted with one or more independently selected $R^6$,
monocyclic 4-6 membered heterocycloalkyl comprising one to three heteroatoms independently selected from N, O, and S, fused to one or two phenyls,
C$_{1-4}$ alkyl optionally substituted with one or more independently selected halo, —NR$^{7a}$R$^{7b}$, or C$_{1-4}$ alkoxy, which alkoxy is optionally substituted with one or more independently selected halo, or
phenyl optionally substituted with one or more independently selected halo or C$_{1-4}$ alkoxy, which alkoxy is optionally substituted with one or more independently selected halo;

$R^6$ is
halo,
=O,
—CN,
—OH,
—C(=O)—C$_{1-4}$ alkoxy optionally substituted with one or more independently selected halo,
—C(=O)—C$_{3-4}$ cycloalkyl,
—S(=O)$_2$—C$_{1-4}$ alkyl,
C$_{1-4}$ alkyl optionally substituted by one or more independently selected C$_{1-3}$ alkoxy, halo, or —OH,
C$_{1-4}$ alkoxy,
phenyl optionally substituted by one or more independently selected halo,
—C(=O)-monocyclic 4-6 membered heterocycloalkyl comprising one to three heteroatoms independently selected from N, O, and S,
—C(=O)NR$^{8a}$R$^{8b}$, or
5-7 membered heteroaryl comprising one to four heteroatoms independently selected from N, O, and S, which heteroaryl is optionally substituted with one or more independently selected C$_{1-4}$ alkyl; and
$R^{7a}$ and $R^{7b}$ are independently H or C$_{1-4}$ alkyl; and
$R^{8a}$ and $R^{8b}$ are independently H or C$_{1-3}$ alkyl;
or a pharmaceutically acceptable salt, or a solvate, orthe salt of a solvate thereof.

2) A compound or pharmaceutically acceptable salt thereof according to clause 1, wherein $Cy_A$ is

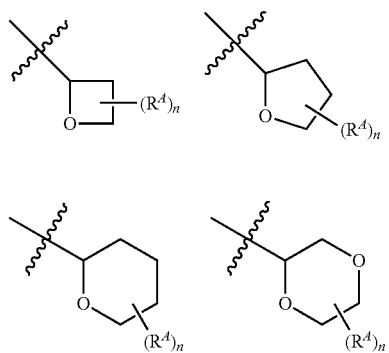

and $R^A$ and the subscript n are as described above.

3) A compound or pharmaceutically acceptable salt thereof according to clause 1 or 2, wherein the subscript n is 1 or 2.

4) A compound or pharmaceutically acceptable salt thereof according to any one of clauses 1-3, wherein each $R^A$ is independently selected from halo, and C$_{1-3}$ alkyl.

5) A compound or pharmaceutically acceptable salt thereof according to any one of clauses 1-3, wherein each $R^A$ is independently selected from F, Cl, —CH$_3$, and —CH$_2$CH$_3$.

6) A compound or pharmaceutically acceptable salt thereof according to clause 1 or 2, wherein the subscript n is 0.

7) A compound or pharmaceutically acceptable salt thereof, according to clause 1 wherein the compound is according to Formula IIa or IIc:

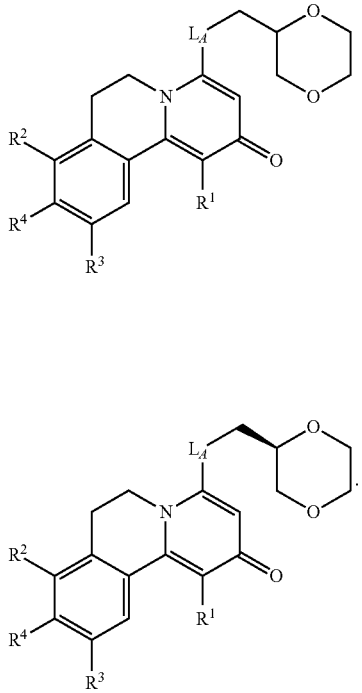

8) A compound or pharmaceutically acceptable salt thereof according to any one of clauses 1-7, wherein $R^2$ is H.
9) A compound or pharmaceutically acceptable salt thereof according to any one of clauses 1-7, wherein $R^2$ is —OH.
10) A compound or pharmaceutically acceptable salt thereof according to any one of clauses 1-7, wherein $R^2$ is —OCH$_3$.
11) A compound or pharmaceutically acceptable salt thereof according to any one of clauses 1-10, wherein $R^3$ is H.
12) A compound or pharmaceutically acceptable salt thereof according to any one of clauses 1-10, wherein $R^3$ is —OCH$_3$.
13) A compound or pharmaceutically acceptable salt thereof according to any one of clauses 1-12, wherein $R^1$ is H.
14) A compound or pharmaceutically acceptable salt thereof according to any one of clauses 1-12, wherein $R^1$ is —CH$_3$, or —CH$_2$CH$_3$.
15) A compound or pharmaceutically acceptable salt thereof according to any one of clauses 1-14, wherein $R^1$ is —CH$_3$.
16) A compound or pharmaceutically acceptable salt thereof according to any one of clauses 1-15, wherein $R^4$ is —CN or —OH.
17) A compound or pharmaceutically acceptable salt thereof according to any one of clauses 1-15, wherein $R^4$ is —OS(=O)$_2$CH$_3$ or —OS(=O)$_2$CF$_3$.

18) A compound or pharmaceutically acceptable salt thereof according to claim 1, wherein the compound is according to Formula IIIa or IIIc:

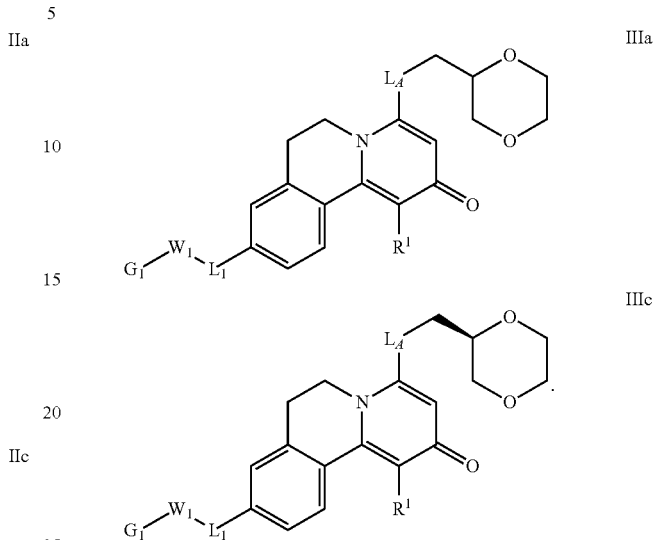

19) A compound or pharmaceutically acceptable salt thereof according to any one of clauses 1-18, wherein $L_1$ is a direct bond.
20) A compound or pharmaceutically acceptable salt thereof according to any one of clauses 1-18, wherein $L_1$ is —O—.
21) A compound or pharmaceutically acceptable salt thereof according to any one of clauses 1-18, wherein $L_1$ is —S—.
22) A compound or pharmaceutically acceptable salt thereof according to any one of clauses 1-18, wherein $L_1$ is —SO$_2$—.
23) A compound or pharmaceutically acceptable salt thereof according to any one of clauses 1-18, wherein $L_1$ is —C(=O)NR$^{5a}$—.
24) A compound or pharmaceutically acceptable salt thereof according to clause 23, wherein $R^{5a}$ is H.
25) A compound or pharmaceutically acceptable salt thereof according to clause 23, wherein $R^{5a}$ is —CH$_3$.
26) A compound or pharmaceutically acceptable salt thereof according to any one of clauses 1-18, wherein $L_1$ is —NR$^{5b}$C(=O)—.
27) A compound or pharmaceutically acceptable salt thereof according to clause 26, wherein $R^{5b}$ is H.
28) A compound or pharmaceutically acceptable salt thereof according to clause 26, wherein $R^{5b}$ is —CH$_3$.
29) A compound or pharmaceutically acceptable salt thereof according to any one of clauses 1-18, wherein $L_1$ is —NR$^{5c}$—.
30) A compound or pharmaceutically acceptable salt thereof according to clause 29, wherein $R^{5c}$ is —CH$_3$.
31) A compound or pharmaceutically acceptable salt thereof according to clause 29, wherein $R^{5c}$ is H.
32) A compound or pharmaceutically acceptable salt thereof according to any one of clauses 1-31, wherein $L_A$ is NH.
33) A compound or pharmaceutically acceptable salt thereof according to any one of clauses 1-31, wherein $L_A$ is O.

34) A compound or pharmaceutically acceptable salt thereof according to clause 1, wherein the compound is according to Formula IVa or IVb:

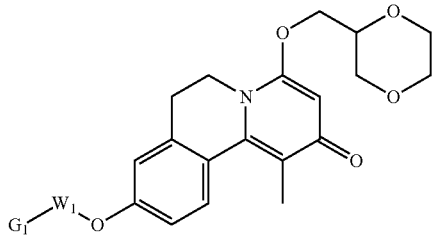

IVa

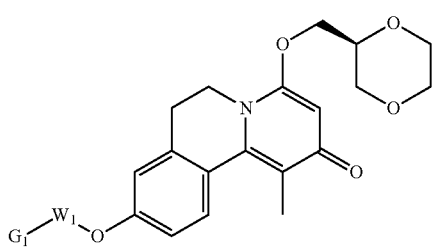

IVb

35) A compound or pharmaceutically acceptable salt thereof according to any one of clauses 1-15 and 18-34, wherein $W_1$ is a direct bond.
36) A compound or pharmaceutically acceptable salt thereof according to any one of clauses 1-15 and 18-34, wherein $W_1$ is $C_{1-2}$ alkylene.
37) A compound or pharmaceutically acceptable salt thereof according to any one of clauses 1-15 and 18-34, wherein $W_1$ is —$CH_2$—, or —$CH_2$—$CH_2$—.
38) A compound or pharmaceutically acceptable salt thereof according to any one of clauses 1-15 and 18-37, wherein $G_1$ is $C_{3-6}$ cycloalkyl.
39) A compound or pharmaceutically acceptable salt thereof according to any one of clauses 1-15 and 18-37, wherein $G_1$ is cyclopropyl, cyclobutyl, cyclopentyl or cyclohexyl.
40) A compound or pharmaceutically acceptable salt thereof according to any one of clauses 1-15 and 18-37, wherein $G_1$ is $C_{3-6}$ cycloalkyl substituted with one or more halo.
41) A compound or pharmaceutically acceptable salt thereof according to any one of clauses 1-15 and 18-37, wherein $G_1$ is cyclopropyl, cyclobutyl, cyclopentyl or cyclohexyl, each of which is substituted with one or more halo.
42) A compound or pharmaceutically acceptable salt thereof according to any one of clauses 1-15 and 18-37, wherein $G_1$ is cyclopropyl, cyclobutyl, cyclopentyl or cyclohexyl, each of which is substituted with one or more F.
43) A compound or pharmaceutically acceptable salt thereof according to any one of clauses 1-15 and 18-37, wherein $G_1$ is 5-6 membered heteroaryl comprising one to four heteroatoms independently selected from N, O, and S.
44) A compound or pharmaceutically acceptable salt thereof according to any one of clauses 1-15 and 18-37, wherein $G_1$ is pyrazolyl, oxadiazolyl, or pyridinyl.
45) A compound or pharmaceutically acceptable salt thereof according to any one of clauses 1-15 and 18-37, wherein $G_1$ is 5-6 membered heteroaryl comprising one to four heteroatoms independently selected from N, O, and S, which heteroaryl is substituted with one or more independently selected $C_{1-4}$ alkyl.
46) A compound or pharmaceutically acceptable salt thereof according to any one of clauses 1-15 and 18-37, wherein $G_1$ is pyrazolyl, oxadiazolyl, or pyridinyl, each of which is substituted with one or more independently selected $C_{1-4}$ alkyl.
47) A compound or pharmaceutically acceptable salt thereof according to any one of clauses 1-15 and 18-37, wherein $G_1$ is 5-7 membered heterocycloalkenyl comprising one double bond, and one to three heteroatoms independently selected from N, O, and S.
48) A compound or pharmaceutically acceptable salt thereof according to any one of clauses 1-15 and 18-37, wherein $G_1$ is 5-7 membered heterocycloalkenyl comprising one double bond, and one to three heteroatoms independently selected from N, O, and S, which heterocycloalkenyl is substituted with one or more independently selected $R^6$.
49) A compound or pharmaceutically acceptable salt thereof according to clause 48, wherein $G_1$ is 1,2,3,6-tetrahydropyridinyl, or 3,6-dihydro-2H-pyran, each of which is substituted with one or more independently selected $R^6$.
50) A compound or pharmaceutically acceptable salt thereof according to clause 48 or 49, wherein each $R^6$ is —C(=O)—$C_{1-4}$ alkoxy.
51) A compound or pharmaceutically acceptable salt thereof according to clause 48 or 49, wherein each $R^6$ is independently —C(=O)OMe, —C(=O)OEt, —C(=O)OiPr, or —C(=O)OtBu.
52) A compound or pharmaceutically acceptable salt thereof according to clause 48 or 49, wherein each $R^6$ is independently —C(=O)—$C_{1-4}$ alkoxy substituted with one or more independently selected halo.
53) A compound or pharmaceutically acceptable salt thereof according to clause 48 or 49, wherein each $R^6$ is —C(=O)OCH$_2$CF$_3$.
54) A compound or pharmaceutically acceptable salt thereof according to any one of clauses 1-15 and 18-37, wherein $G_1$ is monocyclic or spiro bicyclic 4-8 membered heterocycloalkyl comprising one to three heteroatoms independently selected from N, O, and S.
55) A compound or pharmaceutically acceptable salt thereof according to any one of clauses 1-15 and 18-37, wherein $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl.
56) A compound or pharmaceutically acceptable salt thereof according to any one of clauses 1-15 and 18-37, wherein $G_1$ is pyrrolyl fused to two phenyls.
57) A compound or pharmaceutically acceptable salt thereof according to any one of clauses 1-15 and 18-37, wherein $G_1$ is monocyclic or spiro bicyclic 4-8 membered heterocycloalkyl comprising one to three heteroatoms independently selected from N, O, and S, which heterocycloalkyl is substituted with one or more independently selected $R^6$.
58) A compound or pharmaceutically acceptable salt thereof according to any one of clauses 1-15 and 18-37, wherein $G_1$ is azetidinyl, tetrahydrofuranyl, tetrahydropyranyl, dioxanyl, piperidinyl, piperazinyl, morpholinyl, or 2-oxa-6-aza-spiro[3.3]heptanyl, each of which is substituted with one or more independently selected $R^6$.
59) A compound or pharmaceutically acceptable salt thereof according to clause 57 or 58, wherein $R^6$ is halo, =O, —CN, or —OH.
60) A compound or pharmaceutically acceptable salt thereof according to clause 57 or 58, wherein $R^6$ is F.
61) A compound or pharmaceutically acceptable salt thereof according to clause 57 or 58, wherein $R^6$ is —C(=O)—$C_{1-4}$ alkoxy.

62) A compound or pharmaceutically acceptable salt thereof according to clause 57 or 58, wherein $R^6$ is —C(=O)OMe, —C(=O)OEt, —C(=O)OiPr, or —C(=O)OtBu.

63) A compound or pharmaceutically acceptable salt thereof according to clause 57 or 58, wherein $R^6$ is —C(=O)—$C_{1-4}$ alkoxy substituted with one or more independently selected halo.

64) A compound or pharmaceutically acceptable salt thereof according to clause 57 or 58, wherein $R^6$ is —C(=O)OCH$_2$CF$_3$.

65) A compound or pharmaceutically acceptable salt thereof according to clause 57 or 58, wherein $R^6$ is —C(=O)—$C_{3-4}$ cycloalkyl.

66) A compound or pharmaceutically acceptable salt thereof according to clause 57 or 58, wherein $R^6$ is —C(=O) cyclopropyl.

67) A compound or pharmaceutically acceptable salt thereof according to clause 57 or 58, wherein $R^6$ is —S(=O)$_2$—$C_{1-4}$ alkyl.

68) A compound or pharmaceutically acceptable salt thereof according to clause 57 or 58, wherein $R^6$ is —S(=O)$_2$-Me.

69) A compound or pharmaceutically acceptable salt thereof according to clause 57 or 58, wherein $R^6$ is $C_{1-4}$ alkyl.

70) A compound or pharmaceutically acceptable salt thereof according to clause 57 or 58, wherein $R^6$ is —CH$_3$.

71) A compound or pharmaceutically acceptable salt thereof according to clause 57 or 58, wherein $R^6$ is $C_{1-4}$ alkyl substituted by one or more independently selected $C_{1-3}$ alkoxy, halo, or —OH.

72) A compound or pharmaceutically acceptable salt thereof according to clause 57 or 58, wherein $R^6$ is —CH$_3$, —CH$_2$CH$_3$, or —CH(CH$_3$)$_2$, each of which is substituted by one or more independently selected $C_{1-3}$ alkoxy, halo, or —OH.

73) A compound or pharmaceutically acceptable salt thereof according to clause 57 or 58, wherein $R^6$ is —C(CH$_3$)$_2$OH.

74) A compound or pharmaceutically acceptable salt thereof according to clause 57 or 58, wherein $R^6$ is —OCH$_3$, or —OCH$_2$CH$_3$.

75) A compound or pharmaceutically acceptable salt thereof according to clause 57 or 58, wherein $R^6$ is phenyl.

76) A compound or pharmaceutically acceptable salt thereof according to clause 57 or 58, wherein $R^6$ is phenyl substituted with one F.

77) A compound or pharmaceutically acceptable salt thereof according to clause 57 or 58, wherein $R^6$ is —C(=O)-piperidinyl.

78) A compound or pharmaceutically acceptable salt thereof according to clause 57 or 58, wherein $R^6$ is —C(=O)NR$^{8a}$R$^{8b}$, and wherein R$^{8a}$ and R$^{8b}$ are —CH$_3$.

79) A compound or pharmaceutically acceptable salt thereof according to clause 57 or 58, wherein $R^6$ is 5-7 membered heteroaryl comprising one to four heteroatoms independently selected from N, O, and S.

80) A compound or pharmaceutically acceptable salt thereof according to clause 57 or 58, wherein $R^6$ is pyrazolyl.

81) A compound or pharmaceutically acceptable salt thereof according to any one of clauses 1-15 and 18-37, wherein $G_1$ is $C_{1-4}$ alkyl.

82) A compound or pharmaceutically acceptable salt thereof according to any one of clauses 1-15 and 18-37, wherein $G_1$ is —CH$_3$.

83) A compound or pharmaceutically acceptable salt thereof according to any one of clauses 1-15 and 18-37, wherein $G_1$ is $C_{1-4}$ alkyl, substituted with one or more independently selected halo, —NR$^{7a}$R$^{7b}$, or $C_{1-4}$ alkoxy, which alkoxy is optionally substituted with one or more independently selected halo, and wherein R$^{7a}$ and R$^{7b}$ are independently H or $C_{1-4}$ alkyl.

84) A compound or pharmaceutically acceptable salt thereof according to any one of clauses 1-15 and 18-37, wherein $G_1$ is —CH$_3$, or —CH$_2$CH$_3$, each of which is substituted with one or more independently selected halo, —NR$^{7a}$R$^{7b}$, or $C_{1-4}$ alkoxy, which alkoxy is optionally substituted with one or more independently selected halo, and wherein R$^{7a}$ and R$^{7b}$ are independently H or $C_{1-4}$ alkyl.

85) A compound or pharmaceutically acceptable salt thereof according to any one of clauses 1-15 and 18-37, wherein $G_1$ is —CF$_3$, —CHF$_2$, —CH$_2$—CHF$_2$, —CH$_2$—CF$_3$, —CH$_2$—CH$_2$—N(CH$_3$)$_2$, or —CH$_2$—CH$_2$—OCF$_3$.

86) A compound or pharmaceutically acceptable salt thereof according to any one of clauses 1-15 and 18-37, wherein $G_1$ is phenyl.

87) A compound or pharmaceutically acceptable salt thereof according to any one of clauses 1-15 and 18-37, wherein $G_1$ is phenyl substituted with one or more independently selected halo or $C_{1-4}$ alkoxy, which alkoxy is optionally substituted with one or more independently selected halo.

88) A compound or pharmaceutically acceptable salt thereof according to any one of clauses 1-15 and 18-37, wherein $G_1$ is phenyl substituted with one or more independently selected F, or —OCF$_3$.

89) A compound or pharmaceutically acceptable salt thereof according to clause 1, wherein the compound is according to Formula Va or Vb:

Va or

Vb

90) A compound or pharmaceutically acceptable salt thereof according to clause 89, wherein $G_1$ is $C_{3-6}$ cycloalkyl.

91) A compound or pharmaceutically acceptable salt thereof according to clause 89, wherein $G_1$ is cyclopropyl, cyclobutyl, cyclopentyl or cyclohexyl.

92) A compound or pharmaceutically acceptable salt thereof according to clause 89, wherein $G_1$ is $C_{3-6}$ cycloalkyl substituted with one or more halo.

93) A compound or pharmaceutically acceptable salt thereof according to clause 89, wherein $G_1$ is cyclopropyl, cyclobutyl, cyclopentyl or cyclohexyl, each of which is substituted with one or more halo.

94) A compound or pharmaceutically acceptable salt thereof according to clause 89, wherein $G_1$ is cyclopropyl, cyclobutyl, cyclopentyl or cyclohexyl, each of which is substituted with one or more F.
95) A compound or pharmaceutically acceptable salt thereof according to clause 89, wherein $G_1$ is $C_{1-4}$ alkyl, substituted with one or more independently selected halo, $-NR^{7a}R^{7b}$, or $C_{1-4}$ alkoxy, which alkoxy is optionally substituted with one or more independently selected halo, and wherein $R^{7a}$ and $R^{7b}$ are independently H or $C_{1-4}$ alkyl.
96) A compound or pharmaceutically acceptable salt thereof according to clause 89, wherein $G_1$ is $-CH_3$, or $-CH_2CH_3$, each of which is substituted with one or more independently selected halo, $-NR^{7a}R^{7b}$, or $C_{1-4}$ alkoxy, which alkoxy is optionally substituted with one or more independently selected halo, and wherein $R^{7a}$ and $R^{7b}$ are independently H or $C_{1-4}$ alkyl.
97) A compound or pharmaceutically acceptable salt thereof according to clause 89, wherein $G_1$ is $-CF_3$, $-CHF_2$, $-CH_2-CHF_2$, $-CH_2-CF_3$, $-CH_2-CH_2-N(CH_3)_2$, or $-CH_2-CH_2-OCF_3$.
98) A compound or pharmaceutically acceptable salt thereof according to clause 1, wherein the compound or pharmaceutical acceptable salt thereof is 4-[[(2S)-1,4-dioxan-2-yl]methoxy]-1-methyl-9-(2,2,2-trifluoroethoxy)-6,7-dihydrobenzo[a]quinolizin-2-one.
99) A pharmaceutical composition comprising a compound or pharmaceutically acceptable salt thereof, according to any one of clauses 1-98, and a pharmaceutically acceptable carrier.
100) The pharmaceutical composition according to clause 99 comprising a further therapeutic agent.
101) The compound, or pharmaceutically acceptable salt thereof, according to any one of clauses 1-98, or the pharmaceutical composition according to clause 99 or 100, for use as a medicament.
102) The compound, or pharmaceutically acceptable salt thereof, according to any one of clauses 1-98, or the pharmaceutical composition according to clause 99 or 100, for use in the treatment and/or prophylaxis of inflammatory conditions.
103) A method for the treatment or prophylaxis of inflammatory conditions, comprising administering a prophylactically or therapeutically effective amount of a compound according to any one of clauses 1-98, or a composition of clause 99 or 100.
104) The method according to clause 103, wherein a compound, or pharmaceutically acceptable salt thereof, according to any one of clauses 1-98, or the pharmaceutical composition according to clause 99 is administered in combination with a further therapeutic agent.
105) The use according to clause 102, or the method according to clause 103, wherein the inflammatory condition is rheumatoid arthritis, chronic obstructive pulmonary disease, asthma, idiopathic pulmonary fibrosis, psoriasis, Crohn's disease, and/or ulcerative colitis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound. Generally, a compound of the invention is administered in a pharmaceutically effective amount. The amount of a compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, intranasal and inhalation. Depending on the intended route of delivery, a compound of this invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, a compound of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture may be filled into 250 mg capsules (125 mg of active compound per capsule).

Formulation 3—Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Sufficient water may be then added to produce a total volume of 5 mL.

Formulation 4—Tablets

A compound of the invention may be admixed as a dry powder with a dry gelatin binder in an approximate 1:2 weight ratio. A minor amount of magnesium stearate may be added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

A compound of the invention may be used as a therapeutic agent for the treatment of conditions in mammals that are causally related or attributable to aberrant activity of GPR84 and/or aberrant GPR84 expression and/or aberrant GPR84 distribution.

Accordingly, a compound and pharmaceutical compositions of the invention find use as therapeutics for the prophylaxis and/or treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans.

Accordingly, in one aspect, the present invention provides the compound of the invention, or a pharmaceutical composition comprising the compound of the invention for use as a medicament.

In another aspect, the present invention provides the compound of the invention, or a pharmaceutical composition comprising the compound of the invention for use in the manufacture of a medicament.

In yet another aspect, the present invention provides a method of treating a mammal having, or at risk of having a disease disclosed herein. In a particular aspect, the present invention provides a method of treating a mammal having, or at risk of having inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans, said method comprising administering an effective amount of a compound of the invention, or one or more of the pharmaceutical compositions herein described.

In one aspect, the present invention provides the compound of the invention, or a pharmaceutical composition comprising the compound of the invention for use in the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, oesophagitis, neutrophilic dermatoses (e.g., pyoderma gangrenosum, Sweet's syndrome), severe asthma, and skin and/or colon inflammation caused by oncology treatments aimed at activating the immune response.

In another aspect, the present invention provides the compound of the invention, or a pharmaceutical composition comprising the compound of the invention for use in the manufacture of a medicament for the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, oesophagitis, neutrophilic dermatoses (e.g., pyoderma gangrenosum, Sweet's syndrome), severe asthma, and skin and/or colon inflammation caused by oncology treatments aimed at activating the immune response.

In another aspect, the present invention provides a method of treating a mammal having, or at risk of having a disease selected from inflammatory conditions (for example inflammatory bowel diseases (IBD), rheumatoid arthritis, vasculitis), lung diseases (e.g., chronic obstructive pulmonary disease (COPD) and lung interstitial diseases (e.g., idiopathic pulmonary fibrosis (IPF))), neuroinflammatory conditions, infectious diseases, autoimmune diseases, endocrine and/or metabolic diseases, and/or diseases involving impairment of immune cell functions, which method comprises administering an effective amount of a compound of the invention, or one or more of the pharmaceutical compositions herein described.

In additional method of treatment aspects, this invention provides methods of treatment and/or prophylaxis of a mammal susceptible to or afflicted with inflammatory conditions, which method comprises administering an effective amount of a compound of the invention, or one or more of the pharmaceutical compositions herein described. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, oesophagitis, neutrophilic dermatoses (e.g., pyoderma gangrenosum, Sweet's syndrome), severe asthma, and skin and/or colon inflammation caused by oncology treatments aimed at activating the immune response.

In one aspect, the present invention provides the compound of the invention, or a pharmaceutical composition comprising the compound of the invention for use in the prophylaxis and/or treatment of pain. In a specific embodiment, the pain is acute or chronic and is selected from nociceptive pain, inflammatory pain, and neuropathic or dysfunctional pain.

In another aspect, the present invention provides the compound of the invention, or a pharmaceutical composition comprising the compound of the invention for use in the manufacture of a medicament for the prophylaxis and/or treatment of pain. In a specific embodiment, the pain is acute or chronic and is selected from nociceptive pain, inflammatory pain, and neuropathic or dysfunctional pain.

In additional method of treatment aspects, this invention provides methods of treatment and/or prophylaxis of a mammal susceptible to or afflicted with pain, which method comprises administering an effective amount of a compound of the invention, or one or more of the pharmaceutical compositions herein described. In a specific embodiment, the pain is acute or chronic and is selected from nociceptive pain, inflammatory pain, and neuropathic or dysfunctional pain.

In one aspect, the present invention provides a compound of the invention, or a pharmaceutical composition comprising the compound of the invention for use in the prophylaxis and/or treatment of neuroinflammatory conditions, Guillain-Barré syndrome (GBS), multiple sclerosis, axonal degeneration, autoimmune encephalomyelitis.

In another aspect, the present invention provides a compound of the invention, or a pharmaceutical composition comprising the compound of the invention for use in the manufacture of a medicament for the prophylaxis and/or treatment of neuroinflammatory conditions, Guillain-Barré syndrome (GBS), multiple sclerosis, axonal degeneration, autoimmune encephalomyelitis.

In additional method of treatment aspects, this invention provides methods of treatment and/or prophylaxis of a mammal susceptible to or afflicted with neuroinflammatory conditions, Guillain-Barré syndrome (GBS), multiple sclerosis, axonal degeneration, autoimmune encephalomyelitis, which method comprises administering an effective amount of a compound of the invention, or one or more of the pharmaceutical compositions herein described.

In one aspect, the present invention provides a compound of the invention, or a pharmaceutical composition comprising the compound of the invention for use in the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In another aspect, the present invention provides a compound of the invention, or a pharmaceutical composition comprising the compound of the invention for use in the manufacture of a medicament for the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In additional method of treatment aspects, this invention provides methods of treatment and/or prophylaxis of a mammal susceptible to or afflicted with infectious disease(s), which method comprises administering an effective amount of a compound of the invention, or one or more of the pharmaceutical compositions herein described. In a specific embodiment, the infectious disease is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In one aspect, the present invention provides the compound of the invention, or a pharmaceutical composition comprising the compound of the invention for use in the prophylaxis and/or treatment of autoimmune diseases, and/or diseases involving impairment of immune cell functions. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In another aspect, the present invention provides the compound of the invention, or a pharmaceutical composition comprising the compound of the invention for use in the manufacture of a medicament for the prophylaxis and/or treatment of autoimmune diseases and/or diseases involving impairment of immune cell functions. In a specific embodiment, the autoimmune diseases, and/or diseases involving impairment of immune cell functions is selected from COPD, asthma, psoriasis, systemic lupus erythematosis, type I diabetes mellitus, vasculitis and inflammatory bowel disease.

In additional method of treatment aspects, this invention provides methods of treatment and/or prophylaxis of a mammal susceptible to or afflicted with autoimmune diseases and/or diseases involving impairment of immune cell functions, which method comprises administering an effective amount of a compound of the invention, or one or more of the pharmaceutical compositions herein described. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In one aspect, the present invention provides the compound of the invention, or a pharmaceutical composition comprising the compound of the invention for use in the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In another aspect, the present invention provides the compound of the invention, or a pharmaceutical composition comprising the compound of the invention for use in the manufacture of a medicament for the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In additional method of treatment aspects, this invention provides methods of treatment and/or prophylaxis of a mammal susceptible to or afflicted with endocrine and/or metabolic diseases, which method comprises administering an effective amount of a compound of the invention, or one or more of the pharmaceutical compositions herein described. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

As a further aspect of the invention there is provided a compound of the invention for use as a medicament especially in the treatment or prevention of the aforementioned conditions and diseases. Also provided herein is the use of the compound in the manufacture of a medicament for the treatment or prevention of one of the aforementioned conditions and diseases.

A particular regimen of the present method comprises the administration to a subject in suffering from an inflammatory condition, of an effective amount of a compound of the invention for a period of time sufficient to reduce the level of inflammation in the subject, and preferably terminate, the processes responsible for said inflammation. A special embodiment of the method comprises administering of an effective amount of a compound of the invention to a subject suffering from or susceptible to the development of inflammatory condition, for a period of time sufficient to reduce or prevent, respectively, inflammation of said patient, and preferably terminate, the processes responsible for said inflammation.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of an inflammatory condition; particular agents include, but are not limited to, immunoregulatory agents e.g., azathioprine, corticosteroids (e.g., prednisolone or dexamethasone), cyclophosphamide, cyclosporin A, tacrolimus, Mycophenolate Mofetil, muromonab-CD3 (OKT3, e.g., Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g., rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, Golimumab, Certolizumab pegol, Tocilizumab, Interleukin 1 blockers and Abatacept).

In one embodiment, a compound of the invention is co-administered with another therapeutic agent for the treatment and/or prevention of autoimmune diseases; particular agents include but are not limited to: glucocorticoids, cytostatic agents (e.g., purine analogs), alkylating agents, (e.g., nitrogen mustards (cyclophosphamide), nitrosoureas, platinum compounds, and others), antimetabolites (e.g., e.g., methotrexate, azathioprine and mercaptopurine), cytotoxic antibiotics (e.g., e.g., dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g., IFN-β), TNF binding proteins (e.g., infliximab (Remicade®), etanercept (Enbrel®), or adalimumab (Humira®)), mycophenolate, Fingolimod, and Myriocin.

In one embodiment, a compound of the invention is co-administered with another therapeutic agent for the treatment and/or prevention of infectious diseases; particular agents include but are not limited to antibiotics. In a particular embodiment, a compound of the invention is co-administered with another therapeutic agent for the treatment and/or prevention of infections of any organ of the human body; particular agents include but are not limited to: aminoglycosides, ansamycins, carbacephem, carbapenems, cephalosporins, glycopeptides, lincosamides, macrolides, monobactams, nitrofurans, penicillins, polypeptides, quinolones, sulfonamides, tetracyclins, anti-mycobacterial agents, as well as chloramphenicol, fosfomycin, linezolid, metronidazole, mupirocin, rifamycin, thiamphenicol and tinidazole.

In one embodiment, a compound of the invention is co-administered with another therapeutic agent for the treatment and/or prevention of vasculitis, particular agents include but are not limited to steroids (for example prednisone, prednisolone), cyclophosphamide and eventually antibiotics in case of cutaneous infections (for example cephalexin).

In one embodiment, a compound of the invention is co-administered with another therapeutic agent for the treatment and/or prevention of oesophagitis; particular agents include but are not limited to: anti-acids (e.g., formulations containing aluminum hydroxide, magnesium hydroxide, and/or simethicone), H2-antagonists (e.g., cimetidine, ranitidine, famotidine), proton pump inhibitors (e.g., omeprazole, esomeprazole, lansoprazole, rabeprazole, pantoprazole), and glucocorticoids (e.g., prednisone, budesonide).

In one embodiment, a compound of the invention is co-administered with another therapeutic agent for the treatment and/or prevention of IPF, particular agents include but are not limited to pirfenidone and bosentan.

In one embodiment, a compound of the invention is co-administered with another therapeutic agent for the treatment and/or prevention of asthma and/or rhinitis and/or COPD; particular agents include but are not limited to: beta2-adrenoceptor agonists (e.g., salbutamol, levalbuterol, terbutaline and bitolterol), epinephrine (inhaled or tablets), anticholinergics (e.g., ipratropium bromide), glucocorticoids (oral or inhaled) Long-acting β2-agonists (e.g., salmeterol, formoterol, bambuterol, and sustained-release oral albuterol), combinations of inhaled steroids and long-acting bronchodilators (e.g., fluticasone/salmeterol, budesonide/formoterol), leukotriene antagonists and synthesis inhibitors (e.g., montelukast, zafirlukast and zileuton), inhibitors of mediator release (e.g., cromoglycate and ketotifen), phosphodiesterase-4 inhibitors (e.g., Roflumilast), biological regulators of IgE response (e.g., omalizumab), antihistamines (e.g., ceterizine, cinnarizine, fexofenadine), and vasoconstrictors (e.g., oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g., ipratropium), systemic steroids (oral or intravenous, e.g., prednisone, prednisolone, methylprednisolone, dexamethasone, or hydrocortisone), intravenous salbutamol, non-specific beta-agonists, injected or inhaled (e.g., epinephrine, isoetharine, isoproterenol, metaproterenol), anticholinergics (IV or nebulized, e.g., glycopyrrolate, atropine, ipratropium), methylxanthines (theophylline, aminophylline, bamiphylline), inhalation anesthetics that have a bronchodilatory effect (e.g., isoflurane, halothane, enflurane), ketamine, and intravenous magnesium sulfate.

In one embodiment, a compound of the invention is co-administered with another therapeutic agent for the treatment and/or prevention of inflammatory bowel disease (IBD); particular agents include but are not limited to: glucocorticoids (e.g., prednisone, budesonide) synthetic disease modifying, immunomodulatory agents (e.g., methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

In one embodiment, a compound of the invention is co-administered with another therapeutic agent for the treatment and/or prevention of pain, such as non-narcotic and narcotic analgesics; particular agents include but are not limited to: paracetamol, acetylsalicylic acid, NSAID's, codeine, dihydrocodeine, tramadol, pentazocine, pethidine, tilidine, buprenorfine, fentanyl, hydromorfon, methadon, morfine, oxycodon, piritramide, tapentadol or combinations thereof.

Course of treatment for leukemia comprises chemotherapy, biological therapy, targeted therapy, radiation therapy, bone marrow transplantation and/or combinations thereof.

Examples of further therapeutic agents for Acute Lymphoblastic Leukemia (ALL) comprise methotrexate, nelarabine, asparaginase *Erwinia chrysanthemi*, blinatumomab, daunorubicin, clofarabine, cyclophosphamide, cytarabine, dasatinib, doxorubicin, imatinib, ponatinib vincristine, mercaptopurine, pegaspargase, and/or prednisone.

Examples of further therapeutic agents for Acute Myeloid Leukemia (AML) comprise arsenic trioxide, daunorubicin, cyclophosphamide, cytarabine, doxorubicin, idarubicin, mitoxantrone, and/or vincristine.

Examples of further therapeutic agents for Chronic Lymphocytic Leukemia (CLL) comprise alemtuzumab, chlorambucil, ofatumumab, bendamustine, cyclophosphamide, fludarabine, obinutuzumab, ibrutinib, idelalisib, mechlorethamine, prednisone, and/or rituximab.

Examples of further therapeutic agents for Chronic Myelogenous Leukemia (CML) comprise bosutinib, busulfan, cyclophosphamide, cytarabine, dasatinib, imatinib, ponatinib, mechlorethamine, nilotinib, and/or omacetaxine.

Examples of further therapeutic agents for Hairy Cell Leukemia comprise cladiribine, pentostatin, and/or interferon alfa-2b.

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

General Synthetic Procedures

General

A compound of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Wiley-Blackwell; 4th Revised edition edition (2006), and references cited therein (Wuts & Greene 2006).

The following methods are presented with details as to the preparation of representative 6,7-dihydro-pyrido[2,1-a]isoquinolin-2-one compounds that have been listed hereinabove. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica standard (30-70 μm). Thin layer chromatography is carried out using pre-coated silica gel 60 F-254 plates (thickness 0.25 mm). $^1$H NMR spectra are recorded on a Bruker DPX 400 NMR spectrometer (400 MHz) or a Bruker Advance 300 NMR spectrometer (300 MHz). Chemical shifts (δ) for $^1$H NMR spectra are reported in parts per million (ppm) relative to tetramethylsilane (δ 0.00) or the appropriate residual solvent peak as internal reference. Multiplicities are given as singlet (s), doublet (d), doublet of doublet (dd), triplet (t), quartet (q), multiplet (m) and broad (br). Electrospray MS spectra are obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra MS 5 μm C18, 100×4.6 mm. The methods are using either MeCN/H$_2$O gradients (H$_2$O contains either 0.1% TFA or 0.1% NH$_3$) or MeOH/H$_2$O gradients (H$_2$O contains 0.05% TFA). Microwave heating is performed with a Biotage Initiator.

The preparative HPLC purifications are performed with a mass-directed auto-purification system coupled with a ZQ single quadrupole mass spectrometer. All HPLC purifications are performed with a gradient of H$_2$O (different pHs)/MeCN. Preparative HPLC separations under basic conditions are usually carried out using a BEH XBrigde C18 (5 μm, 19×5 mm) precolumn and a BEH XBrigde C18 (5 μm, 19×100 mm). Separations under acidic conditions are usually carried out using CSH Select C18 (5 μm, 19×5 mm) precolumn and a CSH Select C18 (5 μm, 19×100 mm). The focused gradient is from x % to x+25% acetonitrile in water in 5 min with a cycle time of 10 min. The column flow rate is 20 mL/min. The injection volume ranged from 200 to 750 μL. A capillary splitter is used to divert flow after column separation to the mass spectrometer which is diluted by 1 mL/min of make-up flow. The make-up flow is 0.1% formic acid in methanol. All samples are purified by a Waters mass directed fraction collection.

TABLE I

List of abbreviations used in the experimental section:

| Abbreviation | Definition |
| --- | --- |
| μL | microliter |
| AcOH | Acetic acid |
| aq. | aqueous |
| ATP | Adenosine 5'-Triphosphate |
| Boc | tert-Butyloxy-carbonyl |
| Boc$_2$O | Di-tert-butyl dicarbonate |
| br s | broad singlet |
| BrettPhos | 2-(Dicyclohexylphosphino)3, 6-dimethoxy-2', 4', 6'-triisopropyl-1, 1'-biphenyl |
| Brettphos precatalyst | Chloro[2-dicyclohexylphosphino)-3, 6-dimethoxy-2', 4', 6'-triisopropyl-1, 1'-biphenyl][2-(2-aminoethyl)phenyl]palladium(II) (CAS n° 1070663-78-3) |
| Cat. | Catalytic amount |
| d | doublet |
| dd | Doublet of doublet |
| DCM | Dichloromethane |
| Diglyme | Dimethoxy(diethylene glycol) |
| DIPEA | N, N-diisopropylethylamine |
| DMAP | 4-Dimethylaminopyridine |
| DMF | N, N-dimethylformamide |
| DMSO | Dimethylsulfoxide |
| DPBS | Dulbecco's Phosphate-Buffered Saline |
| DPPF | 1, 1'-Bis(diphenylphosphino)ferrocene |
| EtOAc | Ethyl acetate |
| Et$_2$O | Diethyl ether |
| equiv. | equivalent |
| g | gram |
| GTPγS | guanosine 5'-O-[gamma-thio]triphosphate |
| h | Hour |
| HPLC | High-performance liquid chromatography |
| iPrOH | isopropanol |
| iPr$_2$O | Diisopropyl ether |
| LCMS | Liquid Chromatography-Mass Spectrometry |
| L | Liter |
| m | multiplet |
| MeOH | Methanol |
| MeCN | Acetonitrile |

TABLE I-continued

List of abbreviations used in the experimental section:

| Abbreviation | Definition |
|---|---|
| MeI | Methyl iodide |
| mg | milligram |
| min | min |
| MIDA | Methyliminodiacetic acid |
| mL | milliliter |
| mmol | millimole |
| MS | mass spectrometry |
| Mtd | Method |
| MW | Molecular weight |
| MW (obs) | Molecular weight observed |
| MW (calc) | Molecular weight calculated |
| NADP | Nicotinamide adenine dinucleotide phosphate |
| NBS | N-bromosuccinimide |
| ND | Not determined |
| NEAA | Non-Essential Amino Acid |
| NMP | N-Methyl-2-pyrrolidone |
| NMR | Nuclear Magnetic Resonnance |
| obsd | observed |
| OTf | Trifluoromethanesulfonate |
| $Pd(OAc)_2$ | Palladium(II) acetate |
| $Pd(PPh_3)_4$ | Tetrakis(triphenylphosphine)palladium(0) |
| Pd/C | Palladium on Carbon 10% |
| ppm | part-per-million |
| PTFE | Teflon polymer |
| q | quadruplet |
| rpm | revolutions per min |
| Rt | retention time |
| RuPhos | 2-Dicyclohexylphosphino-2', 6'-di-i-propoxy-1, 1'-biphenyl |
| RuPhos Pd G2 | Chloro(2-dicyclohexylphosphino-2', 6'-diisopropoxy-1, 1'-biphenyl)[2-(2'-amino-1, 1'-biphenyl)]palladium(II) (CAS n° 1375325-68-0) |
| s | singlet |
| satd. | saturated |
| SCX | Strong cation exchange |
| SM | Starting material |
| spA | Scintillation proximity assay |
| SPE | Solid phase extraction |
| STAB | sodiumtriacetoxyborohydride |
| t | triplet |
| TBAF | Tetra-n-butylammonium fluoride |
| tBuOMe | Methyl tert-butyl ether |
| TEA | Triethylamine |
| TFA | Trifluoroacetic acid |
| THF | Tetrahydrofuran |
| TLC | Thin layer chromatography |
| XantPhos-Pd-G2 | Chloro[(4, 5-bis(diphenylphosphino)-9, 9-dimethylxanthene)-2-(2'-amino-1, 1'-biphenyl)]palladium(II)-CAS Number 1375325-77-1 |

Synthetic Preparation of the Compounds of the Invention

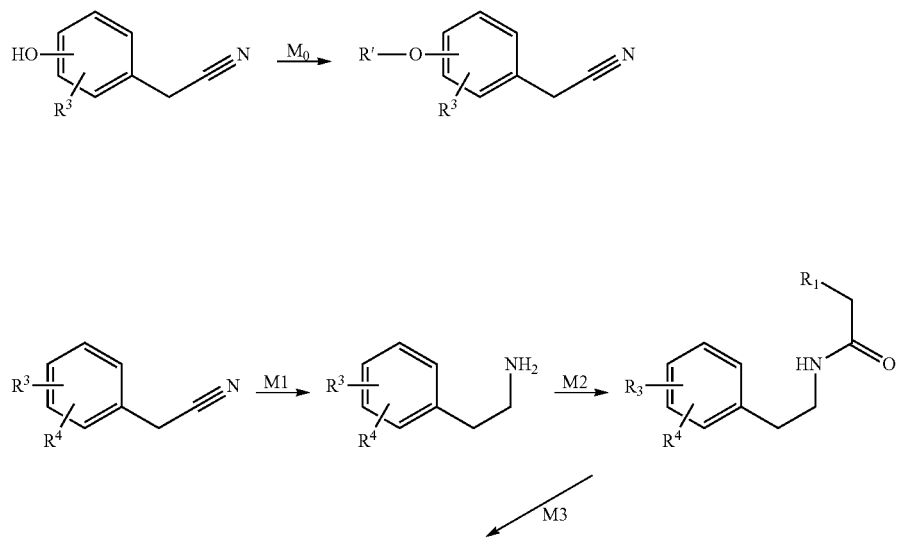

-continued
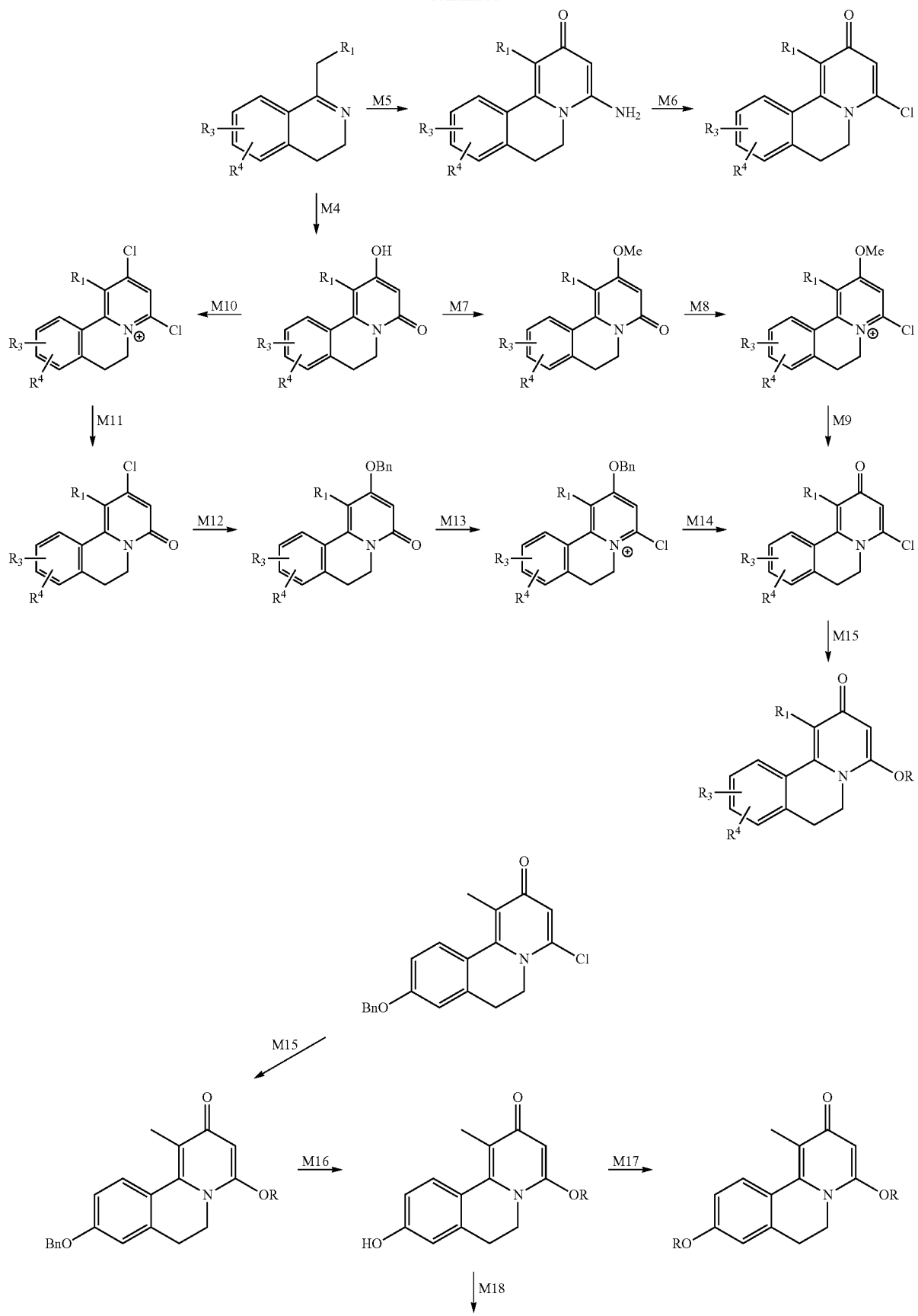

-continued

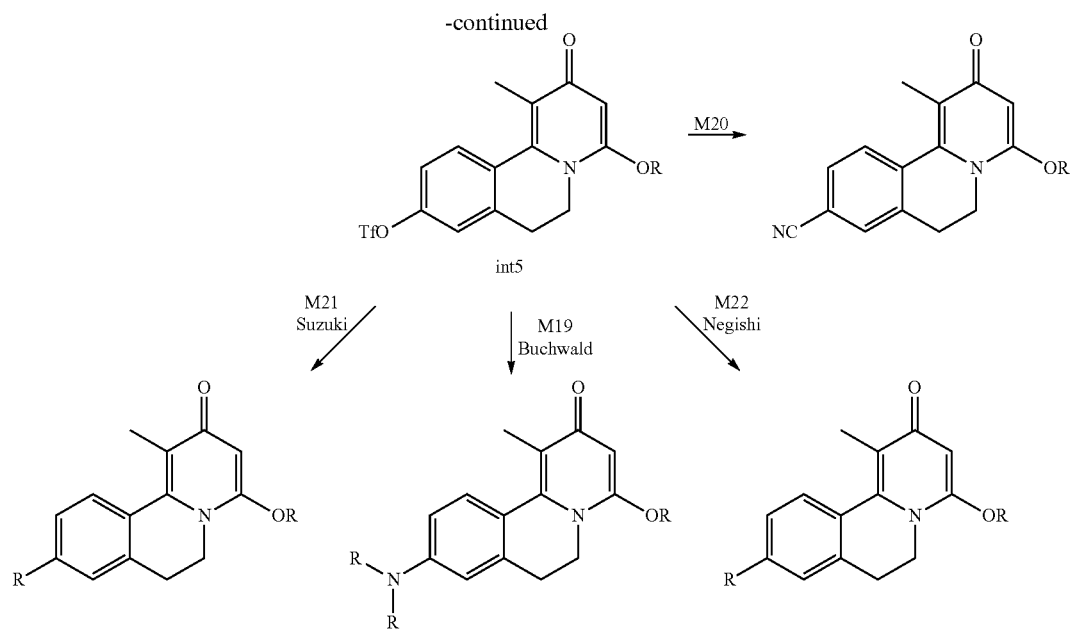

EXAMPLE 1

General Synthetic Methods

1.1. Method 0

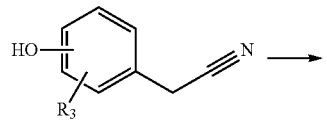

A round bottom flask is loaded with hydroxybenzylcyanide derivative (1.0 equiv.), K$_2$CO$_3$ (3.0 equiv.) and the appropriate alkylating agent (2.0 equiv.). Dry DMF (1.5 mL/mmol) is added. The flask is equipped with a condenser and the mixture is heated at 60° C. until all starting material is consumed. The mixture is diluted with EtOAc and subsequently washed with water, saturated aq. NaHCO$_3$, 1M HCl and brine. The organic layer is then dried over Na$_2$SO$_4$ and concentrated under reduced pressure. The resulting product is used as such.

1.2. Method 1: Reduction of Nitrile Using Raney Ni

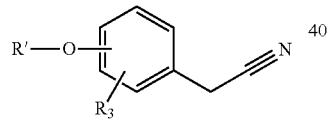

A round bottom flask is loaded with a phenylacetonitrile derivative (1.0 equiv.), raney nickel (50% suspension in water 1.2 equiv.) and 7N NH$_3$ in MeOH (5 mL/mmol) under N$_2$. The system is charged with 1 atmosphere. H$_2$ by doing 2 cycles of vacuum/H$_2$. The suspension is stirred at room temperature overnight leaving the H$_2$ supply connected. The reaction mixture is filtered over a Pall Seitz 300 thick paper filter. The residue is washed 3 times with MeOH and the filtrate is concentrated in vacuo yielding the desired product which is is used without further purification steps.

1.3. Method 2: N-Acylation

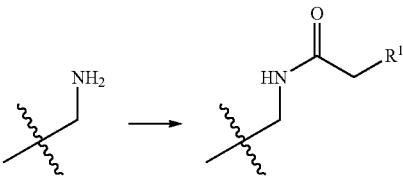

A multineck round bottom flask is loaded with phenethylamine derivative (1.0 equiv.), pyridine (2.1 equiv.) and DCM (2 mL/mmol) under N$_2$. The mixture is cooled to 0° C. (internal temperature) and an acid chloride (1.05 equiv.) is added dropwise. The resulting mixture is left to warm to room temperature. After 30 min the reaction mixture is quenched with 6M HCl and brine. The product is extracted twice with DCM. Combined organics are dried over Na$_2$SO$_4$ and the solvent is evaporated to dryness, to afford the desired product which is used as such without further purification.

1.4. Method 3: Intramolecular Cyclisation Using POCl₃

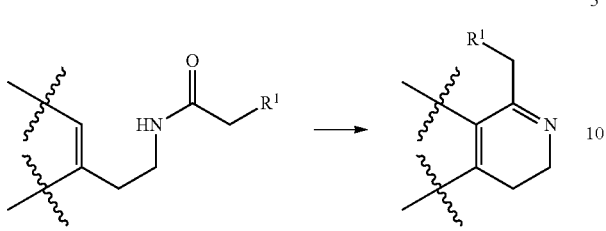

A round bottom flask equipped with a condenser at 0° C. is loaded with phenethylamide derivative (1.0 equiv.) and DCM (0.3 mmol/mL). POCl₃ (4.0 equiv.) is added portion-wise and the ice bath is removed. The resulting mixture is heated at 40° C. overnight. The mixture is concentrated in vacuo and the residue is poured over ice under stirring. Na₂CO₃ is added until a stable pH 8-9 is reached. H₂O is added and compound is extracted with DCM. Combined organics are dried over Na₂SO₄ and evaporated to dryness to afford the desired product which is used as such without further purification.

1.5. Method 4: Malonate Condensation

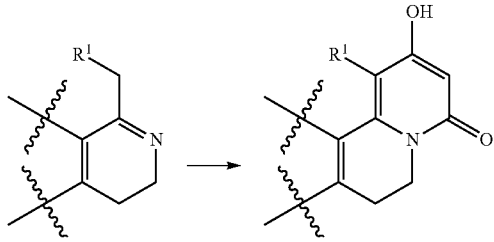

A round bottom flask equipped with a condenser under N₂ is loaded with 3,4-dihydroisoquinoline derivative (1.0 equiv.), di-tBu-malonate (4.0 equiv.) and dry diglyme (0.5 mL/mmol). The mixture is degassed via pump-freeze-thaw cycles and heated at 150° C. until all starting material is consumed. The mixture is cooled down to 10° C. and MTBE is added. The precipitate is separated by filtration and the residue is washed with MeCN/MTBE 1:4. The precipitate is dried in vacuo and used without further purification.

1.6. Method 5

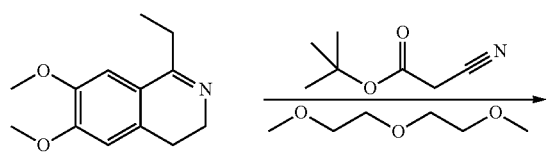

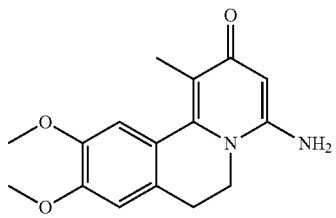

In a round bottom flask placed under nitrogen atmosphere, 1-ethyl-6,7-dimethoxy-3,4-dihydroisoquinoline (1.0 equiv.) is suspended in diglyme (0.7 mL/mmol) and sonicated at 40° C. under nitrogen atmosphere, until a bright yellow suspension is obtained. tert-Butyl cyanoacetate (4.0 equiv.) is added to the mixture. The flask is equipped with a condenser and the mixture is stirred and heated to 140° C. for 48 h. Then, the mixture is cooled down to room temperature. Acetonitrile (15 mL) is added to the reaction mixture. After trituration and sonication, the precipitate is collected, to afford the desired product.

1.7. Method 6

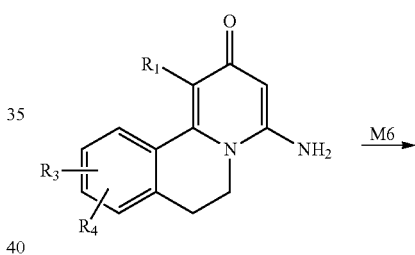

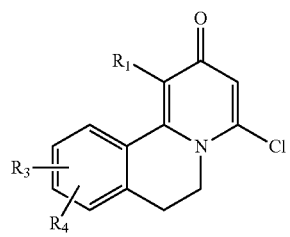

4-Amino-6,7-dihydrobenzo[a]quinolizin-2-one is dissolved in concentrated HCl (4 mL/mmol) and cooled at 0° C. Then a solution of NaNO₂ (4 equiv.) in water (1 mL/mmol) is added while keeping the internal temperature below 5° C. The resulting mixture is allowed to warm to room temperature and is stirred at room temperature until all starting material is consumed. The reaction mixture is then partitioned between water and DCM. The organic layer is dried over Na₂SO₄ and concentrated to dryness to afford 4-chloro-6,7-dihydrobenzo[a]quinolizin-2-one which is used without further purification.

1.8. Method 7: O-Alkylation

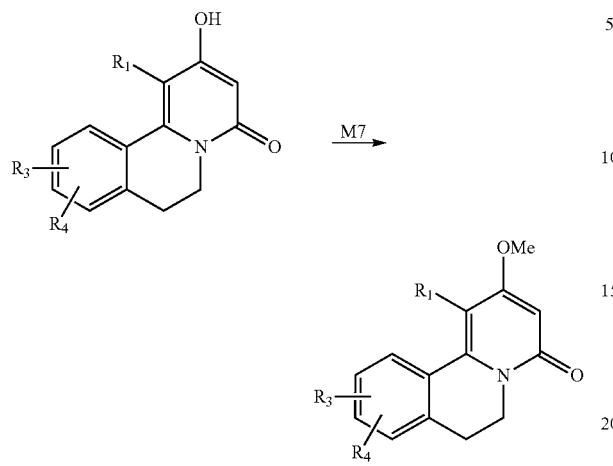

A suspension of 2-hydroxy-6,7-dihydrobenzo[a]quinolizin-4-one derivative (1.0 equiv.), dimethylsulfate (1.5 equiv.), $K_2CO_3$ (2.0 equiv.) and acetone (3 mL/mmol) under $N_2$ is heated at reflux overnight. The mixture is cooled to −10° C. and filtered over a Pall Seitz 300 thick paper filter. The residue is washed with cold acetone. The combined filtrates are concentrated to dryness and separated between DCM and water. The aqueous layer is basified to pH 10 using 2 M NaOH. The organic layer is separated, dried over $Na_2SO_4$ and concentrated. The product is boiled in MTBE for 30 min. The suspension is cooled to 0° C. and filtered. The residue is washed twice with MTBE and dried under vacuo to afford the desired product.

1.9. Method 8: Chlorination

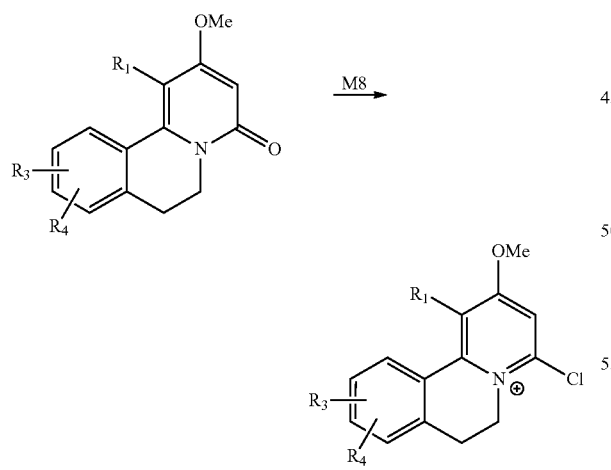

A round bottom flask is loaded with 2-methoxy-6,7-dihydrobenzo[a]quinolizin-4-one derivative (1.0 equiv.) and $POCl_3$ (15 equiv.). The resulting mixture is heated at 80° C. for 50 min. The mixture is cooled to 50° C. and concentrated to dryness. The residue is dissolved in DCM and cooled to 10° C. Water is added while keeping the temperature below 25° C. The pH is adjusted from 1.0 to 6.0 using 40% NaOH. The organic layer is separated, dried over $Na_2SO_4$ and concentrated to dryness to afford the desired product.

1.10. Method 9: Deprotection of Aromatic O-Methyl

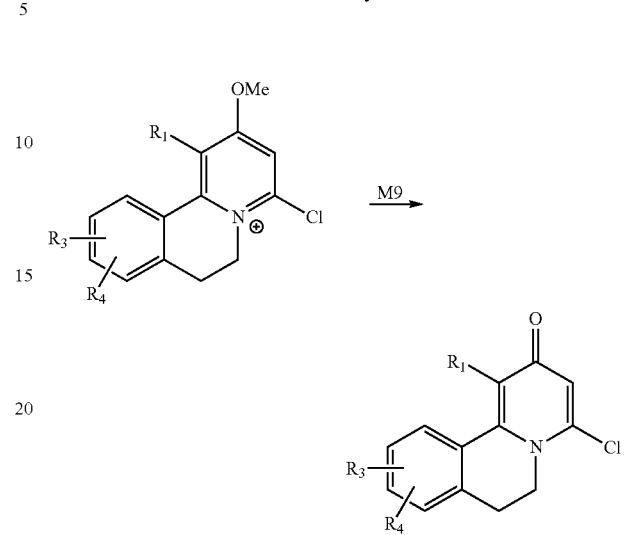

4-Chloro-2-methoxy-6,7-dihydrobenzo[a]quinolizin-5-ium derivative (1.0 equiv.) is added to a suspension of LiCl (3.0 equiv.) in DMF (2 mL/mmol). The mixture is heated at 100° C. for 30 min. The suspension is cooled to room temperature and passed through a filter. The residue is charged to a stirring mixture of saturated aq. $Na_2CO_3$ and water. The resulting suspension is stirred for 1 h and then filtered. The cake is washed with water and dried in vacuo yielding the desired product.

1.11. Method 10 and 11: Chlorination

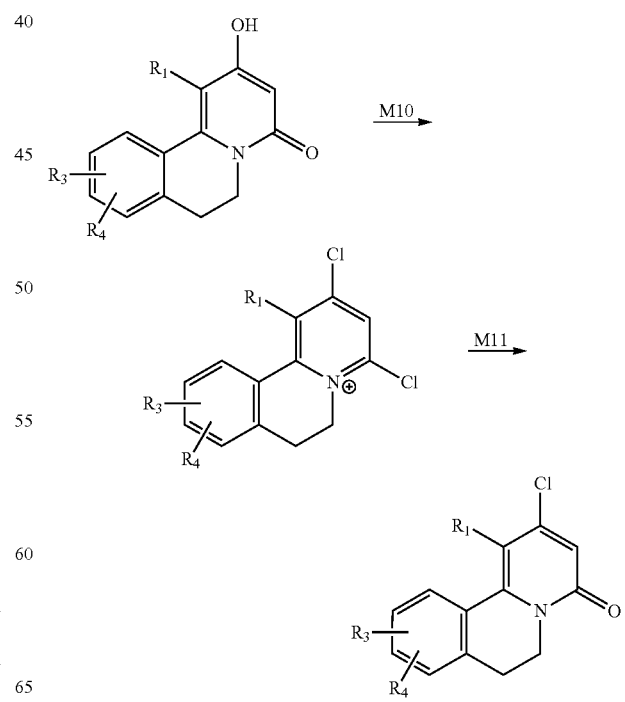

2-Hydroxy-6,7-dihydrobenzo[a]quinolizin-4-one derivative (1.0 equiv.) is mixed with POCl₃ (16 equiv.) under N₂ atmosphere. The mixture is heated to 70° C. and stirred at this temperature for 1.5 h. The reaction mixture is cooled to room temperature and evaporated in vacuo to yield an oil. This oil is treated with ice (120 g) and saturated Na₂CO₃ (120 mL), and stirred until a stable pH (8-9) is reached. EtOAc (120 mL) is added. The layers are separated; the aqueous layer is extracted with EtOAc (100 mL). The combined organic layer is washed with saturated NaCl (25 mL), dried on Na₂SO₄, filtered and evaporated in vacuo to yield the desired product, which is used as such in the next step.

1.12. Method 12: SnAr with Benzyl Alcohol

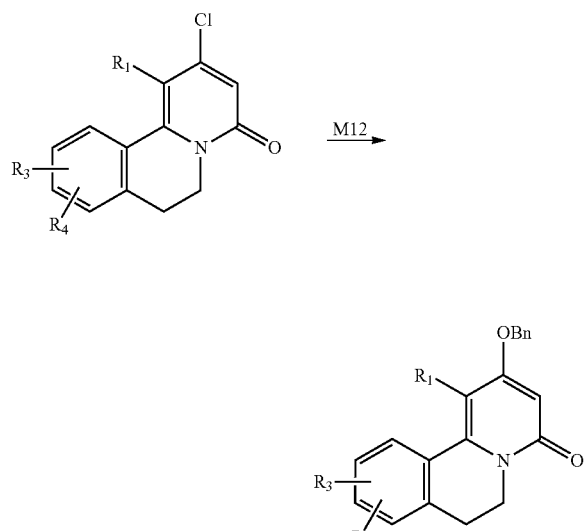

NaH (1.2 equiv., 60% in mineral oil) is mixed with dry THF and dry DMF (1:1 v:v) in a sealed reaction vessel under N₂ atmosphere. Benzyl alcohol (1.3 equiv.) is added, and the mixture is stirred at room temperature for 10 min, until the evolution of gas ceased. The mixture is cooled to 0° C. The solution/suspension of the 2-chloro-6,7-dihydrobenzo[a]quinolizin-4-one derivative (1.0 equiv.) in dry THF+dry DMF (1:1, v:v) is added at once. The tube is removed from the cold bath, heated to 50° C. and stirred at this temperature for 16 h. When LCMS showed complete conversion to the expected intermediate, the reaction mixture is treated with 10 mL saturated NaHCO₃, diluted with H₂O, extracted with EtOAc, the organic layer is washed with H₂O (2×), saturated NaCl (1×), dried on Na₂SO₄, filtered and evaporated in vacuo. The residue is treated with light petroleum ether, sonicated and left to stand in a sealed vessel overnight.

The suspension is allowed to settle, the supernatant removed, and the residue is dried and used as such in the next step.

1.13. Method 13: Chlorination

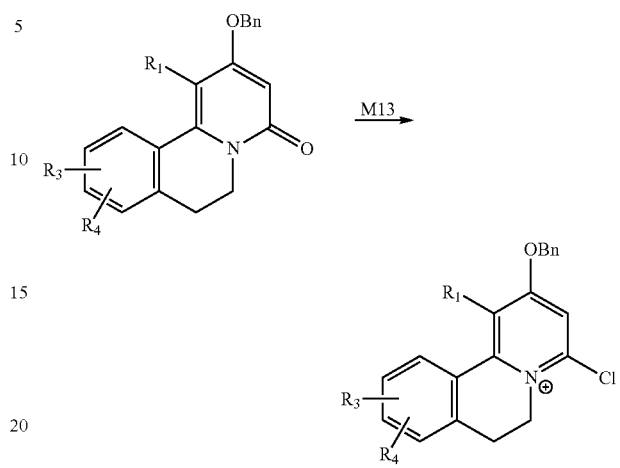

A round bottom flask is loaded with 2-benzoxy-6,7-dihydrobenzo[a]quinolizin-4-one derivative (1.0 equiv.) and POCl₃ (15 equiv.). The resulting mixture is heated at 80° C. for 50 min. The mixture is cooled to 50° C. and concentrated to dryness. The residue is dissolved in DCM and cooled to 10° C. Water is added while keeping the temperature below 25° C. The pH is adjusted from 1.0 to 6.0 using 40% NaOH. The organic layer is separated, dried over Na₂SO₄ and concentrated to dryness in order to afford the desired product.

1.14. Method 14: Deprotection of O-Benzyl

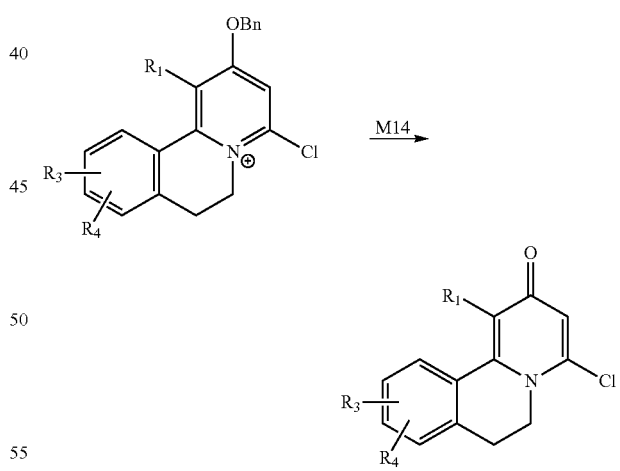

2-Benzoxy-4-chloro-6,7-dihydrobenzo[a]quinolizin-5-ium (1.0 equiv.) is mixed with EtOH (5 mL/mmol) under N₂ in a flask, 5% Palladium on BaSO₄ (5 mol %) is added. The system is sealed, purged by vacuum/N₂, then 3 times by vacuum/H₂ (from a balloon). The mixture is stirred vigorously at room temperature for no more than 5 min. Next, the mixture is filtered and the precipitate is washed with DCM. The filtrate is evaporated in vacuo and the residue is purified by means of column chromatography (DCM with 0 to 3% 0.2 M NH₃ in MeOH).

1.15. Method 15: SnAr with Alcohol

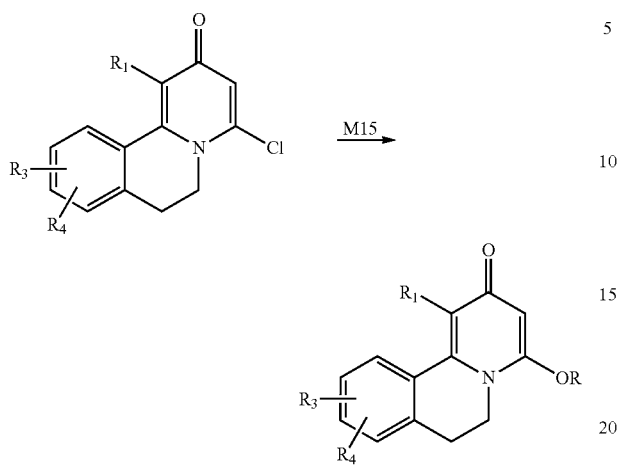

An oven dried multineck round bottom flask equipped with a condenser and an inlet septum under $N_2$ is loaded with NaH (1.25 equiv., 60% in mineral oil) and dry THF (2.67 mL/mmol). An alcohol (1.2 equiv.) is added dropwise and the resulting mixture is stirred at room temperature for 20 min and subsequently heated at 50° C. for 20 min. Then 4-chloro-6,7-dihydrobenzo[a]quinolizin-2-one derivative is added (1.0 equiv.) as a dry solid to the alkoxide mixture (any material that can not be transferred as such is dissolved in dry THF (1.3 mL/mmol) and added to the mixture). The mixture is briefly purged with $N_2$ and heated at 70° C. until all starting material is consumed. The mixture is cooled down to room temperature and quenched with saturated aq. $NaHCO_3$. The mixture is then concentrated in vacuo and partitioned between DCM and brine. The aqueous layer is extracted once with DCM and combined organics are dried over $Na_2SO_4$ and concentrated to dryness. The crude product is dissolved in MeCN and refluxed for 15 min. The mixture is cooled down to room temperature and the precipitate is separated by filtration. The precipitate is discarded and the filtrate is washed with pentane. The MeCN phase is concentrated to dryness affording the desired product.

1.16. Method 16: Deprotection of O-Benzyl

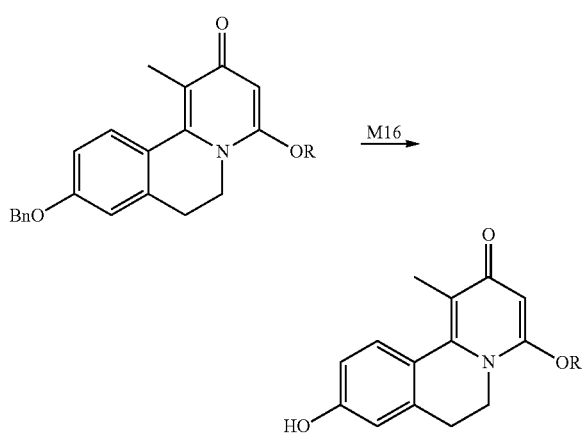

A flask is loaded with 4-alkoxy-9-benzoxy-6,7-dihydrobenzo[a]quinolizin-2-one derivative (1.0 equiv.) and Pd/C (0.02 equiv.). The flask is sealed with an inlet septum and the system is purged with $N_2$. Ethanol is added (5 mL/mmol) and the mixture is purged subsequently twice with vacuum/$N_2$ and three times with $H_2$/vacuum. The mixture is stirred at room temperature with the $H_2$ balloon left connected until all starting material is consumed. The mixture is then flushed with 2 cycles of vacuum/$N_2$ and is then filtered over a Pall Seitz 300 thick paper filter under a constant $N_2$ flow. The filter is washed with 7 M $NH_3$ in MeOH until all product is washed off, and the filtrate is concentrated to dryness yielding the desired product which is used as such.

1.17. Method 17: O-Alkylation

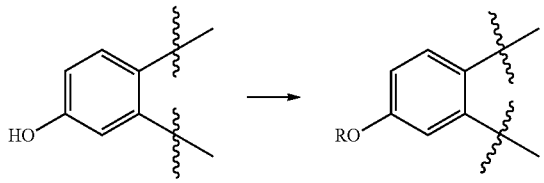

A three necked flask equipped with a thermometer, reflux condenser and inlet septum is loaded with 4-alkoxy-9-hydroxy-6,7-dihydrobenzo[a]quinolizin-2-one derivative (1.0 equiv.), $K_2CO_3$ (3.0 equiv.) and the appropriate alkylating agent (2.1 equiv.). The system is purged with vacuum/$N_2$ and dry DMF is added (2.5 mL/mmol). The resulting mixture is heated to an internal temperature of 100° C. until all starting material is consumed. The reaction mixture is poured in water and extracted with DCM. The aqueous layer is extracted twice more with DCM. The combined organic extracts are washed 3 times with brine, dried over $Na_2SO_4$ and evaporated in vacuo. The obtained solid is triturated with MTBE, separated by filtration and dried under vacuo. The product is then recrystallized from EtOAc to afford the desired product.

1.18. Method 18: O-Triflation of Phenol

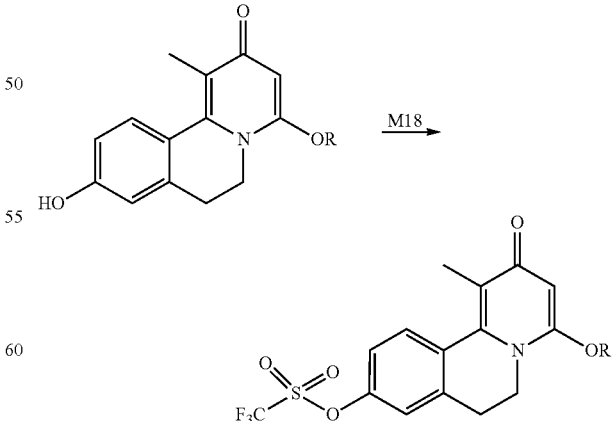

4-Alkoxy-9-hydroxy-6,7-dihydrobenzo[a]quinolizin-2-one derivative (1.0 equiv.) is mixed with DCM and N-phenylbis(trifluoromethanesulfonimide) (1.5 equiv.) under $N_2$.

Triethylamine (1.8 equiv.) is added and the reaction mixture is stirred overnight at room temperature. The reaction mixture is washed with satd. Na₂CO₃, satd. NaCl, dried on Na₂SO₄, filtered and evaporated in vacuo. The crude is further purified by means of automated column chromatography (DCM/methanol) to afford the desired product.

1.18.1. Synthesis of Compound 37

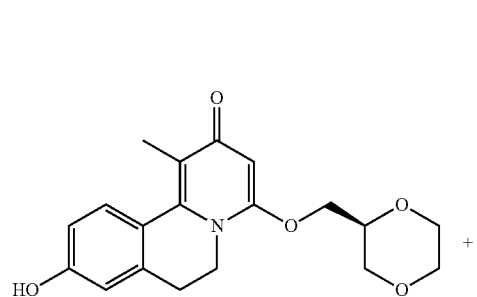

+

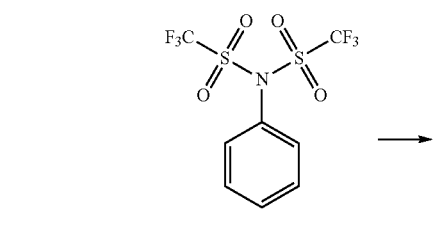

→

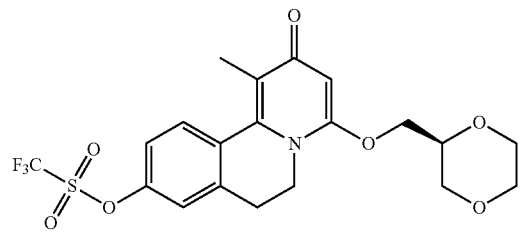

Compound 85 (4.0 g, 11.7 mmol, 1.0 equiv.) is mixed with DCM (117 mL, 10 mL/mmol) and N-phenylbis(trifluoromethanesulfonimide) (6.2 g, 15.5 mmol, 1.5 equiv.) under N₂. Triethylamine (2.9 mL, 21.0 mmol, 1.8 equiv.) is added and the reaction mixture is stirred overnight at room temperature. The reaction mixture is washed with satd. Na₂CO₃, satd. NaCl, dried on Na₂SO₄, filtered and evaporated in vacuo. The crude is further purified by means of automated column chromatography (DCM/methanol) to afford the desired product.

1.19. Method 19: Buchwald Reaction on a Triflate

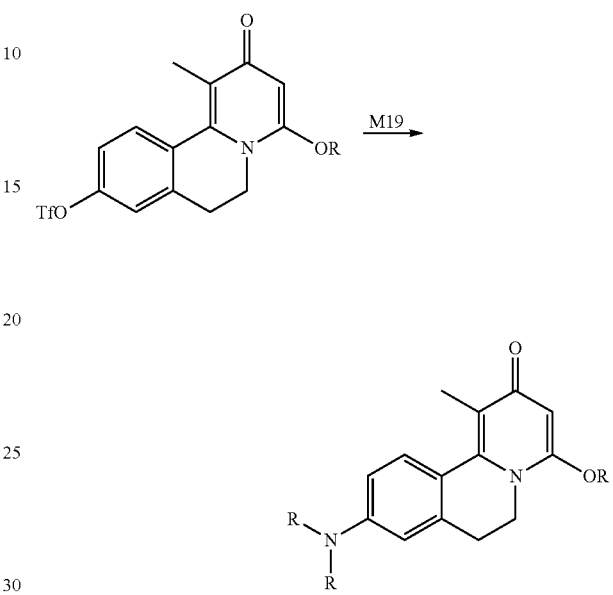

An oven-dried vial is loaded with the triflate derivative (1.0 equiv.), an amine (1.2 equiv.), RuPhos (1 mol %), RuPhos Pd G2 (1 mol %), and Cs₂CO₃ (2.0 equiv.). The vial is sealed, evacuated and backfilled with N₂ and 1,4-dioxane (0.8 mL, 4 mL/mmol) is added. The mixture is stirred to homogeneity and subsequently heated to 100° C. under vigorous stirring for 1 h. The reaction mixture is cooled to room temperature, diluted with DCM/MeOH 95/5, filtered over a plug of Celite® and evaporated in vacuo. The residue is purified by means of preparative HPLC to afford the desired product.

Notes: For primary amines BrettPhos/BrettPhos precatalyst are used. If amines are used as the HCl salt, 3.0 equiv. of Cs₂CO₃ are used.

1.19.1. Procedure Exemplified for Compound 111

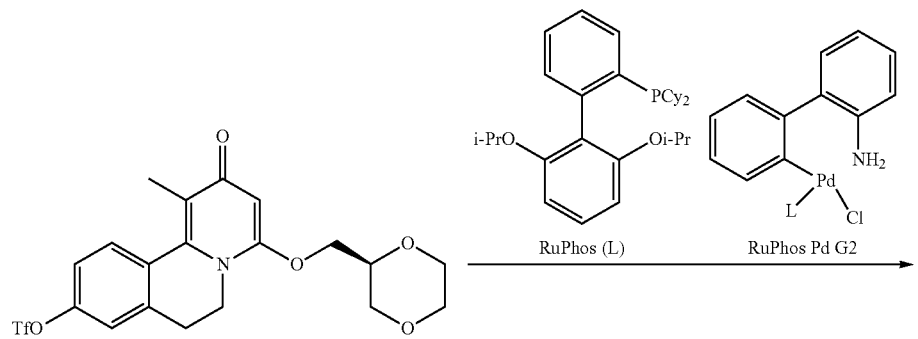

-continued

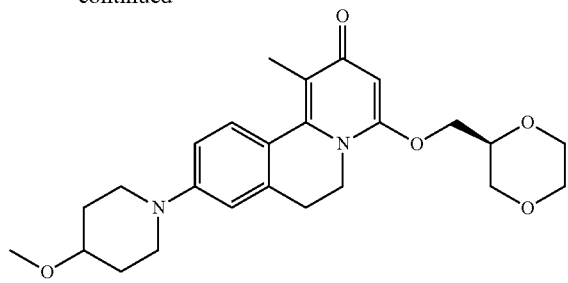

An oven-dried vial is loaded with Compound 37 (95 mg, 0.20 mmol, 1.0 equiv.), 4-methoxypiperidine (28 mg, 0.24 mmol, 1.2 equiv.), RuPhos (0.9 mg, 0.002 mmol, 1 mol %), RuPhos Pd G2 (1.6 mg, 0.002 mmol, 1 mol %), and $Cs_2CO_3$ (130 mg, 0.4 mmol, 2.0 equiv.). The vial is sealed, evacuated and backfilled with $N_2$ and 1,4-dioxane (0.8 mL, 4 mL/mmol) is added. The mixture is stirred to homogeneity and subsequently heated to 100° C. under vigorous stirring for 1 h. The reaction mixture is cooled to room temperature, diluted with DCM/MeOH 95/5, filtered over a plug of Celite® and evaporated in vacuo. The residue is purified by means of preparative HPLC to afford the desired product.

1.20. Method 20: CN Insertion

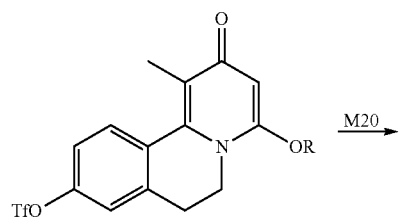

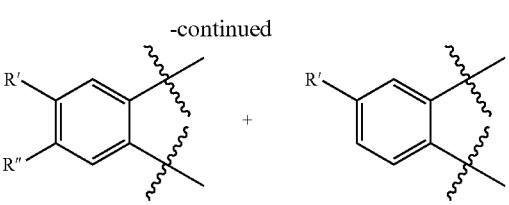

Compound 37 (1.0 equiv.), $Zn(CN)_2$ (1.05 equiv.) and $Pd(PPh_3)_4$ (0.10 equiv.) are weighed in a microwave tube. The tube is sealed and flushed with $N_2$. Dry DMF (5 mL/mmol) is added and the resulting mixture is heated in the microwave for 5 min at 150° C. The mixture is then cooled down to room temperature and separated between EtOAc and saturated aq. $NaHCO_3$. The organic layer is dried over $Na_2SO_4$ and concentrated to dryness. The desired product is isolated by means of preparative HPLC.

1.21. Method 21: Suzuki on Triflate

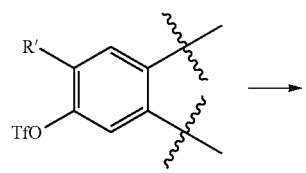

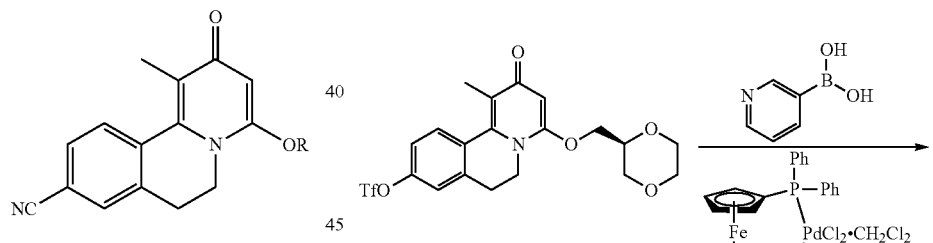

The aryl triflate (1.0 equiv.) is mixed with 3-pyridinylboronic acid (1.1 equiv.) and $Pd(dppfCl_2)$. DCM (5 mol %) in a vial under air. The vial is sealed, evacuated and back-filled with $N_2$, DIPEA (1 mL/mmol) and 1,4-dioxane/$H_2O$ 2:1 (1 mL/mmol) are added and the reaction mixture is heated to 100° C. for 1 h. The reaction mixture is cooled to room temperature, diluted with DCM/MeOH 95/5, filtered over a plug of Celite® and evaporated in vacuo. The residue is purified by means of preparative HPLC to afford the desired product.

1.21.1. Procedure Exemplified for Compound 98

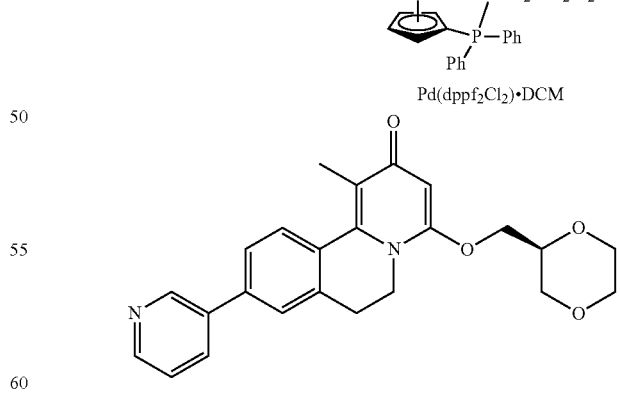

Compound 37 (95 mg, 0.2 mmol, 1.0 equiv.) is mixed with 3-pyridinylboronic acid (27 mg, 0.22 mmol, 1.1 equiv.) and $Pd(dppfCl_2)$. DCM (8 mg, 0.01 mmol, 5 mol %) in a vial under air. The vial is sealed, evacuated and back-filled with $N_2$, DIPEA (0.2 mL, 1 mL/mmol) and dioxane/$H_2O$ 2:1 (0.2 mL, 1 mL/mmol) are added and the reaction mixture is heated to 100° C. for 1 h. The reaction mixture is cooled to room temperature, diluted with DCM/MeOH 95/5, filtered over a plug of Celite® and evaporated in vacuo. The residue is purified by means of preparative HPLC to afford the desired product.

1.21.2. Procedure Exemplified for Compound 101

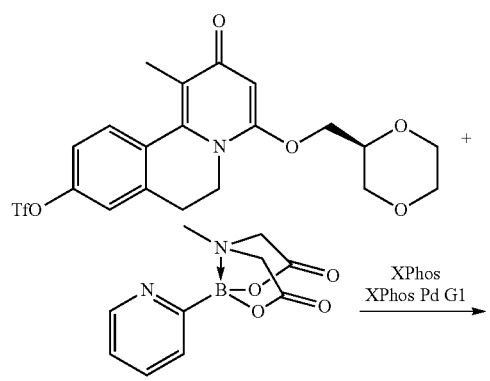

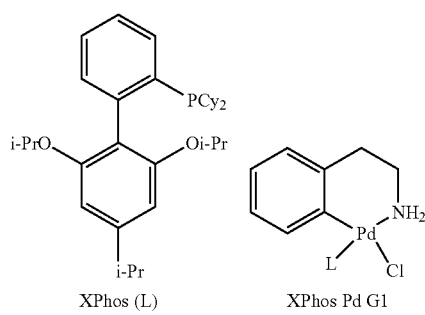

An oven dried vial is loaded with Compound 37 (95 mg, 0.2 mmol, 1.0 equiv.), 2-Pyridylboronic acid MIDA ester (70 mg, 0.30 mmol, 1.5 equiv.), XPhos (4.8 mg, 0.01 mmol, 5 mol %), XPhos Pd G$_1$ (7.4 mg, 0.01 mmol, 5 mol %), K$_3$PO$_4$ (212 mg, 1 mmol, 5.0 equiv.) and Cu(OAc)$_2$ (18 mg, 0.1 mmol, 0.5 equiv.). The vial is sealed and evacuated and back-filled with N$_2$. Dry DMF (1.6 mL, 8 mL/mmol) and diethanolamine (19 µL, 0.2 mmol, 1.0 equiv.) are added and the vial is heated to 100° C. under vigorous stirring for 3 h. The reaction mixture is cooled to room temperature, diluted with DCM/MeOH 95/5, filtered over a plug of Celite® and evaporated in vacuo. The residue is purified by means of preparative HPLC to afford the desired product.

1.22. Method 22: Negishi on a Triflate

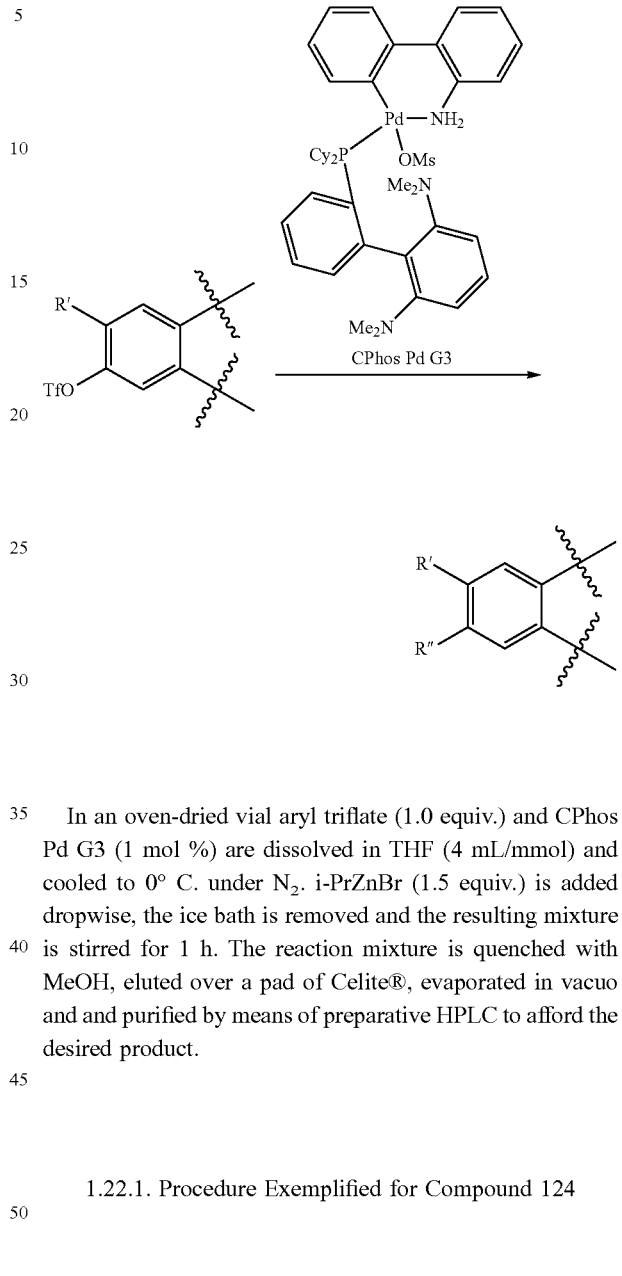

In an oven-dried vial aryl triflate (1.0 equiv.) and CPhos Pd G3 (1 mol %) are dissolved in THF (4 mL/mmol) and cooled to 0° C. under N$_2$. i-PrZnBr (1.5 equiv.) is added dropwise, the ice bath is removed and the resulting mixture is stirred for 1 h. The reaction mixture is quenched with MeOH, eluted over a pad of Celite®, evaporated in vacuo and and purified by means of preparative HPLC to afford the desired product.

1.22.1. Procedure Exemplified for Compound 124

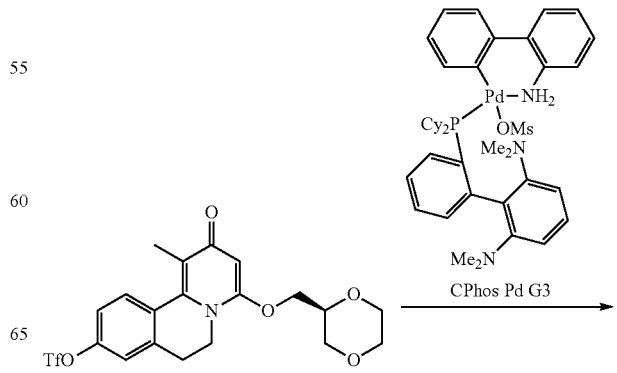

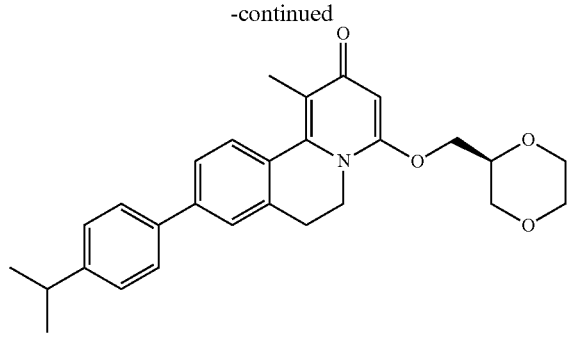

In an oven-dried vial Compound 37 (48 mg, 0.10 mmol, 1.0 equiv.) and CPhos Pd G3 (0.8 mg, 0.001 mmol, 1 mol %) are dissolved in THF (0.4 mL, 4 mL/mmol) and cooled to 0° C. under $N_2$. i-PrZnBr (0.3 mL, 0.5 M in THF, 1.5 equiv.) is added dropwise, the ice bath is removed and the resulting mixture is stirred for 1 h. The reaction mixture is quenched with MeOH, eluted over a pad of Celite®, evaporated in vacuo and purified by means of preparative HPLC to afford the desired product.

1.23. Method 23: SnAr with Amine

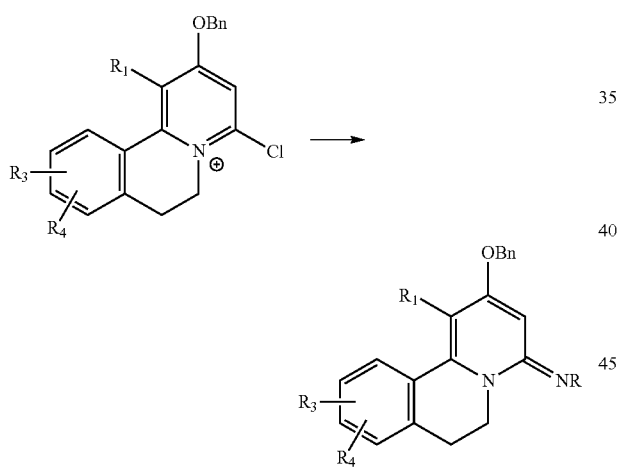

2-Benzoxy-4-chloro-6,7-dihydrobenzo[a]quinolizin-5-ium derivative (1.0 equiv.) is mixed with dry MeCN in a sealed reaction vessel, under $N_2$ atmosphere. The mixture is cooled to 0° C. The appropriate amine or amine hydrochloride (2.5 equiv.) are mixed in a separated vessel under $N_2$ with dry MeCN and triethylamine (5.0 equiv.). This mixture is added dropwise to the mixture containing 2-benzoxy-4-chloro-6,7-dihydrobenzo[a]quinolizin-5-ium derivative, over 5 min. The mixture is stirred for 20 min at 0° C., then at room temperature for 15 min. When LCMS shows complete disappearance of the starting material, the mixture is quenched with saturated $NaHCO_3$, extracted with EtOAc, the organic layer is dried on $Na_2SO_4$, filtered and evaporated in vacuo. The crude is used as such in the next step.

1.24. Method 24: Debenzylation

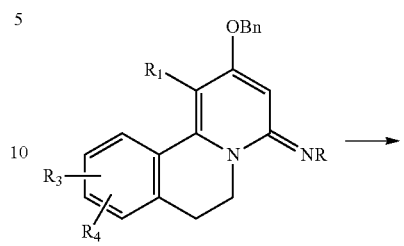

Intermediate from method 23 (1.0 equiv.) is dissolved in EtOH (25 mL/mmol), under $N_2$ atmosphere. 10% Pd on charcoal (0.05 mmol) are added. The mixture is stirred at room temperature, submitted to 3 cycles of evacuation/refill with $N_2$, and a last cycle of evacuation/refill with $H_2$ (from a balloon). The mixture is further stirred at room temperature for 6 h, leaving the $H_2$ balloon connected. LCMS shows complete conversion to an amine. The mixture is filtered though a 0.45 µm PFTE membrane. The filtrate is evaporated in vacuo and thoroughly dried from traces of EtOH, to yield the desired product, which is used as such in the next step.

1.25. Method 25, Exemplified with Compound 2

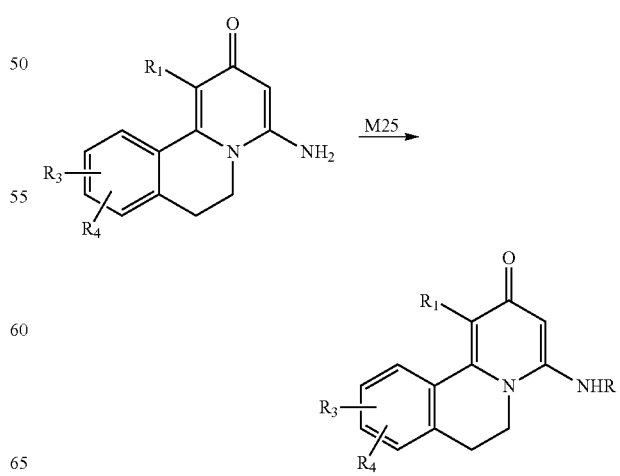

1.25.1. 9,10-dimethoxy-1-methyl-4-(tetrahydrofuran-2-ylmethylamino)-6,7-dihydrobenzo[a]quinolizin-2-one

1.25.1.1. Step 1 (tetrahydrofuran-2-carboxaldehyde)

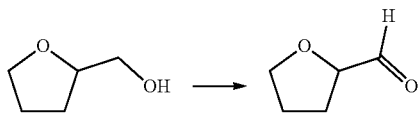 [SMILES: OCC1CCCO1 ; O=CC1CCCO1]

Dess-Martin periodinane (4.98 g, 11.75 mmol, 1.2 equiv.) is added portionwise, at 0° C., and under nitrogen atmosphere to a solution of (tetrahydrofuran-2-yl)methanol (1 g, 9.79 mmol, 1.0 equiv.) in anhydrous DCM (50 mL, 5.1 mL/mmol). The mixture is stirred from 0° C. to room temperature over 1 h, then stirred at room temperature until the full conversion is observed, when monitoring the experiment by TLC. The mixture is diluted with DCM (250 mL) and washed with a mixture (1:1) of saturated aqueous NaHCO$_3$ and saturated aqueous Na$_2$S$_2$O$_3$ (2×125 mL). The organic layer is dried over MgSO$_4$ and evaporated to dryness at 30° C. The resulting crude product is suspended in cold Et$_2$O, triturated and filtered. The filtrate is collected and evaporated to dryness at 30° C., to afford tetrahydrofuran-2-carboxaldehyde.

1.25.2. Step 2

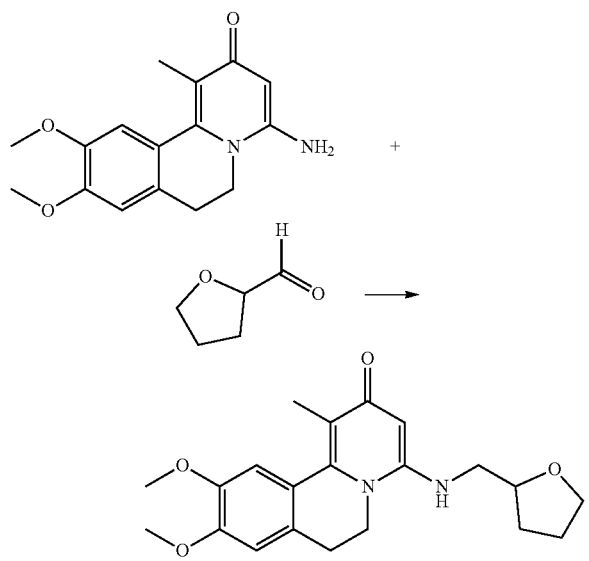

In a 0.5-2.0 mL microwave tube, 4-amino-1-methyl-6,7-dihydrobenzo[a]quinolizin-2-one (50 mg, 0.18 mmol, 1.0 equiv.) and sodium triacetoxyborohydride (94 mg, 0.444 mmol, 2.5 equiv.) are mixed and stirred for 20 min at 0° C. in 400 µL of a mixture (1:1) of anhydrous DCM and trifluoroacetic acid. A solution of tetrahydrofuran-2-carboxaldehyde (23 mg, 0.23 mmol, 1.3 equiv.) in anhydrous DCM (400 µL) is then added at 0° C. to the mixture. The mixture is stirred for 20 min from 0° C. to room temperature. After 2.5 h of stirring at room temperature, the mixture is again cooled down to 0° C. Sodium triacetoxyborohydride (75 mg, 0.35 mmol, 2.0 equiv.) followed by tetrahydrofuran-2-carboxaldehyde (36 mg, 0.36 mmol, 2.1 equiv.) are added, then the mixture is further stirred and brought to room temperature for 1 h. Tetrahydrofuran-2-carboxaldehyde (140 mg, 1.4 mmol, 7.8 equiv.) is added again and the reaction mixture is stirred for 17 h at room temperature. The reaction mixture is diluted with DCM and extracted with saturated aqueous NaHCO$_3$. The organic layer is dried over sodium sulfate and the resulting crude material is purified by preparative HPLC, to isolate the desired product.

1.26. Exemplified with 4-[[(2R)-1,4-dioxan-2-yl]methylamino]-9,10-dimethoxy-1-methyl-6,7-dihydrobenzo[a]quinolizin-2-one (Compound 6)

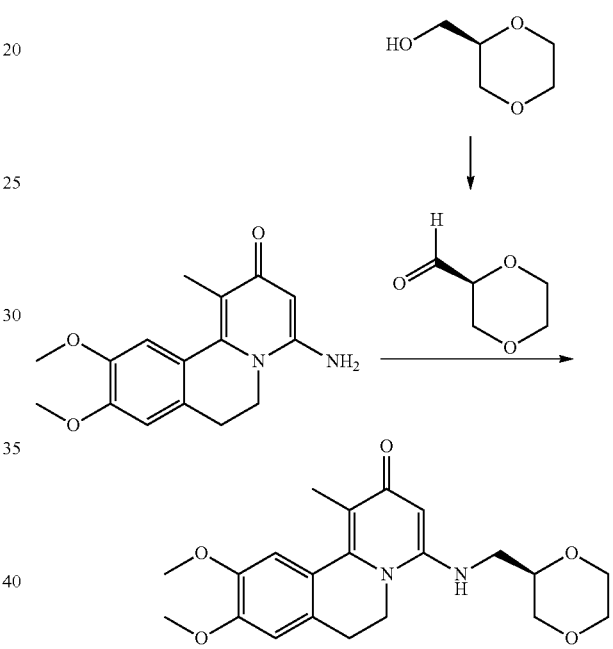

(S)-1,4-dioxan-2-carboxaldehyde is synthesized via the oxidation of (R)-1,4-dioxan-2-yl)methanol, following the same procedure as described in step 1 for the synthesis of Compound 2. This crude aldehyde is used, without further purification, in the reductive alkylation of 4-amino-1-methyl-6,7-dihydrobenzo[a]quinolizin-2-one, according to the procedure described in step 2 for the synthesis of compound Compound 2. The crude product is purified by preparative HPLC, to isolate the desired product.

1.27. Method 27 (Boc Deprotection)

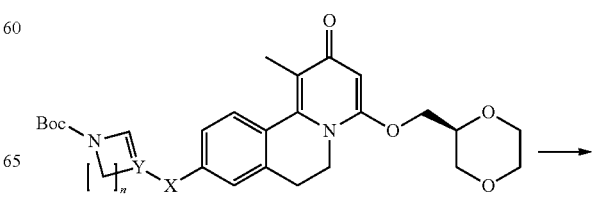

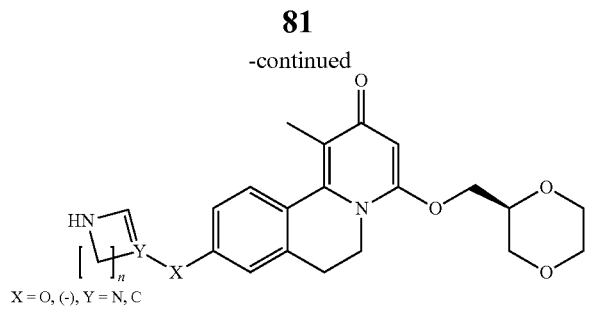

X = O, (-), Y = N, C

A vial is loaded with the boc protected amine derivative (1.0 equiv.), TFA (1.9 mL/mmol) and DCM (3.0 mL/mmol) under a nitrogen atmosphere. The reaction mixture is stirred for 30 min at 30° C. and is subsequently purified by means of SCX chromatography.

1.27.1. Procedure Exemplified for Compound 66

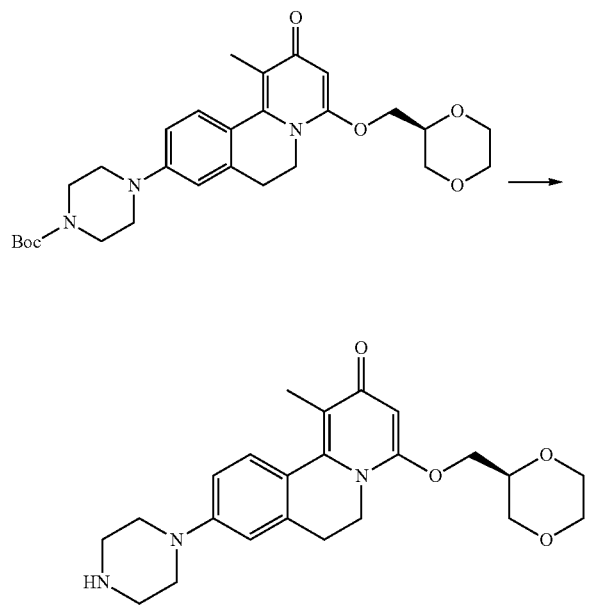

A vial is loaded with Compound 60 (134 mg, 0.33 mmol, 1.0 equiv.), TFA (0.6 mL, 1.9 mL/mmol) and DCM (1 mL, 3.0 mL/mmol) under a nitrogen atmosphere. The reaction mixture is stirred for 30 min at 30° C. and is subsequently purified by means of SCX chromatography.

1.28. Method 28 (N-Functionalization)

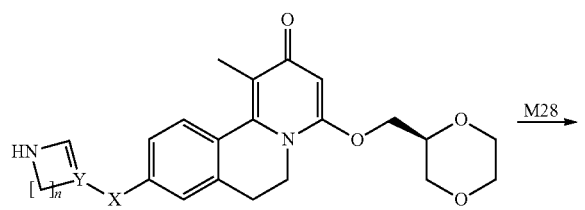

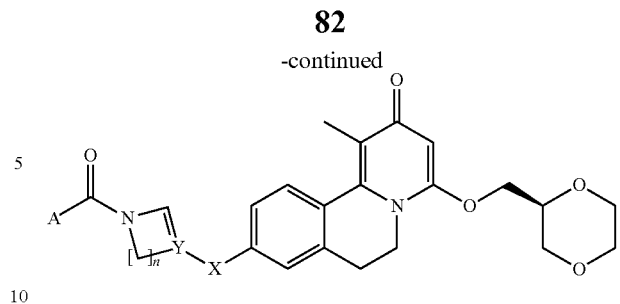

Wherein X is $L_1$, and Y is CH or N

An oven-dried vial is loaded with the amine derivative (1.0 equiv.), Et$_3$N (2.0 equiv.) and DCM (10 mL/mmol) under an nitrogen atmosphere. The vial is cooled to 0° C. and the appropriate acylating agent (1.1 equiv.) is added dropwise. The ice-bath is removed and the reaction mixture is stirred for 1 h at room temperature. Next, the reaction mixture is diluted with DCM and washed with saturated aq. NaHCO$_3$ (1×) and brine (2×). The organic phase is dried over a phase separator and evaporated in vacuo. The residue is purified by means of preparative TLC or preparative HPLC.

1.28.1. Procedure Examplified for Compound 69

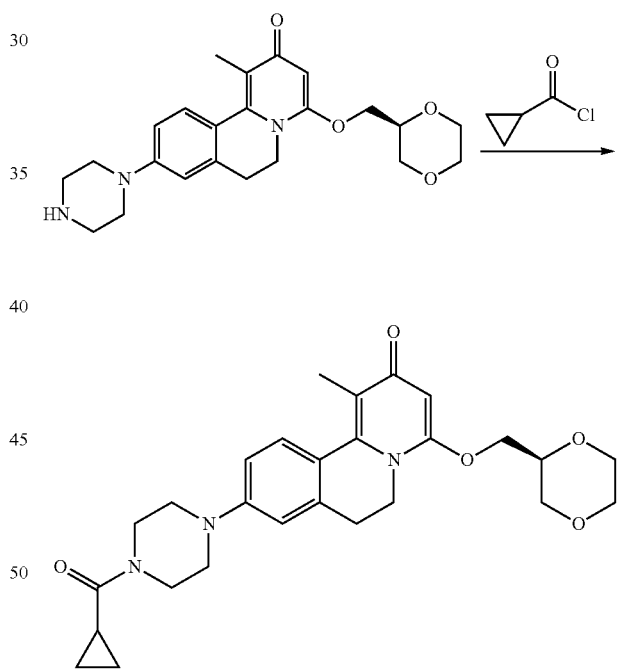

An oven-dried vial is loaded with Compound 66 (45 mg, 0.11 mmol, 1.0 equiv.), Et$_3$N (31 µL, 0.22 mmol, 2.0 equiv.) and DCM (1.1 mL, 10 mL/mmol) under a nitrogen atmosphere. The vial is cooled to 0° C. and cyclopropanecarbonyl chloride (11 µL, 0.12 mmol, 1.1 equiv.) is added dropwise. The ice-bath is removed and the reaction mixture is stirred for 1 h at room temperature. Next, the reaction mixture is diluted with DCM and washed with saturated aq. NaHCO$_3$ (1×) and brine (2×). The organic phase is dried over a phase separator and evaporated in vacuo. The residue is purified by means of preparative thin layer chromatography (DCM/0.2 M NH$_3$ in MeOH 95/5).

1.29. Method 29: Alkene Reduction

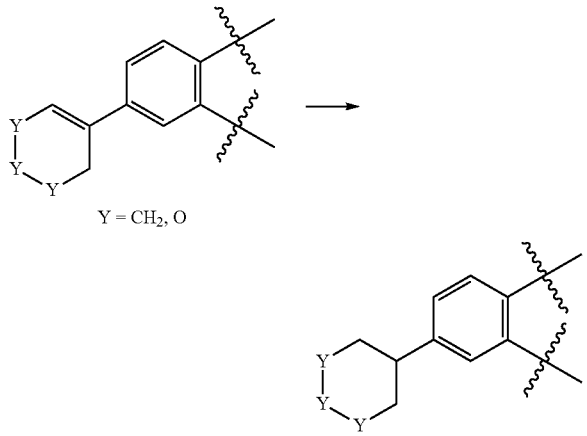

Y = CH₂, O

Pd/C (10% w/w, 0.1 equiv.) is added to the alkene (1.0 equiv.) under nitrogen atmosphere. MeOH is added and the resulting mixture put under hydrogen atmosphere and stirred at room temperature until completion of the reaction. The mixture is filtered through Celite® and the filtrate concentrated under vacuum. The residue is purified by preparative HPLC.

Example 2

Preparation of Illustrative Compounds of the Invention

2.1. Preparation of Intermediates for the Preparation of Illustrative Compounds of the Invention

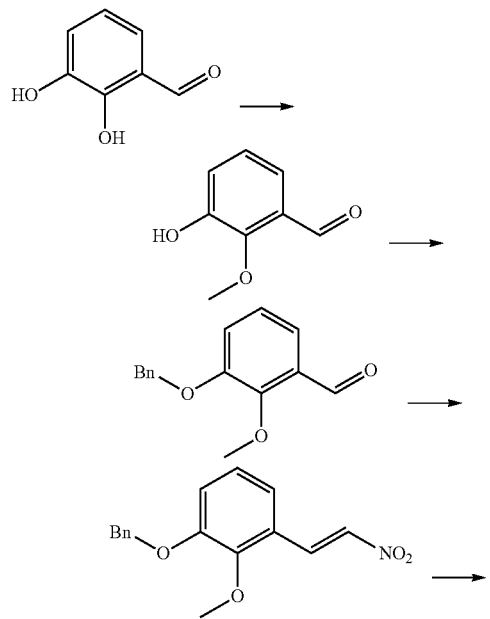

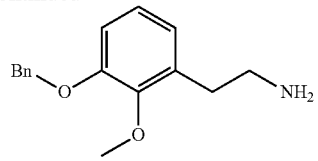

2.1.1. Preparation of Int60

2,3-dihydroxybenzaldehyde (27.6 g) (200 mmol) is mixed with dry DMF (460 mL) and KHCO₃ (80 g, 800 mmol), under N₂ atmosphere. The mixture is stirred at room temperature for 30 min. MeI (51 mL, 820 mmol) is added in one portion. The mixture is further stirred at room temperature for 30 h. The excess MeI is evaporated in vacuo. H₂O (1.1 L) is added, followed by 37% HCl (46 mL) to reach pH ~3.5 after the addition. The mixture is extracted with Et₂O (4×0.55 L then 1×0.28 L). The combined organic layer is further washed with saturated NH₄Cl (2×0.35 L), then brine (1×0.7 L), dried on MgSO₄, filtered and evaporated in vacuo to yield the crude desired product. This crude is dissolved in Et₂O (0.7 L), and extracted with 1M NaOH (2×0.42 L). The combined aqueous layer is treated with 37% HCl (71 mL) to reach pH ~1. The resulting suspension is cooled to 15° C., filtered on a Buchner filter, the solid is washed with H₂O (2×30 mL), dried under suction and then in vacuo at 42° C. to yield the desired product.

2.1.2. Preparation of Int61

Int60 (17 g, 111 mmol) is mixed with dry DMF (280 mL) and K₂CO₃ (23 g, 167 mmol), under N₂ atmosphere. Benzyl bromide (16.5 mL, 139 mmol) is added in one portion. The mixture is stirred at 40° C. for 2.5 h, cooled to room temperature and treated with H₂O (0.5 L) and toluene (0.5 L). The resulting layers are separated, and the aqueous layer is extracted again with toluene (0.25 L). The combined organic layer is washed with 3×0.25 L H₂O, dried on Na₂SO₄, filtered and evaporated in vacuo. The residue is treated with light petroleum ether (100 mL) and stirred until powdery. The suspension is filtered on Buchner, the solid is washed with light petroleum ether (50 mL), dried under suction and then in vacuo at 40° C. to yield the desired product.

2.1.3. Preparation of Int62

Int61 (25.7 g, 106 mmol) is mixed with AcOH (74 mL), nitromethane (17.2 mL, 318 mmol) and ammonium acetate (4.09 g, 53 mmol), under N₂ atmosphere. The mixture is stirred and heated to 100° C. for 12 h. The reaction mixture is poured into a mixture of 50 g ice and 200 mL H₂O. The resulting suspension is extracted with DCM (1×250 mL and 1×100 mL). The combined organic layer is washed with H₂O (170 mL), dried on Na₂SO₄, filtered and evaporated in vacuo to yield the crude desired product. This residue is treated with EtOH (135 mL), under heating until fully dissolved. The warm solution is then allowed to cool down in an ice bath under rapid stirring, yielding a fine suspension. After 30 min of stirring at ~0° C., the suspension is filtered on Buchner, the cake is washed with 80 mL EtOH, dried under suction and then in vacuo at 40° C. to yield the desired product.

2.1.4. Preparation of Intermediate 63

Int62 (18.5 g, 65 mmol) is dissolved in dry THF (65 mL). In another flask, LiAlH$_4$ (8.63 g, 228 mmol) is mixed with dry THF (390 mL), under N$_2$ atmosphere, and the resulting mixture is stirred at 0° C. The solution of int62 is added dropwise, under stirring, keeping the temperature below 10° C. during the addition (about 40 min). The reaction mixture is removed from the cold bath and stirred at room temperature for 2 h. The reaction mixture is then cooled again to 0° C. and sodium sulphate decahydrate (58.5 g) is added portionwise, under stirring, over 10 min, ensuring that the temperature remains below 15° C. during the addition. DCM (400 mL) is added, the biphasic mixture is vacuum filtered on a Pall Seitz 100 filter, the filter is washed with DCM (200 mL). The filtrated is evaporated in vacuo and is used as such in the next step.

2.1.5. Synthesis of Compound 1

2.1.5.2. Step ii: 1-Ethyl-6,7-dimethoxy-3,4-dihydro-isoquinoline (Int103)

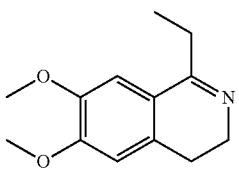

POCl$_3$ (7.8 mL, 84 mmol, 4 equiv.) is added dropwise to an ice cold solution of N-[2-(3,4-dimethoxy-phenyl)-ethyl]-propionamide (5.0 g, 21 mmol, 1 equiv.) in DCM (6 mL) and the mixture is heated to reflux temperature for 24 h. The mixture is concentrated, the remaining residue is poured on ice and basified to pH 7-8 using aq. saturated K$_2$CO$_3$. The aqueous is extracted with DCM (3x), dried (Na$_2$SO$_4$), filtered and concentrated to yield the desired the product which is used without further purification.

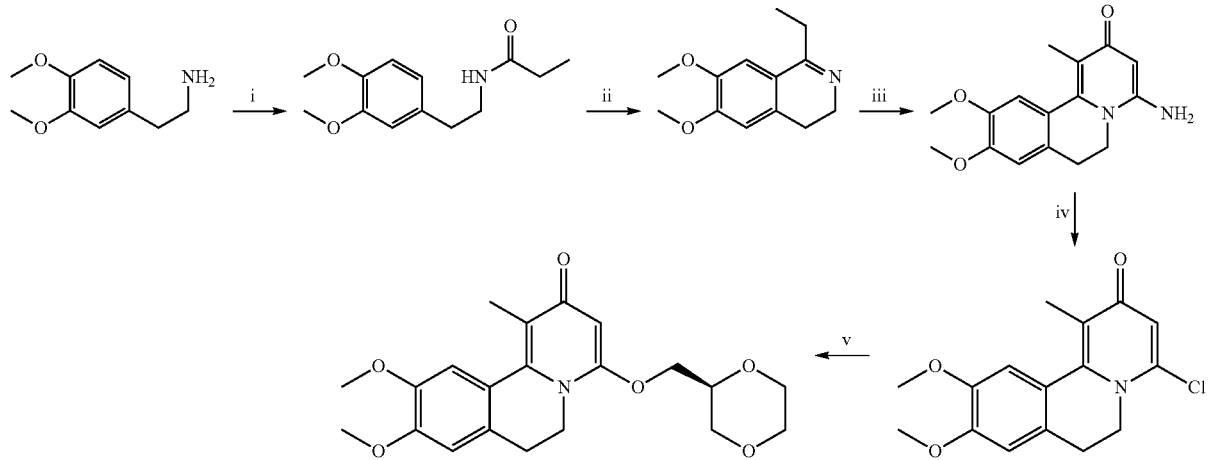

2.1.5.1. Step i: N-[2-(3,4-Dimethoxy-phenyl)-ethyl]-propionamide: Int102

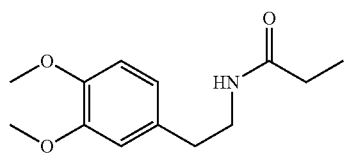 [SMILES: CCC(=O)NCCc1ccc(OC)c(OC)c1]

Pyridine (33 mL, 414 mmol, 3.0 equiv.) is added to a solution of 2-(3,4-dimethoxy-phenyl)-ethylamine (25 g, 138 mmol, 1 equiv.) in DCM (40 mL) and the solution is cooled down to 0° C. Propionyl chloride (17 mL, 207 mmol, 1.5 equiv.) is added dropwise, the reaction is warmed to room temperature and stirred for 24 h. Water is added and the resulting mixture extracted with DCM (3x), dried (Na$_2$SO$_4$), filtered and concentrated under vacuum. The residue is purified by silica gel chromatography (EtOAc/petroleum ether; 50:50 to 75:25) to afford the desired product.

2.1.5.3. Step iii: 9,10-dimethoxy-1-methyl-4-amino-6,7-dihydrobenzo[a]quinolizin-2-one (Int114)

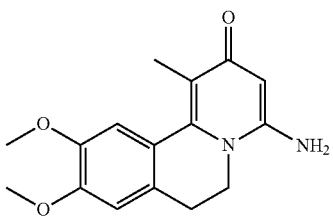

In a 50 mL round bottom flask placed under nitrogen atmosphere, 1-ethyl-6,7-dimethoxy-3,4-dihydroisoquinoline (4.6 mmol, 1.0 equiv.) is suspended in diglyme (3 mL, 0.7 mL/mmol) and sonicated at 40° C. under nitrogen atmosphere, until a bright yellow suspension is obtained. tert-Butyl cyanoacetate (2.6 mL, 18.2 mmol, 4.0 equiv.) is added to the mixture. The flask is equipped with a condenser and the mixture is stirred and heated to 140° C. for 48 h. Then, the mixture is cooled down to room temperature. Acetonitrile (15 mL) is added to the reaction mixture. After trituration and sonication, the precipitate is collected, to afford the desired product.

2.1.5.4. Step iv: 8,9-dimethoxy-4-chloro-1-methyl-6,7-dihydrobenzo[a]quinolizin-2-one (Int 109)

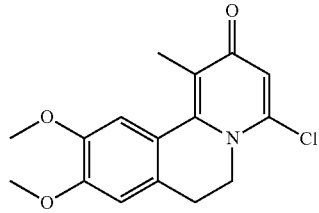

8,9-dimethoxy-1-methyl-4-Amino-6,7-dihydrobenzo[a]quinolizin-2-one (100 mg, 1.0 equiv., 0.35 mmol) is dissolved in concentrated HCl (1.4 mL, 4 mL/mmol) and cooled at 0° C. Then a solution of NaNO$_2$ (97 mg, 4 equiv., 1.40 mmol) in water (350 µL, 1 mL/mmol) is added while keeping the internal temperature below 5° C. The resulting mixture is allowed to warm to room temperature and is stirred at room temperature until all starting material is consumed. The reaction mixture is then partitioned between water and DCM. The organic layer is dried over Na$_2$SO$_4$ and concentrated to dryness to afford the desired product, which is used without further purification.

2.1.5.5. Step v: 4-[[(2S)-1,4-dioxan-2-yl]methoxy]-9,10-dimethoxy-1-methyl-6,7-dihydrobenzo[a]quinolizin-2-one

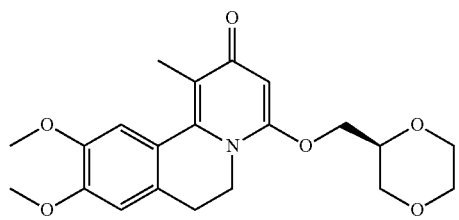 [SMILES: COc1cc2c(cc1OC)-c1c(C)c(=O)cc(OC[C@@H]3COCCO3)n1CC2]

An oven dried microwave tube is loaded with NaH (6.0 equiv., 1.02 mmol, 41 mg, 60% in mineral oil). The tube is sealed and flushed with N$_2$. Dry THF (340 µL, 2 mL/mmol) and (R)-(1,4-dioxan-2-yl)methanol (3.05 equiv., 0.52 mmol, 61 mg) are added. The resulting mixture is stirred at room temperature for 30 min. Then a solution of 8,9-dimethoxy-4-chloro-1-methyl-6,7-dihydrobenzo[a]quinolizin-2-one (1.0 equiv., 0.17 mmol, 53 mg) in dry THF (340 µL, 2 mL/mmol) is added. The mixture is heated at 65° C. until all starting material is consumed. The mixture is cooled down to room temperature and partionated between 1N HCl and DCM. The organic layer is dried over Na$_2$SO$_4$ and concentrated to dryness. The required product is isolated by means of preparative HPLC.

2.1.6. Synthesis of Compound 18

2.1.6.1. 2-(3-benzyloxyphenyl)ethanamine

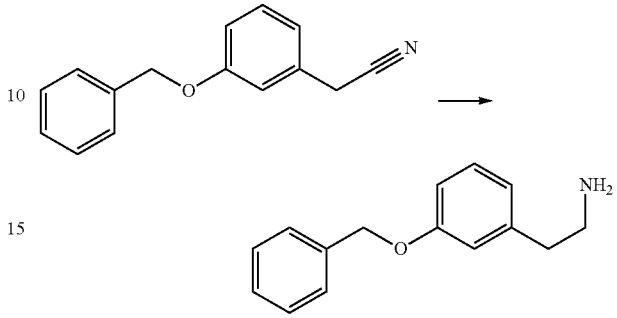

A round bottom flask is loaded with 3-benzyloxyphenylacetonitrile (100 g, 448 mmol, 1.0 equiv.), Raney nickel (50% suspension in water, 63.2 mL, 537 mmol, 1.2 equiv.) and 7N NH$_3$ in MeOH (560 mL, 5 mL/mmol) under N$_2$. The system is filled with 1 atmosphere H$_2$ with cycles of vacuum/H$_2$. The suspension is stirred at room temperature overnight leaving the H$_2$ supply connected. The reaction mixture is filtered over a Pall Seitz 300 thick paper filter. The filter is washed 3 times with MeOH and the filtrate is concentrated in vacuo. The obtained product is used without further purification steps.

$^1$H NMR (DMSO d$_6$): 7.45, 2H, m; 7.40, 2H, m; 7.35, 1H, m; 7.20, 1H, t; 6.84, 2H, m; 6.78, 1H, d; 5.07, 2H, s; 2.76, 2H, t; 2.59, 2H, t.

2.1.6.2. N-[2-(3-benzyloxyphenyl)ethyl]propanamide: Int13

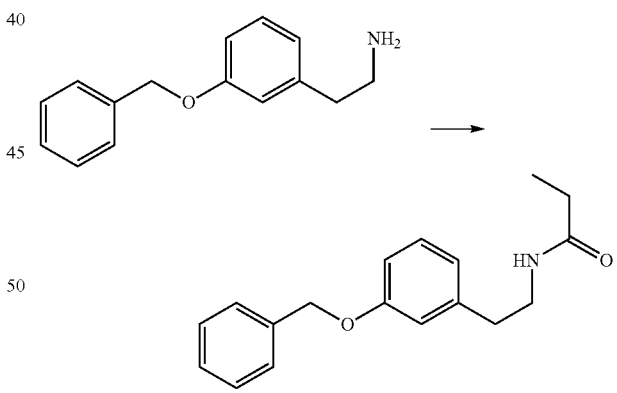

A multineck round bottom flask is loaded with 2-(3-benzyloxyphenyl)ethanamine (97.02 g, 0.427 mol, 1.0 equiv.), pyridine (73 mL, 0.897 mol, 2.10 equiv.) and DCM (218 mL, 2 mL/mmol) under N$_2$. The mixture is cooled to 0° C. (internal temperature) and propionylchloride (39 mL, 0.449 mol, 1.05 equiv.) is added dropwise. The resulting mixture is left to warm to room temperature. After 30 min, the reaction mixture is quenched with 6 M HCl (160 mL) and brine (300 mL). The product is extracted with DCM (2×100 mL). The combined organics are dried over Na$_2$SO$_4$ and concentrated to dryness, to yield the desired product, which is used without further purification.

2.1.6.3. 6-benzyloxy-1-ethyl-3,4-dihydroisoquinoline: Int14

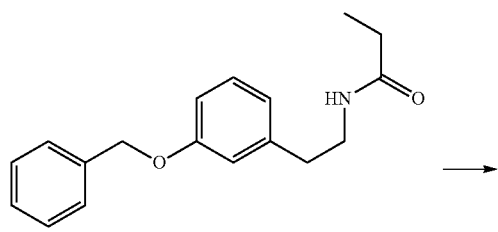

A round bottom flask equipped with a condenser at 0° C. is loaded with N-[2-(3-benzyloxyphenyl)ethyl]propanamide (124 g, 0.417 mol, 1.0 equiv.) and DCM (125 mL, 0.3 mmol/mL). POCl$_3$ (155 mL, 1.667 mol, 4.0 equiv.) is added portionwise and the ice bath is removed. The resulting mixture is heated at 40° C. overnight.

The mixture is concentrated in vacuo and the residue is poured over 300 g of ice under stirring. Na$_2$CO$_3$ is then added until a stable pH 8-9 is reached. H$_2$O (1 L) is added and the resulting mixture is extracted with DCM (3×300 mL). The combined organics are dried over Na$_2$SO$_4$ and concentrated to dryness to afford the desired product, which is used as such.

2.1.6.4. 9-benzyloxy-1-methyl-6,7-dihydrobenzo[a]quinolizine-2,4-dione: Int15

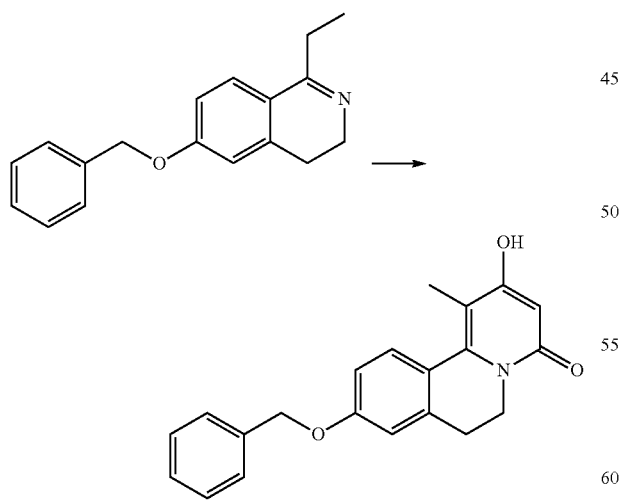

A round bottom flask equipped with a condenser under N$_2$ is loaded with 6-benzyloxy-1-ethyl-3,4-dihydroisoquinoline (50 g, 0.189 mol, 1.0 equiv.), di-tBu-malonate (163 g, 0.755 mol, 4.0 equiv.) and dry diglyme (94 mL 0.5 mL/mmol). The mixture is degassed via pump-freeze-thaw method and heated at 150° C. until all starting material is consumed. The mixture is cooled down to 10° C. and MTBE (200 mL) is added. The precipitate is separated by filtration and the residue is washed with MeCN/MTBE 1:4 (3×250 mL). The precipitate is dried in vacuo and used without further purification.

$^1$H NMR (DMSO d$_6$): 7.60, 1H, d; 7.35-7.43, 6H, m; 7.06, 1H, m; 6.99, 1H, dd; 5.71, 1H, s; 5.17, 2H, s; 3.91, 2H, m; 2.78, 2H, m; 2.13, 3H, s.

2.1.6.5. 2-methoxy-9-benzyloxy-1-methyl-6,7-dihydrobenzo[a]quinolizin-4-one: Int19

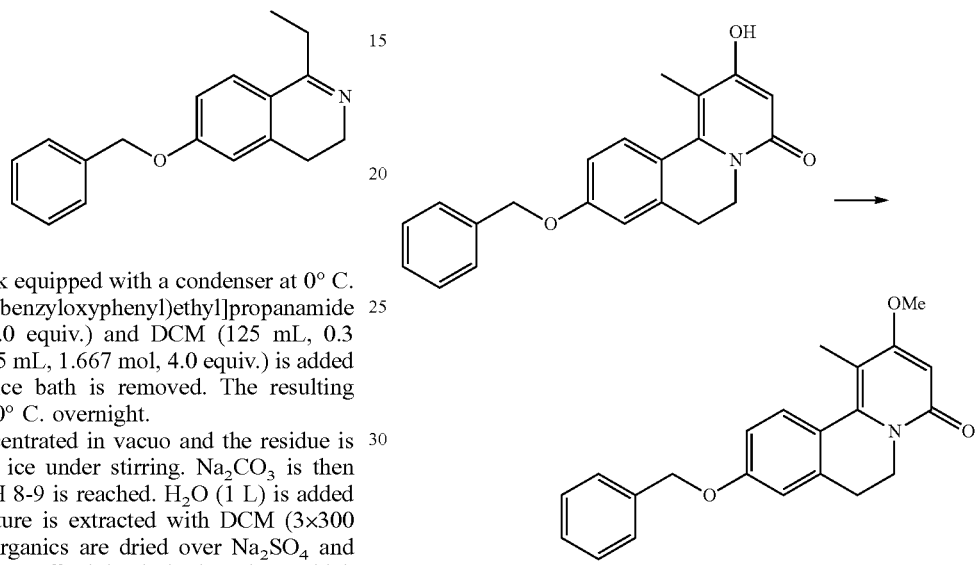

A suspension of 9-benzyloxy-1-methyl-6,7-dihydrobenzo[a]quinolizine-2,4-dione (98.55 g, 0.296 mol, 1.0 equiv.), dimethylsulphate (42 mL, 0.444 mol, 1.5 equiv.), K$_2$CO$_3$ (82 g, 0.592 mol, 2.0 equiv.) and acetone (887 mL, 3 mL/mmol) under N$_2$ is heated at reflux overnight. The mixture is cooled to −10° C. and filtered over a Pall Seitz 300 thick paper filter. The residue is washed with cold acetone (2×50 mL). Combined filtrates are concentrated to dryness and separated between DCM (400 mL) and water (1 L). The aqueous layer is basified to pH 10 using 2 M NaOH. The organic layer is separated, dried over Na$_2$SO$_4$ and concentrated. The product is boiled in MTBE (500 mL) for 30 min. The suspension is cooled to 0° C. and filtered. The residue is washed with MTBE (2×100 mL) and dried under vacuo to afford the desired product.

2.1.6.6. 9-benzyloxy-4-chloro-2-methoxy-1-methyl-6,7-dihydrobenzo[a]quinolizin-5-ium: Int20

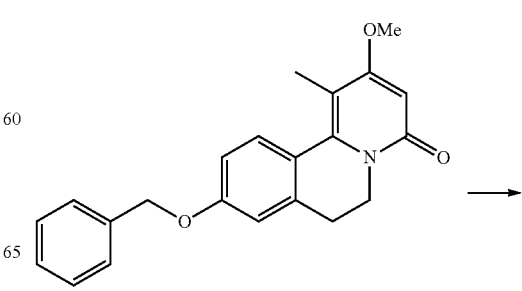

-continued

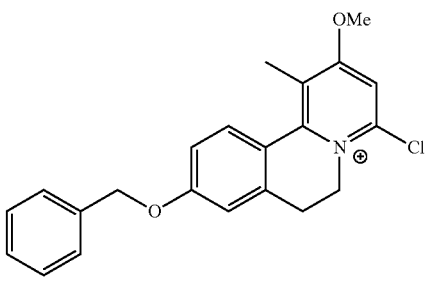

A round bottom flask is loaded with 187 g of 2-methoxy-9-benzyloxy-1-methyl-6,7-dihydrobenzo[a]quinolizin-4-one and POCl₃ (750 mL, 8.070 mol, 15 equiv.). The resulting mixture is heated at 80° C. for 50 min. The mixture is cooled to 50° C. and concentrated to dryness. The residue is dissolved in DCM (3.5 L), cooled to 10° C. Water (2.5 L) is added while keeping the temperature below 25° C. The pH is adjusted from 1.0 to 6.0 using 320 mL 40% NaOH. The organic layer is separated, dried over Na₂SO₄ and concentrated to dryness to afford the desired product.

2.1.6.7. 9-benzyloxy-4-chloro-1-methyl-6,7-dihydrobenzo[a]quinolizin-2-one: Int24

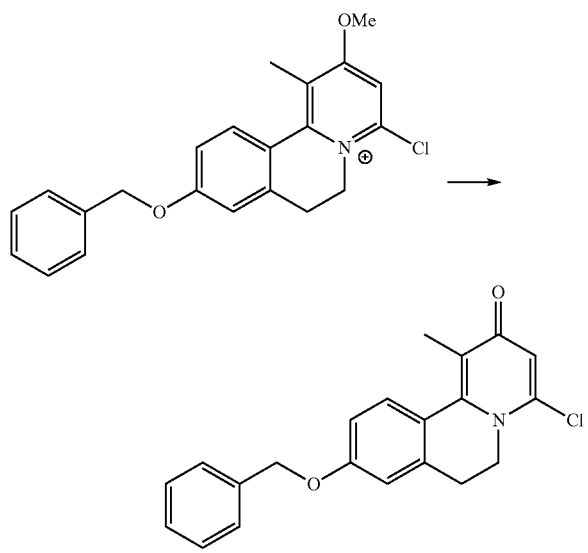

9-benzyloxy-4-chloro-2-methoxy-1-methyl-6,7-dihydrobenzo[a]quinolizin-5-ium (0.538 mol, 1.0 equiv.) is added to a suspension of LiCl (68 g, 1.614 mol, 3.0 equiv.) in DMF (1 L, 2 mL/mmol). The mixture is heated at 100° C. for 30 min. The suspension is cooled to room temperature and passed through a filter. The residue is charged to a stirring mixture of saturated aq. Na₂CO₃ (1 L) and water (1 L). The resulting suspension is stirred for 1 h and then filtered. The cake is washed with water (0.5 L) and dried in vacuo to yield the desired product, which is used as such.

2.1.6.8. 9-benzyloxy-4-[[(2S)-1,4-dioxan-2-yl]methoxy]-1-methyl-6,7-dihydrobenzo[a]quinolizin-2-one

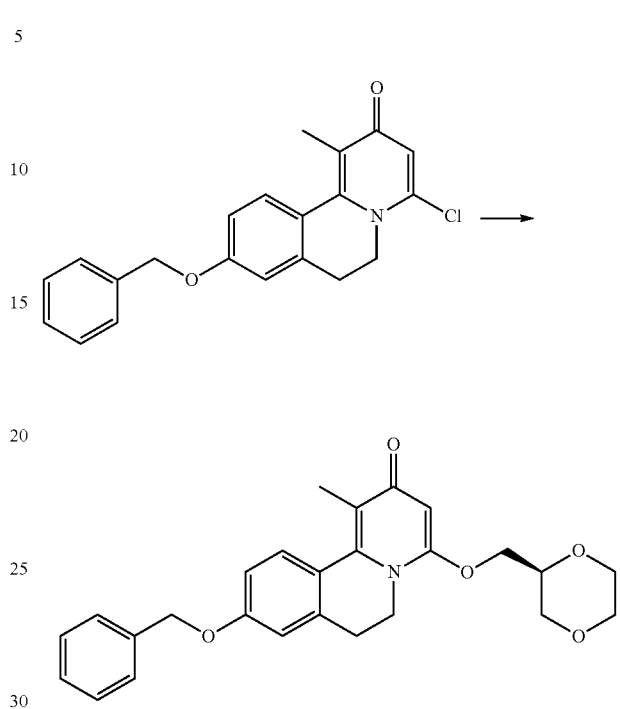

An oven dried multineck round-bottom flask equipped with a condenser and an inlet septum under N₂ is loaded with NaH (7.32 g, 183 mmol, 1.25 equiv.) and dry THF (390 mL, 2.67 mL/mmol). (R)-(1,4-dioxan-2-yl)methanol (20.7 g, 176 mmol, 1.2 equiv.) is added dropwise and the resulting mixture is stirred at room temperature for 20 min and subsequently heated at 50° C. for 20 min. Then 9-benzyloxy-4-chloro-1-methyl-6,7-dihydrobenzo[a]quinolizin-2-one is added (51.5 g, 146 mmol, 1.0 equiv.) as a dry solid to the alkoxide mixture (any material that could not be transferred as such is dissolved in dry THF (194 mL, 1.33 mL/mmol) and added to the mixture). The mixture is purged with N₂ and heated at 70° C. until all starting material is consumed. The mixture is cooled down to room temperature and quenched with 100 mL of saturated aq. NaHCO₃. The mixture is then concentrated in vacuo and separated between DCM (1 L) and brine (400 mL). The aqueous layer is extracted once more with DCM and combined organics are dried over Na₂SO₄ and concentrated to dryness. The crude product is dissolved in 500 mL of MeCN and refluxed for 15 min. The mixture is cooled down to room temperature and the precipitate is separated by filtration. The precipitate is discarded and the filtrate is washed with 350 mL of pentane. The MeCN phase is concentrated to dryness to afford the desired product.

¹H NMR (CDCl₃): 7.58, d, 1H; 7.43, m, 5H; 6.96, dd, 1H; 6.88, d, 1H; 6.48, s, 1H; 5.13, s, 2H; 4.16, t, 2H; 2.95, t, 2H; 2.29, s, 3H.

2.1.6.9. 4-[[(2S)-1,4-dioxan-2-yl]methoxy]-9-hydroxy-1-methyl-6,7-dihydrobenzo[a]quinolizin-2-one

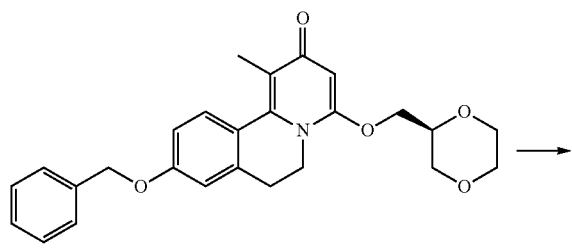

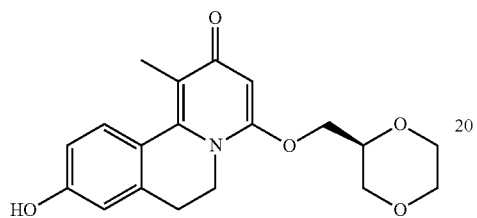

A round-bottom flask is loaded with 9-benzyloxy-4-[[(2S)-1,4-dioxan-2-yl]methoxy]-1-methyl-6,7-dihydrobenzo[a]quinolizin-2-one (58.99 g, 136 mmol, 1.0 equiv.) and Pd/C (2.89 g, 2.72 mmol, 0.02 equiv.). The flask is sealed with an inlet septum and the system is purged with $N_2$. Ethanol is added (680 mL, 5 mL/mmol) and the mixture is purged subsequently twice with vacuum/$N_2$ and three times with $H_2$/vacuum. The mixture is stirred at room temperature with the $H_2$ balloon left connected until all starting material is consumed. The mixture is then flushed with 2 cycles of vacuum/$N_2$ and is then filtered over a Pall Seitz 300 thick paper filter under a constant $N_2$ flow. The filter is washed with 7 M $NH_3$ in MeOH until all product is washed off, and the filtrate is concentrated to dryness, yielding the desired product.

2.1.6.10. Compound 18

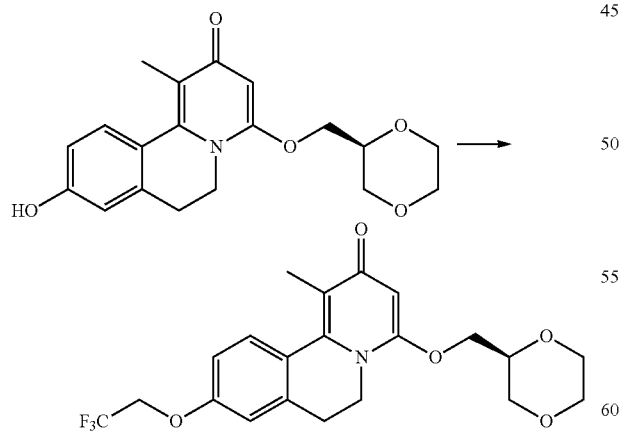

A three necked round-bottom flask equipped with a thermometer, reflux condenser and inlet septum is loaded with 4-[[(2S)-1,4-dioxan-2-yl]methoxy]-9-hydroxy-1-methyl-6,7-dihydrobenzo[a]quinolizin-2-one (50.48 g, 147 mmol, 1.0 equiv.), $K_2CO_3$ (60.4 g, 436.8 mmol, 3.0 equiv.) and 2,2,2-trifluoroethyl-p-toluenesulfonate (78 g, 309 mmol, 2.1 equiv.). The system is purged with vacuum/$N_2$ and dry DMF is added (368 mL, 2.5 mL/mmol). The resulting mixture is heated to an internal temperature of 100° C. until all starting material is consumed. The reaction mixture is poured in water and extracted with DCM (600 mL). The aqueous layer is extracted twice more with DCM (2×150 mL). The combined organics are washed with brine (3×400 mL), dried over $Na_2SO_4$ and evaporated in vacuo. The obtained solid is triturated with MTBE (500 mL), separated by filtration and dried under vacuum. The product is then recrystallized from EtOAc to afford the desired product.

2.1.6.11. 4-[[(2S)-1,4-dioxan-2-yl]methoxy]-1-methyl-9-(2-oxopyrrolidin-1-yl)-6,7-dihydrobenzo[a]quinolizin-2-one (Compound 157)

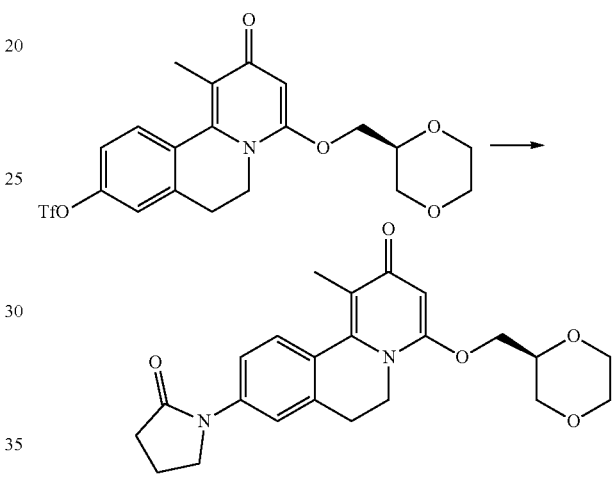

An oven-dried vial is loaded with Pd(OAc)2 (0.22 mg, 0.001 mmol, 0.01 equiv.), tetramethyl t-BuXPhos (1.4 mg, 0.003 mmol, 0.03 equiv.), $H_2O$ (0.072 µL, 0.004 mmol, 0.04 equiv.) and t-BuOH (0.2 mL, 2 mL/mmol) under $N_2$. The mixture is heated for 1.5 min at 110° C. A second oven-dried vial is charged with Compound 37 (48 mg, 0.1 mmol, 1.0 equiv.), $K_2CO_3$ (19 mg, 0.14 mmol, 1.4 equiv.) and 2-pyrrolidinone (9.1 µL, 0.12 mmol, 1.2 equiv.). The vial is evacuated and backfilled with $N_2$ and the activated catalyst solution is transferred from the first microwave vial. The solution is heated to 110° C. for 1 h. The reaction mixture is cooled to room temperature, diluted with DCM/MeOH 95/5, filtered over a plug of Celite®, evaporated in vacuo and purified by means of preparative HPLC.

2.1.6.12. 4-[[(2S)-1,4-dioxan-2-yl]methoxy]-1-methyl-6,7-dihydrobenzo[a]quinolizin-2-one (Compound 156)

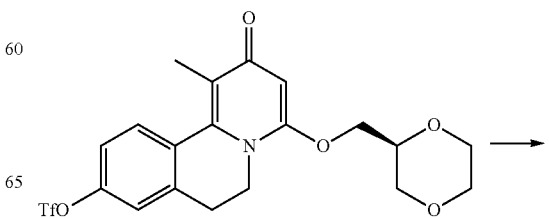

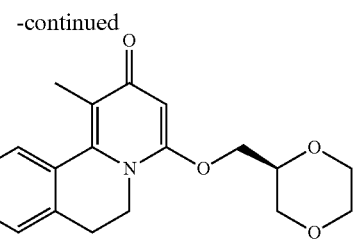

A suspension of Compound 37 (48 mg, 0.1 mmol, 1.0 equiv.), ammonium formate (25 mg, 0.4 mmol, 4 equiv.) and Pd/C (2.4 mg, 5 m/m %) in EtOH (1 mL, 10 mL/mmol) is stirred under $N_2$ at 80° C. for 5 min. The reaction mixture is filtered through a 0.45 µm plug filter and purified by means of preparative HPLC.

2.1.6.13. 3-bromo-4-[[(2S)-1,4-dioxan-2-yl]methoxy]-1-methyl-9-(2,2,2-trifluoroethoxy)-6,7-dihydrobenzo[a]quinolizin-2-one (Int 126)

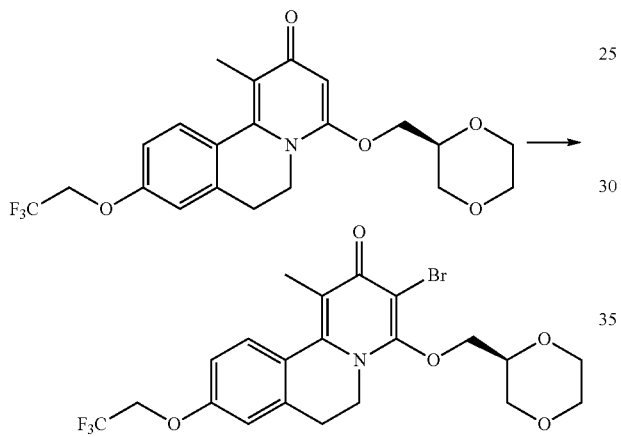

An oven-dried vial is loaded with Compound 18 (100 mg, 0.24 mmol, 1.0 equiv.) and cooled to 0° C. under $N_2$. NBS (43 mg, 0.24 mmol, 1.0 equiv.) is added in one go and the reaction mixture is allowed to warm spontaneously to room temperature. After 30 min, the reaction mixture is diluted with DCM, washed with brine, dried over a phase separator and evaporated in vacuo to afford the desired product. $^1$H NMR (CDCl$_3$): 7.62, d, 1H; 6.92, dd, 1H; 6.88, d, 1H; 4.42, q, 2H; 4.24, dd, 1H; 4.14-4.19, m, 3H; 4.00-4.05, m, 1H; 3.90, dd, 1H; 3.74-3.85, m, 3H; 3.64, ddd, 1H; 3.57, dd, 1H; 2.91, t, 2H; 2.34, s, 3H.

2.1.6.14. 3-deuterio-4-[[(2S)-1,4-dioxan-2-yl]methoxy]-1-methyl-9-(2,2,2-trifluoroethoxy)-6,7-dihydrobenzo[a]quinolizin-2-one (Compound 125)

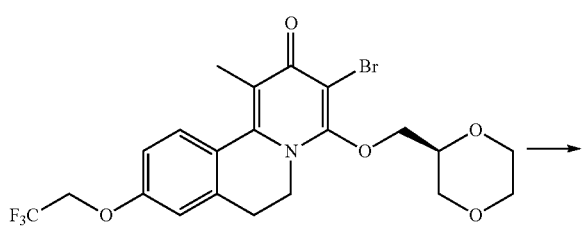

Int 126 (40 mg, 0.08 mmol, 1.0 equiv.) is mixed with MeOD (0.8 mL, 10 mL/mmol) and Pd/C (8 mg, 0.008 mmol, 0.1 equiv.). The system is sealed, purged by vacuum/$N_2$, then 3 times by vacuum/$D_2$. The mixture is stirred at room temperature under $D_2$ (1 atm) for 2 h. The reaction mixture is filtered on a 0.45 µm HPLC membrane filter and purified by means of preparative HPLC.

2.1.6.15. 3-deuterio-9-(1-deuterio-2,2-difluoro-vinyloxy)-4-[[(2S)-1,4-dioxan-2-yl]methoxy]-1-methyl-6,7-dihydrobenzo[a]quinolizin-2-one (Compound 105)

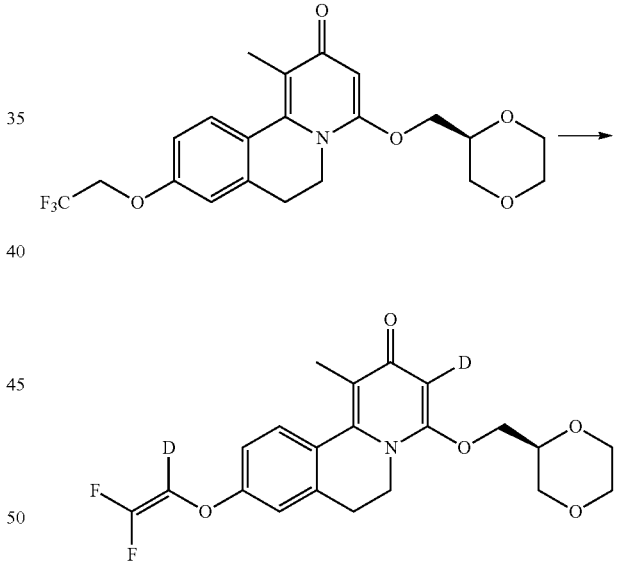

A solution of Compound 18 (50 mg, 0.12 mmol, 1.0 equiv.) in dry THF (1 mL, 8 mL/mmol) is added dropwise to a solution of BuLi (1.98 M in hexane, 0.3 mL, 5.0 equiv.) in dry THF (0.3 mL, 2.5 mL/mmol) maintained at −78° C. under $N_2$. After 30 min, MeOD (0.08 mL) is added and the mixture is allowed to warm to room temperature over 30 min. The reaction mixture is quenched with a few drops of satd. aq. NaHCO$_3$, evaporated in vacuo and extracted with DCM/brine. The combined organic extracts are dried and the solvent is evaporated in vacuo. The residue is purified by means of preparative HPLC to afford the desired product.

2.1.6.16. 3-deuterio-4-[[(2S)-1,4-dioxan-2-yl]methoxy]-1-methyl-9-(1,1,2,2-tetradeuterio-2-fluoro-ethoxy)-6,7-dihydrobenzo[a]quinolizin-2-one (Compound 158)

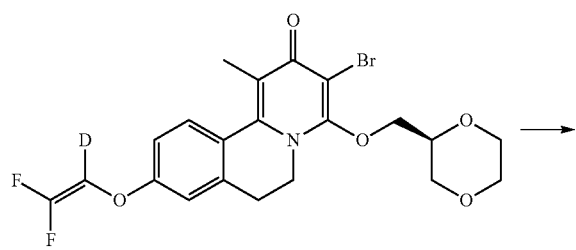

Compound 105 (20 mg, 0.05 mmol, 1.0 equiv.) is mixed with MeOD (0.5 mL, 10 mL/mmol) and Pd/C (5.2 mg, 0.005 mmol, 0.1 equiv.). The system is sealed, purged by vacuum/N₂, then 3 times by vacuum/D₂. The mixture is stirred at room temperature under D₂ (1 atm) for 2 h. The reaction mixture is filtered on a 0.45 μm HPLC membrane filter and purified by means of preparative HPLC.

2.1.6.17. N-cyclopropyl-4-[[(2S)-1,4-dioxan-2-yl]methoxy]-1-methyl-2-oxo-6,7-dihydrobenzo[a]quinolizine-9-carboxamide (Compound 84)

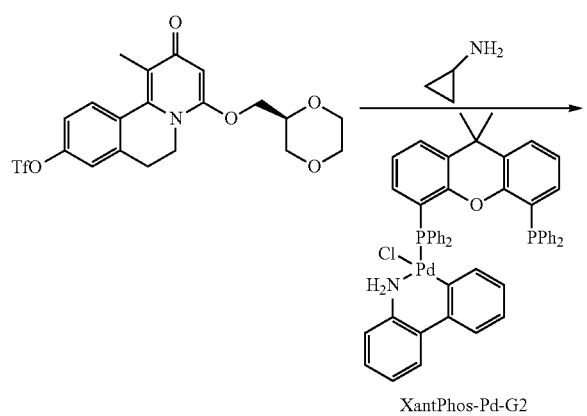

An oven-dried vial is loaded with Compound 37 (70 mg, 0.15 mmol, 1.0 equiv.), cyclopropylamine (20 μL, 0.30 mmol, 2.0 equiv.), XantPhos Pd G2 (2.6 mg, 0.003 mmol, 2 mol %) and Et₃N (41 μL, 0.30 mmol, 2.0 equiv.). The vial is evacuated and back-filled with N₂ and dry dioxane (0.3 mL, 2 mL/mmol) is added. A stream of CO gas is passed into the solution for 1-2 min and the contents are heated to 45° C. under a CO atmosphere for 2 days. Next, the reaction mixture is cooled to room temperature, filtered over a plug of Celite® and evaporated in vacuo. The residue is purified by means of preparative HPLC to afford the desired product.

2.1.6.18. N-[4-[[(2S)-1,4-dioxan-2-yl]methoxy]-1-methyl-2-oxo-6,7-dihydrobenzo[a]quinolizin-9-yl]-N-methyl-cyclopropanecarboxamide (Compound 73)

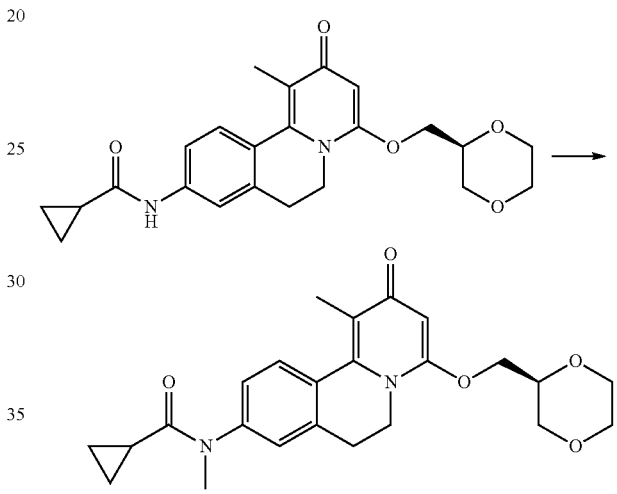

To a solution of Compound 70 (25 mg, 0.06 mmol, 1.0 equiv.) in DMF (0.6 mL, 10 mL/mmol) is added NaH (60% in mineral oil, 7.2 mg, 0.18 mmol, 3.0 equiv.). The reaction mixture is stirred for 20 min at room temperature and MeI (7.4 μL, 0.12 mmol, 2.0 equiv.) is subsequently added. The reaction mixture is stirred at room temperature for 3 h. Next, the reaction mixture is quenched with saturated aq. NaHCO₃ and evaporated in vacuo. The residue is partitioned between DCM and H₂O and the aqueous phase is extracted 2× with DCM. The combined organic extracts are dried over a phase separator, evaporated in vacuo and purified by means of preparative HPLC.

2.1.6.19. 4-[[(2S)-1,4-dioxan-2-yl]methoxy]-1-methyl-9-phenylsulfanyl-6,7-dihydrobenzo[a]quinolizin-2-one (Compound 64)

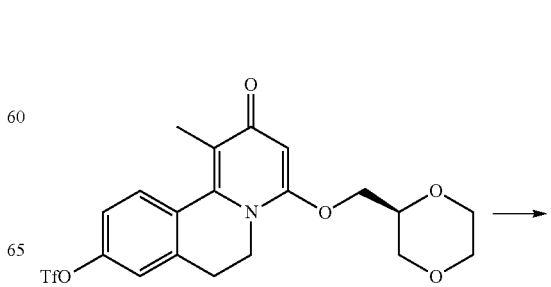

-continued

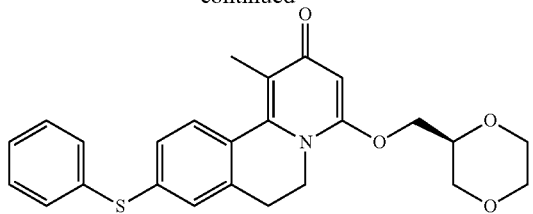

An oven-dried vial is loaded with Compound 37 (119 mg, 0.25 mmol, 1.0 equiv.), Thiophenol (30 μL, 0.30 mmol, 1.2 equiv.), Pd$_2$(dba)$_3$ (6.8 mg, 0.008 mol, 3 mol %), XantPhos (8.6 mg, 0.016 mmol, 6 mol %) and DIPEA (88 μL, 0.5 mmol, 2.0 equiv.). The vial is sealed, evacuated and backfilled with nitrogen gas (3×), dry toluene (1.2 mL, 5 mL/mmol) is added and the mixture is stirred at 100° C. for 1 h. The reaction mixture is cooled to room temperature, separated by filtration and evaporated in vacuo. The residue is dissolved in DCM and washed once with H$_2$O. The organic phase is dried over a phase separator and evaporated in vacuo. The residue is purified by means of preparative TLC (DCM/MeOH 95/5).

2.1.6.20. 9-(benzenesulfonyl)-4-[[(2S)-1,4-dioxan-2-yl]methoxy]-1-methyl-6,7-dihydrobenzo[a]quinolizin-2-one (Compound 67)

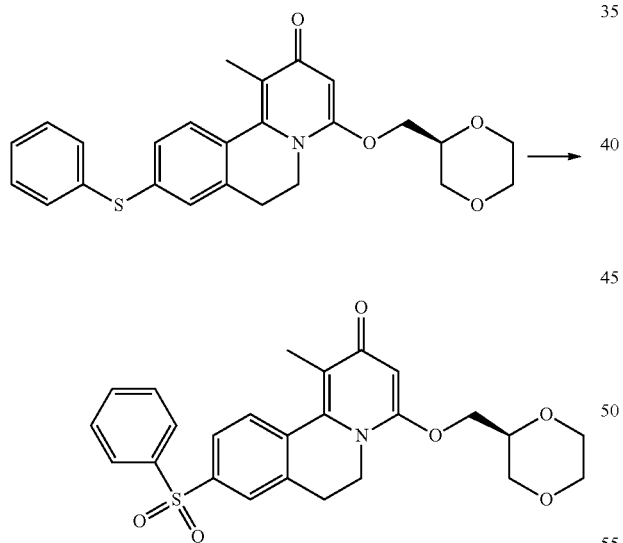

A vial is loaded with Compound 64 (40 mg, 0.09 mmol, 1.0 equiv.) and DCM (0.5 mL, 5 mL/mmol). m-CPBA (40 mg, 0.23 mmol, 2.5 equiv.) is added, the tube is sealed and stirred at room temperature for 1.5 h. The reaction mixture is diluted with DCM and washed with saturated aq. Na$_2$CO$_3$. The organic layer is dried and concentrated in vacuo. The resulting residue is purified by means of preparative TLC (DCM/0.2 M NH$_3$ in MeOH 95/5) to afford the desired product.

2.1.6.21. 9-(difluoromethoxy)-4-[[(2S)-1,4-dioxan-2-yl]methoxy]-1-methyl-6,7-dihydrobenzo[a]quinolizin-2-one (Compound 59)

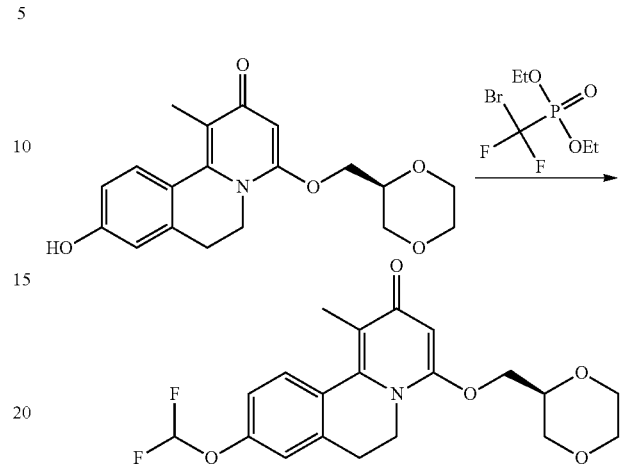

Diethyl(bromodifluoromethyl)phosphonate (89 μL, 0.5 mmol, 2.0 equiv.) is added dropwise to a cooled (dry ice/CH$_3$CN:H$_2$O 1:1) solution of Compound 85 (86 mg, 0.25 mmol, 1.0 equiv.) and KOH (330 mg, 5 mmol, 20 equiv.) in CH$_3$CN:H$_2$O 1:1 (2.5 mL, 10 mL/mmol) under a nitrogen atmosphere. The reaction mixture is allowed to warm to room temperature and stirred overnight. Next, the reaction mixture is diluted with DCM and H$_2$O, the organic phase is separated over a phase separator and evaporated in vacuo. The residue is purified by means of preparative HPLC to afford the desired product.

2.1.6.22. [4-[[(2S)-1,4-dioxan-2-yl]methoxy]-1-methyl-2-oxo-6,7-dihydrobenzo[a]quinolizin-9-yl] methanesulfonate (Compound 56)

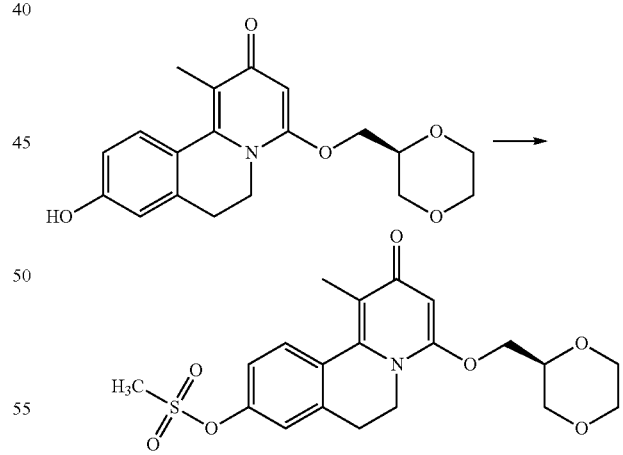

Compound 85 (400 mg, 1.2 mmol, 1.0 equiv.) is mixed with DCM (12 mL, 10 mL/mmol) and Et$_3$N (291 μL, 2.1 mmol, 1.8 equiv.) in a tube under a nitrogen atmosphere. Mesyl chloride (122 μL, 1.6 mmol, 1.4 equiv.) is added in one go, the tube is sealed and stirred at room temperature overnight. Next, the reaction mixture is washed with satd. aq. Na$_2$CO$_3$, satd. NaCl, dried on Na$_2$SO$_4$, filtered and evaporated in vacuo. The residue is purified by means of column chromatography (DCM/MeOH).

2.1.6.23. 9-benzyloxy-4-[[(2R)-1,4-dioxan-2-yl]methylamino]-1-methyl-6,7-dihydrobenzo[a]quinolizin-2-one (Compound 34)

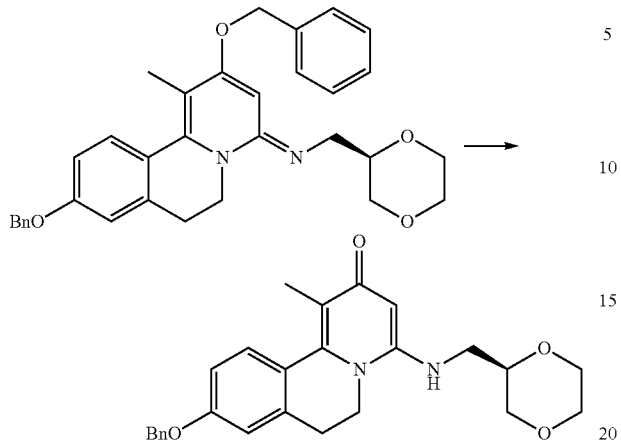

Int27 (50 mg, 0.1 mmol, 1.0 equiv.) is mixed with MeOH (1 mL, 10 mL/mmol) and 5% Pd on BaSO$_4$ (10 mg, 0.005 mmol, 5 mol %). The system is sealed, purged by vacuum/N$_2$, then 3 times by vacuum/H$_2$. The mixture is stirred overnight at room temperature, with the H$_2$ balloon left connected through a septum. Next, The reaction mixture is separated by filtration, evaporated in vacuo and purified by means of preparative HPLC.

2.1.6.24. 4-(1,4-dioxan-2-ylmethylamino)-9-hydroxy-8-methoxy-6,7-dihydrobenzo[a]quinolizin-2-one and 4-(1,4-dioxan-2-ylmethylamino)-8-hydroxy-9-methoxy-6,7-dihydrobenzo[a]quinolizin-2-one (Compound 22)

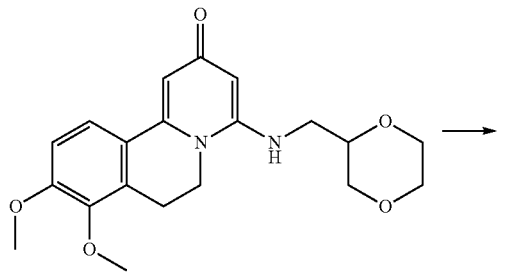

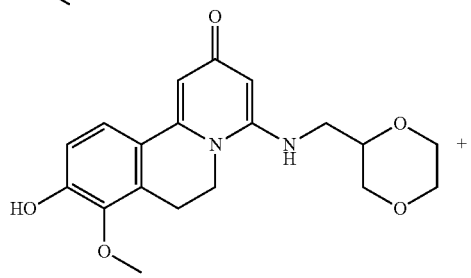

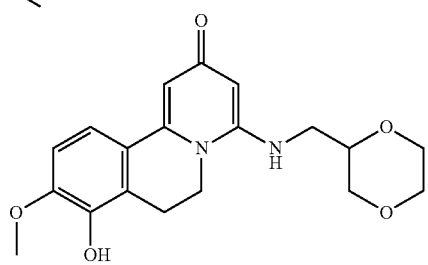

A vial is loaded with Compound 19 (50 mg, 0.13 mmol, 1 equiv.) and NaSMe (19 mg, 0.26 mmol, 2.0 equiv.), the vial is evacuated and back-filled with N$_2$ and NMP (1 mL, 8 mL/mmol) is added. The resulting mixture is heated to 140° C. for 20 min. Next, EtOAc is added to the reaction mixture and the formed precipitate is separated by filtration. The precipitate is then partitioned between DCM and 1M HCl. The organic layer is separated, dried, evaporated in vacuo and purified by means of preparative HPLC to afford the desired product.

2.1.6.25. 1-methyl-4-(tetrahydrofuran-2-ylmethylamino)-9-(2,2,2-trifluoroethoxy)-6,7-dihydrobenzo[a]quinolizin-2-one (Compound 8) and-Methyl-4-[(tetrahydro-furan-2-ylmethyl)-amino]-9-(tetrahydro-furan-2-yloxy)-6,7-dihydro-yrido[2,1-a]isoquinolin-2-one (Compound 9)

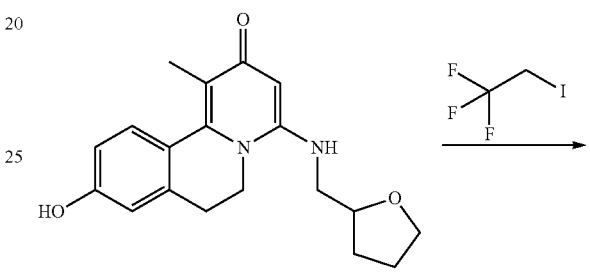

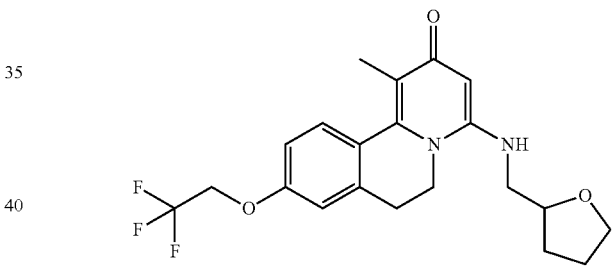

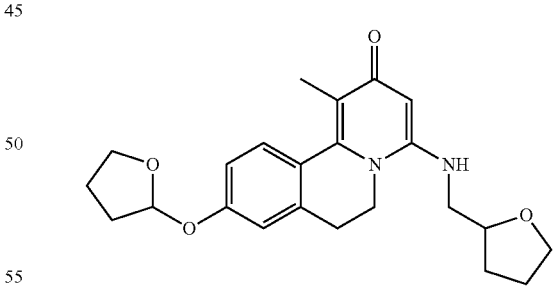

Int2 (42 mg, 1.00 Eq) is mixed with dry THF (0.5 mL), dry DMF (0.25 mL) and K$_2$CO$_3$ (28 mg, 2.00 eq) in a microwave tube, under nitrogen atmosphere. 1,1,1-trifluoro-2-iodoethane (10.3 µL, 1.05 eq) is then added. The tube is sealed and stirred at room temperature for 50 h. The temperature is increased to 100° C. and stirring is continued for another 92 h. The reaction mixture is cooled to room temperature, partitioned between EtOAc and saturated aqueous NaHCO$_3$. The organic layer is dried on Na$_2$SO$_4$, filtered and evaporated in vacuo, to yield a residue which is purified by preparative HPLC to yield the desired products.

TABLE II

Intermediate for the synthesis of illustrative compounds of the invention

| Int # | Structure | Name | SM | Mtd | MW | Mes |
|---|---|---|---|---|---|---|
| Int 1 | 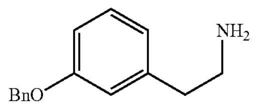 [SMILES: NCCc1cccc(OCc2ccccc2)c1] | 2-(3-benzyloxyphenyl)ethanamine | commercial | — | — | — |
| Int 2 | 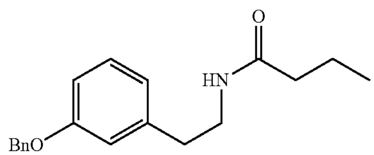 [SMILES: CCCC(=O)NCCc1cccc(OCc2ccccc2)c1] | N-[2-(3-benzyloxphenyl)ethyl]butanamide | Int 1 | M2 | 207 | — |
| Int 3 | 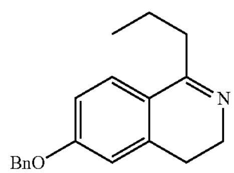 [SMILES: CCCC1=NCCc2cc(OCc3ccccc3)ccc21] | 6-benzyloxy-1-propyl-3,4-dihydroisoquinoline | Int 2 | M3 | 189 | 190 |
| Int 4 | 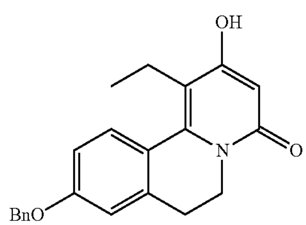 [SMILES: CCc1c(O)cc(=O)n2c1-c1ccc(OCc3ccccc3)cc1CC2] | 9-benzyloxy-1-ethyl-2-hydroxy-6,7-dihydrobenzo[a]quinolizin-4-one | Int 3 | M4 | 347 | 348 |
| Int 5 | 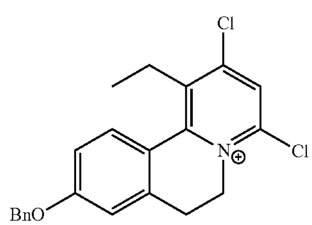 [SMILES: CCc1c(Cl)cc(Cl)[n+]2c1-c1ccc(OCc3ccccc3)cc1CC2] | 9-benzyloxy-2,4-dichloro-1-ethyl-6,7-dihydrobenzo[a]quinolizin-5-ium | Int 4 | M10 | 385 | 384/386 |
| Int 6 | 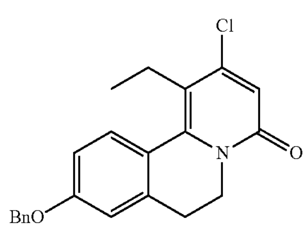 [SMILES: CCc1c(Cl)cc(=O)n2c1-c1ccc(OCc3ccccc3)cc1CC2] | 9-benzyloxy-2-chloro-1-ethyl-6,7-dihydrobenzo[a]quinolizin-4-one | Int 5 | M11 | 366 | 366 |
| Int 7 | 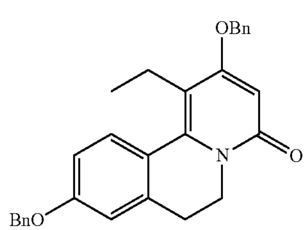 [SMILES: CCc1c(OCc2ccccc2)cc(=O)n2c1-c1ccc(OCc3ccccc3)cc1CC2] | 2,9-dibenzyloxy-1-ethyl-6,7-dihydrobenzo[a]quinolizin-4-one | Int 6 | M12 | 438 | 438 |

TABLE II-continued

Intermediate for the synthesis of illustrative compounds of the invention

| Int # | Structure | Name | SM | Mtd | MW | Mes |
|---|---|---|---|---|---|---|
| Int 8 | 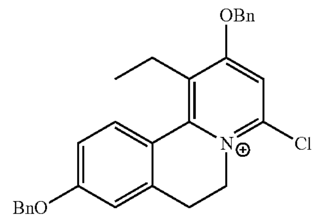 [SMILES: CCc1c(OCc2ccccc2)cc(Cl)[n+]2c1-c1ccc(OCc3ccccc3)cc1CC2] | 2,9-dibenzyloxy-4-chloro-1-ethyl-6,7-dihydrobenzo[a]quinolizin-5-ium | Int 7 | M13 | 457 | 456 |
| Int 9 | 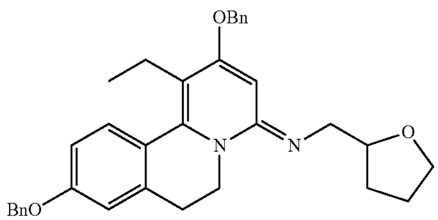 [SMILES: CCc1c(OCc2ccccc2)c/c(=N\CC2CCCO2)n2c1-c1ccc(OCc3ccccc3)cc1CC2] | 2,9-dibenzyloxy-1-ethyl-N-(tetrahydrofuran-2-ylmethyl)-6,7-dihydrobenzo[a]quinolizin-4-imine | Int 8 | M23 | 521 | 521 |
| Int 10 | 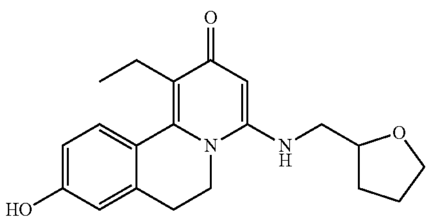 [SMILES: CCc1c2n(c(NCC3CCCO3)cc1=O)CCc1cc(O)ccc1-2] | 1-ethyl-9-hydroxy-4-(tetrahydrofuran-2-ylmethylamino)-6,7-dihydrobenzo[a]quinolizin-2-one | Int 9 | M24 | 340 | 341 |
| Int 11 | 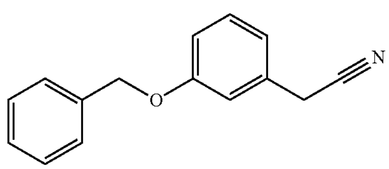 [SMILES: N#CCc1cccc(OCc2ccccc2)c1] | 3-benzyloxyphenylacetonitrile | commercial | — | 223 | 224 |
| Int 12 | 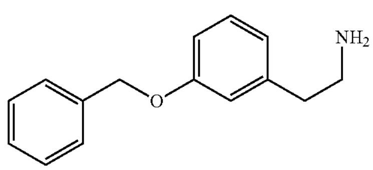 [SMILES: NCCc1cccc(OCc2ccccc2)c1] | 2-(3-benzyloxyphenyl)ethanamine | Int 11 | M1 | 227 | 228 |
| Int 13 | 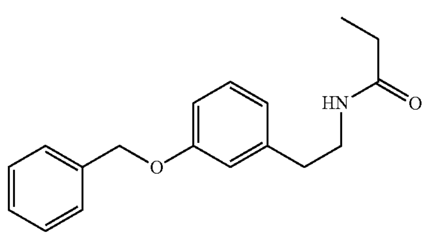 [SMILES: CCC(=O)NCCc1cccc(OCc2ccccc2)c1] | N-[2-(3-benzyloxyphenyl)ethyl]propanamide | Int 12 | M2 | 283 | 284 |
| Int 14 | 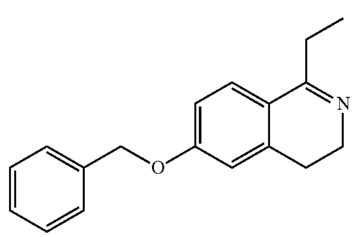 [SMILES: CCC1=NCCc2cc(OCc3ccccc3)ccc21] | 6-benzyloxy-1-ethyl-3,4-dihydroisoquinoline | Int 13 | M3 | 265 | 266 |

TABLE II-continued

Intermediate for the synthesis of illustrative compounds of the invention

| Int # | Structure | Name | SM | Mtd | MW | Mes |
|---|---|---|---|---|---|---|
| Int 15 | 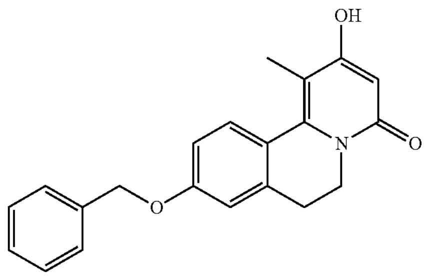 [SMILES: Cc1c(O)cc(=O)n2c1-c1ccc(OCc3ccccc3)cc1CC2] | 9-benzyloxy-1-methyl-6,7-dihydrobenzo[a]quinolizine-2,4-dione | Int 14 | M4 | 333 | 334 |
| Int 16 | 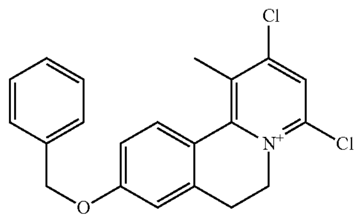 [SMILES: Cc1c(Cl)cc(Cl)[n+]2c1-c1ccc(OCc3ccccc3)cc1CC2] | 9-Benzyloxy-2,4-dichloro-1-methyl-6,7-dihydro-pyrido[2,1-a]isoquinolinylium | Int 15 | M10 | 371 | 370/372 (Cl) |
| Int 17 | 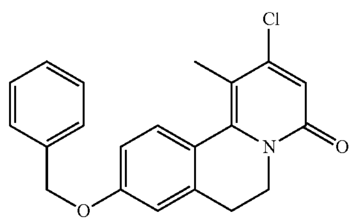 [SMILES: Cc1c(Cl)cc(=O)n2c1-c1ccc(OCc3ccccc3)cc1CC2] | 9-Benzyloxy-2-chloro-1-methyl-6,7-dihydro-pyrido[2,1-a]isoquinolin-4-one | Int 16 | M11 | 352 | 352/354 (Cl) |
| Int 18 | 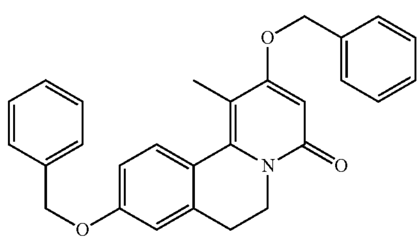 [SMILES: Cc1c(OCc2ccccc2)cc(=O)n2c1-c1ccc(OCc3ccccc3)cc1CC2] | 2,9-Bis-benzyloxy-1-methyl-6,7-dihydro-pyrido[2,1-a]isoquinolin-4-one | Int 17 | M12 | 424 | 424 |
| Int 19 | 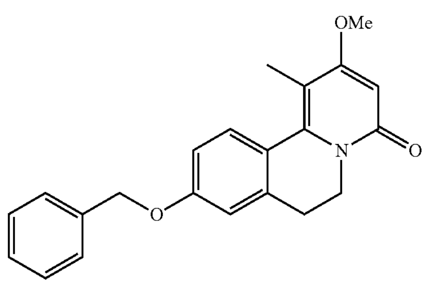 | 2-methoxy-9-benzyloxy-1-methyl-6,7-dihydrobenzo[a]quinolizin-4-one | Int 15 | M7 | 347 | 348 |
| Int 20 | 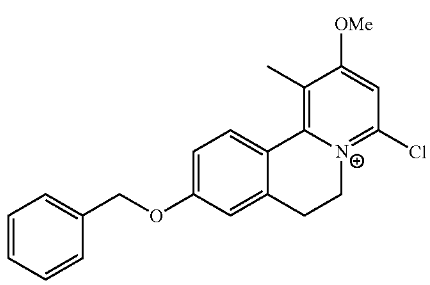 [SMILES: COc1cc(Cl)[n+]2c(c1C)-c1ccc(OCc3ccccc3)cc1CC2] | 9-benzyloxy-4-chloro-2-methoxy-1-methyl-6,7-dihydrobenzo[a]quinolizin-5-ium chloride | Int 19 | M8 | 366 | 366/368 (Cl) |

TABLE II-continued

Intermediate for the synthesis of illustrative compounds of the invention

| Int # | Structure | Name | SM | Mtd | MW | Mes |
|---|---|---|---|---|---|---|
| Int 21 | 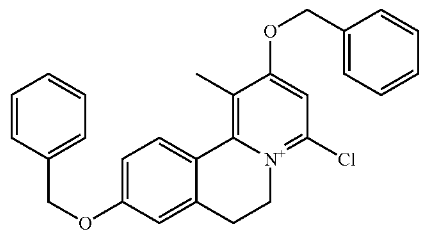 [SMILES: Cc1c(OCc2ccccc2)cc(Cl)[n+]2c1-c1ccc(OCc3ccccc3)cc1CC2] | 2,9-Bis-benzyloxy-4-chloro-1-methyl-6,7-dihydro-pyrido[2,1-a]isoquinolinylium | Int 18 | M13 | 443 | 442/447 (Cl) |
| Int 22 | 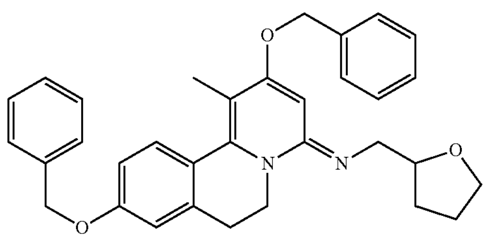 [SMILES: Cc1c(OCc2ccccc2)c/c(=N\CC2CCCO2)n2c1-c1ccc(OCc3ccccc3)cc1CC2] | [2,9-Bis-benzyloxy-1-methyl-6,7-dihydro-pyrido[2,1-a]isoquinolin-(4E)-ylidene]-(tetrahydro-furan-2-ylmethyl)-amine | Int 21 | M23 | 506 | 507 |
| Int 23 | 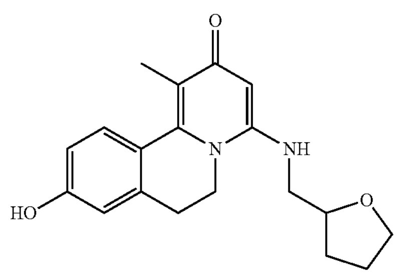 [SMILES: Cc1c2n(c(NCC3CCCO3)cc1=O)CCc1cc(O)ccc1-2] | 9-Hydroxy-1-methyl-4-[(tetrahydro-furan-2-ylmethyl)-amino]-6,7-dihydro-pyrido[2,1-a]isoquinolin-2-one | Int 22 | M24 | 326 | 327 |
| Int 24 | 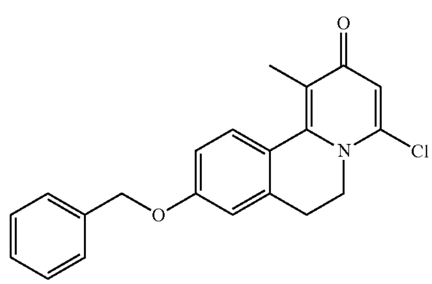 [SMILES: Cc1c2n(c(Cl)cc1=O)CCc1cc(OCc3ccccc3)ccc1-2] | 9-benzyloxy-4-chloro-1-methyl-6,7-dihydrobenzo[a]quinolizin-2-one | Int 20 | M9 | 351 | 352/354 (Cl) |
| Int 25 | 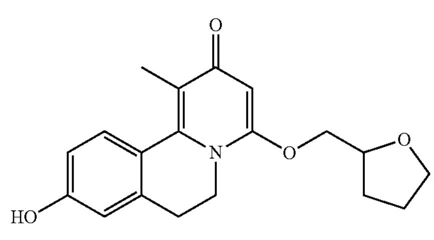 [SMILES: Cc1c2n(c(OCC3CCCO3)cc1=O)CCc1cc(O)ccc1-2] | 9-hydroxy-1-methyl-4-(tetrahydrofuran-2-ylmethoxy)-6,7-dihydrobenzo[a]quinolizin-2-one | Cpd 108 | M16 | 327 | 328 |
| Int 26 | 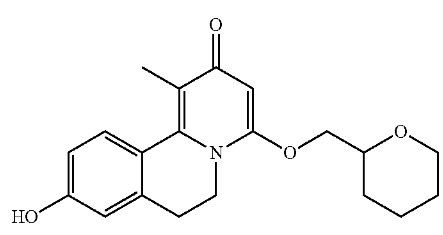 [SMILES: Cc1c2n(c(OCC3CCCCO3)cc1=O)CCc1cc(O)ccc1-2] | 9-hydroxy-1-methyl-4-(tetrahydropyran-2-ylmethoxy)-6,7-dihydrobenzo[a]quinolizin-2-one | Cpd 109 | M16 | 341 | 342 |

TABLE II-continued

Intermediate for the synthesis of illustrative compounds of the invention

| Int # | Structure | Name | SM | Mtd | MW | Mes |
|---|---|---|---|---|---|---|
| Int 27 | 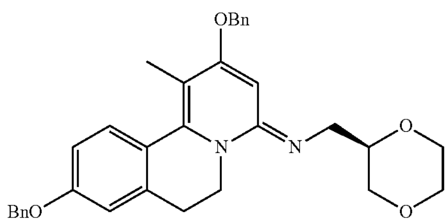 [SMILES: Cc1c(OCc2ccccc2)c/c(=N\C[C@@H]2COCCO2)n2c1-c1ccc(OCc3ccccc3)cc1CC2] | 2,9-dibenzyloxy-N-[[(2R)-1,4-dioxan-2-yl]methyl]-1-methyl-6,7-dihydrobenzo[a]quinolizin-4-imine | Int 1 | M23 | 523 | 523 |
| Int 28 | 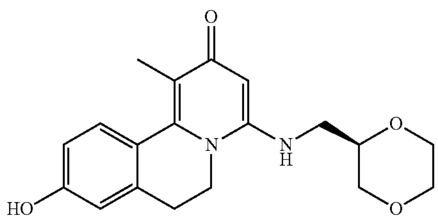 | 4-[[(2R)-1,4-dioxan-2-yl]methylamino]-9-hydroxy-1-methyl-6,7-dihydrobenzo[a]quinolizin-2-one | Int 27 | M24 | 342 | 343 |
| Int 29 | 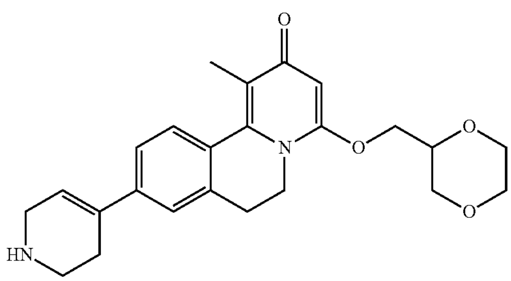 [SMILES: Cc1c2n(c(OCC3COCCO3)cc1=O)CCc1cc(C3=CCNCC3)ccc1-2] | 4-(1,4-dioxan-2-ylmethoxy)-1-methyl-9-(1,2,3,6-tetrahydropyridin-4-yl)-6,7-dihydrobenzo[a]quinolizin-2-one | Cpd 74 | M27 | 408 | 409 |
| Int 30 | 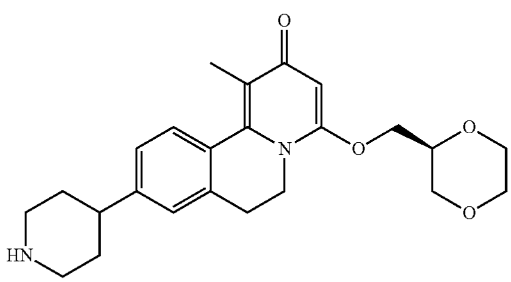 [SMILES: Cc1c2n(c(OC[C@@H]3COCCO3)cc1=O)CCc1cc(C3CCNCC3)ccc1-2] | 4-(1,4-dioxan-2-ylmethoxy)-1-methyl-9-(4-piperidyl)-6,7-dihydrobenzo[a]quinolizin-2-one | Cpd 75 | M27 | 411 | 411 |
| Int 31 | 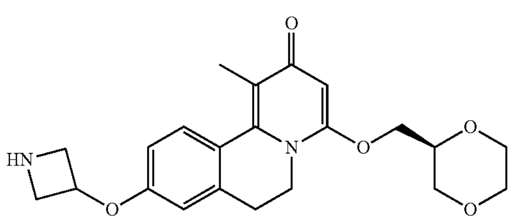 [SMILES: Cc1c2n(c(OC[C@@H]3COCCO3)cc1=O)CCc1cc(OC3CNC3)ccc1-2] | 9-(azetidin-3-yloxy)-4-[[(2S)-1,4-dioxan-2-yl]methoxyl-1-methyl-6,7-dihydrobenzo[a]quinolizin-2-one | Cpd 104 | M27 | 398 | 399 |
| Int 32 | 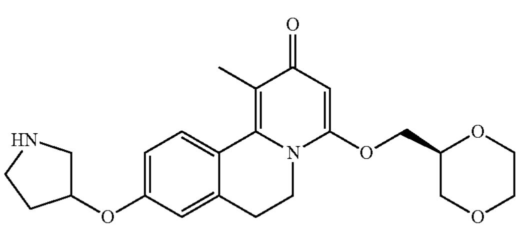 [SMILES: Cc1c2n(c(OC[C@@H]3COCCO3)cc1=O)CCc1cc(OC3CCNC3)ccc1-2] | 4-[[(2S)-1,4-dioxan-2-yl]methoxy]-1-methyl-9-pyrrolidin-3-yloxy-6,7-dihydrobenzo[a]quinolizin-2-one | Cpd 127 | M27 | 412 | 413 |

TABLE II-continued

Intermediate for the synthesis of illustrative compounds of the invention

| Int # | Structure | Name | SM | Mtd | MW | Mes |
|---|---|---|---|---|---|---|
| Int 33 | 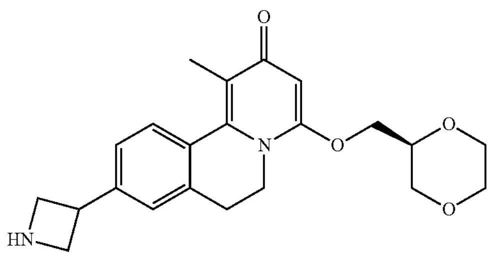 [SMILES: Cc1c2n(c(OC[C@@H]3COCCO3)cc1=O)CCc1cc(C3CNC3)ccc1-2] | 9-(azetidin-3-yl)-4-[[(2S)-1,4-dioxan-2-yl]methoxy]-1-methyl-6,7-dihydrobenzo[a]quinolizin-2-one | Cpd 71 | M27 | 382 | 383 |
| Int 34 | 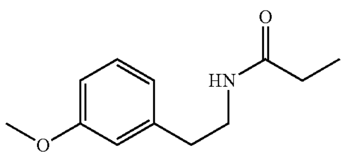 | N-[2-(3-methoxyphenyl)ethyl]propanamide | (commercial) | M2 | 207 | — |
| Int 35 | 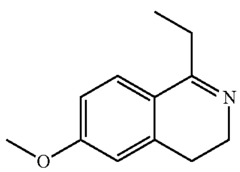 | 1-ethyl-6-methoxy-3,4-dihydroisoquinoline | Int 34 | M3 | 279 | 280 |
| Int 36 | 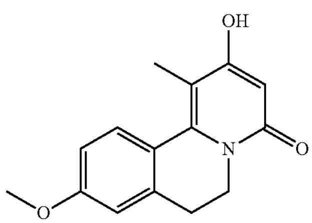 [SMILES: COc1ccc2c(c1)CCn1c-2c(C)c(O)cc1=O] | 2-hydroxy-9-methoxy-1-methyl-6,7-dihydrobenzo[a]quinolizin-4-one | Int 35 | M4 | 257 | 258 |
| Int 37 | 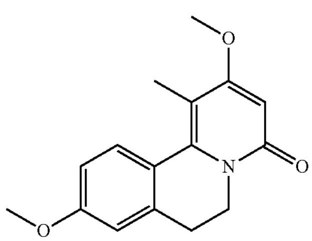 [SMILES: COc1ccc2c(c1)CCn1c-2c(C)c(OC)cc1=O] | 2,9-dimethoxy-1-methyl-6,7-dihydrobenzo[a]quinolizin-4-one | Int 36 | M7 | 271 | 272 |
| Int 38 | 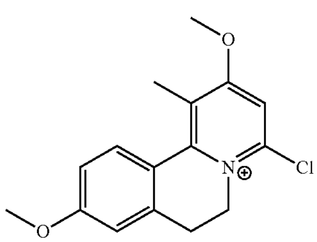 [SMILES: COc1ccc2c(c1)CC[n+]1c(Cl)cc(OC)c(C)c1-2] | 4-chloro-2,9-dimethoxy-1-methyl-6,7-dihydrobenzo[a]quinolizin-5-ium | Int 37 | M8 | 291 | 292 |
| Int 39 | 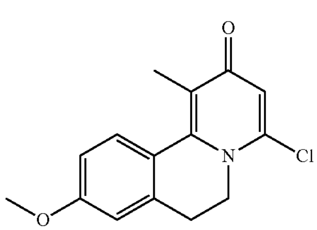 [SMILES: COc1ccc2c(c1)CCn1c(Cl)cc(=O)c(C)c1-2] | 4-chloro-9-methoxy-1-methyl-6,7-dihydrobenzo[a]quinolizin-2-one | Int 38 | M9 | 276 | 276 |

TABLE II-continued

Intermediate for the synthesis of illustrative compounds of the invention

| Int # | Structure | Name | SM | Mtd | MW | Mes |
|---|---|---|---|---|---|---|
| Int 40 | 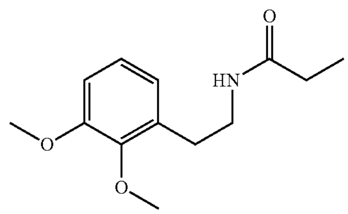 [SMILES: CCC(=O)NCCc1cccc(OC)c1OC] | N-[2-(2,3-dimethoxyphenyl)ethyl]propanamide | (commercial) | M2 | 237 | — |
| Int 41 | 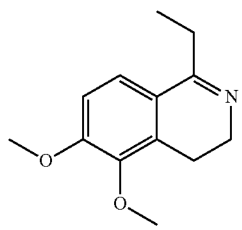 [SMILES: CCC1=NCCc2c1ccc(OC)c2OC] | 1-ethyl-5,6-dimethoxy-3,4-dihydroisoquinoline | Int 40 | M3 | 219 | 220 |
| Int 42 | 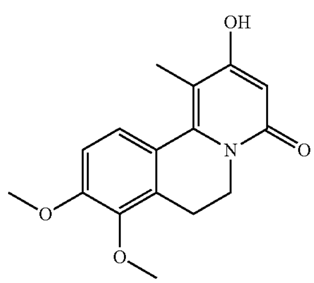 [SMILES: COc1ccc2c(c1OC)CCn1c-2c(C)c(O)cc1=O] | 2-hydroxy-8,9-dimethoxy-1-methyl-6,7-dihydrobenzo[a]quinolizin-4-one | Int 41 | M4 | 287 | 288 |
| Int 43 | 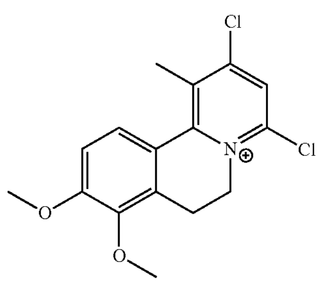 [SMILES: COc1ccc2c(c1OC)CC[n+]1c(Cl)cc(Cl)c(C)c1-2] | 2,4-dichloro-8,9-dimethoxy-1-methyl-6,7-dihydrobenzo[a]quinolizin-5-ium | Int 42 | M10 | 325 | 324/326 |
| Int 44 | 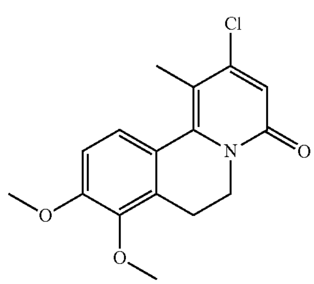 [SMILES: COc1ccc2c(c1OC)CCn1c-2c(C)c(Cl)cc1=O] | 2-chloro-8,9-dimethoxy-1-methyl-6,7-dihydrobenzo[a]quinolizin-4-one | Int 43 | M11 | 306 | 306 |
| Int 45 | 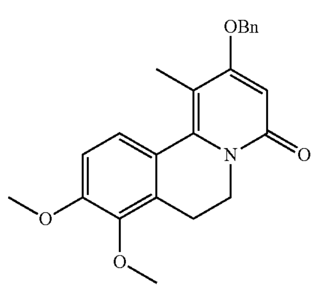 [SMILES: COc1ccc2c(c1OC)CCn1c-2c(C)c(OCc2ccccc2)cc1=O] | 2-benzyloxy-8,9-dimethoxy-1-methyl-6,7-dihydrobenzo[a]quinolizin-4-one | Int 44 | M12 | 377 | 378 |

TABLE II-continued

Intermediate for the synthesis of illustrative compounds of the invention

| Int # | Structure | Name | SM | Mtd | MW | Mes |
|---|---|---|---|---|---|---|
| Int 46 | 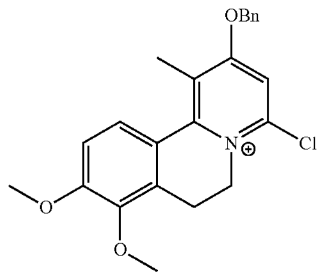 [SMILES: COc1ccc2c(c1OC)CC[n+]1c(Cl)cc(OCc3ccccc3)c(C)c1-2] | 2-benzyloxy-4-chloro-8,9-dimethoxy-1-methyl-6,7-dihydrobenzo[a]quinolizin-5-ium | Int 45 | M13 | 397 | 396 |
| Int 47 | 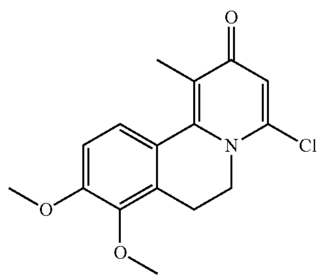 [SMILES: COc1ccc2c(c1OC)CCn1c(Cl)cc(=O)c(C)c1-2] | 4-chloro-8,9-dimethoxy-1-methyl-6,7-dihydrobenzo[a]quinolizin-2-one | Int 46 | M14 | 306 | 306 |
| Int 48 | 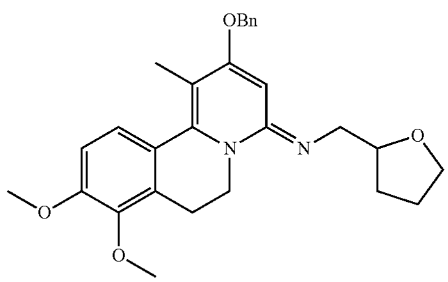 [SMILES: COc1ccc2c(c1OC)CCn1c-2c(C)c(OCc2ccccc2)c/c1=N\CC1CCCO1] | 2-benzyloxy-8,9-dimethoxy-1-methyl-N-(tetrahydrofuran-2-ylmethyl)-6,7-dihydrobenzo[a]quinolizin-4-imine | Int 46 | M23 | 461 | 461 |
| Int 49 | 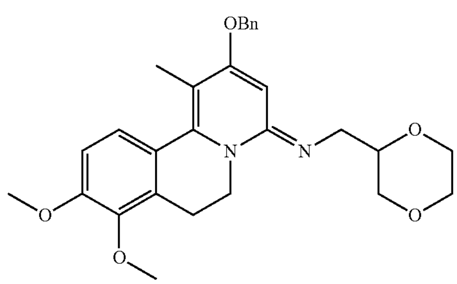 [SMILES: COc1ccc2c(c1OC)CCn1c-2c(C)c(OCc2ccccc2)c/c1=N\CC1COCCO1] | 2-benzyloxy-N-(1,4-dioxan-2-ylmethyl)-8,9-dimethoxy-1-methyl-6,7-dihydrobenzo[a]quinolizin-4-imine | Int 46 | M23 | 477 | 477 |
| Int 50 | 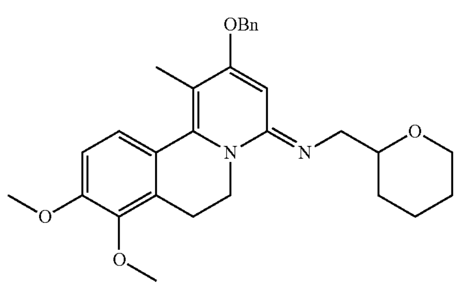 [SMILES: COc1ccc2c(c1OC)CCn1c-2c(C)c(OCc2ccccc2)c/c1=N\CC1CCCCO1] | 2-benzyloxy-8,9-dimethoxy-1-methyl-N-(tetrahydropyran-2-ylmethyl)-6,7-dihydrobenzo[a]quinolizin-4-imine | Int 46 | M23 | 475 | 475 |

TABLE II-continued

Intermediate for the synthesis of illustrative compounds of the invention

| Int # | Structure | Name | SM | Mtd | MW | Mes |
|---|---|---|---|---|---|---|
| Int 51 | 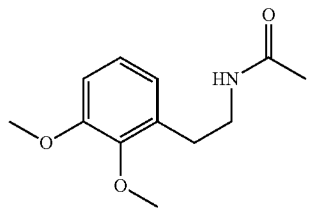 [SMILES: COc1cccc(CCNC(C)=O)c1OC] | N-[2-(2,3-dimethoxyphenyl)ethyl]acetamide | (commercial) | M2 | 223 | — |
| Int 52 | 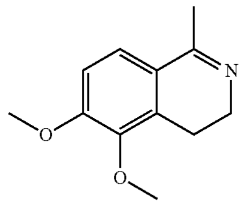 | 5,6-dimethoxy-1-methyl-3,4-dihydroisoquinoline | Int 51 | M3 | 205 | 206 |
| Int 53 | 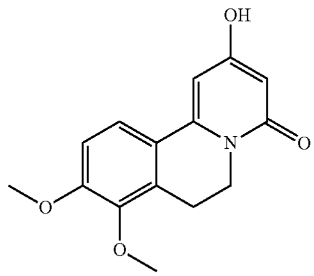 [SMILES: COc1ccc2c(c1OC)CCn1c-2cc(O)cc1=O] | 2-hydroxy-8,9-dimethoxy-6,7-dihydrobenzo[a]quinolizin-4-one | Int 52 | M4 | 273 | 274 |
| Int 54 | 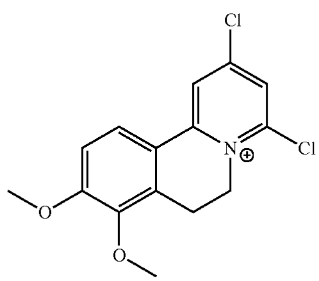 [SMILES: COc1ccc2c(c1OC)CC[n+]1c(Cl)cc(Cl)cc1-2] | 2,4-dichloro-8,9-dimethoxy-6,7-dihydrobenzo[a]quinolizin-5-ium | Int 53 | M10 | 311 | 310/312 |
| Int 55 | 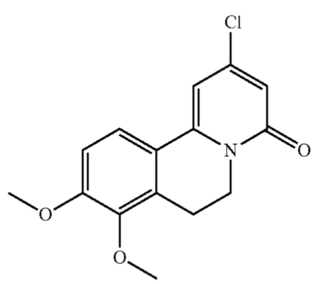 [SMILES: COc1ccc2c(c1OC)CCn1c-2cc(Cl)cc1=O] | 2-chloro-8,9-dimethoxy-6,7-dihydrobenzo[a]quinolixin-4-one | Int 54 | M11 | 292 | 292 |
| Int 56 | 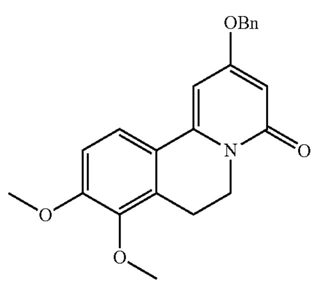 [SMILES: COc1ccc2c(c1OC)CCn1c-2cc(OCc2ccccc2)cc1=O] | 2-benzyloxy-8,9-dimethoxy-6,7-dihydrobenzo[a]quinolizin-4-one | Int 55 | M12 | 363 | 364 |

TABLE II-continued

Intermediate for the synthesis of illustrative compounds of the invention

| Int # | Structure | Name | SM | Mtd | MW | Mes |
|---|---|---|---|---|---|---|
| Int 57 | 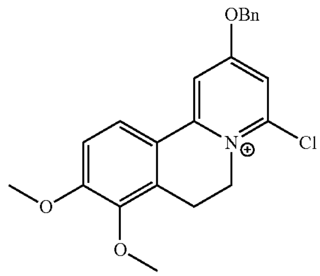 [SMILES: COc1ccc2c(c1OC)CC[n+]1c(Cl)cc(OCc3ccccc3)cc1-2] | 2-benzyloxy-4-chloro-8,9-dimethoxy-6,7-dihydrobenzo[a]quinolizin-5-ium | Int 56 | M13 | 383 | 382 |
| Int 58 | 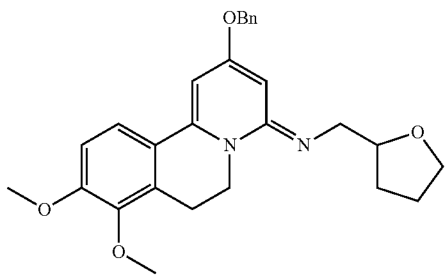 [SMILES: COc1ccc2c(c1OC)CCn1c-2cc(OCc2ccccc2)c/c1=N\CC1CCCO1] | 2-benzyloxy-8,9-dimethoxy-N-(tetrahydrofuran-2-ylmethyl)-6,7-dihydrobenzo[a]quinolizin-4-imine | Int 57 | M23 | 447 | 447 |
| Int 59 | 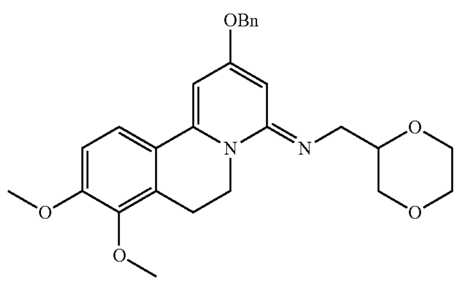 [SMILES: COc1ccc2c(c1OC)CCn1c-2cc(OCc2ccccc2)c/c1=N\CC1COCCO1] | 2-benzyloxy-N-(1,4-dioxan-2-ylmethyl)-8,9-dimethoxy-6,7-dihydrobenzo[a]quinolizin-4-imine | Int 57 | M23 | 463 | 463 |
| Int 60 | 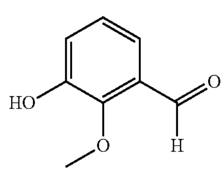 | 3-Hydroxy-2-methoxy-benzaldehyde | commercial | — | 152 | N/A |
| Int 61 | 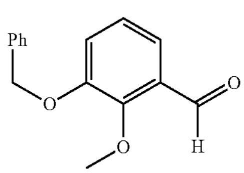 [SMILES: COc1c(C=O)cccc1OCc1ccccc1] | 3-Benzyloxy-2-methoxy-benzaldehyde | Int 60 | Described above | 242 | N/A |
| Int 62 | 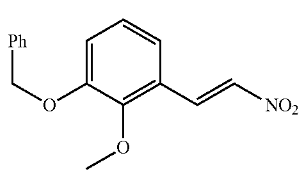 [SMILES: COc1c(/C=C/[N+](=O)[O-])cccc1OCc1ccccc1] | 1-Benzyloxy-2-methoxy-3-(2-nitro-vinyl)-benzene | Int 61 | Described above | 285 | N/A |
| Int 63 | 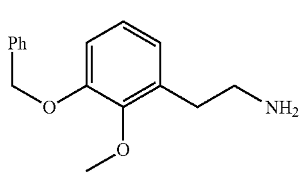 [SMILES: COc1c(CCN)cccc1OCc1ccccc1] | 2-(3-Benzyloxy-2-methoxy-phenyl)-ethylamine | Int 62 | Described above | 257 | 258 |

TABLE II-continued

Intermediate for the synthesis of illustrative compounds of the invention

| Int # | Structure | Name | SM | Mtd | MW | Mes |
|---|---|---|---|---|---|---|
| Int 64 | 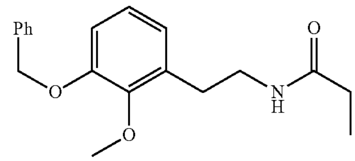 [SMILES: CCC(=O)NCCc1cccc(OCc2ccccc2)c1OC] | N-[2-(3-Benzyloxy-2-methoxy-phenyl)-ethyl]-propionamide | Int 63 | M2 | 313 | 314 |
| Int 65 | 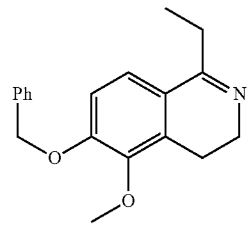 [SMILES: CCC1=NCCc2c1ccc(OCc1ccccc1)c2OC] | 6-Benzyloxy-1-ethyl-5-methoxy-3,4-dihydro-isoquinoline | Int 64 | M3 | 295 | 296 |
| Int 66 | 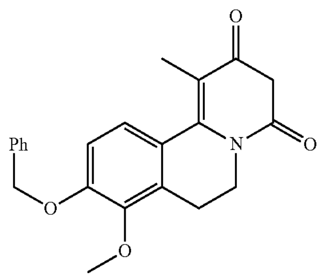 [SMILES: COc1c(OCc2ccccc2)ccc2c1CCN1C(=O)CC(=O)C(C)=C21] | 9-Benzyloxy-8-methoxy-1-methyl-6,7-dihydro-pyrido[2,1-a]isoquinoline-2,4-dione | Int 65 | M4 | 363 | 364 |
| Int 67 | 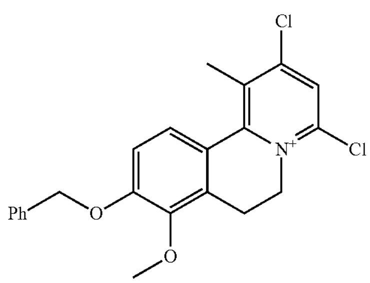 [SMILES: COc1c(OCc2ccccc2)ccc2c1CC[n+]1c(Cl)cc(Cl)c(C)c1-2] | -Benzyloxy-2,4-dichloro-8-methoxy-1-methyl-6,7-dihydro-pyrido[2,1-a]isoquinolinylium | Int 66 | M10 | 401 | 400/402 (Cl2+) |
| Int 68 | 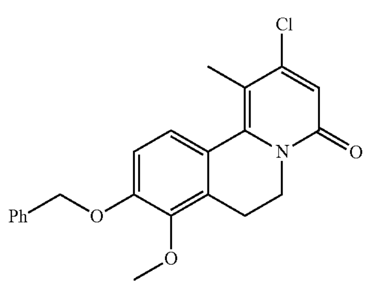 [SMILES: COc1c(OCc2ccccc2)ccc2c1CCn1c-2c(C)c(Cl)cc1=O] | 9-Benzyloxy-2-chloro-8-methoxy 1-methyl-6,7-dihydro-pyrido[2,1-a]isoquinolin-4-one | Int 67 | M11 | 382 | 382/384 (Cl) |
| Int 69 | 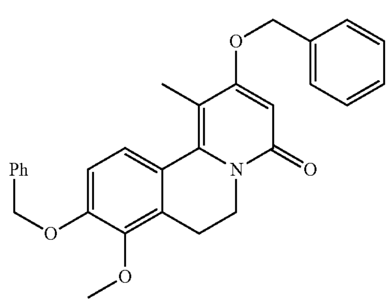 [SMILES: COc1c(OCc2ccccc2)ccc2c1CCn1c-2c(C)c(OCc2ccccc2)cc1=O] | 2,9-Bis-benzyloxy-8-methoxy-1-methyl-6,7-dihydro-pyrido[2,1-a]isoquinolin-4-one | Int 68 | M12 | 454 | 454 |

TABLE II-continued

Intermediate for the synthesis of illustrative compounds of the invention

| Int # | Structure | Name | SM | Mtd | MW | Mes |
|---|---|---|---|---|---|---|
| Int 70 | 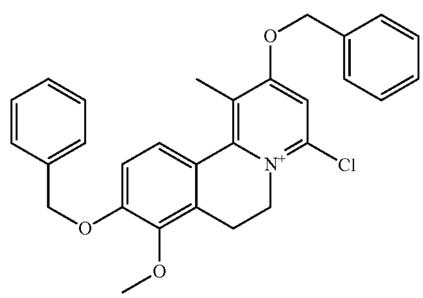 [SMILES: COc1c(OCc2ccccc2)ccc2c1CC[n+]1c(Cl)cc(OCc3ccccc3)c(C)c1-2] | 2,9-Bis-benzyloxy-4-chloro-8-methoxy-1-methyl-6,7-dihydro-pyrido[2,1-a]isoquinolinylium | Int 69 | M13 | 473 | 472/ 474 (Cl+) |
| Int 71 | 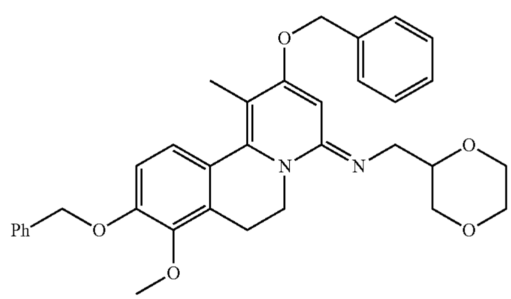 [SMILES: COc1c(OCc2ccccc2)ccc2c1CCn1c-2c(C)c(OCc2ccccc2)c/c1=N\CC1COCCO1] | [2,9-Bis-benzyloxy-8-methoxy-1-methyl-6,7-dihydro-pyrido[2,1-a]isoquinolin-(4E)-ylidene]-[1,4]dioxan-2-ylmethyl-amine | Int 70 | M23 | 553 | 553 |
| Int 72 | 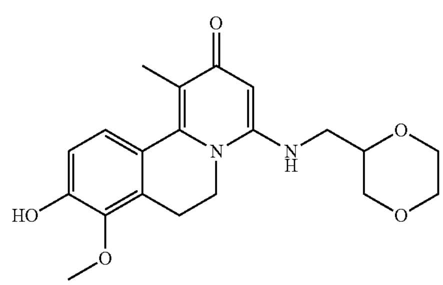 [SMILES: COc1c(O)ccc2c1CCn1c(NCC3COCCO3)cc(=O)c(C)c1-2] | 4-[([1,4]Dioxan-2-ylmethyl)-amino]-9-hydroxy-8-methoxy-1-methyl-6,7-dihydro-pyrido[2,1-a]isoquinolin-2-one | Int 71 | M24 | 372 | 373 |
| Int 73 | 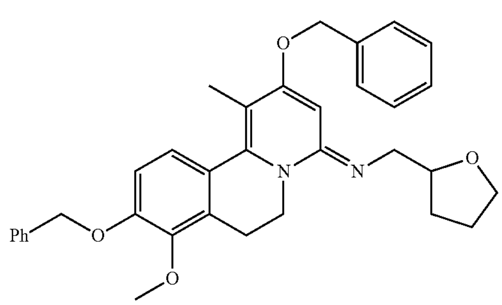 [SMILES: COc1c(OCc2ccccc2)ccc2c1CCn1c-2c(C)c(OCc2ccccc2)c/c1=N\CC1CCCO1] | [2,9-Bis-benzyloxy-8-methoxy-1-methyl-6,7-dihydro-pyrido[2,1-a]isoquinolin-(4E)-ylidene]-(tetrahydro-furan-2-ylmethyl)-amine | Int 69 | M23 | 537 | 537 |
| Int 74 | 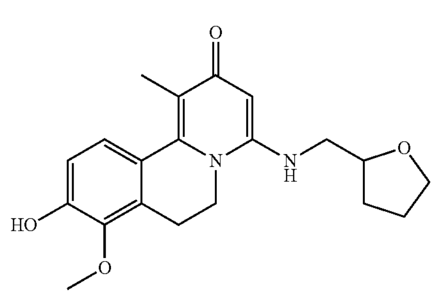 [SMILES: COc1c(O)ccc2c1CCn1c(NCC3CCCO3)cc(=O)c(C)c1-2] | 9-Hydroxy-8-methoxy-1-methyl-4-[(tetrahydro-furan-2-ylmethyl)-amino]-6,7-dihydro-pyrido[2,1-a]isoquinolin-2-one | Int 73 | M24 | 356 | 357 |

TABLE II-continued

Intermediate for the synthesis of illustrative compounds of the invention

| Int # | Name | SM | Mtd | MW | Mes |
|---|---|---|---|---|---|
| Int 75 | N-[2-(3,5-dimethoxyphenyl)ethyl]acetamide | (commercial) | M2 | 223 | — |
| Int 76 | 6,8-dimethoxy-1-methyl-3,4-dihydroisoquinoline | Int 75 | M3 | 205 | 206 |
| Int 77 | 2-hydroxy-9,11-dimethoxy-6,7-dihydrobenzo[a]quinolizin-4-one | Int 76 | M4 | 273 | 274 |
| Int 78 | 2,4-dichloro-9,11-dimethoxy-6,7-dihydrobenzo[a]quinolizin-5-ium | Int 77 | M10 | 311 | 310/312 |
| Int 79 | 2-chloro-9,11-dimethoxy-6,7-dihydrobenzo[a]quinolizin-4-one | Int 78 | M11 | 292 | 292 |
| Int 80 | 2-benzyloxy-9,11-dimethoxy-6,7-dihydrobenzo[a]quinolizin-4-one | Int 79 | M12 | 363 | 364 |
| Int 81 | 2-benzyloxy-4-chloro-9,11-dimethoxy-6,7-dihydrobenzo[a]quinolizin-5-ium | Int 80 | M13 | 383 | 382 |

TABLE II-continued

Intermediate for the synthesis of illustrative compounds of the invention

| Int # | Structure | Name | SM | Mtd | MW | Mes |
|---|---|---|---|---|---|---|
| Int 82 | 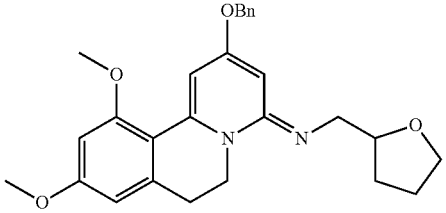 [SMILES: COc1cc2c(c(OC)c1)-c1cc(OCc3ccccc3)c/c(=N\CC3CCCO3)n1CC2] | 2-benzyloxy-9,11-dimethoxy-N-(tetrahydrofuran-2-ylmethyl)-6,7-dihydrobenzo[a]quinolizin-4-imine | Int 81 | M23 | 447 | 447 |
| Int 83 | 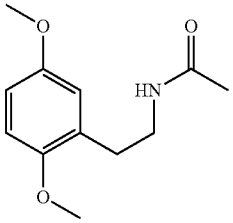 [SMILES: COc1ccc(OC)c(CCNC(C)=O)c1] | N-[2-(2,5-dimethoxyphenyl)ethyl]acetamide | (commercial) | M2 | 223 | — |
| Int 84 | 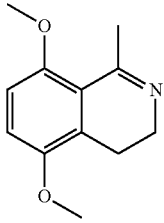 | 5,8-dimethoxy-1-methyl-3,4-dihydroisoquinoline | Int 83 | M3 | 205 | 206 |
| Int 85 | 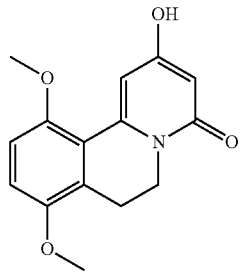 [SMILES: COc1ccc(OC)c2c1CCn1c-2cc(O)cc1=O] | 2-hydroxy-8,11-dimethoxy-6,7-dihydrobenzo[a]quinolizin-4-one | Int 84 | M4 | 273 | 274 |
| Int 86 | 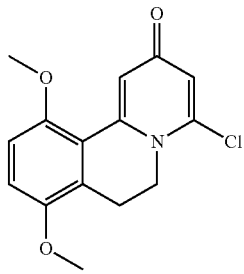 [SMILES: COc1ccc(OC)c2c1CCn1c(Cl)cc(=O)cc1-2] | 4-chloro-8,11-dimethoxy-6,7-dihydrobenzo[a]quinolizin-2-one | Int 85 | M13 | 292 | 292 |
| Int 87 | 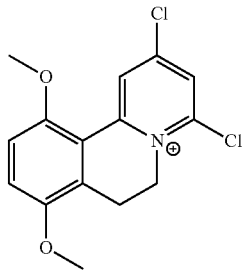 [SMILES: COc1ccc(OC)c2c1CC[n+]1c(Cl)cc(Cl)cc1-2] | 2,4-dichloro-8,11-dimethoxy-6,7-dihydrobenzo[a]quinolizin-5-ium | Int 86 | M10 | 311 | 310/312 |

TABLE II-continued

Intermediate for the synthesis of illustrative compounds of the invention

| Int # | Structure | Name | SM | Mtd | MW | Mes |
|---|---|---|---|---|---|---|
| Int 88 | 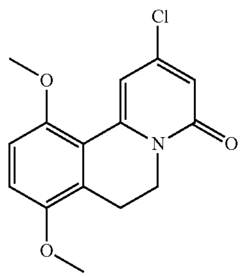 [SMILES: COc1ccc(OC)c2c1CCn1c-2cc(Cl)cc1=O] | 2-chloro-8,11-dimethoxy-6,7-dihydrobenzo[a]quinolizin-4-one | Int 87 | M11 | 292 | 292 |
| Int 89 | 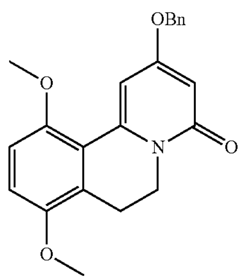 [SMILES: COc1ccc(OC)c2c1CCn1c-2cc(OCc2ccccc2)cc1=O] | 2-benzyloxy-8,11-dimethoxy-6,7-dihydrobenzo[a]quinolizin-4-one | Int 88 | M12 | 363 | 364 |
| Int 90 | 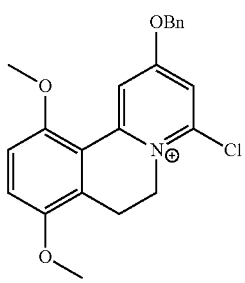 [SMILES: COc1ccc(OC)c2c1CC[n+]1c(Cl)cc(OCc3ccccc3)cc1-2] | 2-benzyloxy-4-chloro-8,11-dimethoxy-6,7-dihydrobenzo[a]quinolizin-5-ium | Int 89 | M13 | 383 | 382 |
| Int 91 | 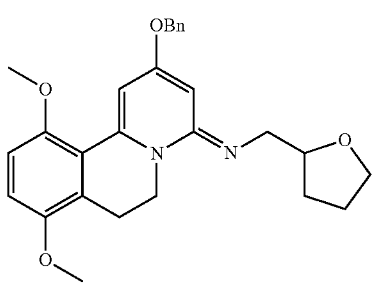 [SMILES: COc1ccc(OC)c2c1CCn1c-2cc(OCc2ccccc2)c/c1=N\CC1CCCO1] | 2-benxyloxy-8,11-dimethoxy-N-(tetrahydrofuran-2-ylmethyl)-6,7-dihydrobenzo[a]quinolizin-4-imine | Int 90 | M23 | 447 | 447 |
| Int 92 | 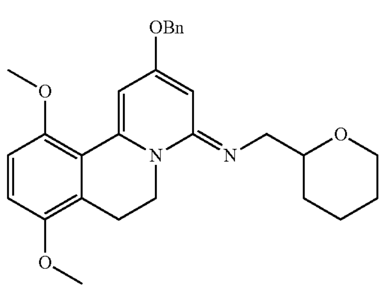 [SMILES: COc1ccc(OC)c2c1CCn1c-2cc(OCc2ccccc2)c/c1=N\CC1CCCCO1] | 2-benzyloxy-8,11-dimethoxy-N-(tetrahydropyran-2-ylmethyl)-6,7-dihydrobenzo[a]quinolizin-4-imine | Int 90 | M23 | 461 | 461 |

TABLE II-continued

Intermediate for the synthesis of illustrative compounds of the invention

| Int # | Structure | Name | SM | Mtd | MW | Mes |
|---|---|---|---|---|---|---|
| Int 93 | 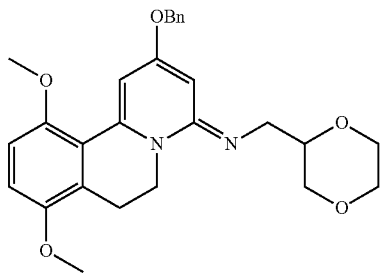 [SMILES: COc1ccc(OC)c2c1CCn1c-2cc(OCc2ccccc2)c/c1=N\CC1COCCO1] | 2-benzoloxy-N-(1,4-dioxan-2-ylmethyl)-8,11-dimethoxy-6,7-dihydrobenzo[a]quinolizin-4-imine | Int 90 | M23 | 463 | 463 |
| Int 94 | 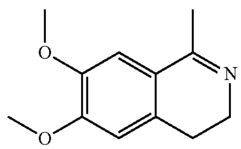 | 6,7-Dimethoxy-1-methyl-3,4-dihydro-isoquinoline | N.A. (commercial) | N.A. (commercial) | 205 | 206 |
| Int 95 | 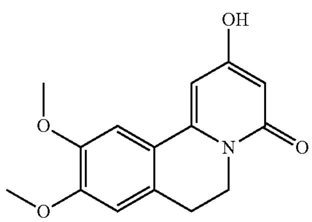 [SMILES: COc1cc2c(cc1OC)-c1cc(O)cc(=O)n1CC2] | 2-Hydroxy-9,10-dimethoxy-6,7-dihydro-pyrido[2,1-a]isoquinolin-4-one | Int 94 | M4 | 273 | 274 |
| Int 96 | 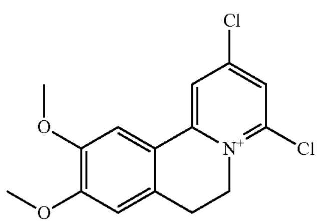 [SMILES: COc1cc2c(cc1OC)-c1cc(Cl)cc(Cl)[n+]1CC2] | 2,4-Dichloro-9,10-dimethoxy-6,7-dihydro-pyrido[2,1-a]isoquinolinylium | Int 95 | M10 | 311 | 310/312 (Cl2+) |
| Int 97 | 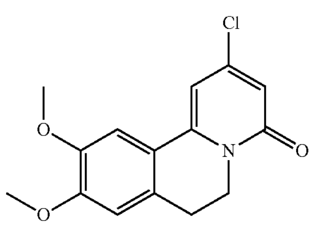 [SMILES: COc1cc2c(cc1OC)-c1cc(Cl)cc(=O)n1CC2] | 2-Chloro-9,10-dimethoxy-6,7-dihydro-pyrido[2,1-a]isoquinolin-4-one | Int 96 | M11 | 292 | 292/294 (Cl) |
| Int 98 | 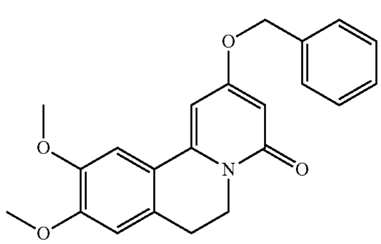 [SMILES: COc1cc2c(cc1OC)-c1cc(OCc3ccccc3)cc(=O)n1CC2] | 2-Benzyloxy-9,10-dimethoxy-6,7-dihydro-pyrido[2,1-a]isoquinolin-4-one | Int 97 | M12 | 363 | 364 |

TABLE II-continued

Intermediate for the synthesis of illustrative compounds of the invention

| Int # | Structure | Name | SM | Mtd | MW | Mes |
|---|---|---|---|---|---|---|
| Int 99 | 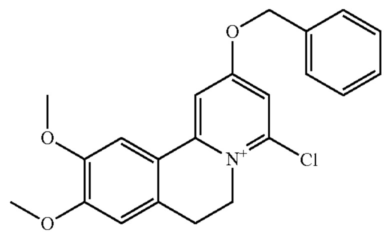 [SMILES: COc1cc2c(cc1OC)-c1cc(OCc3ccccc3)cc(Cl)[n+]1CC2] | 2-Benzyloxy-4-chloro-9,10-dimethoxy-6,7-dihydro-pyrido[2,1-a]isoquinolinylium | Int 98 | M13 | 383 | 382/384 (Cl+) |
| Int 100 | 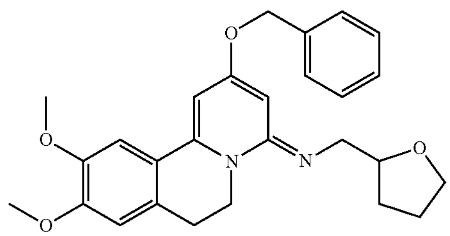 [SMILES: COc1cc2c(cc1OC)-c1cc(OCc3ccccc3)c/c(=N\CC3CCCO3)n1CC2] | [2-Benzyloxy-9,10-dimethoxy-6,7-dihydro-pyrido[2,1-a]isoquinolin-(4E)-ylidene]-(tetrahydro-furan-2-ylmethyl)-amine | Int 99 | M23 | 447 | 447 |
| Int 101 | 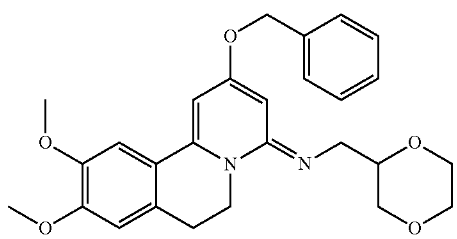 [SMILES: COc1cc2c(cc1OC)-c1cc(OCc3ccccc3)c/c(=N\CC3COCCO3)n1CC2] | [2-Benzyloxy-9,10-dimethoxy-6,7-dihydro-pyrido[2,1-a]isoquinolin-(4E)-ylidene]-[1,4]dioxan-2-ylmethyl-amine | Int 99 | M23 | 463 | 463 |
| Int 102 | 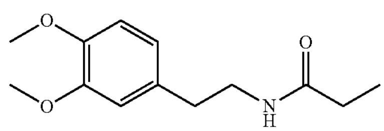 [SMILES: CCC(=O)NCCc1ccc(OC)c(OC)c1] | N-[2-(3,4dimethoxyphenyl)ethyl]propanamide | 2-(3,4-di-meth-oxy-phenyl-ethyl-amine | M2 | 237 | 238.1 |
| Int 103 | 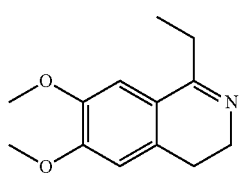 [SMILES: CCC1=NCCc2cc(OC)c(OC)cc21] | 6,7-dimethoxy-1-ethyl-3,4-dihydroisoquinoline | Int 102 | M3 | 219 | 220.2 |
| Int 104 | 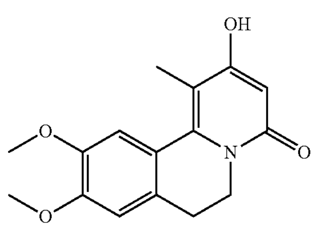 [SMILES: COc1cc2c(cc1OC)-c1c(C)c(O)cc(=O)n1CC2] | 2-hydroxy-9,10-dimethoxy-1-methyl-6,7-dihydrobenzo[a]quinolizin-4-one | Int 103 | M4 | 287 | 288 |
| Int 105 | 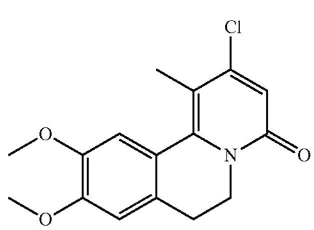 [SMILES: COc1cc2c(cc1OC)-c1c(C)c(Cl)cc(=O)n1CC2] | 2-chloro-9,10-dimethoxy-1-methyl-6,7-dihydrobenzo[a]quinolizin-4-one | Int 104 | M10 + 11 | 305 | 306 |

TABLE II-continued

Intermediate for the synthesis of illustrative compounds of the invention

| Int # | Structure | Name | SM | Mtd | MW | Mes |
|---|---|---|---|---|---|---|
| Int 106 | 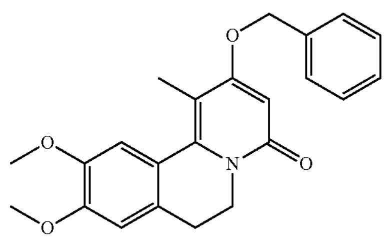 [SMILES: COc1cc2c(cc1OC)-c1c(C)c(OCc3ccccc3)cc(=O)n1CC2] | 2-benzyloxy-9,10-dimethoxy-1-methyl-6,7-dihydrobenzo[a]quinolizin-4-one | Int 105 | M12 | 377 | 378 |
| Int 107 | 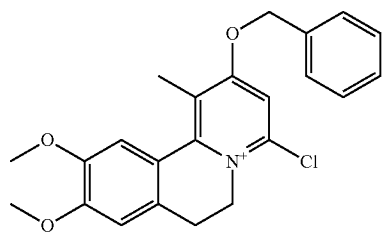 [SMILES: COc1cc2c(cc1OC)-c1c(C)c(OCc3ccccc3)cc(Cl)[n+]1CC2] | 2-benzyloxy-4-chloro-9,10-dimethoxy-1-methyl-6,7-dihydrobenzo[a]quinolizin-5-ium | Int 106 | M13 | 396 | 397 |
| Int 108 | 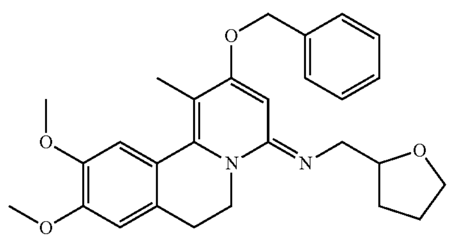 [SMILES: COc1cc2c(cc1OC)-c1c(C)c(OCc3ccccc3)c/c(=N\CC3CCCO3)n1CC2] | 2-benzyloxy-9,10-dimethoxy-1-methyl-N-(tetrahydrofuran-2-ylmethyl)-6,7-dihydrobenzo[a]quinolizin-4-imine | Int 107 | M21 | 460 | 461 |
| Int 109 | 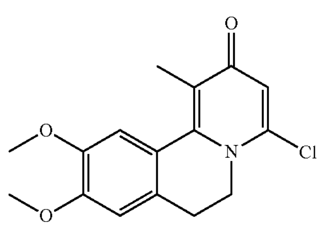 [SMILES: COc1cc2c(cc1OC)-c1c(C)c(=O)cc(Cl)n1CC2] | 4-chloro-9,10-dimethoxy-1-methyl-6,7-dihydrobenzo[a]quinolizin-2-one | Int 114 | M6 | 305 | 306 |
| Int 110 | 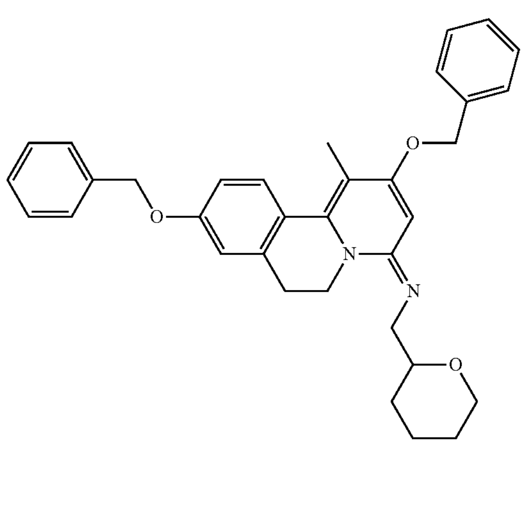 [SMILES: Cc1c(OCc2ccccc2)c/c(=N/CC2CCCCO2)n2c1-c1ccc(OCc3ccccc3)cc1CC2] | 2,9-dibenzyloxy-1-methyl-N-(tetrahydropyran-2-ylmethyl)-6,7-dihydrobenzo[a]quinolizin-4-imine | Int 21 | M23 | 520 | 521 |

TABLE II-continued

Intermediate for the synthesis of illustrative compounds of the invention

| Int # | Structure | Name | SM | Mtd | MW | Mes |
|---|---|---|---|---|---|---|
| Int 111 | 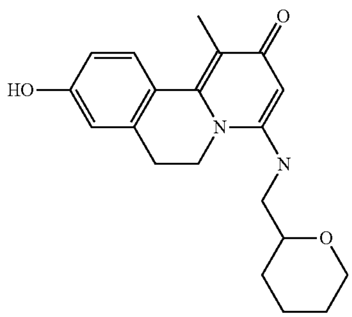 [SMILES: Cc1c2n(c(NCC3CCCCO3)cc1=O)CCc1cc(O)ccc1-2] | 9-hydroxy-1-methyl-4-(tetrahydropyran-2-ylmethylamino)-6,7-dihydrobenzo[a]quinolizin-2-one | Int 110 | M24 | 340 | 341 |
| Int 112 | racemic | 9-benzyloxy-4-[[1,4-dioxan-2-yl]methoxy]-1-methyl-6,7-dihydrobenzo[a]quinolizin-2-one | Int 24 | M15 | 434 | 434 |
| Int 113 | racemic | 4-[[1,4-dioxan-2-yl]methoxy]-9-hydroxy-1-methyl-6,7-dihydrobenzo[a]quinolizin-2-one | Int 112 | M16 | 343 | 344 |
| Int 114 | 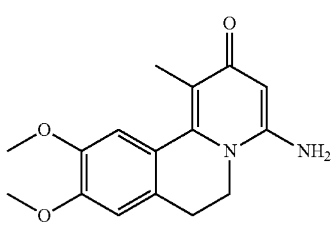 [SMILES: COc1cc2c(cc1OC)-c1c(C)c(=O)cc(N)n1CC2] | 9,10-dimethoxy-1-methyl-4-amino-6,7-dihydrobenzo[a]quinolizin-2-one | Int 103 | M5 | 286 | 287 |
| Int 115 | 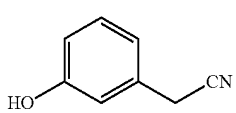 | Meta-hydroxy benzyl cyanide | commercial | NA | 133 | NA |
| Int 116 | 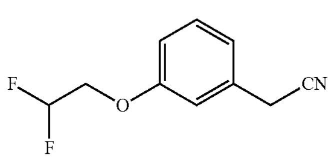 [SMILES: N#CCc1cccc(OCC(F)F)c1] | 3-(2,2-difluoroethoxy)phenylacetonitrile | Int 115 | M0 | 197 | 198 |
| Int 117 | 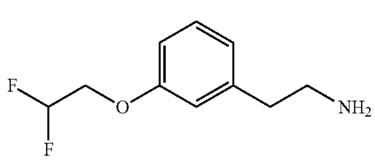 [SMILES: NCCc1cccc(OCC(F)F)c1] | 2-(3-(2,2-difluoroethoxy)phenyl)ethanamine | Int 116 | M1 | 201 | 202 |

TABLE II-continued

Intermediate for the synthesis of illustrative compounds of the invention

| Int # | Structure | Name | SM | Mtd | MW | Mes |
|---|---|---|---|---|---|---|
| Int 118 | 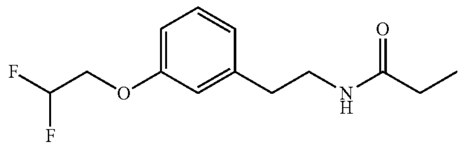 [SMILES: CCC(=O)NCCc1cccc(OCC(F)F)c1] | N-[2-(3-(2,2-difluoroethoxy)phenyl)ethyl]propanamide | Int 117 | M2 | 257 | 258 |
| Int 119 | 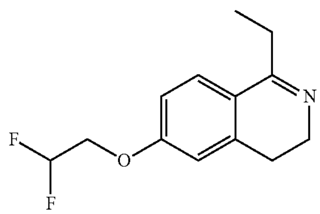 [SMILES: CCC1=NCCc2cc(OCC(F)F)ccc21] | 6-(2,2-difluoroethoxy)-1-ethyl-3,4-dihydroisoquinoline | Int 118 | M3 | 239 | 240 |
| Int 120 | 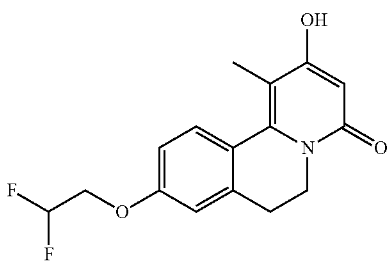 | 2-hydroxy-9-(2,2-difluoroethoxy)-1-methyl-6,7-dihydrobenzo[a]quinolizin-4-one | Int 119 | M4 | 307 | 308 |
| Int 121 | 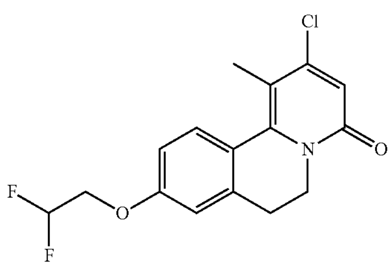 [SMILES: Cc1c(Cl)cc(=O)n2c1-c1ccc(OCC(F)F)cc1CC2] | 2-chloro-9-(2,2-difluoroethoxy)-1-methyl-6,7-dihydrobenzo[a]quinolizin-4-one | Int 120 | M10 + 11 | 325 | 326 |
| Int 122 | 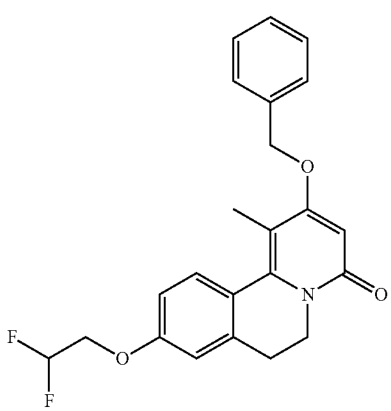 [SMILES: Cc1c(OCc2ccccc2)cc(=O)n2c1-c1ccc(OCC(F)F)cc1CC2] | 2-benzyloxy-9-(2,2-difluoroethoxy)-1-methyl-6,7-dihydrobenzo[a]quinolizin-4-one | Int 121 | M12 | 397 | 398 |

TABLE II-continued

Intermediate for the synthesis of illustrative compounds of the invention

| Int # | Structure | Name | SM | Mtd | MW | Mes |
|---|---|---|---|---|---|---|
| Int 123 | 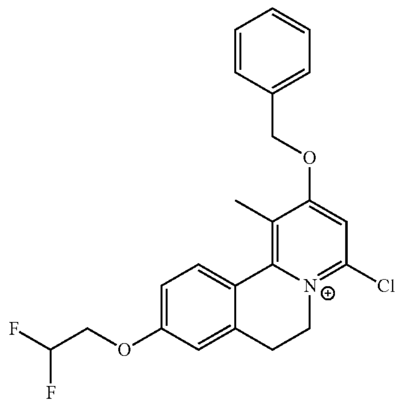 [SMILES: Cc1c(OCc2ccccc2)cc(Cl)[n+]2c1-c1ccc(OCC(F)F)cc1CC2] | 2-benzoloxy-4-chloro-9(2,2-difluoroethoxy)-1-methyl-6,7-dihydrobenzo[a]quinolizin-5-ium | Int 122 | M13 | 416 | 416 |
| Int 124 | 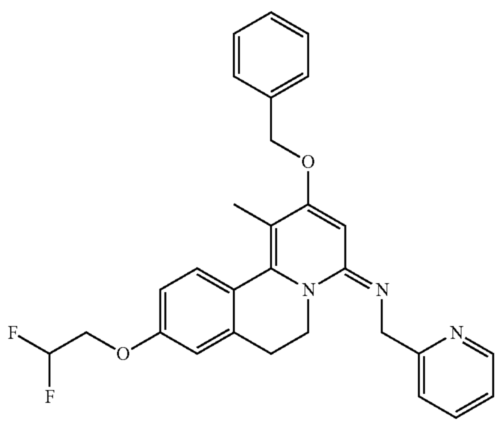 [SMILES: Cc1c(OCc2ccccc2)c/c(=N/Cc2ccccn2)n2c1-c1ccc(OCC(F)F)cc1CC2] | 2-benzyloxy-9-(2,2-difluoroethoxy)-1-methyl-N-(2-pyridylmethyl)-6,7-dihydrobenzo[a]quinolizin-4-imine | Int 123 | M23 | 487 | 488 |
| Int 125 | 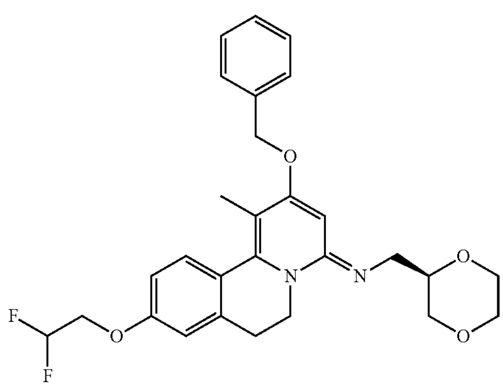 [SMILES: Cc1c(OCc2ccccc2)c/c(=N\C[C@@H]2COCCO2)n2c1-c1ccc(OCC(F)F)cc1CC2] | 2-benzyloxy-9-(2,2-difluoroethoxy)-1-methyl-N-((2R)-1,4-dioxan-2-ylmethyl)-6,7-dihydrobenzo[a]quinolizin-4-imine | Int 123 | M23 | 496 | 497 |
| Int 126 | 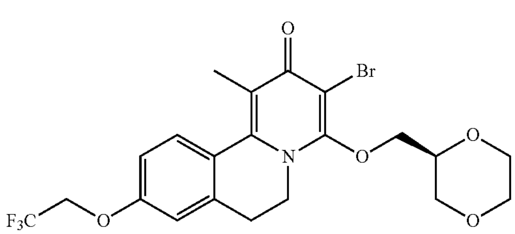 [SMILES: Cc1c2n(c(OC[C@@H]3COCCO3)c(Br)c1=O)CCc1cc(OCC(F)(F)F)ccc1-2] | 3-bromo-4-[[(2S)-1,4-dioxan-2-yl]methoxy]-1-methyl-9-(2,2,2-trifluoroethoxy)-6,7-dihydrobenzo[a]quinolizin-2-one | Cpd 18 | Described abobe | 343 | 344 |

TABLE III

Illustrative compound of the invention

| Cpd # | Structure | Name | SM | Mtd | MW | Mes |
|---|---|---|---|---|---|---|
| 1 | 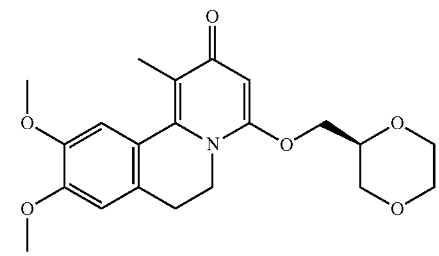 [SMILES: COc1cc2c(cc1OC)-c1c(C)c(=O)cc(OC[C@@H]3COCCO3)n1CC2] | 4-[[(2S)-1,4-dioxan-2-yl]methoxy]-9,10-dimethoxy-1-methyl-6,7-dihydrobenzo[a]quinolizin-2-one | Int 109 | Described above | 387 | 388 |
| 2 | 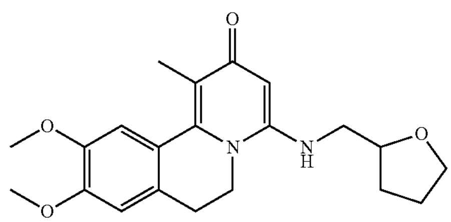 [SMILES: COc1cc2c(cc1OC)-c1c(C)c(=O)cc(NCC3CCCO3)n1CC2] | 9,10-dimethoxy-1-methyl-4-(tetrahydrofuran-2-ylmethylamino)-6,7-dihydrobenzo[a]quinolizin-2-one | Int 108 | Described above | 370 | 371 |
| 3 | 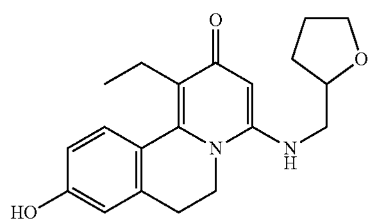 [SMILES: CCc1c2n(c(NCC3CCCO3)cc1=O)CCc1cc(O)ccc1-2] | 1-ethyl-9-hydroxy-4-(tetrahydrofuran-2-ylmethylamino)-6,7-dihydrobenzo[a]quinolizin-2-one | Int 9 | M24 | 340 | 341 |
| 4 | 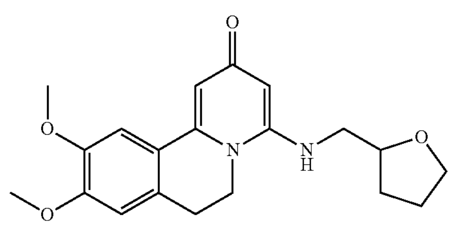 [SMILES: COc1cc2c(cc1OC)-c1cc(=O)cc(NCC3CCCO3)n1CC2] | 9,10-Dimethoxy-4-[(tetrahydro-furan-2-ylmethyl)-amino]-6,7-dihydro-pyrido[2,1-a]isoquinolin-2-one | Int 108 | M24 | 356 | 357 |
| 5 | 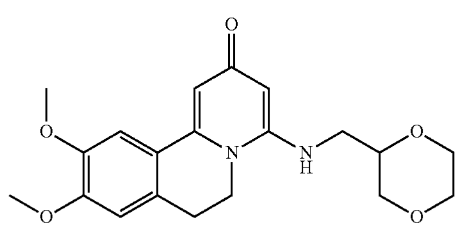 [SMILES: COc1cc2c(cc1OC)-c1cc(=O)cc(NCC3COCCO3)n1CC2] | 4-[([1,4]Dioxan-2-ylmethyl)-amino]-9,10-dimethoxy-6,7-dihydro-pyrido[2,1-a]isoquinolin-2-one | Int 101 | M24 | 372 | 373 |
| 6 | 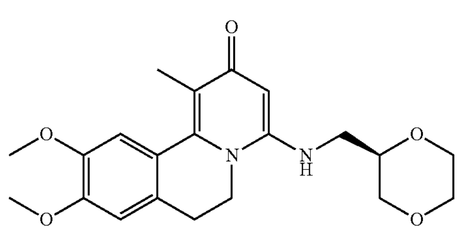 [SMILES: COc1cc2c(cc1OC)-c1c(C)c(=O)cc(NC[C@@H]3COCCO3)n1CC2] | 4-[[(2R)-1,4-dioxan-2-yl]methylamino]-9,10-dimethoxy-1-methyl-6,7-dihydrobenzo[a]quinolizin-2-one | Int 78 chiral | Described above | 386 | 387.0 |

TABLE III-continued

Illustrative compound of the invention

| Cpd # | Structure | Name | SM | Mtd | MW | Mes |
|---|---|---|---|---|---|---|
| 7 | 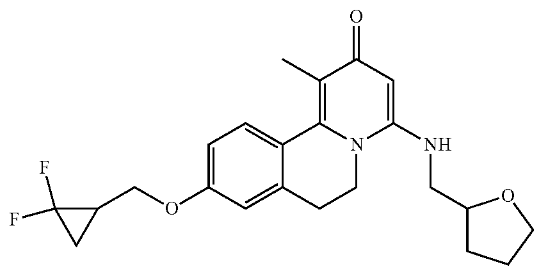 [SMILES: Cc1c2n(c(NCC3CCCO3)cc1=O)CCc1cc(OCC3CC3(F)F)ccc1-2] | 9-(2,2-Difluoro-cyclopropylmethoxy)-1-methyl-4-[(tetrahydro-furan-2-ylmethyl)-amino]-6,7-dihydro-pyrido[2,1-a]isoquinolin-2-one | Int 23 | M17 | 416 | 417 |
| 8 | 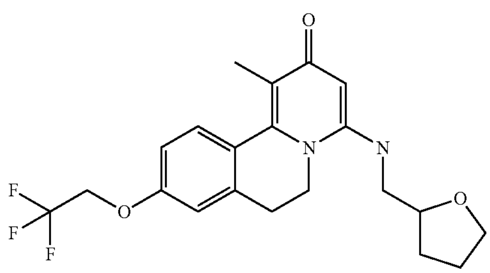 [SMILES: Cc1c2n(c(NCC3CCCO3)cc1=O)CCc1cc(OCC(F)(F)F)ccc1-2] | 1-methyl-4-(tetrahydrofuran-2-ylmethylamino)-9-(2,2,2-trifluoroethoxy)-6,7-dihydrobenzo[a]quinolizin-2-one | Int 23 | M17 | 408 | 409 |
| 9 | 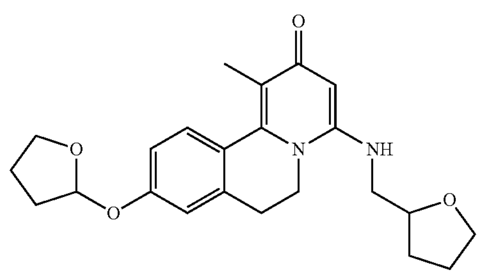 [SMILES: Cc1c2n(c(NCC3CCCO3)cc1=O)CCc1cc(OC3CCCO3)ccc1-2] | -Methyl-4-[(tetrahydro-furan-2-ylmethyl)-amino]-9-(tetrahydro-furan-2-yloxy)-6,7-dihydro-pyrido[2,1-a]isoquinolin-2-one | Int 23 | M17 (by product) | 396 | 409, 398, 327 |
| 10 | 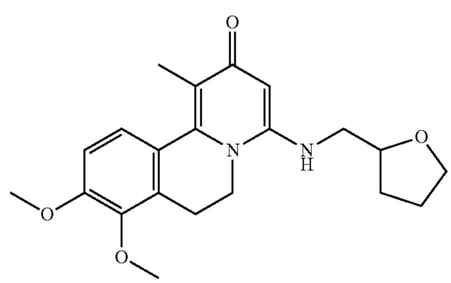 [SMILES: COc1ccc2c(c1OC)CCn1c(NCC3CCCO3)cc(=O)c(C)c1-2] | 8,9-dimethoxy-1-methyl-4-(tetrahydrofuran-2-ylmethylamino)-6,7-dihydrobenzo[a]quinolizin-2-one | Int 58 | M24 | 370 | 371 |
| 12 | 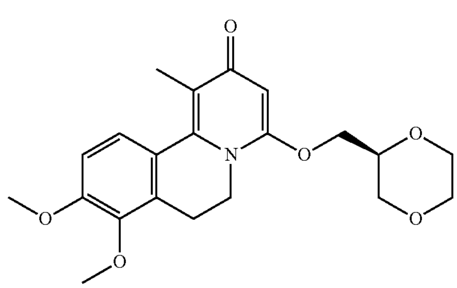 [SMILES: COc1ccc2c(c1OC)CCn1c(OC[C@@H]3COCCO3)cc(=O)c(C)c1-2] | 4-[[(2S)-1,4-dioxan-2-yl]methoxy]-8,9-dimethoxy-1-methyl-6,7-dihydrobenzo[a]quinolizin-2-one | Int 47 | M15 | 387 | 388 |

TABLE III-continued

Illustrative compound of the invention

| Cpd # | Structure | Name | SM | Mtd | MW | Mes |
|---|---|---|---|---|---|---|
| 13 | 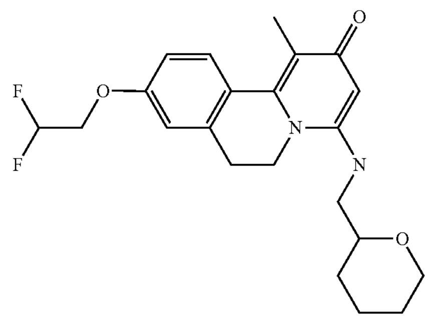 [SMILES: Cc1c2n(c(NCC3CCCCO3)cc1=O)CCc1cc(OCC(F)F)ccc1-2] | 9-(2,2-difluoroethoxy)-1-methyl-4-(tetrahydropyran-2-ylmethylamino)-6,7-dihydrobenzo[a]quinolizin-2-one | Int 111 | M17 | 405 | 405 |
| 14 | 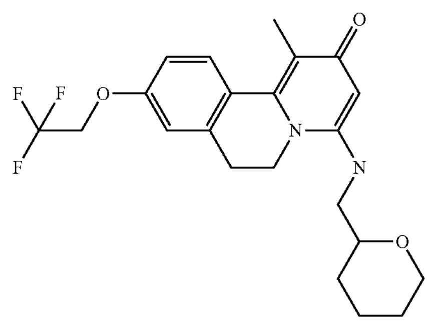 [SMILES: Cc1c2n(c(NCC3CCCCO3)cc1=O)CCc1cc(OCC(F)(F)F)ccc1-2] | 1-methyl-4-(tetrahydropyran-2-ylmethylamino)-9-(2,2,2-trifluoroethoxy)-6,7-dihydrobenzo[a]quinolizin-2-one | Int 111 | M17 | 422 | 423 |
| 16 | 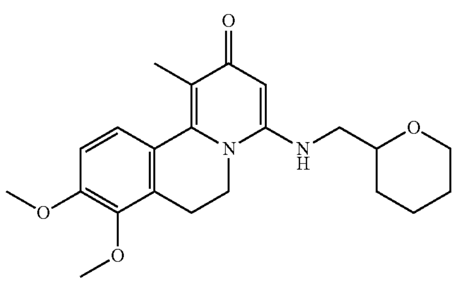 [SMILES: COc1ccc2c(c1OC)CCn1c(NCC3CCCCO3)cc(=O)c(C)c1-2] | 8,9-dimethoxy-1-methyl-4-(tetrahydropyran-2-ylmethylamino)-6,7-dihydrobenzo[a]quinolizin-2-one | Int 50 | M24 | 384 | 385 |
| 17 | 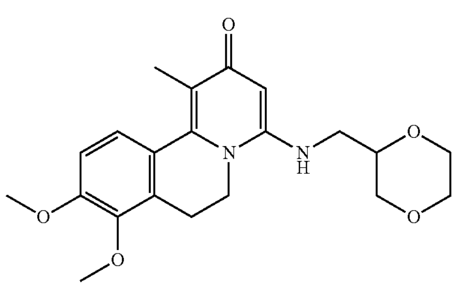 [SMILES: COc1ccc2c(c1OC)CCn1c(NCC3COCCO3)cc(=O)c(C)c1-2] | 4-(1,4-dioxan-2-ylmethylamino)-8,9-dimethoxy-1-methyl-6,7-dihydrobenzo[a]quinolizin-2-one | Int 49 | M24 | 386 | 387 |
| 18 | 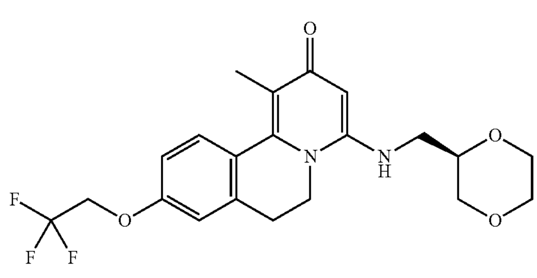 [SMILES: Cc1c2n(c(NC[C@@H]3COCCO3)cc1=O)CCc1cc(OCC(F)(F)F)ccc1-2] | 4-[[(2S)-1,4-dioxan-2-yl]methoxy]-1-methyl-9-(2,2,2-trifluoroethoxy)-6,7-dihydrobenzo[a]quinolizin-2-one | Cpd 85 | M17 | 425 | 426 |

TABLE III-continued

Illustrative compound of the invention

| Cpd # | Structure | Name | SM | Mtd | MW | Mes |
|---|---|---|---|---|---|---|
| 19 | 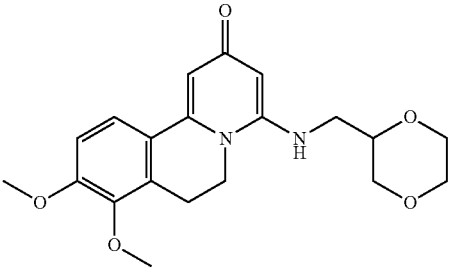 [SMILES: COc1ccc2c(c1OC)CCn1c(NCC3COCCO3)cc(=O)cc1-2] | 4-(1,4-dioxan-2-ylmethylamino)-8,9-dimethoxy-6,7-dihydrobenzo[a]quinolizin-2-one | Int 59 | M24 | 372 | 373 |
| 20 | 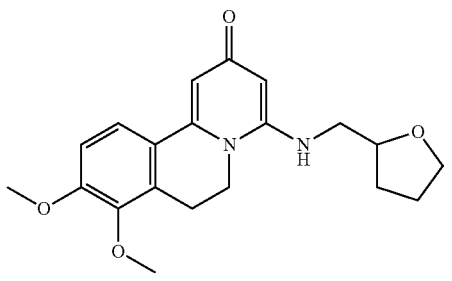 [SMILES: COc1ccc2c(c1OC)CCn1c(NCC3CCCO3)cc(=O)cc1-2] | 8,9-dimethoxy-4-(tetrahydrofuran-2-ylmethylamino)-6,7-dihydrobenzo[a]quinolizin-2-one | Int 58 | M24 | 356 | 357 |
| 21 | 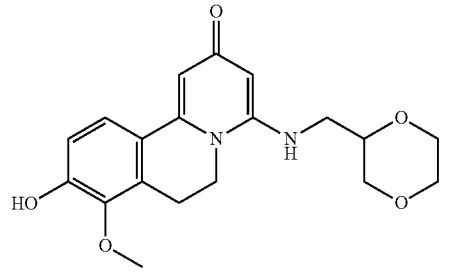 [SMILES: COc1c(O)ccc2c1CCn1c(NCC3COCCO3)cc(=O)cc1-2] | 4-(1,4-dioxan-2-ylmethylamino)-9-hydroxy-8-methoxy-6,7-dihydrobenzo[a]quinolizin-2-one | Cpd 19 | Described above | 358 | 359 |
| 22 | 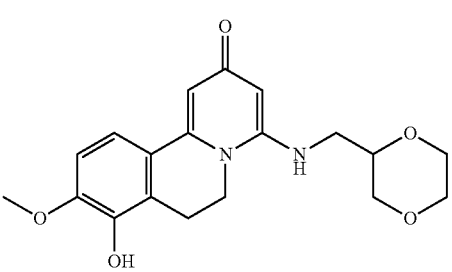 [SMILES: COc1ccc2c(c1O)CCn1c(NCC3COCCO3)cc(=O)cc1-2] | 4-(1,4-dioxan-2-ylmethylamino)-8-hydroxy-9-methoxy-6,7-dihydrobenzo[a]quinolizin-2-one | Cpd 19 | Described above | 358 | 359 |
| 23 | 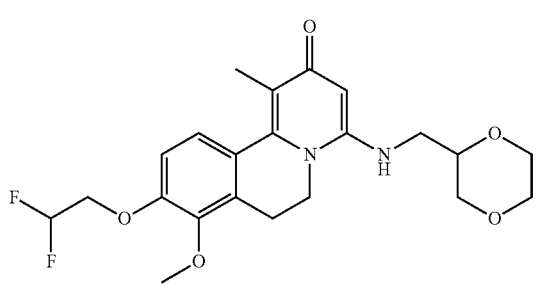 [SMILES: COc1c(OCC(F)F)ccc2c1CCn1c(NCC3COCCO3)cc(=O)c(C)c1-2] | 9-(2,2-Difluoro-ethoxy)-4-[([1,4]dioxan-2-ylmethyl)-amino]-8-methoxy-1-methyl-6,7-dihydro-pyrido[2,1-a]isoquinolin-2-one | Cpd 21 | M17 | 436 | 437 |

TABLE III-continued

Illustrative compound of the invention

| Cpd # | Structure | Name | SM | Mtd | MW | Mes |
|---|---|---|---|---|---|---|
| 24 | 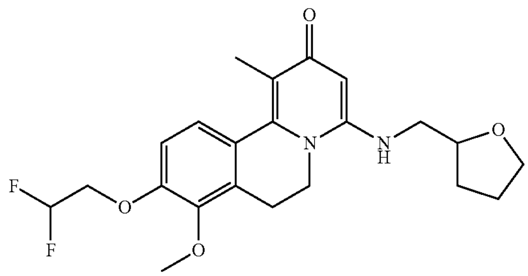 [SMILES: COc1c(OCC(F)F)ccc2c1CCn1c(NCC3CCCO3)cc(=O)c(C)c1-2] | 9-(2,2-Difluoro-ethoxy)-8-methoxy-1-methyl-4-[(tetrahydro-furan-2-ylmethyl)-amino]-6,7-dihydro-pyrido[2,1-a]isoquinolin-2-one | Int 74 | M17 | 420 | 421 |
| 25 | 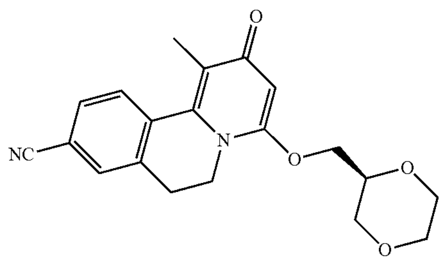 [SMILES: Cc1c2n(c(OC[C@@H]3COCCO3)cc1=O)CCc1cc(C#N)ccc1-2] | 4-[[(1S)-1,4-dioxan-2-yl]methoxy]-1-methyl-2-oxo-6,7-dihydrobenzo[a]quinolizine-9-carbonitrile | Cpd 37 | M20 | 352 | 353 |
| 26 | 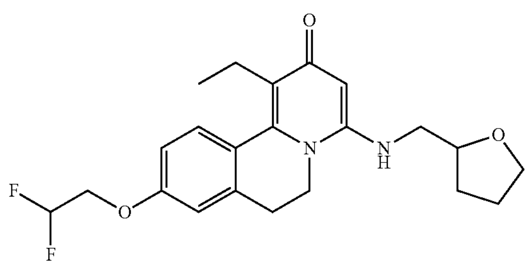 [SMILES: CCc1c2n(c(NCC3CCCO3)cc1=O)CCc1cc(OCC(F)F)ccc1-2] | 9-(2,2-difluoroethoxy)-1-ethyl-4-(tetrahydrofuran-2-ylmethylamino)-6,7-dihydrobenzo[a]quinolizin-2-one | Int 10 | M17 | 404 | 405 |
| 27 | 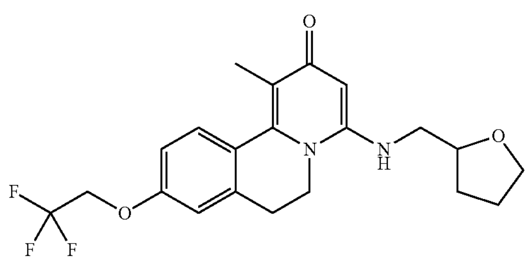 [SMILES: Cc1c2n(c(NCC3CCCO3)cc1=O)CCc1cc(OCC(F)(F)F)ccc1-2] | 1-ethyl-4-(tetrahydrofuran-2-ylmethylamino)-9-(2,2,2-trifluoroethoxy)-6,7-dihydrobenzo[a]quinolizin-2-one | Int 10 | M17 | 422 | 423 |
| 28 | 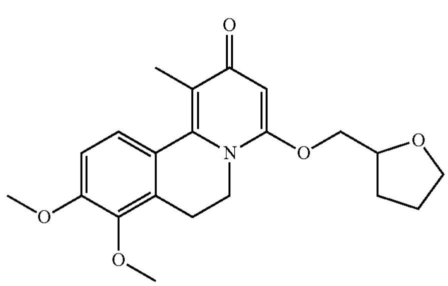 [SMILES: COc1ccc2c(c1OC)CCn1c(OCC3CCCO3)cc(=O)c(C)c1-2] | 8,9-dimethoxy-1-methyl-4-(tetrahydrofuran-2-ylmethoxy)-6,7-dihydrobenzo[b]quinolizin-2-one | Int 47 | M15 | 371 | 372 |

TABLE III-continued

Illustrative compound of the invention

| Cpd # | Structure | Name | SM | Mtd | MW | Mes |
|---|---|---|---|---|---|---|
| 29 | 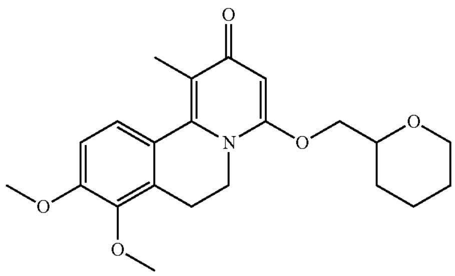 [SMILES: COc1ccc2c(c1OC)CCn1c(OCC3CCCCO3)cc(=O)c(C)c1-2] | 8,9-dimethoxy-1-methyl-4-(tetrahydropyran-2-ylmethoxy)-6,7-dihydrobenzo[b]quinolizin-2-one | Int 47 | M15 | 385 | 386 |
| 30 | 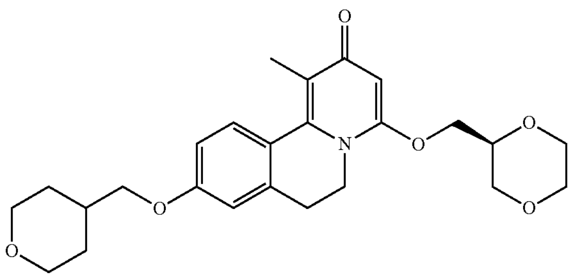 [SMILES: Cc1c2n(c(OC[C@@H]3COCCO3)cc1=O)CCc1cc(OCC3CCOCC3)ccc1-2] | 4-[[(2S)-1,4-dioxan-2-yl]methoxy]-1-methyl-9-(tetrahydropyran-4-ylmethoxy)-6,7-dihydrobenzo[b]quinolizin-2-one | Cpd 85 | M17 | 442 | 442 |
| 31 | 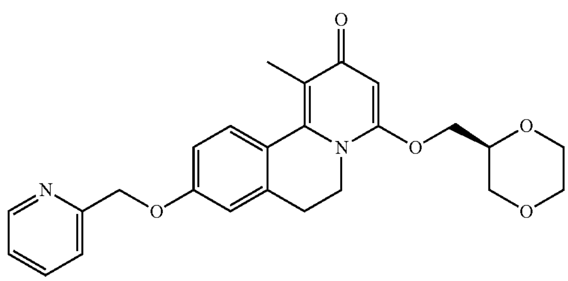 [SMILES: Cc1c2n(c(OC[C@@H]3COCCO3)cc1=O)CCc1cc(OCc3ccccn3)ccc1-2] | 4-[[(2S)-1,4-dioxan-2-yl]methoxy]-1-methyl-9-(2-pyridylmethoxy)-6,7-dihydrobenzo[b]quinolizin-2-one | Cpd 85 | M17 | 434 | 435 |
| 32 | 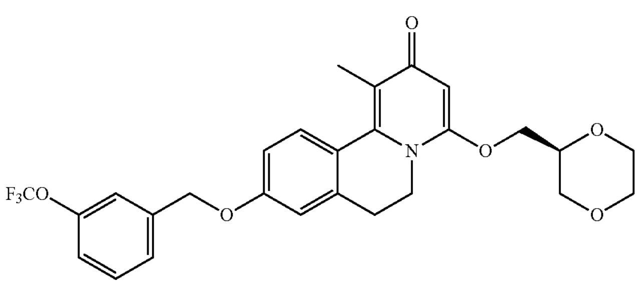 [SMILES: Cc1c2n(c(OC[C@@H]3COCCO3)cc1=O)CCc1cc(OCc3cccc(OC(F)(F)F)c3)ccc1-2] | 4-[[(2S)-1,4-dioxan-2-yl]methoxy]-1-methyl-9-[[3-(trifluoromethoxy)phenyl]methoxy]-6,7-dihydrobenzo[a]quinolizin-2-one | Cpd 85 | M17 | 518 | 518 |
| 33 | 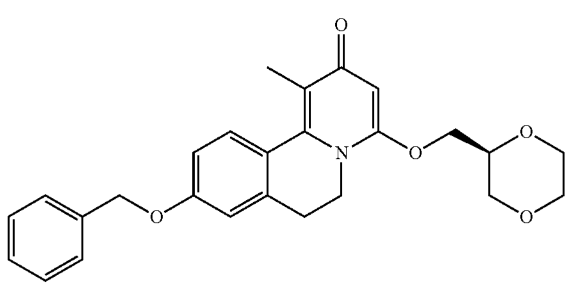 [SMILES: Cc1c2n(c(OC[C@@H]3COCCO3)cc1=O)CCc1cc(OCc3ccccc3)ccc1-2] | 9-benzyloxy-4-[[(2S)-1,4-dioxan-2-yl]methoxy]-1-methyl-6,7-dihydrobenzo[a]quinolizin-2-one | Int 24 | M17 | 434 | 434 |

TABLE III-continued

Illustrative compound of the invention

| Cpd # | Structure | Name | SM | Mtd | MW | Mes |
|---|---|---|---|---|---|---|
| 34 | 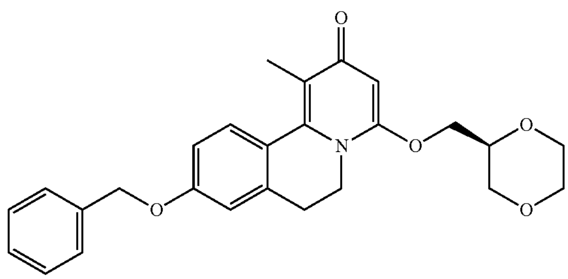 [SMILES: Cc1c2n(c(OC[C@@H]3COCCO3)cc1=O)CCc1cc(OCc3ccccc3)ccc1-2] | 9-benzyloxy-4-[[(2R)-1,4-dioxan-2-yl]methylamino]-1-methyl-6,7-dihydrobenzo[a]quinolizin-2-one | Int 28 | M24 | 433 | 433 |
| 35 | 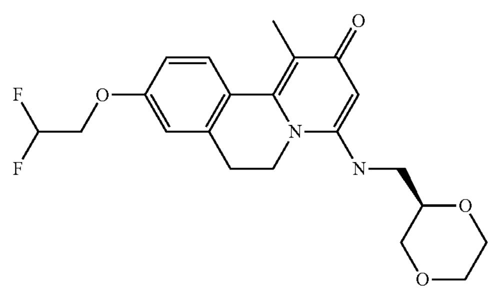 [SMILES: Cc1c2n(c(NC[C@@H]3COCCO3)cc1=O)CCc1cc(OCC(F)F)ccc1-2] | 9-(2,2-difluoroethoxy)-4-[[(2R)-1,4-dioxan-2-yl]methylamino]-1-methyl-6,7-dihydrobenzo[b]quinolizin-2-one | Int 28 | M17 | 406 | 407 |
| 36 | 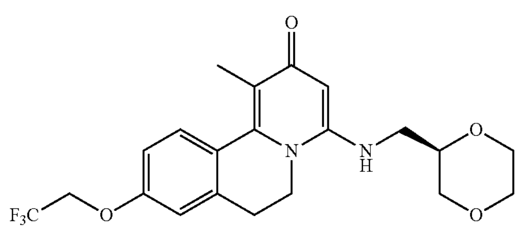 [SMILES: Cc1c2n(c(NC[C@@H]3COCCO3)cc1=O)CCc1cc(OCC(F)(F)F)ccc1-2] | 4-[[(2R)-1,4-dioxan-2-yl]methylamino]-1-mehtyl-9-(2,2,2-trifluoroethoxy)-6,7-dihydrobenzo[a]quinolizin-2-one | Int 28 | M17 | 424 | 425 |
| 37 | 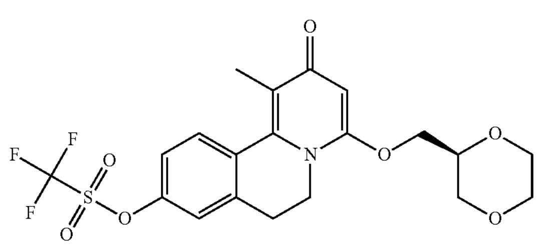 [SMILES: Cc1c2n(c(OC[C@@H]3COCCO3)cc1=O)CCc1cc(OS(=O)(=O)C(F)(F)F)ccc1-2] | [4-[[(2S)-1,4-dioxan-2-yl]methoxy]-1-methyl-2-oxo-6,7-dihydrobenzo[a]quinolizin-9-yl] trifluoromethanesulfonate | Cpd 85 | M18 | 475 | |
| 38 | 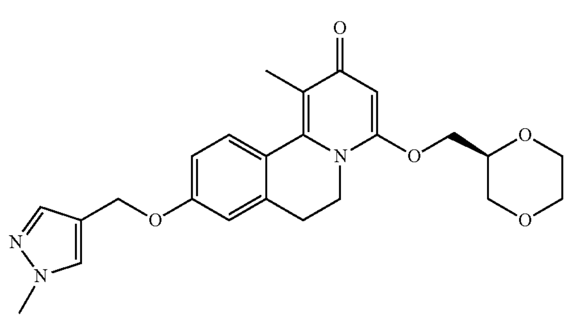 [SMILES: Cc1c2n(c(OC[C@@H]3COCCO3)cc1=O)CCc1cc(OCc3cnn(C)c3)ccc1-2] | 4-[[(2S)-1,4-dioxan-2-yl]methoxy]-1-methyl-9-[(1-methylpyrazol-4-yl)methoxy]-6,7-dihydrobenzo[a]quinolizin-2-one | Cpd 85 | M17 | 438 | 438 |

TABLE III-continued

Illustrative compound of the invention

| Cpd # | Structure | Name | SM | Mtd | MW | Mes |
|---|---|---|---|---|---|---|
| 39 | 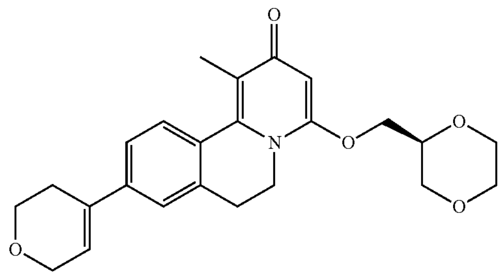 [SMILES: Cc1c2n(c(OC[C@@H]3COCCO3)cc1=O)CCc1cc(C3=CCOCC3)ccc1-2] | 9-(3,6-dihydro-2H-pyran-4-yl)-4-[[(2S)-1,4-dioxan-2-yl]methoxy]-1-methyl-6,7-dihydrobenzo[a]quinolizin-2-one | Cpd 37 | M21 | 409 | 410 |
| 40 | 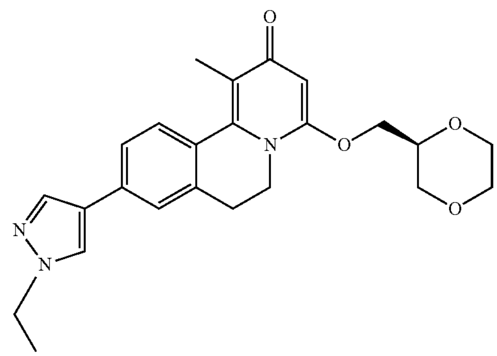 | 4-[[(2S)-1,4-dioxan-2-yl]methoxy]-9-(1-ethylpyrazol-4-yl)-1-methyl-6,7-dihydrobenzo[a]quinolizin-2-one | Cpd 37 | M21 | 422 | 42 |
| 41 | 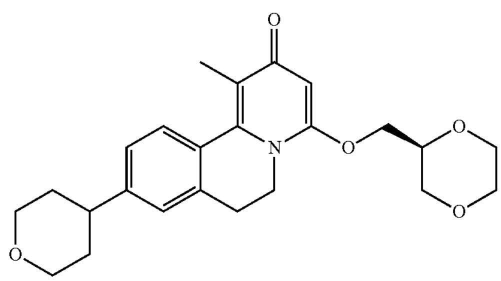 [SMILES: Cc1c2n(c(OC[C@@H]3COCCO3)cc1=O)CCc1cc(C3CCOCC3)ccc1-2] | 4-[[(2S)-1,4-dioxan-2-yl]methoxy]-1-methyl-9-tetrahydropyran-4-yl-6,7-dihydrobenzo[a]quinolizin-2-one | Cpd 39 | M29 | 412 | 412 |
| 42 | 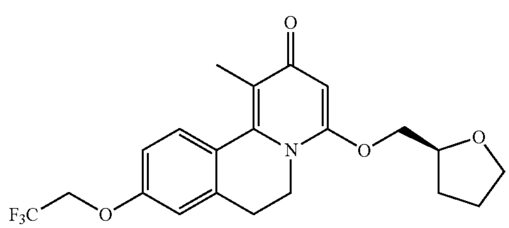 [SMILES: Cc1c2n(c(OC[C@@H]3CCCO3)cc1=O)CCc1cc(OCC(F)(F)F)ccc1-2] | 1-methyl-4-[[(2S)-tetrahydrofuran-2-yl]methylamino]-9-(2,2,2-trifluoroethoxy)-6,7-dihydrobenzo[a]quinolizin-2-one | Int 23 | M17 | 408 | 409 |
| 43 | 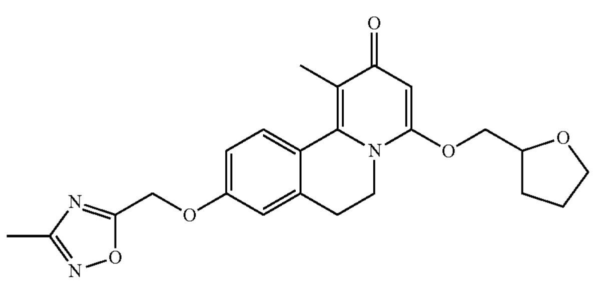 [SMILES: Cc1noc(COc2ccc3c(c2)CCn2c(OCC4CCCO4)cc(=O)c(C)c2-3)n1] | 1-methyl-9-[(3-methyl-1,2,4-oxadiazol-5-yl)methoxy]-4-(tetrahydrofuran-2-ylmethoxy)-6,7-dihydrobenzo[a]quinolizin-2-one | Int 25 | M17 | 423 | 424 |

TABLE III-continued

Illustrative compound of the invention

| Cpd # | Structure | Name | SM | Mtd | MW | Mes |
|---|---|---|---|---|---|---|
| 44 | 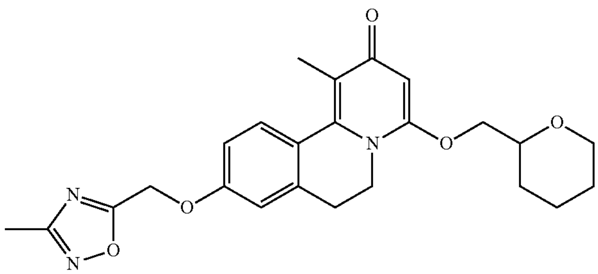 [SMILES: Cc1noc(COc2ccc3c(c2)CCn2c(OCC4CCCCO4)cc(=O)c(C)c2-3)n1] | 1-methyl-9-[(3-methyl-1,2,4-oxadiazol-5-yl)methoxy]-4-(tetrahydropyran-2-ylmethoxy)-6,7-dihydrobenzo[a]quinolizin-2-one | Int 26 | M17 | 438 | 438 |
| 45 | 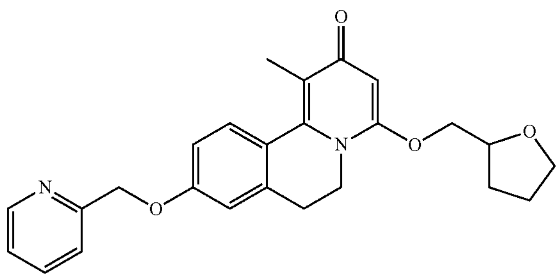 [SMILES: Cc1c2n(c(OCC3CCCO3)cc1=O)CCc1cc(OCc3ccccn3)ccc1-2] | 1-methyl-9-(2-pyridylmethoxy)-4-(tetrahydrofuran-2-ylmethoxy)-6,7-dihydrobenzo[a]quinolizin-2-one | Int 25 | M17 | 418 | 419 |
| 46 | 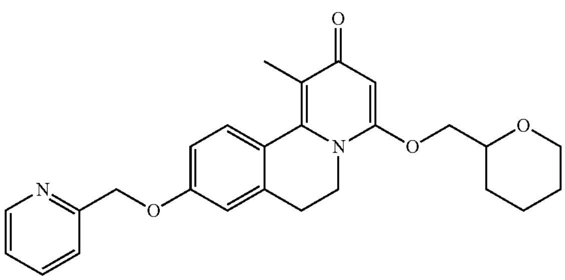 [SMILES: Cc1c2n(c(OCC3CCCCO3)cc1=O)CCc1cc(OCc3ccccn3)ccc1-2] | 1-methyl-9-(2-pyridylmethoxy)-4-(tetrahydropyran-2-ylmethoxy)-6,7-dihydrobenzo[a]quinolizin-2-one | Int 26 | M17 | 433 | 433 |
| 47 | 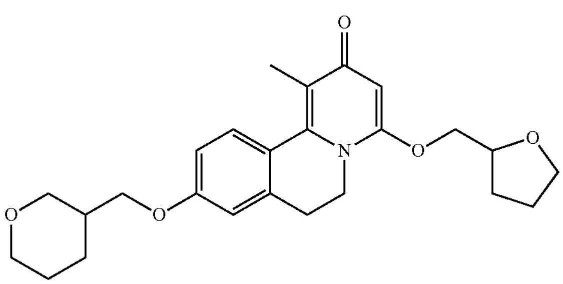 [SMILES: Cc1c2n(c(OCC3CCCO3)cc1=O)CCc1cc(OCC3CCCOC3)ccc1-2] | 1-methyl-4-(tetrahydrofuran-2-ylmethoxy)-9-(tetrahydropyran-3-ylmethoxy)-6,7-dihydrobenzo[a]quinolizin-2-one | Int 25 | M17 | 426 | 426 |
| 48 | 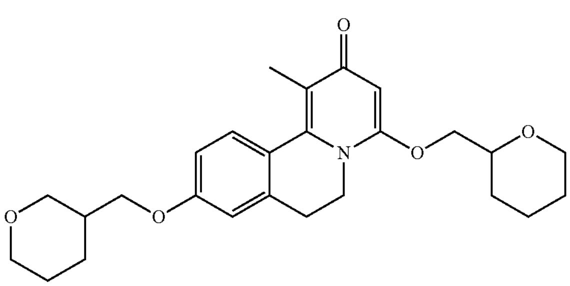 [SMILES: Cc1c2n(c(OCC3CCCCO3)cc1=O)CCc1cc(OCC3CCCOC3)ccc1-2] | 1-methyl-4-(tetrahydropyran-2-ylmethoxy)-9-(tetrahydropyran-3-ylmethoxy)-6,7-dihydrobenzo[a]quinolizin-2-one | Int 26 | M17 | 440 | 440 |

TABLE III-continued

Illustrative compound of the invention

| Cpd # | Structure | Name | SM | Mtd | MW | Mes |
|---|---|---|---|---|---|---|
| 49 | 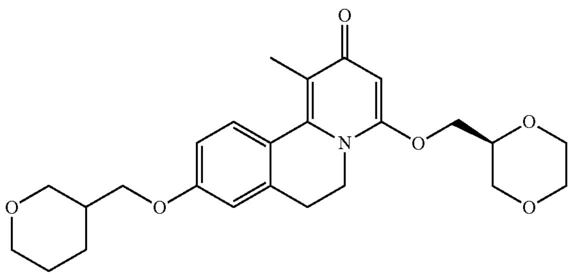 [SMILES: Cc1c2n(c(OC[C@@H]3COCCO3)cc1=O)CCc1cc(OCC3CCCOC3)ccc1-2] | 4-[[(2S)-1,4-dioxan-2-yl]methoxy]-1-methyl-9-(tetrahydropyran-3-ylmethoxy)-6,7-dihydrobenzo[a]quinolizin-2-one | Cpd 85 | M17 | 442 | 442 |
| 50 | 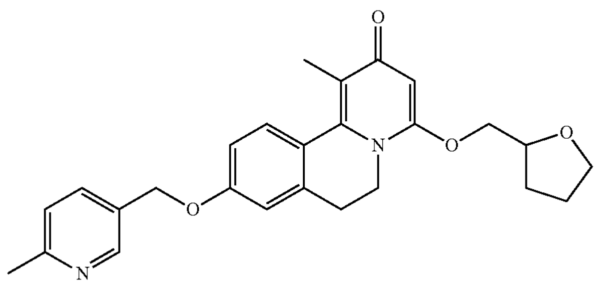 [SMILES: Cc1ccc(COc2ccc3c(c2)CCn2c(OCC4CCCO4)cc(=O)c(C)c2-3)cn1] | 1-methyl-9-[(6-methyl-3-pyridyl)methoxy]-4-(tetrahydrofuran-2-ylmethoxy)-6,7-dihydrobenzo[a]quinolizin-2-one | Int 25 | M17 | 433 | 433 |
| 51 | 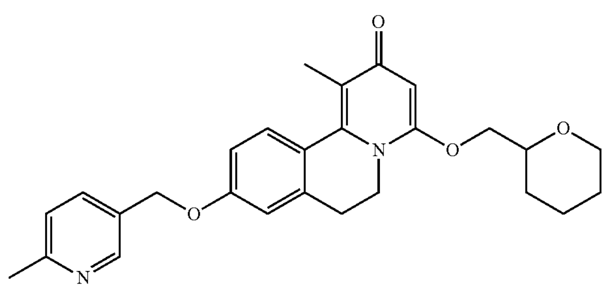 [SMILES: Cc1ccc(COc2ccc3c(c2)CCn2c(OCC4CCCCO4)cc(=O)c(C)c2-3)cn1] | 1-methyl-9-[(6-methyl-3-pyridyl)methoxy]-4-(tetrahydropyran-2-ylmethoxy)-6,7-dihydrobenzo[a]quinolizin-2-one | Int 26 | M17 | 447 | 447 |
| 52 | 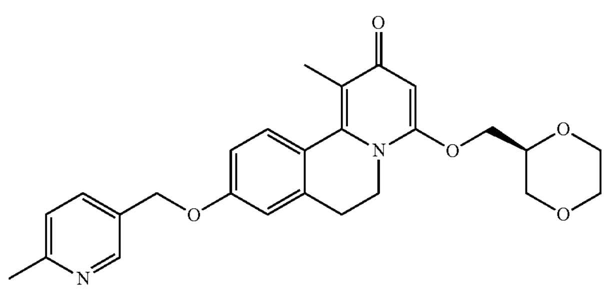 [SMILES: Cc1ccc(COc2ccc3c(c2)CCn2c(OC[C@@H]4COCCO4)cc(=O)c(C)c2-3)cn1] | 4-[[(2S)-1,4-dioxan-2-yl]methoxy]-1-methyl-9-[(6-methyl-3-pyridyl)methoxy]-6,7-dihydrobenzo[a]quinolizin-2-one | Cpd 85 | M17 | 449 | 449 |
| 53 | 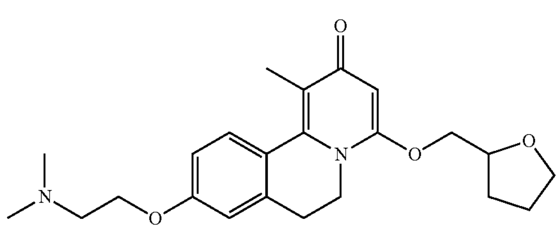 [SMILES: Cc1c2n(c(OCC3CCCO3)cc1=O)CCc1cc(OCCN(C)C)ccc1-2] | 9-(2-dimethylaminoethyloxy)-1-methyl-4-(tetrahydrofuran-2-ylmethoxy)-6,7-dihydrobenzo[a]quinolizin-2-one | Int 25 | M17 | 399 | 399 |

TABLE III-continued

Illustrative compound of the invention

| Cpd # | Structure | Name | SM | Mtd | MW | Mes |
|---|---|---|---|---|---|---|
| 54 | 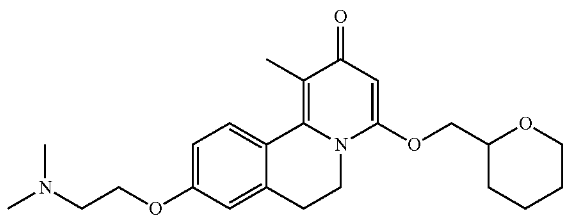 [SMILES: Cc1c2n(c(OCC3CCCCO3)cc1=O)CCc1cc(OCCN(C)C)ccc1-2] | 9-(2-dimethylaminoethyloxy)-1-methyl-4-(tetrahydropyran-2-ylmethoxy)-6,7-dihydrobenzo[a]quinolizin-2-one | Int 26 | M17 | 413 | 413 |
| 55 | 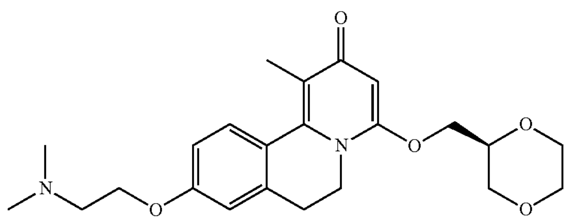 [SMILES: Cc1c2n(c(OC[C@@H]3COCCO3)cc1=O)CCc1cc(OCCN(C)C)ccc1-2] | 9-(2-dimethylaminoethyloxy)-4-[[(2S)-1,4-dioxan-2-yl]methoxy]-1-methyl-6,7-dihydrobenzo[a]quinolizin-2-one | Cpd 85 | M17 | 415 | 415 |
| 56 | 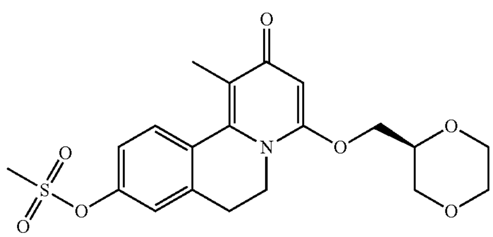 [SMILES: Cc1c2n(c(OC[C@@H]3COCCO3)cc1=O)CCc1cc(OS(C)(=O)=O)ccc1-2] | [4-[[(2S)-1,4-dioxan-2-yl]methoxy]-1-methyl-2-oxo-6,7-dihydrobenzo[a]quinolizin-9-yl] methanesulfonate | Cpd 85 | M17 | 421 | 422 |
| 57 | 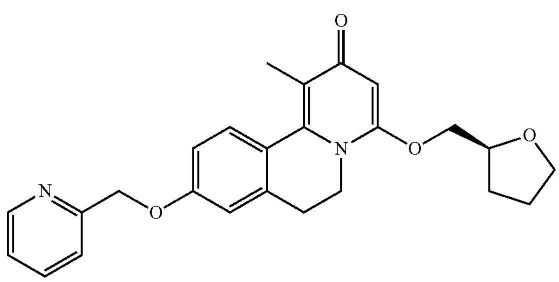 [SMILES: Cc1c2n(c(OC[C@@H]3CCCO3)cc1=O)CCc1cc(OCc3ccccn3)ccc1-2] | 1-methyl-9-(2-pyridylmethoxy)-4-[[(2S)-tetrahydrofuran-2-yl]methoxy]-6,7-dihydrobenzo[a]quinolizin-2-one | Int 25 | M17 | 418 | 419 |
| 58 | 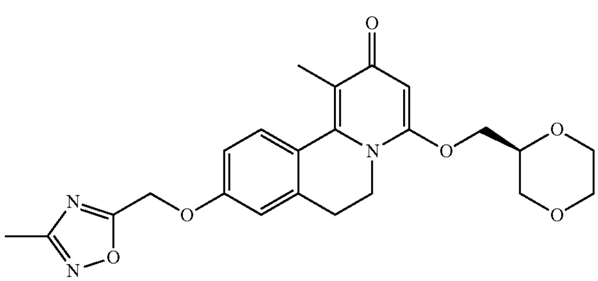 [SMILES: Cc1noc(COc2ccc3c(c2)CCn2c(OC[C@@H]4COCCO4)cc(=O)c(C)c2-3)n1] | 4-[[(2S)-1,4-dioxan-2-yl]methoxy]-1-methyl-9-[(3-methyl-1,2,4-oxadiazol-5-yl)methoxy]-6,7-dihydrobenzo[a]quinolizin-2-one | Cpd 85 | M17 | 439 | 440 |
| 59 | 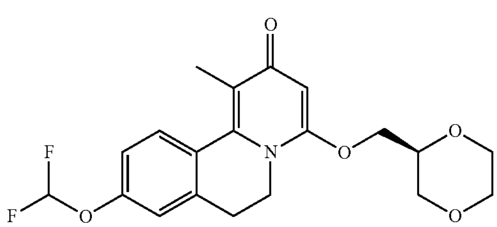 [SMILES: Cc1c2n(c(OC[C@@H]3COCCO3)cc1=O)CCc1cc(OC(F)F)ccc1-2] | 9-(difluoromethoxy)-4-[[(2S)-1,4-dioxan-2-yl]methoxy]-1-methyl-6,7-dihydrobenzo[a]quinolizin-2-one | Cpd 85 | Described above | 393 | 394 |

TABLE III-continued

Illustrative compound of the invention

| Cpd # | Structure | Name | SM | Mtd | MW | Mes |
|---|---|---|---|---|---|---|
| 60 | 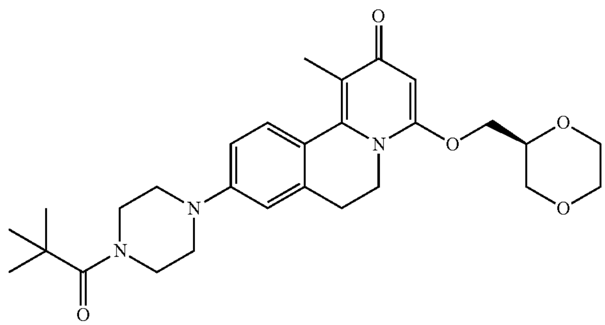 [SMILES: Cc1c2n(c(OC[C@@H]3COCCO3)cc1=O)CCc1cc(N3CCN(C(=O)C(C)(C)C)CC3)ccc1-2] | tert-butyl 4-[4-[[(2S)-1,4-dioxan-2-yl]methoxy]-1-methyl-2-oxo-6,7-dihydrobenzo[a]quinolizin-9-yl]piperazine-1-carboxylate | Cpd 37 | M19 | 512 | 512 |
| 61 | 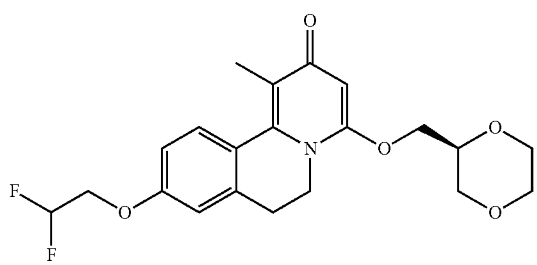 [SMILES: Cc1c2n(c(OC[C@@H]3COCCO3)cc1=O)CCc1cc(OCC(F)F)ccc1-2] | 9-(2,2-difluoroethoxy)-4-[[(2S)-1,4-dioxan-2-yl]methoxy]-1-methyl-6,7-dihydrobenzo[a]quinolizin-2-one | Cpd 85 | M17 | 407 | 408 |
| 62 | 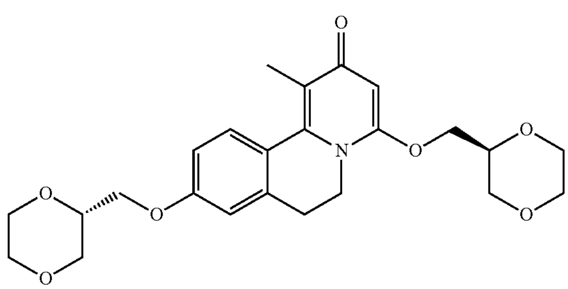 [SMILES: Cc1c2n(c(OC[C@@H]3COCCO3)cc1=O)CCc1cc(OC[C@@H]3COCCO3)ccc1-2] | 4,9-bis[[(2S)-1,4-dioxan-2-yl]methoxy]-1-methyl-6,7-dihydrobenzo[a]quinolizin-2-one | Cpd 85 | M17 | 443 | 444 |
| 63 | 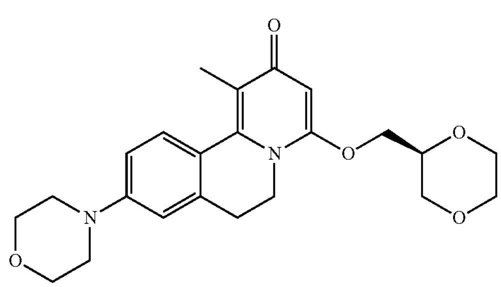 | 4-[[(2S)-1,4-dioxan-2-yl]methoxy]-1-methyl-9-morpholino-6,7-dihydrobenzo[a]quinolizin-2-one | Cpd 37 | M19 | 412 | 413 |
| 64 | 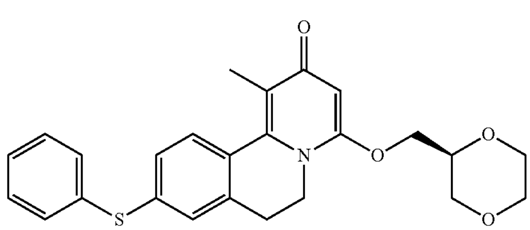 [SMILES: Cc1c2n(c(OC[C@@H]3COCCO3)cc1=O)CCc1cc(Sc3ccccc3)ccc1-2] | 4-[[(2S)-1,4-dioxan-2-yl]methoxy]-1-methyl-9-phenylsulfanyl-6,7-dihydrobenzo[a]quinolizin-2-one | Cpd 37 | Described above | 436 | 436 |

TABLE III-continued

Illustrative compound of the invention

| Cpd # | Structure | Name | SM | Mtd | MW | Mes |
|---|---|---|---|---|---|---|
| 65 | 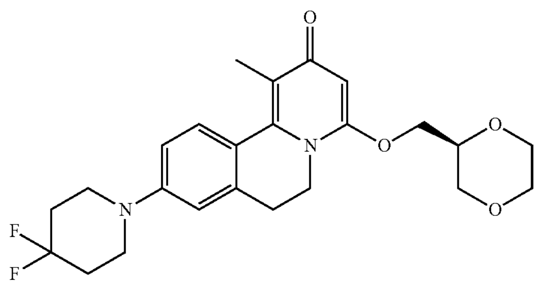 [SMILES: Cc1c2n(c(OC[C@@H]3COCCO3)cc1=O)CCc1cc(N3CCC(F)(F)CC3)ccc1-2] | 9-(4,4-difluoro-1-piperidyl)-4-[[(2S)-1,4-dioxan-2-yl]methoxy]-1-methyl-6,7-dihydrobenzo[a]quinolizin-2-one | Cpd 37 | M19 | 446 | 447 |
| 66 | 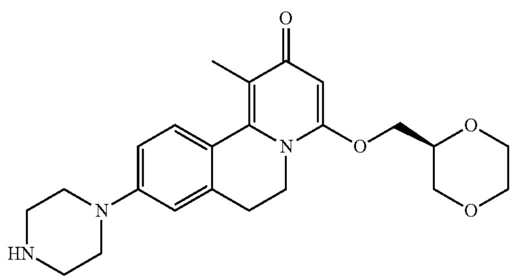 | 4-[[(2S)-1,4-dioxan-2-yl]methoxy]-1-methyl-9-piperazin-1-yl-6,7-dihydrobenzo[a]quinolizin-2-one | Cpd 60 | M27 | 412 | 412 |
| 67 | 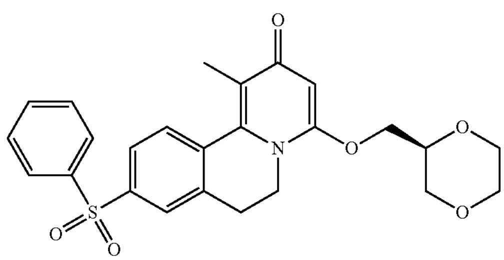 [SMILES: Cc1c2n(c(OC[C@@H]3COCCO3)cc1=O)CCc1cc(S(=O)(=O)c3ccccc3)ccc1-2] | 9-(benzenesulfonyl)-4-[[(2S)-1,4-dioxan-2-yl]methoxy]-1-methyl-6,7-dihydrobenzo[a]quinolizin-2-one | Cpd 64 | Described above | 468 | 468 |
| 68 | 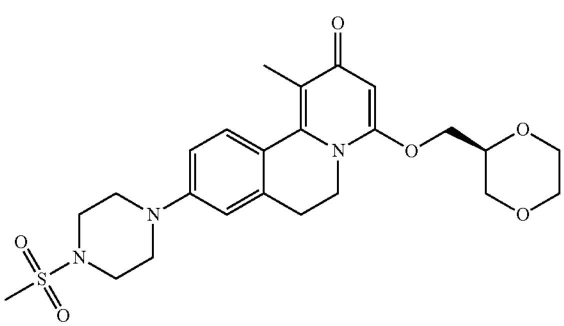 [SMILES: Cc1c2n(c(OC[C@@H]3COCCO3)cc1=O)CCc1cc(N3CCN(S(C)(=O)=O)CC3)ccc1-2] | 4-[[(2S)-1,4-dioxan-2-yl]methoxy]-1-methyl-9-(4-methylsulfonyl)piperazin-1-yl)-6,7-dihydrobenzo[a]quinolizin-2-one | Cpd 66 | M28 | 490 | 490 |
| 69 | 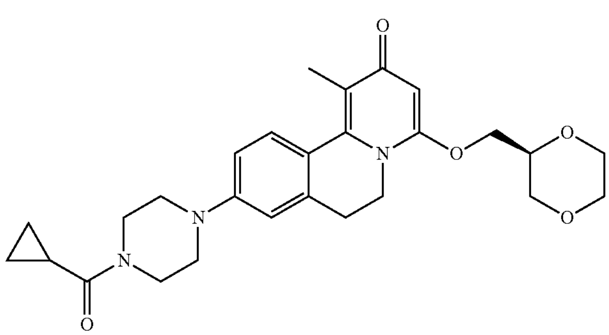 [SMILES: Cc1c2n(c(OC[C@@H]3COCCO3)cc1=O)CCc1cc(N3CCN(C(=O)C4CC4)CC3)ccc1-2] | 9-[4-(cyclopropanecarbonyl)piperazin-1-yl]-4-[[(2S)-1,4-dioxan-2-yl]methoxy]-1-methyl-6,7-dihydrobenzo[a]quinolizin-2-one | Cpd 66 | M28 | 480 | 480 |

TABLE III-continued

Illustrative compound of the invention

| Cpd # | Structure | Name | SM | Mtd | MW | Mes |
|---|---|---|---|---|---|---|
| 70 | 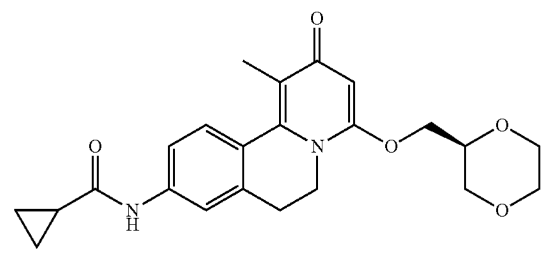 [SMILES: Cc1c2n(c(OC[C@@H]3COCCO3)cc1=O)CCc1cc(NC(=O)C3CC3)ccc1-2] | N-[4-[[(2S)-1,4-dioxan-2-yl]methoxy]-1-methyl-2-oxo-6,7-dihydrobenzo[a]quinolizin-9-yl]cyclopropane carboxamide | Cpd 37 | Water activated Buchwald | 410 | 411 |
| 71 | 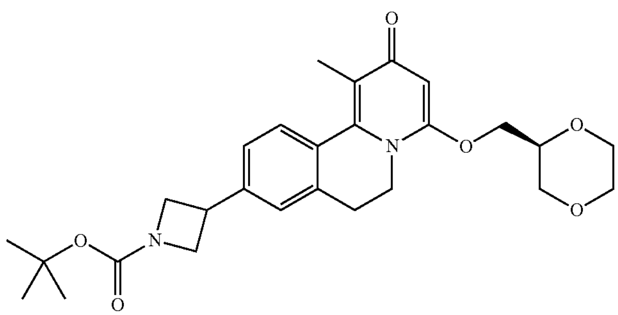 [SMILES: Cc1c2n(c(OC[C@@H]3COCCO3)cc1=O)CCc1cc(C3CN(C(=O)OC(C)(C)C)C3)ccc1-2] | tert-butyl 3-[4-[[(2S)-1,4-dioxan-2-yl]methoxy]-1-methyl-2-oxo-6,7-dihydrobenzo[a]quinolizin-9-yl]azetidine-1-carboxylate | Cpd 37 | M22 | 483 | 483 |
| 72 | 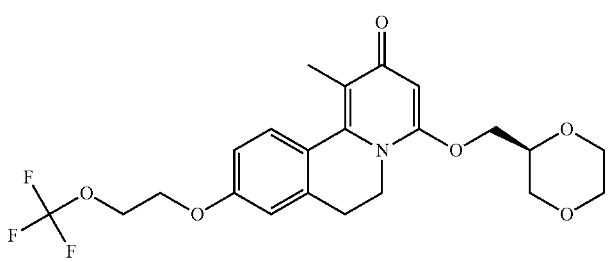 [SMILES: Cc1c2n(c(OC[C@@H]3COCCO3)cc1=O)CCc1cc(OCCOC(F)(F)F)ccc1-2] | 4-[[(2S)-1,4-dioxan-2-yl]methoxy]-1-methyl-9-[2-(trifluoromethoxy)ethoxy]-6,7-dihydrobenzo[a]quinolizin-2-one | Cpd 85 | M17 | 455 | 456 |
| 73 | 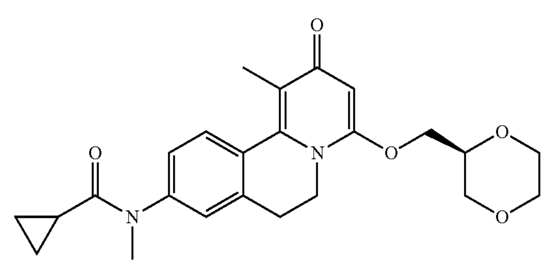 [SMILES: Cc1c2n(c(OC[C@@H]3COCCO3)cc1=O)CCc1cc(N(C)C(=O)C3CC3)ccc1-2] | N-[4-[[(2S)-1,4-dioxan-2-yl]methoxy]-1-methyl-2-oxo-6,7-dihydrobenzo[a]quinolizin-9-yl]-N-methyl-cyclopropanecarboxamide | Cpd 70 | described above | 425 | 425 |
| 74 | 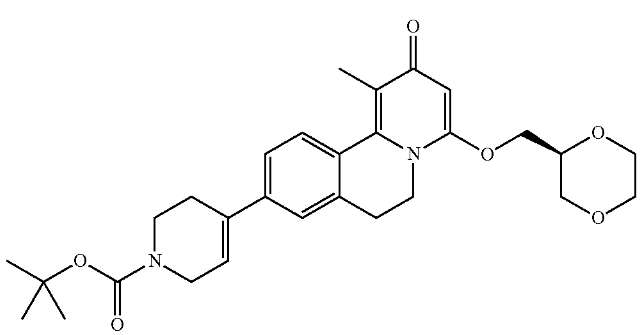 [SMILES: Cc1c2n(c(OC[C@@H]3COCCO3)cc1=O)CCc1cc(C3=CCN(C(=O)OC(C)(C)C)CC3)ccc1-2] | tert-butyl 4-[4-[[(2S)-1,4-dioxan-2-yl]methoxy]-1-methyl-2-oxo-6,7-dihydrobenzo[a]qunolizin-9-yl]-3,6-dihydro-2H-pyridine-1-carboxylate | Cpd 37 | M21 | 509 | 509 |

TABLE III-continued

Illustrative compound of the invention

| Cpd # | Structure | Name | SM | Mtd | MW | Mes |
|---|---|---|---|---|---|---|
| 75 | 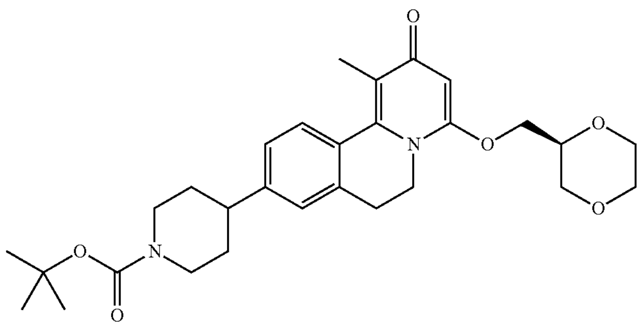 [SMILES: Cc1c2n(c(OC[C@@H]3COCCO3)cc1=O)CCc1cc(C3CCN(C(=O)OC(C)(C)C)CC3)ccc1-2] | tert-butyl 4-[4-[[(2S)-1,4-dioxan-2-yl]methoxy]-1-methyl-2-oxo-6,7-dihydrobenzo[a]quinolizin-9-yl]piperidine-1-carboxylate | Cpd 74 | M29 | 511 | 511 |
| 76 | 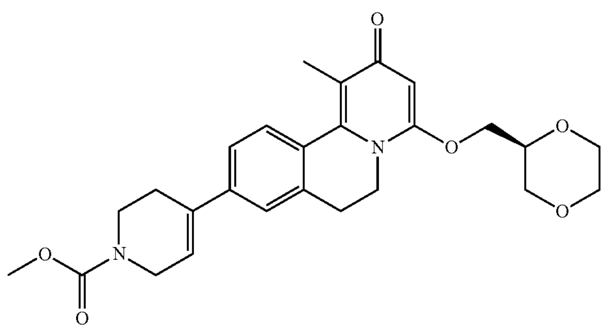 [SMILES: COC(=O)N1CC=C(c2ccc3c(c2)CCn2c(OC[C@@H]4COCCO4)cc(=O)c(C)c2-3)CC1] | methyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate | Int 29 | M28 | 467 | 467 |
| 77 | 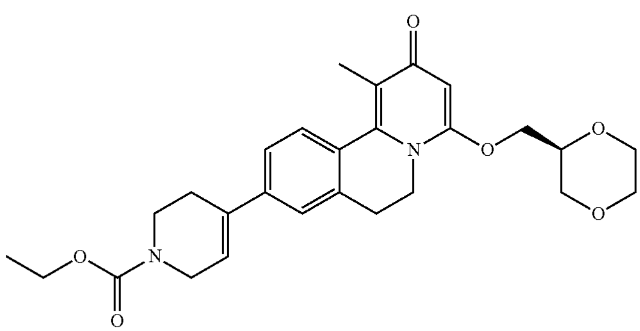 [SMILES: CCOC(=O)N1CC=C(c2ccc3c(c2)CCn2c(OC[C@@H]4COCCO4)cc(=O)c(C)c2-3)CC1] | ethyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate | Int 29 | M28 | 481 | 481 |
| 78 | 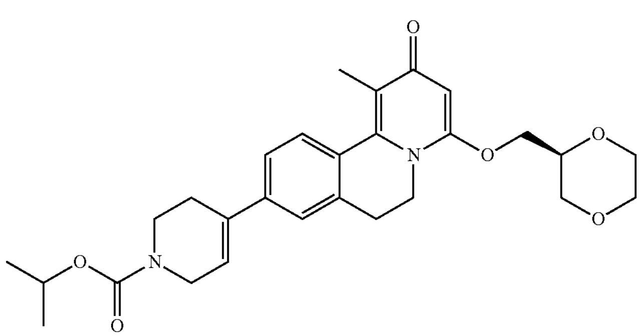 [SMILES: Cc1c2n(c(OC[C@@H]3COCCO3)cc1=O)CCc1cc(C3=CCN(C(=O)OC(C)C)CC3)ccc1-2] | isopropyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate | Int 29 | M28 | 495 | 495 |

TABLE III-continued

Illustrative compound of the invention

| Cpd # | Structure | Name | SM | Mtd | MW | Mes |
|---|---|---|---|---|---|---|
| 79 | 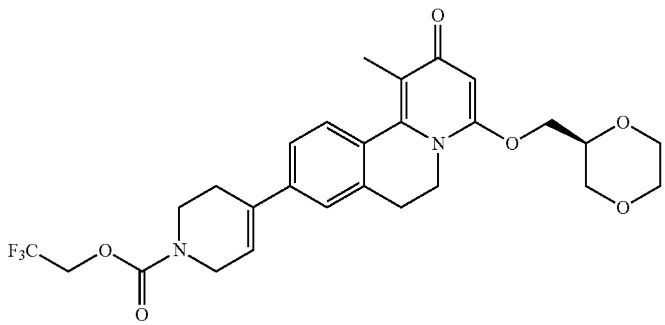 [SMILES: Cc1c2n(c(OC[C@@H]3COCCO3)cc1=O)CCc1cc(C3=CCN(C(=O)OCC(F)(F)F)CC3)ccc1-2] | 2,2,2-trifluoroethyl 4-[4-[[(2S)-1,4-dioxan-2-yl]methoxy]-1-methyl-2-oxo-6,7-dihydrobenzo[a]quinolizin-9-yl]-3,6-dihydro-2H-pyridine-1-carboxylate | Int 29 | M28 | 535 | 535 |
| 80 | 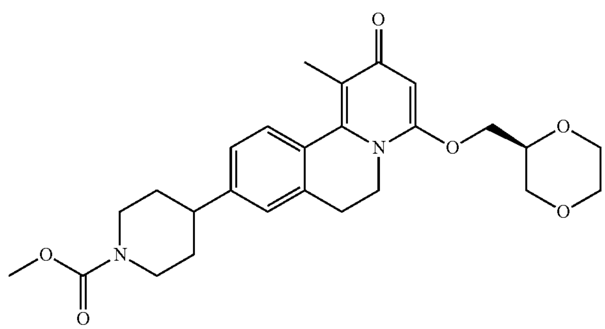 [SMILES: COC(=O)N1CCC(c2ccc3c(c2)CCn2c(OC[C@@H]4COCCO4)cc(=O)c(C)c2-3)CC1] | methyl 4-[4-[[(2S)-1,4-dioxan-2-yl]methoxy]-1-methyl-2-oxo-6,7-dihydrobenzo[a]quinolizin-9-yl]piperidine-1-carboxylate | Int 30 | M28 | 469 | 469 |
| 81 | 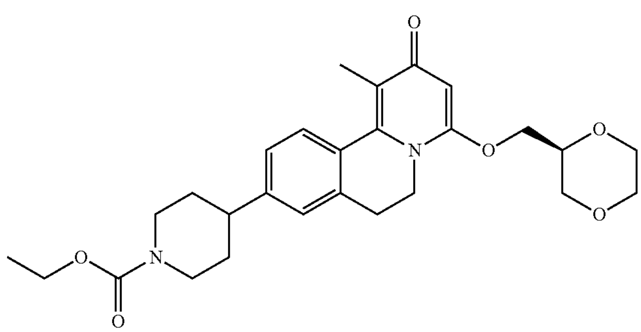 [SMILES: CCOC(=O)N1CCC(c2ccc3c(c2)CCn2c(OC[C@@H]4COCCO4)cc(=O)c(C)c2-3)CC1] | ethyl 4-[4-[[(2S)-1,4-dioxan-2-yl]methoxy]-1-methyl-2-oxo-6,7-dihydrobenzo[a]quinolizin-9-yl]piperidine-1-carboxylate | Int 30 | M28 | 483 | 483 |
| 82 | 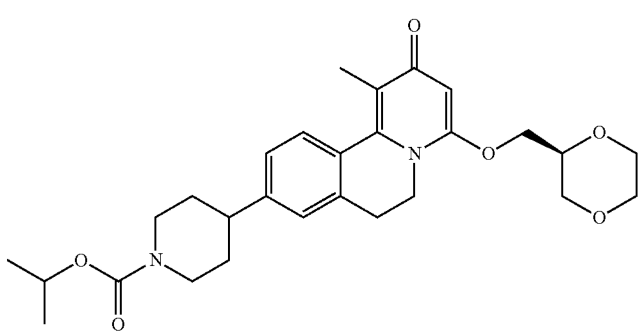 [SMILES: Cc1c2n(c(OC[C@@H]3COCCO3)cc1=O)CCc1cc(C3CCN(C(=O)OC(C)C)CC3)ccc1-2] | isopropyl 4-[4-[[(2S)-1,4-dioxan-2-yl]methoxy]-1-methyl-2-oxo-6,7-dihydrobenzo[a]quinolizin-9-yl]piperidine-1-carboxylate | Int 30 | M28 | 497 | 497 |

TABLE III-continued

Illustrative compound of the invention

| Cpd # | Structure | Name | SM | Mtd | MW | Mes |
|---|---|---|---|---|---|---|
| 83 | 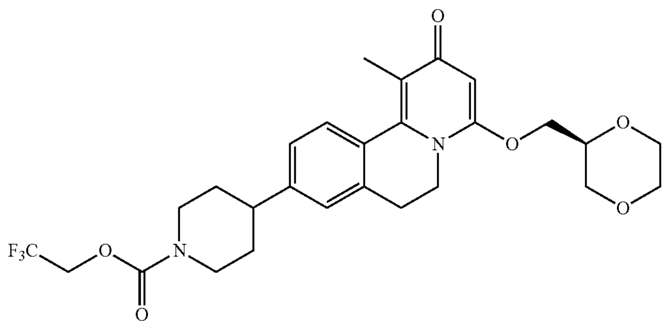 [SMILES: Cc1c2n(c(OC[C@@H]3COCCO3)cc1=O)CCc1cc(C3CCN(C(=O)OCC(F)(F)F)CC3)ccc1-2] | 2,2,2-trifluoroethyl 4-[4-[[(2S)-1,4-dioxan-2-yl]methoxy]-1-methyl-2-oxo-6,7-dihydrobenzo[a]quinolizin-9-yl]piperidine-1-carboxylate | Int 30 | M28 | 537 | 537 |
| 84 | 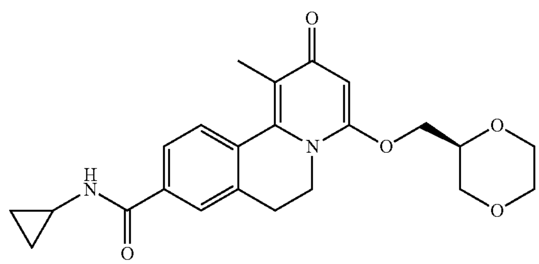 [SMILES: Cc1c2n(c(OC[C@@H]3COCCO3)cc1=O)CCc1cc(C(=O)NC3CC3)ccc1-2] | N-cyclopropyl-4-[[(2S)-1,4-dioxan-2-yl]methoxy]-1-methyl-2-oxo-6,7-dihydrobenzo[a]quinolizine-9-carboxamide | Cpd 37 | Described above | 410 | 411 |
| 85 | 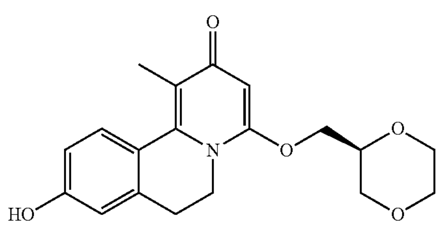 [SMILES: Cc1c2n(c(OC[C@@H]3COCCO3)cc1=O)CCc1cc(O)ccc1-2] | 4-[[(2S)-1,4-dioxan-2-yl]methoxy]-9-hydroxy-1-methyl-6,7-dihydrobenzo[a]quinolizin-2-one | Cpd 33 | Described above | 343 | 344 |
| 86 | 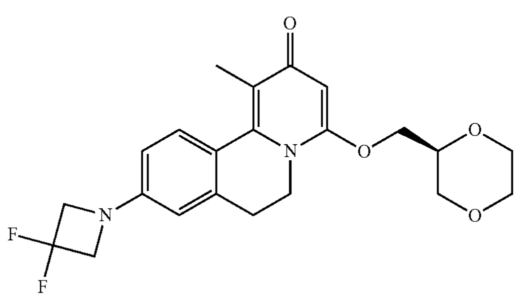 [SMILES: Cc1c2n(c(OC[C@@H]3COCCO3)cc1=O)CCc1cc(N3CC(F)(F)C3)ccc1-2] | 9-(3,3-difluoroazetidin-1-yl)-4-[[(2S)-1,4-dioxan-2-yl]methoxy]-1-methyl-6,7-dihydrobenzo[a]quinolizin-2-one | Cpd 37 | M19 | 418 | 419 |
| 87 | 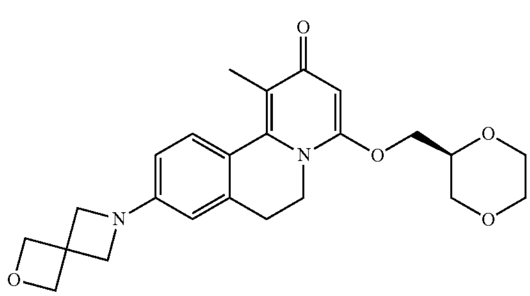 [SMILES: Cc1c2n(c(OC[C@@H]3COCCO3)cc1=O)CCc1cc(N3CC4(COC4)C3)ccc1-2] | 4-[[(2S)-1,4-dioxan-2-yl]methoxy]-1-methyl-9-(6-oxa-2-azaspiro[3.3]heptan-2-yl)-6,7-dihydrobenzo[a]quinolizin-2-one | Cpd 37 | M19 | 424 | 425 |

TABLE III-continued

Illustrative compound of the invention

| Cpd # | Structure | Name | SM | Mtd | MW | Mes |
|---|---|---|---|---|---|---|
| 88 | 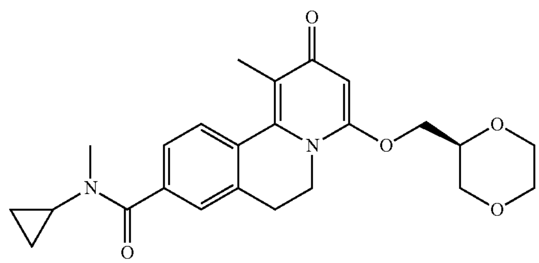 [SMILES: Cc1c2n(c(OC[C@@H]3COCCO3)cc1=O)CCc1cc(C(=O)N(C)C3CC3)ccc1-2] | N-cyclopropyl-4-[[(2)S-1,4-dioxan-2-yl]methoxy]-N,1-dimethyl-2-oxo-6,7-dihydrobenzo[a]quinolizine-9-carboxamide | Cpd 37 | Pd-Catalyzed Aminocarbonylation | 425 | 425 |
| 89 | 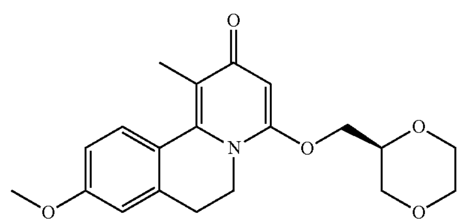 [SMILES: COc1ccc2c(c1)CCn1c(OC[C@@H]3COCCO3)cc(=O)c(C)c1-2] | 4-[[(2S)-1,4-dioxan-2-yl]methoxy]-9-methoxy-1-methyl-6,7-dihydrobenzo[a]quinolizin-2-one | Cpd 85 | M17 | 357 | 358 |
| 90 | racemic | 4-(1,4-dioxan-2-ylmethoxy)-1-methyl-9-(2,2,2-trifluoroethoxy)-6,7-dihydrobenzo[a]quinolizin-2-one | Int 113 | M17 | 425 | 426 |
| 91 | 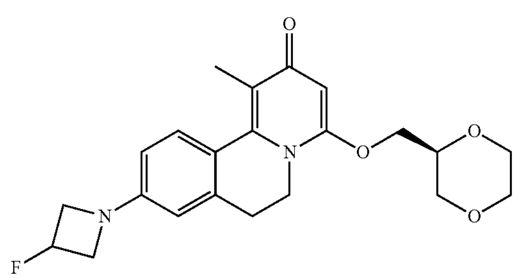 [SMILES: Cc1c2n(c(OC[C@@H]3COCCO3)cc1=O)CCc1cc(N3CC(F)C3)ccc1-2] | 4-[[(2S)-1,4-dioxan-2-yl]methoxy]-9-(3-fluoroazetidin-1-yl)-1-methyl-6,7-dihydrobenzo[a]quinolizin-2-one | Cpd 37 | M19 | 400 | 401 |
| 92 | 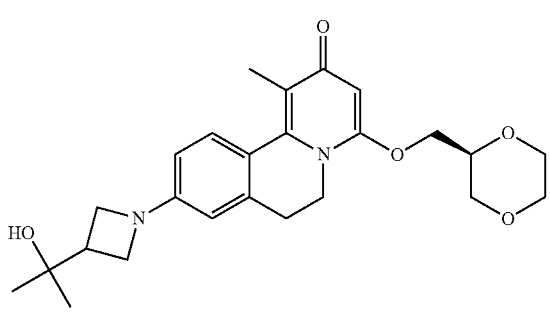 [SMILES: Cc1c2n(c(OC[C@@H]3COCCO3)cc1=O)CCc1cc(N3CC(C(C)(C)O)C3)ccc1-2] | 4-[[(2S)-1,4-dioxan-2-yl]methoxy]-9-[3-(1-hydroxy-1-methyl-ethyl)azetidin-1-yl]-1-methyl-6,7-dihydrobenzo[a]quinolizin-2-one | Cpd 37 | M19 | 441 | 441 |

TABLE III-continued

Illustrative compound of the invention

| Cpd # | Structure | Name | SM | Mtd | MW | Mes |
|---|---|---|---|---|---|---|
| 93 | 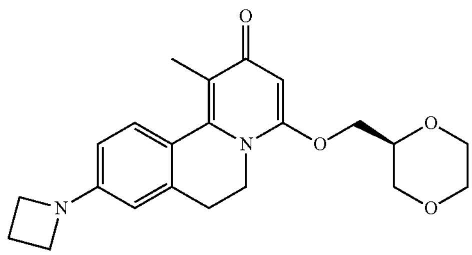 [SMILES: Cc1c2n(c(OC[C@@H]3COCCO3)cc1=O)CCc1cc(N3CCC3)ccc1-2] | 9-(azetidin-1-yl)-4-[[(2S)-1,4-dioxan-2-yl]methoxy]-1-methyl-6,7-dihydrobenzo[a]quinolizin-2-one | Cpd 37 | M19 | 382 | 383 |
| 94 | 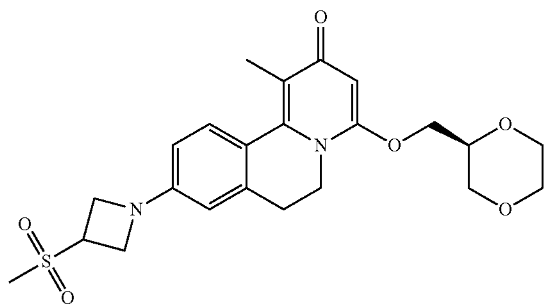 [SMILES: Cc1c2n(c(OC[C@@H]3COCCO3)cc1=O)CCc1cc(N3CC(S(C)(=O)=O)C3)ccc1-2] | 4-[[(2S)-1,4-dioxan-2-yl]methoxy]-1-methyl-9-(3-methylsulfonylazetidin-1-yl)-6,7-dihydrobenzo[a]quinolizin-2-one | Cpd 37 | M19 | 461 | 461 |
| 95 | 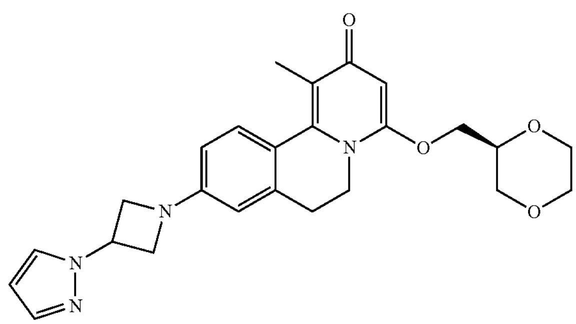 [SMILES: Cc1c2n(c(OC[C@@H]3COCCO3)cc1=O)CCc1cc(N3CC(n4cccn4)C3)ccc1-2] | 4-[[(2S)-1,4-dioxan-2-yl]methoxy]-1-methyl-9-(3-pyrazol-1-ylazetidin-1-yl)-6,7-dihydrobenzo[a]quinolizin-2-one | Cpd 37 | M19 | 449 | 449 |
| 96 | 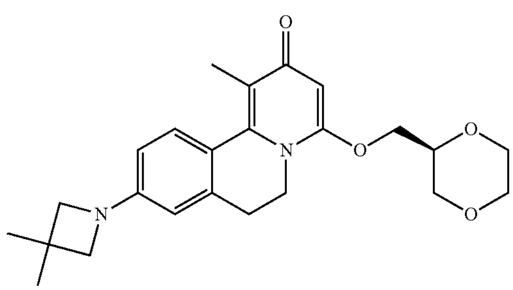 [SMILES: Cc1c2n(c(OC[C@@H]3COCCO3)cc1=O)CCc1cc(N3CC(C)(C)C3)ccc1-2] | 9-(3,3-dimethylazetidin-1-yl)-4-[[(2S)-1,4-dioxan-2-yl]methoxy]-1-methyl-6,7-dihydrobenzo[a]quinolizin-2-one | Cpd 37 | M19 | 411 | 411 |
| 97 | 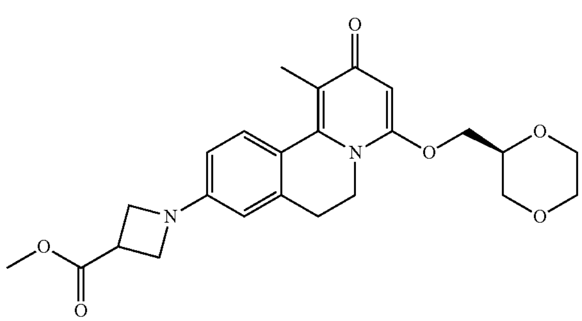 [SMILES: COC(=O)C1CN(c2ccc3c(c2)CCn2c(OC[C@@H]4COCCO4)cc(=O)c(C)c2-3)C1] | methyl 1-[4-[[(2S)-1,4-dioxan-2-yl]methoxy]-1-methyl-2-oxo-6,7-dihydrobenzo[a]quinolliz-in-9-yl]azetidine-3-carboxylate | Cpd 37 | M19 | 440 | 441 |

TABLE III-continued

Illustrative compound of the invention

| Cpd # | Structure | Name | SM | Mtd | MW | Mes |
|---|---|---|---|---|---|---|
| 98 | 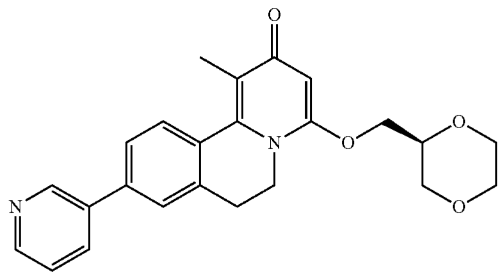 [SMILES: Cc1c2n(c(OC[C@@H]3COCCO3)cc1=O)CCc1cc(-c3cccnc3)ccc1-2] | 4-[[(2S)-1,4-dioxan-2-yl]methoxy]-1-methyl-9-(3-pyridyl)-6,7-dihydrobenzo[a]quinolizin-2-one | Cpd 37 | M21 | 404 | 405 |
| 99 | 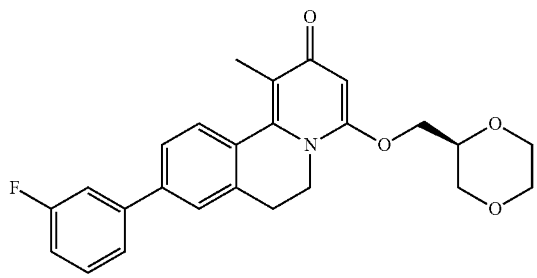 [SMILES: Cc1c2n(c(OC[C@@H]3COCCO3)cc1=O)CCc1cc(-c3cccc(F)c3)ccc1-2] | 4-[[(2S)-1,4-dioxan-2-yl]methoxy]-9-(3-fluorophenyl)-1-methyl-6,7-dihydrobenzo[a]quinolizin-2-one | Cpd 37 | M21 | 421 | 421 |
| 100 | 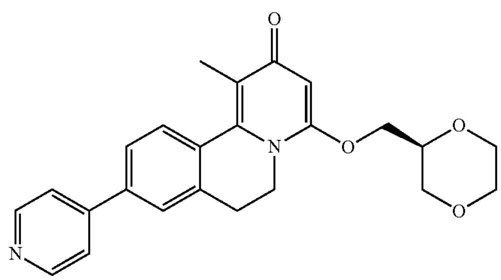 [SMILES: Cc1c2n(c(OC[C@@H]3COCCO3)cc1=O)CCc1cc(-c3ccncc3)ccc1-2] | 4-[[(2S)-1,4-dioxan-2-yl]methoxy]-1-methyl-9-(4-pyridyl)-6,7-dihydrobenzo[a]quinolizin-2-one | Cpd 37 | M21 | 404 | 405 |
| 101 | 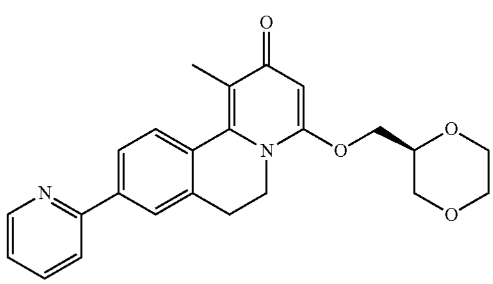 [SMILES: Cc1c2n(c(OC[C@@H]3COCCO3)cc1=O)CCc1cc(-c3ccccn3)ccc1-2] | 4-[[(2S)-1,4-dioxan-2-yl]methoxy]-1-methyl-9-(2-pyridyl)-6,7-dihydrobenzo[a]quinolizin-2-one | Cpd 37 | M21 | 404 | 405 |
| 102 | 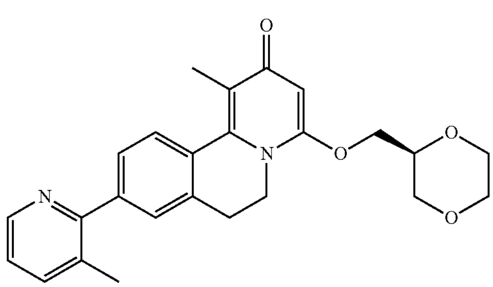 [SMILES: Cc1cccnc1-c1ccc2c(c1)CCn1c(OC[C@@H]3COCCO3)cc(=O)c(C)c1-2] | 4-[[(2S)-1,4-dioxan-2-yl]methoxy]-1-methyl-9-(3-methyl-2-pyridyl)-6,7-dihydrobenzo[a]quinolizin-2-one | Cpd 37 | M21 | 418 | 419 |

TABLE III-continued

Illustrative compound of the invention

| Cpd # | Structure | Name | SM | Mtd | MW | Mes |
|---|---|---|---|---|---|---|
| 103 | 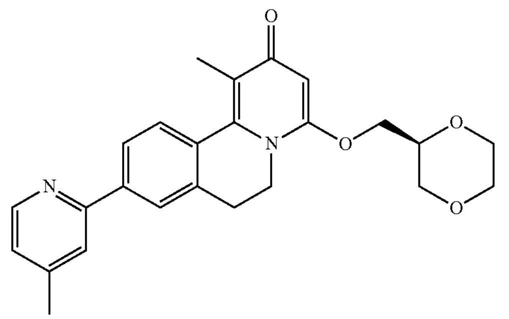 [SMILES: Cc1ccnc(-c2ccc3c(c2)CCn2c(OC[C@@H]4COCCO4)cc(=O)c(C)c2-3)c1] | 4-[[(2S)-1,4-dioxan-2-yl]methoxy]-1-methyl-9-(4-methyl-2-pyridyl)-6,7-dihydrobenzo[a]quinolizin-2-one | Cpd 37 | M21 | 418 | 419 |
| 104 | 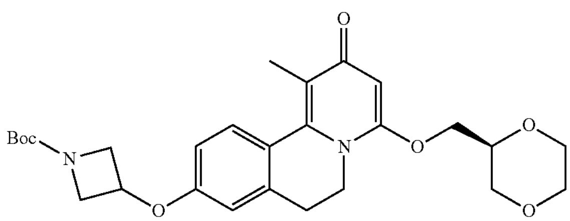 [SMILES: Cc1c2n(c(OC[C@@H]3COCCO3)cc1=O)CCc1cc(OC3CN(C(=O)OC(C)(C)C)C3)ccc1-2] | tert-butyl 3-[[4-[[(2S)-1,4-dioxan-2-yl]methoxy]-1-methyl-2-oxo-6,7-dihydrobenzo[a]quinolizin-9-yl]oxy]azetidine-1-carboxylate | Cpd 85 | M17 | 499 | 499 |
| 105 | 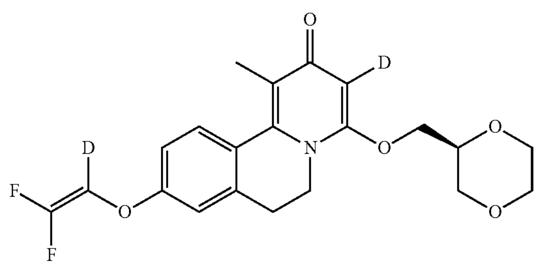 [SMILES: [2H]C(Oc1ccc2c(c1)CCn1c(OC[C@@H]3COCCO3)c([2H])c(=O)c(C)c1-2)=C(F)F] | 3-deuterio-9-(1-deuterio-2,2-difluoro-vinyloxy)-4-[[(2S)-1,4-dioxan-2-yl]methoxy]-1-methyl-6,7-dihydrobenzo[a]quinolizin-2-one | Cpd 18 | Lithiation-deuteration | 407 | 408 |
| 106 | 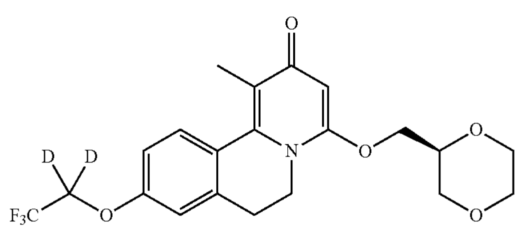 [SMILES: [2H]C([2H])(Oc1ccc2c(c1)CCn1c(OC[C@@H]3COCCO3)cc(=O)c(C)c1-2)C(F)(F)F] | 9-(1,1-dideuterio-2,2,2-trifluoro-ethoxy)-4-[[(2S)-1,4-dioxan-2-yl]methoxy]-1-methyl-6,7-dihydrobenzo[a]quinolizin-2-one | Cpd 85 | M17 | 427 | 428 |
| 107 | 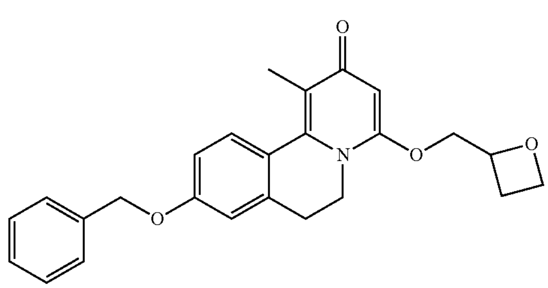 [SMILES: Cc1c2n(c(OCC3CCO3)cc1=O)CCc1cc(OCc3ccccc3)ccc1-2] | 9-benzyloxy-1-methyl-4-(oxetan-2-ylmethoxy)-6,7-dihydrobenzo[a]quinolizin-2-one | Int 24 | M15 | 403 | 404 |

TABLE III-continued

Illustrative compound of the invention

| Cpd # | Structure | Name | SM | Mtd | MW | Mes |
|---|---|---|---|---|---|---|
| 108 | 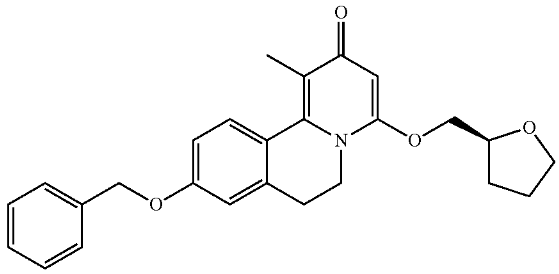 [SMILES: Cc1c2n(c(OC[C@@H]3CCCO3)cc1=O)CCc1cc(OCc3ccccc3)ccc1-2] | 9-benzyloxy-1-methyl-4-[[(2S)-tetrahydrofuran-2-yl]methoxy]-6,7-dihydrobenzo[a]quinolizin-2-one | Int 24 | M15 | 418 | 418 |
| 109 | 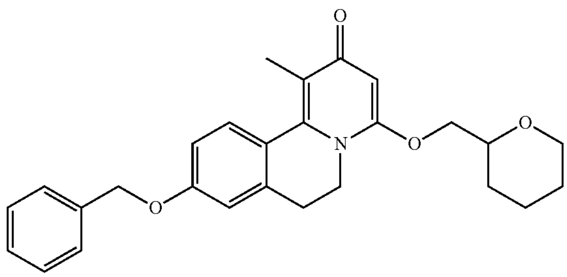 [SMILES: Cc1c2n(c(OCC3CCCCO3)cc1=O)CCc1cc(OCc3ccccc3)ccc1-2] | 9-benzyloxy-1-methyl-4-(tetrahydropyran-2-ylmethoxy)-6,7-dihydrobenzo[a]quinolizin-2-one | Int 24 | M15 | 432 | 432 |
| 110 | 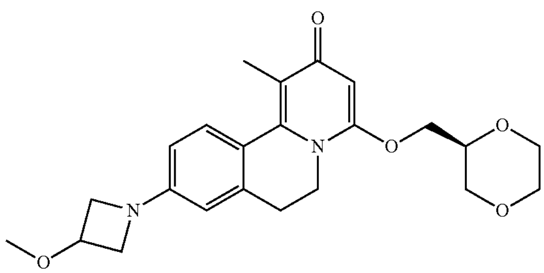 [SMILES: COC1CN(c2ccc3c(c2)CCn2c(OC[C@@H]4COCCO4)cc(=O)c(C)c2-3)C1] | 4-[[(2S)-1,4-dioxan-2-yl]methoxy]-9-(3-methoxyazetidin-1-yl)-1-methyl-6,7-dihydrobenzo[a]quinolizin-2-one | Cpd 37 | M19 | 412 | 413 |
| 111 | 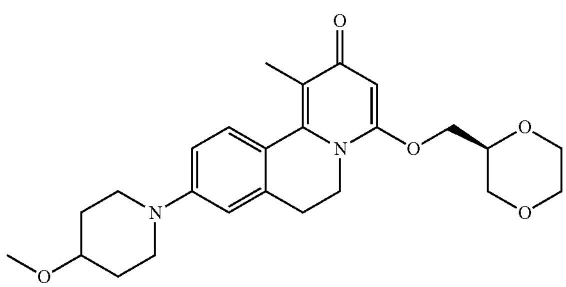 [SMILES: COC1CCN(c2ccc3c(c2)CCn2c(OC[C@@H]4COCCO4)cc(=O)c(C)c2-3)CC1] | 4-[[(2S)-1,4-dioxan-2-yl]methoxy]-9-(4-methoxy-1-piperidyl)-1-methyl-6,7-dihydrobenzo[a]quinolizin-2-one | Cpd 37 | M19 | 441 | 441 |
| 112 | 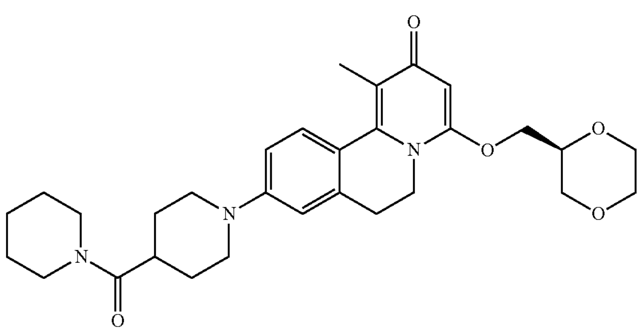 [SMILES: Cc1c2n(c(OC[C@@H]3COCCO3)cc1=O)CCc1cc(N3CCC(C(=O)N4CCCCC4)CC3)ccc1-2] | 4-[[(2S)-1,4-dioxan-2-yl]methoxy]-1-methyl-9-[4-(piperidine-1-carbonyl)-1-piperidyl]-6,7-dihydrobenzo[a]quinolizin-2-one | Cpd 37 | M19 | 522 | 522 |

TABLE III-continued

Illustrative compound of the invention

| Cpd # | Structure | Name | SM | Mtd | MW | Mes |
|---|---|---|---|---|---|---|
| 113 | 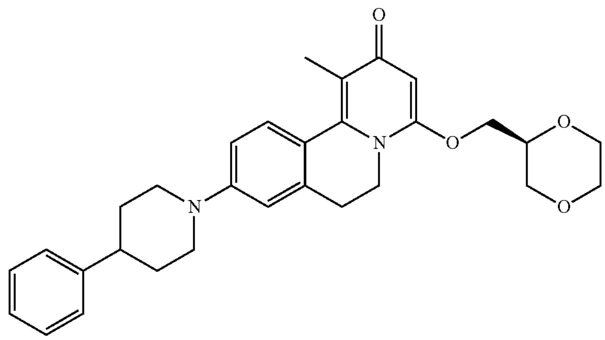 [SMILES: Cc1c2n(c(OC[C@@H]3COCCO3)cc1=O)CCc1cc(N3CCC(c4ccccc4)CC3)ccc1-2] | 4-[[(2S)-1,4-dioxan-2-yl]methoxy]-1-methyl-9-(4-phenyl-1-piperidyl)-6,7-dihydrobenzo[a]quinolizin-2-one | Cpd 37 | M19 | 487 | 487 |
| 114 | | methyl 1-[4-[[(2S)-1,4-dioxan-2-yl]methoxy]-1-methyl-2-oxo-6,7-dihydrobenzo[a]quinolizin-9-yl]piperidine-4-carboxylate | Cpd 37 | M19 | 469 | 469 |
| 114 | | 4-[[(2S)-1,4-dioxan-2-yl]methoxy]-9-[4-(ethoxymethyl)-1-piperidyl]-1-methyl-6,7-dihydrobenzo[a]quinolizin-2-one | Cpd 37 | M19 | 469 | 469 |
| 115 | 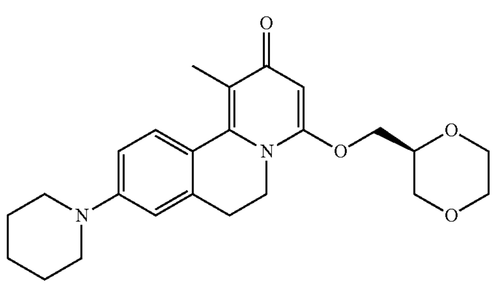 [SMILES: Cc1c2n(c(OC[C@@H]3COCCO3)cc1=O)CCc1cc(N3CCCCC3)ccc1-2] | 4-[[(2S)-1,4-dioxan-2-yl]methoxy]-1-methyl-9-(1-piperidyl)-6,7-dihydrobenzo[a]quinolizin-2-one | Cpd 37 | M19 | 411 | 411 |
| 116 | 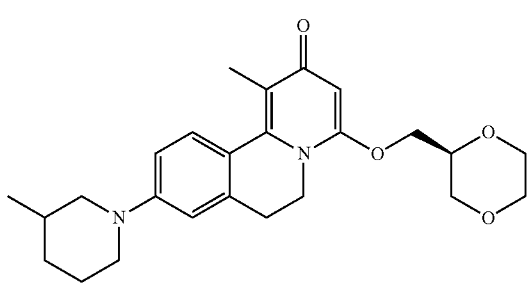 [SMILES: Cc1c2n(c(OC[C@@H]3COCCO3)cc1=O)CCc1cc(N3CCCC(C)C3)ccc1-2] | 4-[[(2S)-1,4-dioxan-2-yl]methoxy]-1-methyl-9-(3-methyl-1-piperidyl)-6,7-dihydrobenzo[a]quinolizin-2-one | Cpd 37 | M19 | 425 | 425 |

TABLE III-continued

Illustrative compound of the invention

| Cpd # | Structure | Name | SM | Mtd | MW | Mes |
|---|---|---|---|---|---|---|
| 117 | 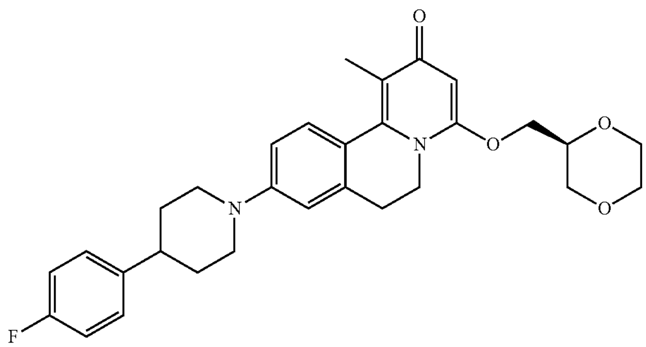 [SMILES: Cc1c2n(c(OC[C@@H]3COCCO3)cc1=O)CCc1cc(N3CCC(c4ccc(F)cc4)CC3)ccc1-2] | 4-[[(2S)-1,4-dioxan-2-yl]methoxy]-9-[4-(4-fluorophenyl)-1-piperidyl]-1-methyl-6,7-dihydrobenzo[a]quinolizin-2-one | Cpd 37 | M19 | 505 | 505 |
| 118 | 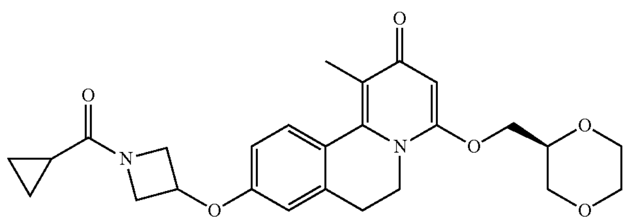 [SMILES: Cc1c2n(c(OC[C@@H]3COCCO3)cc1=O)CCc1cc(OC3CN(C(=O)C4CC4)C3)ccc1-2] | 9-[1-(cyclopropanecarbonyl)azetidin-3-yl]oxy-4-[[(2S)-1,4-dioxan-2-yl]methoxy]-1-methyl-6,7-dihydrobenzo[a]quinolizin-2-one | Int 31 | M28 | 467 | 467 |
| 119 | 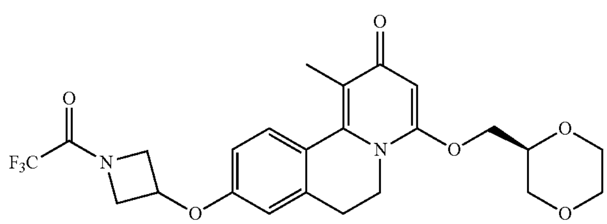 [SMILES: Cc1c2n(c(OC[C@@H]3COCCO3)cc1=O)CCc1cc(OC3CN(C(=O)C(F)(F)F)C3)ccc1-2] | 4-[[(2)S-1,4-dioxan-2-yl]methoxy]-1-methyl-9-[1-(2,2,2-trifluoroacetyl)azetidin-3-yl]oxy-6,7-dihydrobenzo[a]quinolizin-2-one | Int 31 | M28 | 494 | 495 |
| 120 | 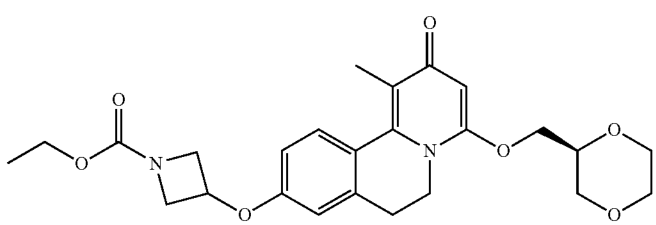 [SMILES: CCOC(=O)N1CC(Oc2ccc3c(c2)CCn2c(OC[C@@H]4COCCO4)cc(=O)c(C)c2-3)C1] | ethyl 3-[[4-[[(2S)-1,4-dioxan-2-yl]methoxy]-1-methyl-2-oxo-6,7-dihydrobenzo[a]quinolizin-9-yl]oxy]azetidine-1-carboxylate | Int 31 | M28 | 471 | 471 |
| 121 | 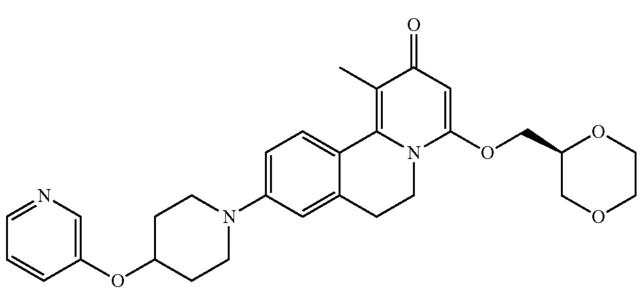 [SMILES: Cc1c2n(c(OC[C@@H]3COCCO3)cc1=O)CCc1cc(N3CCC(Oc4cccnc4)CC3)ccc1-2] | 4-[[(2S)-1,4-dioxan-2-yl]methoxy]-1-methyl-9-[4-(3-pyridyloxy)-1-piperidyl]-6,7-dihydrobenzo[a]quinolizin-2-one | Cpd 37 | M19 | 504 | 504 |

TABLE III-continued

Illustrative compound of the invention

| Cpd # | Structure | Name | SM | Mtd | MW | Mes |
|---|---|---|---|---|---|---|
| 122 | 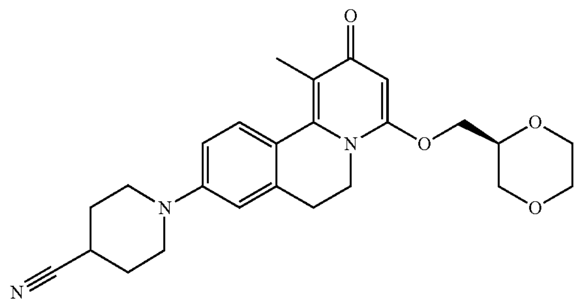 [SMILES: Cc1c2n(c(OC[C@@H]3COCCO3)cc1=O)CCc1cc(N3CCC(C#N)CC3)ccc1-2] | 1-[4-[[(2)S-1,4-dioxan-2-yl]methoxy]-1-methyl-2-oxo-6,7-dihydrobenzo[a]quinolizin-9-yl]piperidine-4-carbonitrile | Cpd 37 | M19 | 436 | 436 |
| 123 | 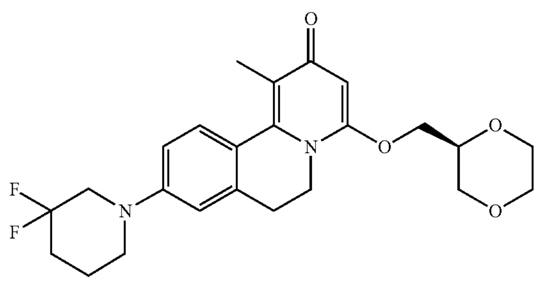 [SMILES: Cc1c2n(c(OC[C@@H]3COCCO3)cc1=O)CCc1cc(N3CCCC(F)(F)C3)ccc1-2] | 9-(3,3-difluoro-1-piperidyl)-4-[[(2S)-1,4-dioxan-2-yl]methoxy]-1-methyl-6,7-dihydrobenzo[a]quinolizin-2-one | Cpd 37 | M19 | 446 | 447 |
| 124 | 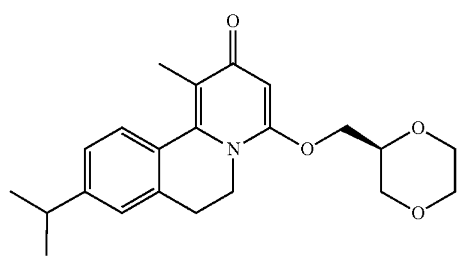 [SMILES: Cc1c2n(c(OC[C@@H]3COCCO3)cc1=O)CCc1cc(C(C)C)ccc1-2] | 4-[[(2S)-1,4-dioxan-2-yl]methoxy]-9-isopropyl-1-methyl-6,7-dihydrobenzo[a]quinolizin-2-one | Cpd 37 | M22 | 369 | 370 |
| 125 | 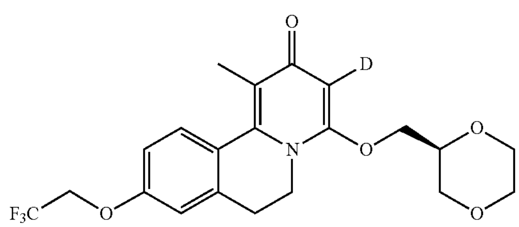 | 3-deuterio-4-[[(2S)-1,4-dioxan-2-yl]methoxy]-1-methyl-9-(2,2,2-trifluoroethoxy)-6,7-dihydrobenzo[a]quinolizin-2-one | Int 126 | Described above | 426 | 427 |
| 126 | 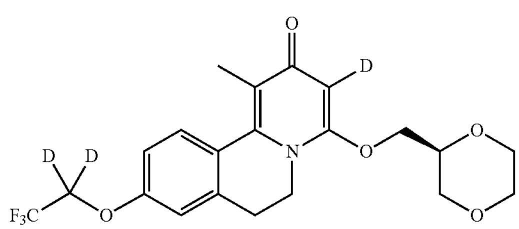 [SMILES: [2H]c1c(OC[C@@H]2COCCO2)n2c(c(C)c1=O)-c1ccc(OC([2H])([2H])C(F)(F)F)cc1CC2] | 3-deuterio-4-[[(2S)-1,4-dioxan-2-yl]methoxy]-1-methyl-9-(1,1,2,2-tetradeuterio-2-fluoro-ethoxy)-6,7-dihydrobenzo[a]quinolizin-2-one | Cpd 105 | Described above | 394 | 395 |
| 127 | 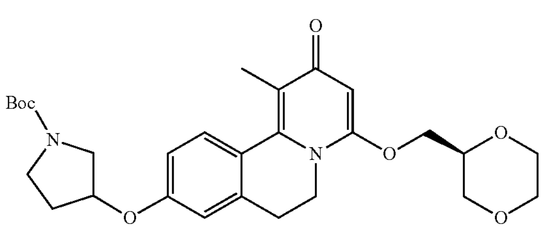 [SMILES: Cc1c2n(c(OC[C@@H]3COCCO3)cc1=O)CCc1cc(OC3CCN(C(=O)OC(C)(C)C)C3)ccc1-2] | tert-butyl 3-[[4-[[(2S)-1,4-dioxan-2-yl]methoxy]-1-methyl-2-oxo-6,7-dihydrobenzo[a]quinolizin-9-yl]oxy]pyrrolidine-1-carboxylate | Cpd 85 | M17 | 513 | 513 |

TABLE III-continued

Illustrative compound of the invention

| Cpd # | Structure | Name | SM | Mtd | MW | Mes |
|---|---|---|---|---|---|---|
| 128 | 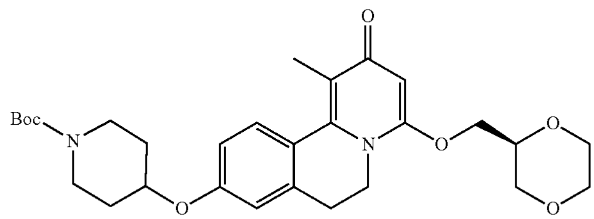 [SMILES: Cc1c2n(c(OC[C@@H]3COCCO3)cc1=O)CCc1cc(OC3CCN(C(=O)OC(C)(C)C)CC3)ccc1-2] | tert-butyl 4-[[4-[[(2S)-1,4-dioxan-2-yl]methoxy]-1-methyl-2-oxo-6,7-dihydrobenzo[a]quinolizin-9-yl]oxy]piperidine-1-carboxylate | Cpd 85 | M17 | 527 | 527 |
| 129 | 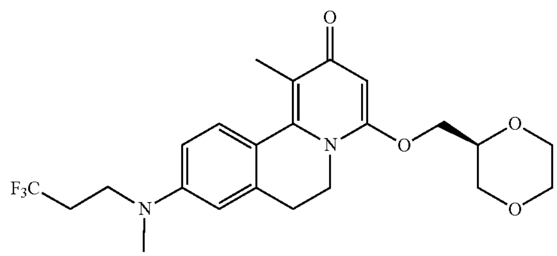 [SMILES: Cc1c2n(c(OC[C@@H]3COCCO3)cc1=O)CCc1cc(N(C)CCC(F)(F)F)ccc1-2] | 4-[[(2S)-1,4-dioxan-2-yl]methoxy]-1-methyl-9-[methyl(3,3,3-trifluoropropyl)amino]-6,7-dihydrobenzo[a]quinolizin-2-one | Cpd 37 | M19 | 453 | 453 |
| 130 | 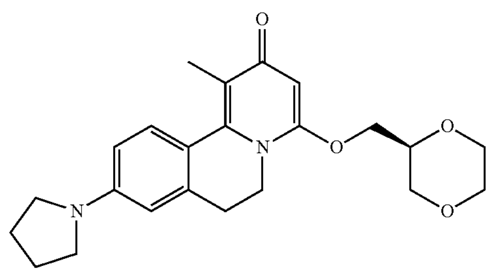 [SMILES: Cc1c2n(c(OC[C@@H]3COCCO3)cc1=O)CCc1cc(N3CCCC3)ccc1-2] | 4-[[(2S)-1,4-dioxan-2-yl]methoxy]-1-methyl-9-pyrrolidin-1-yl-6,7-dihydrobenzo[a]quinolizin-2-one | Cpd 37 | M19 | 396 | 397 |
| 131 | 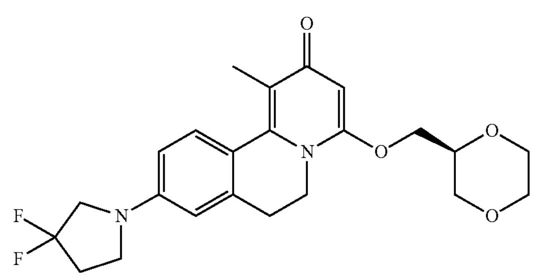 [SMILES: Cc1c2n(c(OC[C@@H]3COCCO3)cc1=O)CCc1cc(N3CCC(F)(F)C3)ccc1-2] | 9-(3,3-difluoropyrrolidin-1-yl)-4-[[(2S)-1,4-dioxan-2-yl]methoxy]-1-methyl-6,7-dihydrobenzo[a]quinolizin-2-one | Cpd 37 | M19 | 432 | 433 |
| 132 | 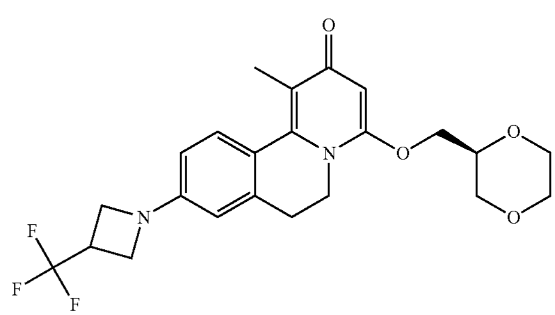 [SMILES: Cc1c2n(c(OC[C@@H]3COCCO3)cc1=O)CCc1cc(N3CC(C(F)(F)F)C3)ccc1-2] | 4-[[(2S)-1,4-dioxan-2-yl]methoxy]-1-methyl-9-[3-(trifluoromethyl)azetidin-1-yl]-6,7-dihydrobenzo[a]quinolizin-2-one | Cpd 37 | M19 | 450 | 451 |

TABLE III-continued

Illustrative compound of the invention

| Cpd # | Structure | Name | SM | Mtd | MW | Mes |
|---|---|---|---|---|---|---|
| 133 | 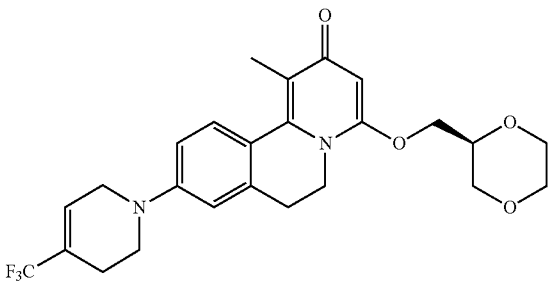 [SMILES: Cc1c2n(c(OC[C@@H]3COCCO3)cc1=O)CCc1cc(N3CC=C(C(F)(F)F)CC3)ccc1-2] | 4-[[(2S)-1,4-dioxan-2-yl]methoxy]-1-methyl-9-[4-(trifluoromethyl)-3,6-dihydro-2H-pyridin-1-yl]-6,7-dihydrobenzo[a]quinolizin-2-one | Cpd 37 | M19 | 476 | 477 |
| 134 | 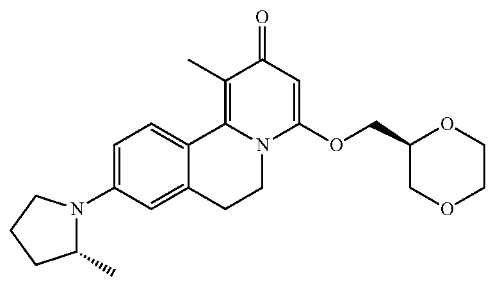 [SMILES: Cc1c2n(c(OC[C@@H]3COCCO3)cc1=O)CCc1cc(N3CCC[C@H]3C)ccc1-2] | 4-[[(2S)-1,4-dioxan-2-yl]methoxy]-1-methyl-9-[(2R)-2-methylpyrrolidin-1-yl]-6,7-dihydrobenzo[a]quinolizin-2-one | Cpd 37 | M19 | 411 | 411 |
| 135 | 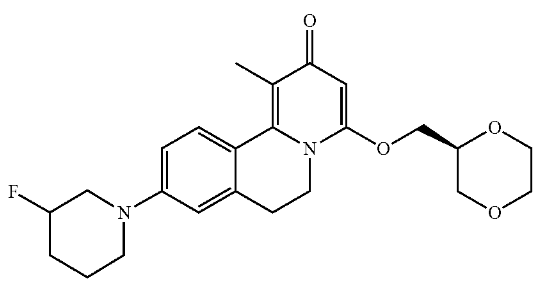 [SMILES: Cc1c2n(c(OC[C@@H]3COCCO3)cc1=O)CCc1cc(N3CCCC(F)C3)ccc1-2] | 4-[[(2S)-1,4-dioxan-2-yl]methoxy]-9-(3-fluoro-1-piperidyl)-1-methyl-6,7-dihydrobenzo[a]quinolizin-2-one | Cpd 37 | M19 | 429 | 429 |
| 136 | 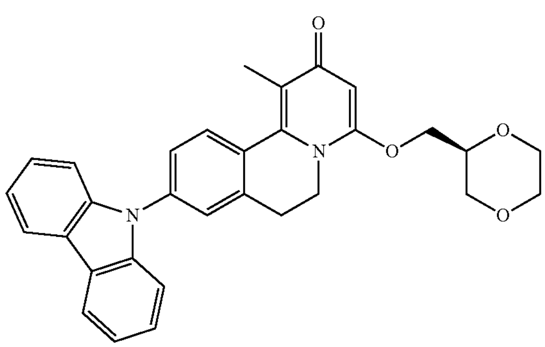 [SMILES: Cc1c2n(c(OC[C@@H]3COCCO3)cc1=O)CCc1cc(-n3c4ccccc4c4ccccc43)ccc1-2] | 9-carbazol-9-yl-4-[[(2S)-1,4-dioxan-2-yl]methoxy]-1-methyl-6,7-dihydrobenzo[a]quinolizin-2-one | Cpd 37 | M19 | 493 | 493 |
| 137 | 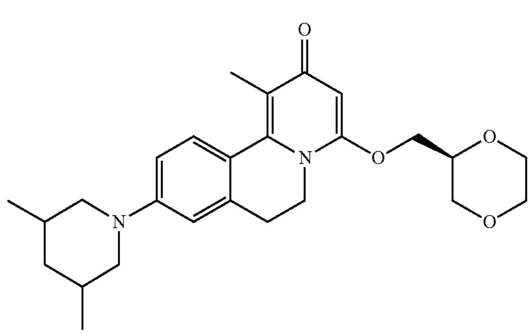 [SMILES: Cc1c2n(c(OC[C@@H]3COCCO3)cc1=O)CCc1cc(N3CC(C)CC(C)C3)ccc1-2] | 9-(3,5-dimethyl-1-piperidyl)-4-[[(2S)-1,4-dioxan-2-yl]methoxy]-1-methyl-6,7-dihydrobenzo[a]quinolizin-2-one | Cpd 37 | M19 | 439 | 439 |

TABLE III-continued

Illustrative compound of the invention

| Cpd # | Structure | Name | SM | Mtd | MW | Mes |
|---|---|---|---|---|---|---|
| 138 | 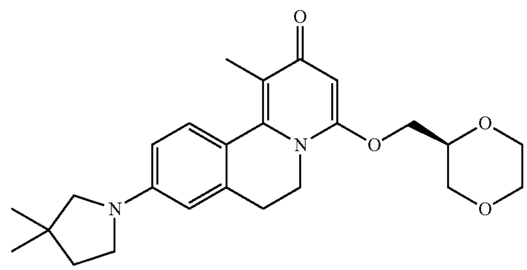 [SMILES: Cc1c2n(c(OC[C@@H]3COCCO3)cc1=O)CCc1cc(N3CCC(C)(C)C3)ccc1-2] | 9-(3,3-dimethylpyrrolidin-1-yl)-4-[[(2S)-1,4-dioxan-2-yl]methoxy]-1-methyl-6,7-dihydrobenzo[a]quinolizin-2-one | Cpd 37 | M19 | 425 | 425 |
| 139 | 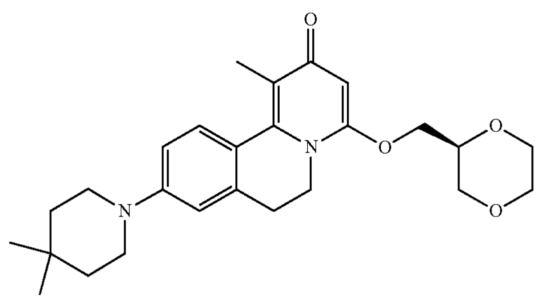 [SMILES: Cc1c2n(c(OC[C@@H]3COCCO3)cc1=O)CCc1cc(N3CCC(C)(C)CC3)ccc1-2] | 9-(4,4-dimethyl-1-piperidyl)-4-[[(2S)-1,4-dioxan-2-yl]methoxy]-1-methyl-6,7-dihydrobenzo[a]quinolizin-2-one | Cpd 37 | M19 | 439 | 439 |
| 140 | 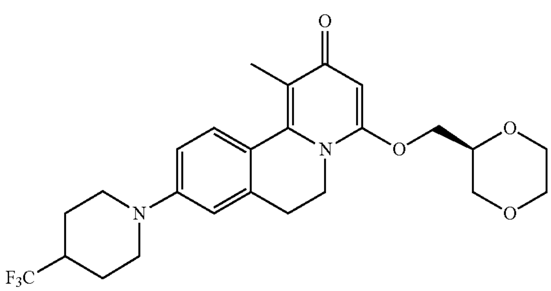 [SMILES: Cc1c2n(c(OC[C@@H]3COCCO3)cc1=O)CCc1cc(N3CCC(C(F)(F)F)CC3)ccc1-2] | 4-[[(2S)-1,4-dioxan-2-yl]methoxy]-1-methyl-9-[4-(trifluoromethyl)-1-piperidyl]-6,7-dihydrobenzo[a]quinolizin-2-one | Cpd 37 | M19 | 479 | 479 |
| 141 | 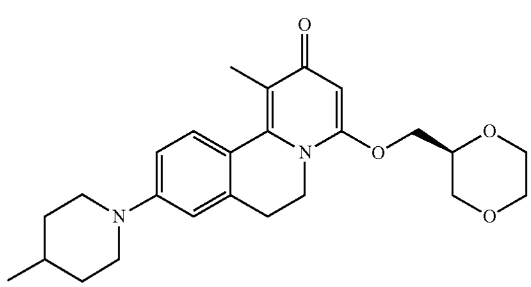 [SMILES: Cc1c2n(c(OC[C@@H]3COCCO3)cc1=O)CCc1cc(N3CCC(C)CC3)ccc1-2] | 4-[[(2S)-1,4-dioxan-2-yl]methoxy]-1-methyl-9-(4-methyl-1-piperidyl)-6,7-dihydrobenzo[a]quinolizin-2-one | Cpd 37 | M19 | 425 | 425 |
| 142 | 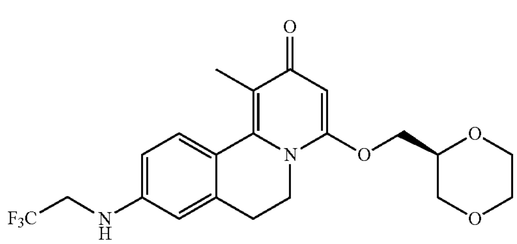 [SMILES: Cc1c2n(c(OC[C@@H]3COCCO3)cc1=O)CCc1cc(NCC(F)(F)F)ccc1-2] | 4-[[(2S)-1,4-dioxan-2-yl]methoxy]-1-methyl-9-(2,2,2-trifluoroethylamino)-6,7-dihydrobenzo[a]quinolizin-2-one | Cpd 37 | M19 | 424 | 425 |

TABLE III-continued

Illustrative compound of the invention

| Cpd # | Structure | Name | SM | Mtd | MW | Mes |
|---|---|---|---|---|---|---|
| 143 | 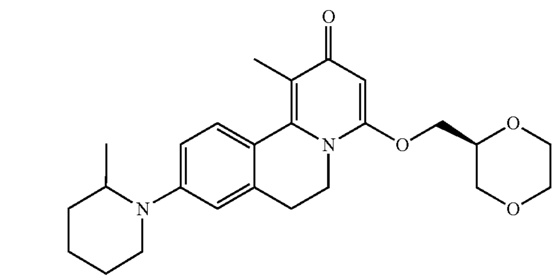 [SMILES: Cc1c2n(c(OC[C@@H]3COCCO3)cc1=O)CCc1cc(N3CCCCC3C)ccc1-2] | 4-[[(2S)-1,4-dioxan-2-yl]methoxy]-1-methyl-9-(2-methyl-1-piperidyl)-6,7-dihydrobenzo[a]quinolizin-2-one | Cpd 37 | M19 | 425 | 426 |
| 144 | 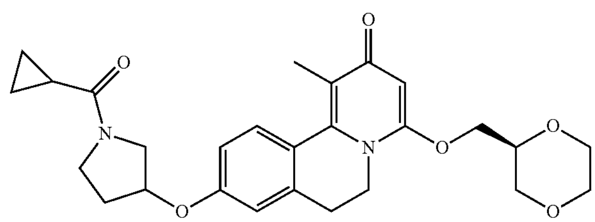 [SMILES: Cc1c2n(c(OC[C@@H]3COCCO3)cc1=O)CCc1cc(OC3CCN(C(=O)C4CC4)C3)ccc1-2] | 9-[1-(cyclopropanecarbonyl)pyrrolidin-3-yl]oxy-4-[[(2S)-1,4-dioxan-2-yl]methoxy]-1-methyl-6,7-dihydrobenzo[a]quinolizin-2-one | Int 32 | M28 | 481 | 481 |
| 145 | 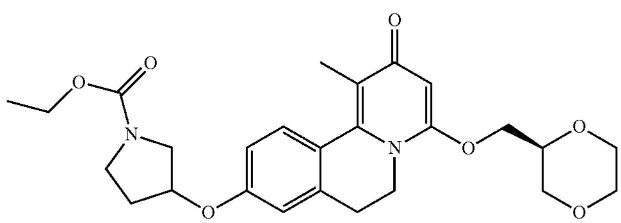 [SMILES: CCOC(=O)N1CCC(Oc2ccc3c(c2)CCn2c(OC[C@@H]4COCCO4)cc(=O)c(C)c2-3)C1] | ethyl 3-[[4-[[(2S)-1,4-dioxan-2-yl]methoxy]-1-methyl-2-oxo-6,7-dihydrobenzo[a]quinolizin-9-yl]oxy]pyrrolidine-1-carboxylate | Int 32 | M28 | 485 | 485 |
| 146 | 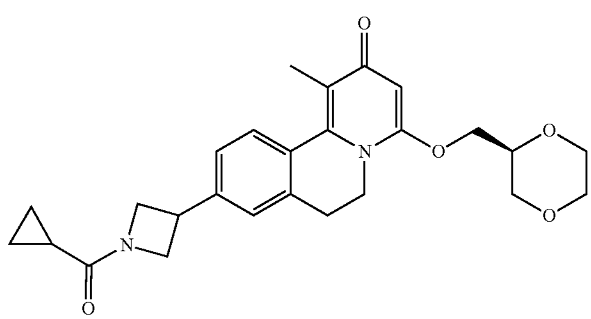 [SMILES: Cc1c2n(c(OC[C@@H]3COCCO3)cc1=O)CCc1cc(C3CN(C(=O)C4CC4)C3)ccc1-2] | 9-[1-(cyclopropanecarbonyl)azetidin-3-yl]-4-[[(2S)-1,4-dioxan-2-yl]methoxy]-1-methyl-6,7-dihydrobenzo[a]quinolizin-2-one | Int 33 | M28 | 451 | 451 |
| 147 | 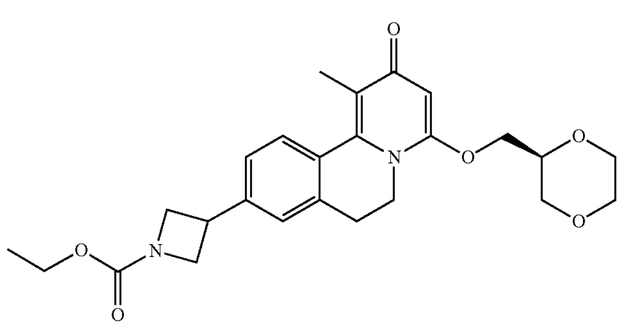 [SMILES: CCOC(=O)N1CC(c2ccc3c(c2)CCn2c(OC[C@@H]4COCCO4)cc(=O)c(C)c2-3)C1] | ethyl 3-[4-[[(2S)-1,4-dioxan-2-yl]methoxy]-1-methyl-2-oxo-6,7-dihydrobenzo[a]quinolizin-9-yl]azetidine-1-carboxylate | Int 33 | M28 | 455 | 455 |

TABLE III-continued

Illustrative compound of the invention

| Cpd # | Structure | Name | SM | Mtd | MW | Mes |
|---|---|---|---|---|---|---|
| 148 | 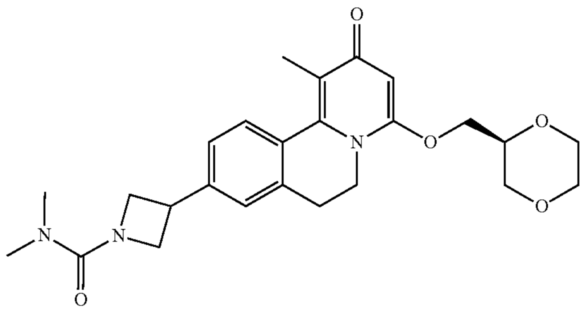 [SMILES: Cc1c2n(c(OC[C@@H]3COCCO3)cc1=O)CCc1cc(C3CN(C(=O)N(C)C)C3)ccc1-2] | 3-[4-[[(2S)-1,4-dioxan-2-yl]methoxy]-1-methyl-2-oxo-6,7-dihydrobenzo[a]quinolizin-9-yl]-N,N-dimethyl-azetidine-1-carboxamide | Int 33 | M28 | 454 | 454 |
| 149 | 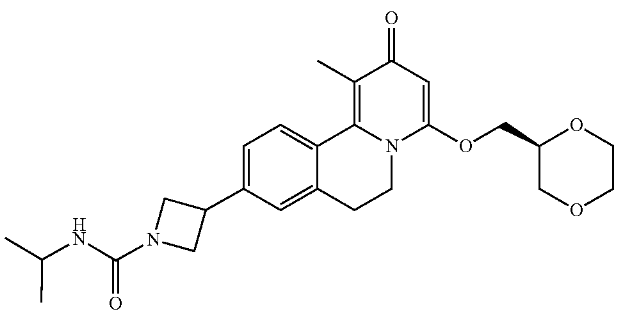 [SMILES: Cc1c2n(c(OC[C@@H]3COCCO3)cc1=O)CCc1cc(C3CN(C(=O)NC(C)C)C3)ccc1-2] | 3-[4-[[(2S)-1,4-dioxan-2-yl]methoxy]-1-methyl-2-oxo-6,7-dihydrobenzo[a]quinolizin-9-yl]-N-isopropyl-azetidine-1-carboxamide | Int 33 | M28 | 468 | 468 |
| 150 | 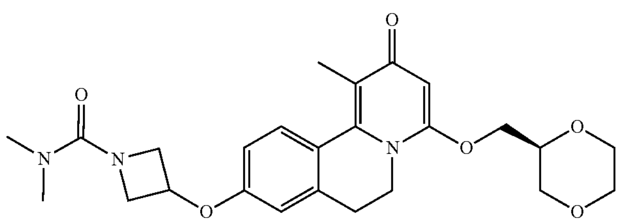 [SMILES: Cc1c2n(c(OC[C@@H]3COCCO3)cc1=O)CCc1cc(OC3CN(C(=O)N(C)C)C3)ccc1-2] | 3-[[4-[[(2S)-1,4-dioxan-2-yl]methoxy]-1-methyl-2-oxo-6,7-dihydrobenzo[a]quinolizin-9-yl]oxy]-N,N-dimethyl-azetidine-1-carboxamide | Int 33 | M28 | 470 | 470 |
| 151 | 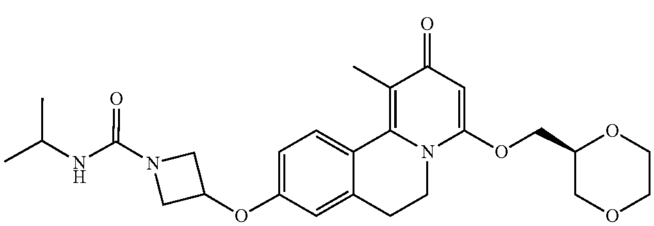 [SMILES: Cc1c2n(c(OC[C@@H]3COCCO3)cc1=O)CCc1cc(OC3CN(C(=O)NC(C)C)C3)ccc1-2] | 3-[4-[[(2S)-1,4-dioxan-2-yl]methoxy]-1-methyl-2-oxo-6,7-dihydrobenzo[a]quinolizin-9-yl]-N-isopropyl-azetidine-1-carboxamide | Int 33 | M28 | 484 | 484 |
| 152 | 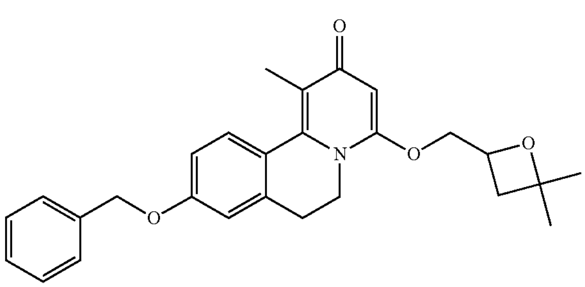 [SMILES: Cc1c2n(c(OCC3CC(C)(C)O3)cc1=O)CCc1cc(OCc3ccccc3)ccc1-2] | 9-benzyloxy-4-[(4,4-dimethyloxetan-2-yl)methoxy]-1-methyl-6,7-dihydrobenzo[a]quinolizin-2-one | Int 3 | M15 | 432 | 432 |

TABLE III-continued

Illustrative compound of the invention

| Cpd # | Structure | Name | SM | Mtd | MW | Mes |
|---|---|---|---|---|---|---|
| 153 | 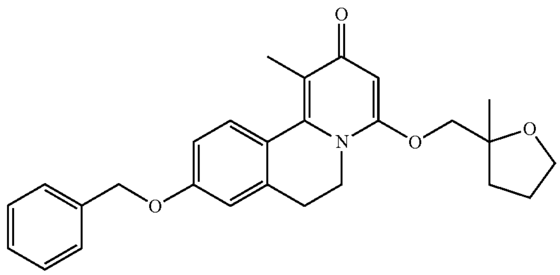 [SMILES: Cc1c2n(c(OCC3(C)CCCO3)cc1=O)CCc1cc(OCc3ccccc3)ccc1-2] | 9-benzyloxy-1-methyl-4-[(2-methyltetrahydrofuran-2-yl)methoxy]-6,7-dihydrobenzo[a]quinolizin-2-one | Int 24 | M15 | 432 | 432 |
| 154 | 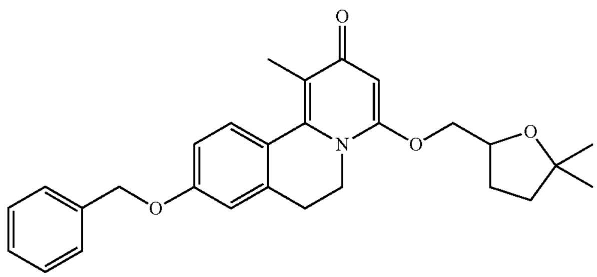 [SMILES: Cc1c2n(c(OCC3CCC(C)(C)O3)cc1=O)CCc1cc(OCc3ccccc3)ccc1-2] | 9-benzyloxy-4-[(5,5-dimethyltetrahydrofuran-2-yl)methoxy]-1-methyl-6,7-dihydrobenzo[a]quinolizin-2-one | Int 24 | M15 | 446 | 446 |
| 155 | 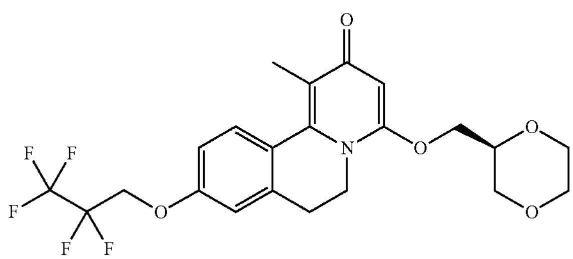 [SMILES: Cc1c2n(c(OC[C@@H]3COCCO3)cc1=O)CCc1cc(OCC(F)(F)C(F)(F)F)ccc1-2] | 4-[[(2S)-1,4-dioxan-2-yl]methoxy]-1-methyl-9-(2,2,3,3,3-pentafluoropropoxy)-6,7-dihydrobenzo[a]quinolizin-2-one | Cpd 85 Cpd 85 | M17 | 327 | 328 |
| 156 | 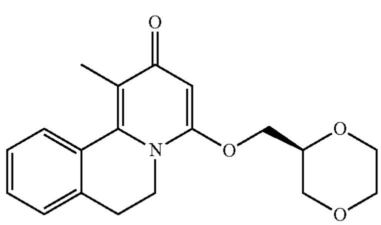 [SMILES: Cc1c2n(c(OC[C@@H]3COCCO3)cc1=O)CCc1ccccc1-2] | 4-[[(2S)-1,4-dioxan-2-yl]methoxy]-1-methyl-6,7-dihydrobenzo[a]quinolizin-2-one | Cpd 37 | Described above | 327 | 328 |
| 157 | 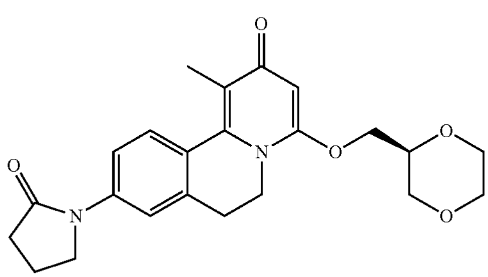 [SMILES: Cc1c2n(c(OC[C@@H]3COCCO3)cc1=O)CCc1cc(N3CCCC3=O)ccc1-2] | 4-[[(2S)-1,4-dioxan-2-yl]methoxy]-1-methyl-9-(2-oxopyrrolidin-1-yl)-6,7-dihydrobenzo[a]quinolizin-2-one | Cpd 37 | Described above | 410 | 411 |

TABLE III-continued

Illustrative compound of the invention

| Cpd # | Structure | Name | SM | Mtd | MW | Mes |
|---|---|---|---|---|---|---|
| 158 | 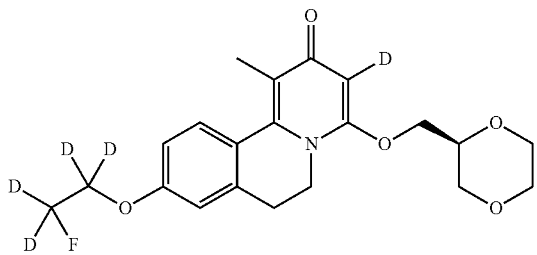 [SMILES: [2H]c1c(OC[C@@H]2COCCO2)n2c(c(C)c1=O)-c1ccc(OC([2H])([2H])C([2H])([2H])F)cc1CC2] | 3-deuterio-4-[[(2S)-1,4-dioxan-2-yl]methoxy]-1-methyl-9-(1,1,2,2-tetradeuterio-2-fluoroethoxy)-6,7-dihydrobenzo[a]quinolizin-2-one | Cpd 105 | Described above | 395 | ND |
| 159 | 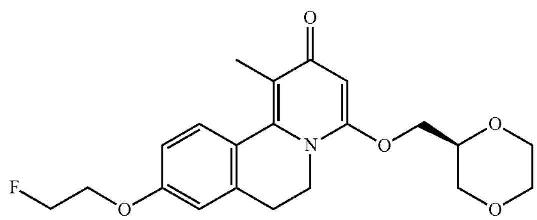 [SMILES: Cc1c2n(c(OC[C@@H]3COCCO3)cc1=O)CCc1cc(OCCF)ccc1-2] | 4-[[(2S)-1,4-dioxan-2-yl]methoxy]-9-(2-fluoroethoxy)-1-methyl-6,7-dihydrobenzo[a]quinolizin-2-one | Cpd 85 | M17 | 389 | 390 |

TABLE IV

NMR data of illustrative compounds of the invention

Cpd # NMR

1. $^1$H NMR (CDCl$_3$): 7.15, s, 1 H; 6.75, s, 1 H; 5.83, s, 1 H; 4.05, m, 1 H; 4.01, m, 2 H; 3.97, m, 2H; 3.92, s, 3H; 3.87, s, 3H; 3.83, m, 2H; 3.75, m, 2H; 3.65, m, 1 H; 3.50, m, 1 H; 2.84, t, 2H; 2.30, s, 3H

2. $^1$H NMR (DMSO-d$_6$): 7.11(1 H, s), 6.99 (1 H, s), 5.97 (1 H, t), 5.40 (1 H, s), 4.05 (1 H, m), 4.12 (1 H, m), 3.80 (3 H, s), 3.75 (3 H, s), 3.84-3.60 (3 H, m), 3.08 (2 H, m), 2.82 (2 H, t), 2.08 (3 H, s), 1.98 (1 H, m), 1.85 (2 H, m), 1.60 (1 H, m).

3. $^1$H NMR (DMSO-d$_6$): 8.50, s, 1 H; 7.50, d, 1 H; 6.85, d, 2H; 6.10, s, 1 H; 4.20, m, 1 H; 3.95, m, 3H; 3.80, q, 1 H; 3.40, dd, 1 H; 3.30, m, 1 H; 2.90, t, 2H; 2.70, q, 2H; 2.15, m, 1 H; 2.00, m, 2H; 1.70, m, 1H; 1.30, t, 3H.

4. $^1$H NMR (DMSO-d$_6$): 7.22, s, 1.0 H; 6.94, s, 1.0 H; 6.33, d, 1.0 H; 6.07, t, 1.0 H; 5.33, s, 1.0 H; 4.06, m, 1.0 H; 3.9 ÷ 3.75, m + d?, 9 H; 3.65, m, 1 H; 3.05, m, 2 H; 2.9, m, 2 H; 1.98, m, 1 H; 1.86, m, 2 H; 1.62, m, 1 H.

5. $^1$H NMR (DMSO-d$_6$): 7.22, s, 1 H; 6.94, s, 1.0 H; 6.35, s, 1.0 H; 6.13, t, 1 H; 5.31, d, 1.0 H; 3.85-3.72, various signals, 11 H; 3.72 ÷ 3.55, m, 2 H; 3.55 ÷ 3.45, m, 2 H; 3.05, m, 2 H; 2.90, m, 2H.

6. $^1$H NMR (DMSO-d$_6$): 7.11(1 H, s), 6.99 (1 H, s), 6.04 (1 H, t), 5.39 (1 H, s), 3.82 (3 H, s), 3.75 (3 H, s), 3.85-3.60 (4 H, m), 3.59 (1 H, dt), 3.49 (2 H, m), 3.26 (2 H, AB system), 3.05 (2 H, m), 2.82 (2 H, t), 2.09 (3 H, s).

7. $^1$H NMR (DMSO-d$_6$): 7.50, d, 1.0 H; 6.99, d, 1.0 H; 6.91, dd, 1.0 H; 5.97, t, 1 H; 5.38, s, 1 H; 4.22, m, 1 H; 4.05, m, 2 H; 3.78, m, 3 H; 3.65, m, 1 H; 3.07, m, 2 H; 2.85, m, 2 H; 2.25, m, 1 H; 2.0, s, 3.0 H; 2.0 ÷ 1.9, 1 H; 1.9 ÷ 1.68, m, 3 H; 1.68 ÷ 1.4, 2 m, 2 H.

8. $^1$H NMR (DMSO-d$_6$): 7.55, d, 1.0 H; 7.10, d, 1 H; 7.02, dd, 1 H; 5.98, t, 1.0 H; 5.39, s, 1.0 H; 4.83, q, 2 H; 4.05, m, 1 H; 3.75, m, 3 H; 3.65, m, 1 H; 3.06, m, 2 H; 2.88, m, 2 H; 2.02, s, 3 H; 2.0 ÷ 1.9, m, 1 H; 2.9 ÷ 2.75, m, 2 H; 1.6, m, 1 H.

10. $^1$H NMR (CDCl$_3$): 8.50, br, 1 H; 7.25, d, 1 H; 6.88, d, 1 H; 6.50, s, 1 H; 6.18, br, 1 H; 4.20, m, 1 H; 4.10-4.0, m, 1 H; 3.90, s, 3H; 3.90-3.80, m, 4H; 3.80-3.60, m, 1 H; 3.40-3.30, m, 1 H; 3.20-3.15, m, 1 H; 3.10-2.90, m, 2H; 2.22, s, 3H; 2.10-2.00, m, 1 H; 2.00-1.90, m, 2H; 1.70-1.60, m, 1 H

12. $^1$H NMR (CDCl$_3$): 7.81, s, 1 H; 7.44, d, 1 H; 6.98, d, 1 H; 4.33-4.36, m, 2 H; 4.20-4.24, m, 2 H; 4.02-4.06, m, 1 H; 3.98, s, 3 H; 3.88, s, 3 H; 3.81-3.84, m, 2 H; 3.75-3.80, m, 2 H; 3.62-3.68, m, 1 H; 3.52, dd, 1 H; 3.08, t, 2 H; 2.39, s, 3 H

13. $^1$H NMR (CDCl$_3$): 7.53, d, 1 H; 6.89, dd, 1 H; 6.84, d, 1 H; 6.14, s, 1 H; 6.11, tt, CF$_2$H, 1 H; 5.42, b, 1 H; 4.24, td, 2H; 4.05, m, 1 H; 3.91, m, 2H; 3.63, m, 1 H; 3.43, m, 1 H; 3.22, m, 1 H; 3.10, m, 1 H; 2.95, t, 2H; 2.28, s, 3H; 1.84, b, 1 H; 1.65, d, 1 H; 1.52, b, 3H; 1.32, m, 1 H.

14. $^1$H NMR (CDCl$_3$): 7.53, d, 1 H; 6.89, m, 2H; 6.14, s, 1 H; 5.50, b, 1 H; 4.41, q, 2H; 4.08, m, 1 H; 3.91, m, 2H; 3.63, t, 1 H; 3.43, m, 1 H; 3.22, m, 1 H; 3.10, m, 1 H; 2.95, t, 2H; 2.28, s, 3H; 1.84, b, 1 H; 1.65, d, 1 H; 1.52, b, 3H; 1.32, m, 1 H.

16. $^1$H NMR (CDCl$_3$): 7.30, d, 1 H; 6.85, d, 1 H; 5.75, s, 1 H; 4.52, br, 1 H; 4.00-3.92, m, 1 H; 3.90, s, 3H; 3.90-3.85, m, 1 H; 3.82, s, 3H; 3.75-3.65, m, 1 H; 3.62-3.54, m, 1 H; 3.48-3.40, m, 1 H; 3.20-3.12, m, 1 H; 3.08-3.00, m, 3H; 2.97-2.90, m, 1 H; 2.23, s, 3H; 1.85, br, 1 H, 1.13, m, 1 H; 1.55-1.50, m, 2H; 1.90-1.80, m, 2H.

TABLE IV-continued

NMR data of illustrative compounds of the invention

| Cpd # | NMR |
|---|---|
| 17 | $^1$H NMR (CDCl$_3$): 7.33, d, 1 H; 6.91, d, 1 H; 6.30, s, 1 H; 4.95, br, 1 H; 3.95, s, 3H; 3.85, s, 3H; 3.80-3.70, m, 4H; 3.65-3.60, m, 4H; 3.45, m, 1 H; 3.25, br, 1 H; 3.15-3.05, br, 2H; 3.00, br, 1 H; 2.30, s, 3H. |
| 18 | $^1$H NMR (CDCl$_3$): 7.63, d, 1 H; 6.92, dd, 1 H 6.88, d, 1 H; 6.14, s, 1 H; 4.42, q, 2H; 4.10, m, 2H; 4.02, m, 3H; 3.85, td, 2H, 3.80, dd, 1 H; 3.76, m, 1 H; 3.65, m, 1 H; 3.52, m, 1 H; 2.93, t, 2H; 2.29, s, 3H. |
| 19 | $^1$H NMR (CDCl$_3$): 7.26, d, 1 H; 6.82, d, 1 H; 6.70, 1 H; 6.20, br, 1 H; 5.84, s, 1 H; 4.02-3.98, m, 2H; 3.98-3.84, m, 4H; 3.83, m, 1 H; 3.81, s, 3H; 3.80-3.74, m, 3H; 3.62-3.58, m, 1 H; 3.40, dd, 1 H; 3.20-310, br, 2H; 3.15-3.00, br t, 2H. |
| 20 | $^1$H NMR (CDCl$_3$): 7.31, d, 1 H; 6.92, m, 2H; 6.28, br, 1 H; 6.10, s, 1 H; 4.20, br, 1 H; 4.10-4.00, m, 1 H; 4.00-3.90, m, 1 H; 3.78, s, 3H; 3.85, m, 1 H; 3.82, s, 3H; 3.81-3.75, m, 1 H; 3.30, br, 1 H; 3.20-3.00, br, 3H; 2.10, m, 1 H; 2.00-1.90, m, 2H; 1.70-1.50, m, 1 H. |
| 23 | $^1$H NMR (DMSO-d$_6$): 7.32, d, 1.0 H; 7.10, d, 1.0 H; 6.46, tt, 1.0 H; 6.00, m, 1.0 H; 5.37, s, 1.0 H; 4.42, td, 2 H; 3.85, dd, 1 H; 3.82, s, 3 H; 3.76, m, 3 H; 3.7 ÷ 3.4, m's, 1 + 1 + 2 H; 3.3 ÷ 3.2, m, 1 H; 3.05, m, 2 H; 2.85, m, 2.0 H; 2.03, sm 3 H. |
| 24 | $^1$H NMR (DMSO-d$_6$): 7.32, d, 1.0 H; 7.09, d, 1.0 H; 6.46, tt, 1 H; 5.95, m, 1.0 H; 5.39, s, 1.0 H; 4.43, td, 2 H; 4.04, m, 1 H; 3.85 ÷ 3.70, m + s, 3 + 3 H; 3.65, m, 1 H; 3.1, m, 2 H; 2.9, m, 2 H; 2.02, s, 3 H; 1.97, m, 1 H; 1.84, m, 2 H; 1.60, m, 1 H. |
| 25 | $^1$HNMR (CDCl$_3$): 7.77, d, 1 H; 7.67, dd, 1 H; 7.61, d, 1 H; 6.19, s, 1 H; 4.09, m, 5H; 3.83, m, 4H; 3.65, td, 1 H; 3.52, t, 1 H; 2.99, t, 2H; 2.31, s, 3H. |
| 26 | $^1$H NMR (CDCl$_3$): 7.58, d, 1 H; 6.88, d, 1 H; 6.82, s, 1 H; 6.30-5.95, tt, 1 H; 5.28, s, 1 H; 4.40, br, 1 H; 4.30-4.10, m, 3H; 4.00-3.90, m, 1 H; 3.90-3.65, m, 3H; 3.24, m, 1 H; 3.05, m, 1 H; 2.95-2.80, m, 2H; 2.80-2.60, m, 2H; 2.10-2.00, m, 1 H; 2.95, q, 2H; 1.65, m, 1 H; 1.68, t, 3H. |
| 27 | $^1$H NMR (CDCl$_3$): 7.60, d, 1 H; 6.91, d, 1 H; 6.88, s, 1 H; 5.70, s, 1 H; 4.50, br, 1 H; 4.92, q, 2H; 4.17m, 1 H; 4.00, m, 1 H; 3.90-3.80, m, 1 H; 3.80-3.70, m, 2H; 3.30-3.20, m, 1 H; 3.10-3.00, m, 1 H; 2.95-2.85, m, 2H; 2.80-2.60, m, 2H; 2.10-2.00, m, 1 H; 1.95-1.90, q, 2H; 1.70-1.60, m, 1 H; 1.28, t, 3H. |
| 28 | $^1$H NMR (CDCl$_3$): 7.40, d, 1 H; 6.80, d, 1 H; 5.95, s, 1 H; 4.30, qd, 1 H; 4.10, dd, 1 H; 4.05-3.95, m, 3H; 3.92-3.90, m, 5H; 3.85, s, 3H; 2.95, t, 2H; 2.28, s, 3H; 2.15-2.05, m, 1 H; 2.00-1.90, m, 2H; 1.75-1.65, m, 1 H. |
| 29 | $^1$H NMR (CDCl$_3$): 7.40, d, 1 H; 6.90, d, 1 H; 5.92, s, 1 H; 4.05-3.95, m, 5H; 3.92, s, 3H; 3.85, s, 3H; 3.78-7.70, m, 1 H; 3.50-3.40, td, 1 H; 2.95, t, 2H; 2.28, s, 3H; 2.95-2.90, m, 1 H; 1.7-1.4, m, 5H |
| 30 | $^1$H NMR (CDCl$_3$): 7.57, d, 1 H; 6.85, dd, 1 H; 6.78, d, 1 H; 5.93, s, 1 H; 3.98-4.09, m, 7 H; 3.81-3.90, m, 4 H; 3.74-3.79, m, 2 H; 3.65, ddd, 1 H; 3.42-3.54, m, 3 H; 2.88, t, 2 H; 2.28, s, 3 H; 2.06-2.12, m, 1 H; 1.75-1.79, m, 2 H; 1.51, dd, 1 H; 1.44, dd, 1 H |
| 31 | $^1$H NMR (CDCl$_3$): 8.62, d, 1 H; 7.75, td, 1 H; 7.59, d, 1 H; 7.52, d, 1 H; 7.27, d, 1 H; 6.97, dd, 1 H, 6.90, d, 1 H; 6.21, s, 1 H; 5.27, s, 2 H; 4.04-4.13, m, 2 H; 3.99-4.04, m, 3 H; 3.85-3.88, m, 1 H; 3.81-3.83, m, 1 H; 3.74-3.79, m, 2 H; 3.64, ddd, 1 H; 3.51, dd, 1 H; 2.89, t, 2 H; 2.29, s, 3 H |
| 32 | $^1$H NMR (CDCl$_3$): 7.61, d, 1 H; 7.44, t, 1 H; 7.36, d, 1 H; 7.31, s, 1 H; 7.20, d, 1 H; 6.95, dd, 1 H; 6.89, d, 1 H; 6.28, s, 1 H; 5.14, s, 2 H; 4.10-4.14, m, 2 H; 3.99-4.08, m, 3 H; 3.81-3.89, m, 2 H; 3.75-3.79, m, 2 H; 3.65, ddd, 1 H, 3.52, dd, 1 H; 2.91, t, 2 H; 2.30, s, 3 H. |
| 34 | $^1$H NMR (CDCl$_3$): 7.52, d, 1 H; 7.39-7.46, m, 4 H; 7.33-7.37, m, 1 H; 6.94, dd, 1 H; 6.88, d, 1 H; 6.06, s, 1 H; 5.31, br s, 1 H; 5.13, s, 2 H; 4.00-4.05, m, 1 H; 3.07-3.92, m, 2 H, 3.81, dd, 1 H; 3.69-3.75, m, 3 H; 3.57, ddd, 1 H; 3.41, dd, 1 H; 3.18-3.24, m, 1 H; 3.09-3.15, m, 1 H; 2.93, t, 2 H; 2.30, s, 3 H |
| 35 | $^1$H NMR (CDCl$_3$): 7.52, d, 1 H; 6.88, dd, 1 H; 6.83, d, 1 H; 6.11, tt, 1 H; 6.01, s, 1 H; 5.68, b, 1 H; 4.24, td, 2H; 4.01, m, 1 H; 3.87, m, 2H; 3.80, m, 1 H; 3.75, m, 1 H; 3.68, d, 2H; 3.56, m, 1 H; 3.37, t, 1 H; 3.15, m, 2H; 2.93, t, 2H; 2.26, s, 3H |
| 36 | $^1$H NMR (CDCl$_3$): 7.54, d, 1 H; 6.89, dd, 1 H; 6.86, d, 1 H; 5.78, s, 1 H, 4.60, br, 1 H; 4.41, q, 2 H; 3.93-3.99, m, 1 H; 3.85-3.90, m, 1 H; 3.76-3.82, m, 3 H, 3.71-3.74, m, 2 H; 3.60, ddd, 1 H; 3.42, dd, 1 H; 3.12-3.17, m, 1 H; 3.03-3.09, m, 1 H, 2.93, t, 2 H; 2.25, s, 3 H |
| 38 | $^1$H NMR (CDCl$_3$): 7.60, d, 1 H; 7.57, s, 1 H; 7.47, s, 1 H; 6.94, dd, 1 H; 6.86, d, 1 H; 6.52, s, 1 H; 5.02, s, 2 H; 4.14-4.16, m, 2 H; 4.08-4.10, t, 2 H; 4.01-4.05, m, 1 H; 3.92, s, 3 H; 3.87, dd, 1 H; 3.81-3.84, m, 1 H; 3.75-3.79, m, 2 H; 3.66, ddd, 1 H; 3.53, dd, 1 H; 2.91, t, 2 H; 2.32, s, 3 H. |
| 39 | $^1$H NMR (CDCl$_3$): 7.63, d, 1 H; 7.39, dd, 1 H; 7.30, d, 1 H; 6.26-6.27, m, 1 H; 6.25, s, 1 H; 4.36, dd, 2 H; 4.01-4.13, m, 4 H; 3.96, t, 2 H; 3.75-3.89, m, 5 H; 3.65, ddd, 1 H; 3.52, dd, 1 H; 2.94, t, 2 H; 2.54-2.57, m, 2 H; 2.32, s, 3 H. |
| 40 | $^1$H NMR (CDCl$_3$): 7.83, s, 1 H; 7.73, s, 1 H; 7.63, d, 1 H; 7.45, dd, 1 H; 7.39, d, 1 H; 6.21, s, 1 H; 4.23, q, 2 H; 4.00-4.14, m, 5 H; 3.85-3.89, m, 2 H; 3.77-3.82, m, 1 H; 3.74-3.77, m, 1 H; 3.64, ddd, 1 H; 3.52, dd, 1 H; 2.95, t, 2 H; 2.32, s, 3 H, 1.54, t, 3 H. |
| 41 | $^1$H NMR (CDCl$_3$): 7.60, d, 1 H; 7.22, dd, 1 H; 7.14, d, 1 H; 6.23, s, 1 H; 4.09-4.14, m, 3 H; 4.00-4.07, m, 3 H; 3.81-3.89, m, 2 H; 3.75-3.80, m, 2 H; 3.50-3.67, m, 5 H; 2.92, t, 2 H; 2.79-2.84, m, 1 H; 2.32, s, 3 H; 1.78-1.87, m, 4 H. |
| 42 | $^1$H NMR (CDCl$_3$): 7.54, d, 1 H; 6.89, dd, 1 H; 6.85, d, 1 H; 5.80, s, 1 H; 4.84, br, 1 H; 4.40, q, 2 H; 4.14-4.21, m, 1 H, 3.97-4.03, m, 1 H; 3.83-3.88, m, 1 H; 3.71-3.80, m, 2H; 3.22-3.27, m,; 1.94, p, 2 H; 1.62-1.69, m, 1 H. |
| 43 | $^1$H NMR (CDCl$_3$): 7.62, d, 1 H; 6.97, dd, 1 H; 6.92, d, 1 H; 6.31, s, 1 H; 5.33, s, 2 H; 4.32, ddd, 1 H; 4.10-4.17, m, 2 H; 4.03-4.07, m, 2 H; 3.83-3.93, m, 2H; 2.91, t, 2 H; 2.45, s, 3 H; 2.30, s, 3 H; 2.09-2.14, m, 1 H; 1.95-2.01, m, 2 H; 1.68-1.73, m, 1 H |
| 44 | $^1$H NMR (CDCl$_3$): 7.62, d, 1 H; 6.96, dd, 1 H; 6.91, d, 1 H; 6.26, s, 1 H; 5.33, s, 2H; 4.00-4.13, m, 5H; 3.71-3.75, m, 1 H; 3.45-3.51, m, 1 H; 2.90, t, 2H; 2.45, s, 3H; 2.29, s, 3H; 1.91-1.94, m, 1 H; 1.54-1.66, m, 4H; 1.41-1.48, m, 1 H |

TABLE IV-continued

NMR data of illustrative compounds of the invention

| Cpd # | NMR |
|---|---|
| 45 | $^1$H NMR (CDCl$_3$): 8.6, d, 1 H; 7.7, m, 1 H; 7.51, dd, 2H; 7.23, 1 H; 6.92, d, 1 H; 6.85, s, 1 H; 5.95, s, 1 H; 5.22, s, 2H; 4.28, m, 1 H; 4.10-3.90, m, 4H; 3.90-3.75, m, 2H; 2.84, t, 2H; 2.22, s, 3H; 2.10-2.00, m, 1 H; 1.85-2.00, m, 2H; 1.70-1.60, m, 1 H. |
| 47 | $^1$H NMR (CDCl$_3$): 7.55, d, 1 H; 6.85, d, 1 H; 6.78, s, 1 H; 6.03, s, 1 H; 4.30, qd, 1 H; 4.10-3.95, m, 5H; 3.95-3.80, m, 5H; 3.50-3.40, m, 1 H; 3.37, dd, 1 H; 2.85, t, 2H; 2.28, s, 3H; 2.20-2.00, m, 2H; 2.00-1.85, m, 3H; 1.70-1.60, m, 3H; 1.50-1.40, m, 1 H |
| 50 | $^1$H NMR (CDCl$_3$): 8.58, s, 1 H; 7.75, d, 1 H; 7.68, d, 1 H; 7.19, d, 1 H; 6.90, d, 1 H; 6.81, s, 1 H; 5.99, s, 1 H; 5.10, s, H; 4.25, m, 1 H; 4.19-3.95, m, 4H; 3.94-3.80, m, 2H; 2.85, t, 2H; 2.78, s, 3H; 2.24, s, 3H; 2.20-2.00, m, 1 H; 2.00-1.90, m, 2H; 1.86-1.80, m, 1 H. |
| 53 | $^1$H NMR (CD$_3$OD): 7.72, d, 1 H; 7.06-7.09, m, 2 H; 6.04, s, 1 H; 4.47, t, 2 H; 4.37, ddd, 1 H; 4.26, dd, 1 H; 4.09-4.20, m, 3 H; 3.85-3.98, m, 2 H; 3.61, t, 2 H; 2.97-3.00, m, 2 H; 2.98, s, 6 H; 2.28, s, 3 H; 2.13-2.21, m, 1 H; 1.98-2.06, m, 2 H; 1.78-1.87, m, 1 H. |
| 54 | $^1$H NMR (CD$_3$OD): 7.71, d, 1 H; 7.05-7.08, m, 2 H; 6.03, s, 1 H; 4.47, t, 2 H; 4.11-4.21, m, 4 H; 4.01-4.05, m, 1 H; 3.80-3.86, m, 1 H; 3.61, t, 2 H; 3.53-3.58, m, 1 H; 2.96-2.99, m, 2 H; 2.98, s, 6 H; 2.27, s, 3 H; 1.95-1.98, m, 1 H; 1.72-1.75, m, 1 H; 1.59-1.68, m, 3 H; 1.48-1.55, m, 1 H. |
| 55 | $^1$H NMR (CD$_3$OD): 7.72, d, 1 H; 7.06-7.09, m, 2 H; 6.03, s, 1 H; 4.48, t, 2 H; 4.21, d, 2 H; 4.13, t, 2 H; 4.04-4.08, m, 1 H; 3.85-3.94, m, 2 H; 3.75-3.83, m, 2 H; 3.55-3.69, m, 4 H; 2.97-3.00, m, 2 H; 2.99, s, 6 H; 2.27, s, 3 H. |
| 57 | $^1$H NMR (CDCl$_3$): 8.65-8.55, d, 1 H; 7.80-7.70, dd, 1 H; 7.62-7.58, d, 1 H; 7.54-7.50, d, 1 H; 7.30-7.20, m, 1 H; 6.98-6.92, dd, 1 H, 6.88, s, 1 H; 6.05, s, 1 H; 5.25, s, 2H; 4.38-4.28, m, 1 H; 4.20-4.00, m, 5H; 3.95-3.80, m, 2H; 2.85, t, 2H; 2.28, s, 3H; 2.15-2.05, m, 1 H; 2.00-1.90, m, 2H; 1.75-1.60, m, 1 H. |
| 58 | $^1$H NMR (CDCl$_3$): 7.56, d, 1 H; 6.92, dd, 1 H; 6.86, d, 1 H; 5.82, s, 1 H; 5.28, s, 2H; 4.03-3.95, m, 5H; 3.84-3.69, m, 4H; 3.63-3.60, ddd, 1 H; 3.49-3.42, dd, 1 H; 2.87-2.71, t, 2H; 2.40, s, 3.H; 2.20, s, 3H. |
| 61 | $^1$H NMR (CDCl$_3$): 7.59, d, 1 H; 6.88, dd, 1 H; 6.82, d, 1 H; 6.11-5.96, tt, 1 H; 5.81, s, 1 H; 4.24, td, 2H; 4.07-3.98, m, 5H; 3.89-3.73, m, 4H; 3.65, td, 1 H; 3.50, dd, 1 H; 2.89, dd, 2H; 2.25, s, 3H. |
| 62 | $^1$H NMR (CDCl$_3$): 7.56, d, 1 H; 6.86, dd, 1 H; 6.79, d, 1 H; 5.88, s, 1 H; 3.46-4.08, m, 20 H; 2.86, t, 2 H; 2.26, s, 3 H. |
| 63 | $^1$H NMR (DMSO-d$_6$): 7.51, d, 1 H; 6.89-6.94, m, 2 H; 5.669, s, 1 H; 4.03-4.10, m, 2 H; 3.88-3.96, m, 3 H; 3.61-3.88, m, 8 H; 3.45-3.53, m, 1 H; 3.42, dd, 1 H; 3.23, br t, 4 H; 2.84, t, 2 H; 2.08, s, 3 H. |
| 64 | $^1$H NMR (CDCl$_3$): 7.66, s, 1 H; 7.51-7.56, m, 3 H; 7.42-7.45, m, 3 H; 7.13, d, 1 H; 7.10, s, 1 H; 4.31, br d, 4 H; 4.06, br s, 1 H; 3.72-3.89, m, 4 H; 3.63, td, 1 H; 3.51, t, 1 H; 2.96, br s, 2 H; 2.35, s, 3 H. |
| 65 | $^1$H NMR (CDCl$_3$): 7.55, d, 1 H; 6.87, dd, 1 H; 6.76, d, 1 H; 6.26, s, 1 H; 3.95-4.14, m, 5 H; 3.74-3.88, m, 4 H; 3.64, ddd, 1 H; 3.49-3.54, m, 5 H; 2.88, t, 2 H; 2.29, s, 3 H; 2.05-2.15, m, 4 H. |
| 66 | $^1$H NMR (CDCl$_3$): 7.53, d, 1 H; 6.82, dd, 1 H; 6.72, d, 1 H; 5.84, s, 1 H; 3.96-4.09, m, 5 H; 3.73-3.89, m, 4 H; 3.64, ddd, 1 H; 3.50, dd, 1 H; 3.30, br t, 4 H; 3.06, br t, 4 H; 2.85, t, 2 H; 2.27, s, 3 H; NH not observed. |
| 67 | $^1$H NMR (CDCl$_3$): 7.96-7.99, m, 2 H; 7.86-7.90, m, 2 H; 7.75, d, 1 H; 7.58-7.63, m, 1 H; 7.52-7.56, m, 2 H; 5.95, s, 1 H; 3.97-4.09, m, 5 H; 3.73-3.86, m, 4 H; 3.63, ddd, 1 H; 3.49, dd, 1 H; 2.98, t, 2 H; 2.24, s, 3 H. |
| 69 | $^1$H NMR (CDCl$_3$): 7.57, d, 1 H; 6.84, dd, 1 H; 6.74, d, 1 H; 6.17, s, 1 H; 3.99-4.13, m, 5 H; 3.74-3.88, m, 8 H; 3.65, ddd, 1 H; 3.51, dd, 1 H; 3.35, br d, 4 H; 2.88, t, 2 H; 2.30, s, 3 H; 1.74-1.81, m, 1 H; 1.01-1.05, m, 2 H; 0.79-0.85, m, 2 H. |
| 70 | $^1$H NMR (CDCl$_3$): 9.72, br s, 1 H; 7.91, s, 1 H; 7.51, d, 1 H; 7.39, dd, 1 h; 5.87, s, 1 H; 3.96-4.06, m, 5 H; 3.72-3.85, m, 4 H; 3.62, ddd, 1 H; 3.48, dd, 1 H; 2.86, t, 2 H; 2.27, s, 3 H; 1.84, septet, 1 H; 1.04-1.08, m, 2 H; 0.79-0.84, m, 2 H. |
| 71 | $^1$H NMR (CDCl$_3$): 7.63, d, 1 H; 7.28, dd, 1 H; 7.26, d, 1 H; 6.10, s, 1 H; 4.37, t, 2 H; 3.98-4.12, m, 7 H; 3.75-3.89, m, 5 H; 3.65, ddd, 1 H; 3.52, dd, 1 H; 2.93, t, 2 H; 2.31, s, 3 H; 1.47, s, 9 H. |
| 72 | $^1$H NMR (CDCl$_3$): 7.58, d, 1 H; 6.87, dd, 1 H; 6.82, d, 1 H; 5.88, s, 1 H; 4.30-4.33, m, 2 H; 4.24-4.27, m, 2 H; 3.98-4.08, m, 5 H; 3.73-3.87, m, 4 H; 3.65, ddd, 1 H; 3.50, dd, 1 H; 2.88, t, 2 H; 2.27, s, 3 H. |
| 73 | $^1$H NMR (CDCl$_3$): major rotamer: 7.72, d, 1 H; 7.32, dd, 1 H; 7.27, d, 1 H; 6.46, s, 1 H; 3.97-4.23, m, 5 H; 3.75-3.91, m, 5 H; 3.64, ddd, 1 H; 3.53, dd, 1 H; 2.36, s, 3 H; 2.98, t, 2 H; 2.36, s, 3 H; 1.07-1.11, m, 2 H; 0.70-0.74, m, 2 H; minor rotamer not resolved |
| 74 | $^1$H NMR (CDCl$_3$): 7.61, d, 1 H; 7.35, d, 1 h; 7.27, s, 1 H; 6.15, br s, 1 H; 5.92, br s, 1 H; 4.02-4.10, m, 5 H; 3.73-3.88, m, 4 H; 3.63-3.66, m, 3 H; 3.47-3.53, m, 3 H; 2.92, t, 2 H; 2.54, br s, 2 H; 2.30, s, 3 H; 1.49, s, 9 H. |
| 75 | $^1$H NMR (CDCl$_3$): 7.61, d, 1 H; 7.21, dd, 1 H; 7.14, d, 1 H; 6.48, br s, 1 H; 4.00-4.29, m, 7 H; 3.61-3.89, m, 5 H; 3.52, dd, 1 H; 2.93, t, 2 H; 2.82, br t, 2 H; 2.71, tt, 1 H; 2.34, s, 3 H; 1.85, br d, 2 H; 1.51-1.70, m, 2 H; 1.49, s, 9 H. |
| 76 | $^1$H NMR (CDCl$_3$): 7.61, d, 1 H; 7.34, d,, 1 H; 7.26, s, 1 H; 6.15, br s, 1 H; 5.95, s, 1 H; 4.15, br s, 2 H; 3.98-4.12, m, 5 H; 3.75-3.92, m, 4 H; 3.74, 3, 3 H; 3.61-3.72, m, 3 H; 3.50, dd, 1 H; 2.91, t, 2 H; 2.56, br s, 2 H; 2.29, s, 3 H. |
| 77 | $^1$H NMR (CDCl$_3$): 7.61, d, 1 H; 7.34, dd, 1 H; 7.26, s, 1 H; 6.15, br s, 1 H; 5.96, s, 1 H; 4.18, q, 2 H; 4.15-4.17, m, 1 H; 3.98-4.10, m, 5 H; 3.67-3.88, m, 6 H; 3.64, ddd, 1 H; 3.50, dd, 1 H; 2.91, t, 2 H; 2.56, br s, 2 H; 2.29, s, 3 H; 1.28, t, 3 H. |
| 78 | $^1$H NMR (CDCl$_3$): 7.62, d, 1 H; 7.35, dd, 1 H; 7.27, d, 1 H; 6.16, br s, 1 H; 6.00, s, 1 H; 4.97, septet, 1 H; 3.98-4.14, m, 7 H; 3.67-3.88, m, 6 H; 3.64, ddd, 1 H; 3.51, dd, 1 H; 2.92, t, 2 H; 2.56, br s, 2 H; 2.29, s, 3 H; 1.27, d, 6 H. |

TABLE IV-continued

NMR data of illustrative compounds of the invention

| Cpd # | NMR |
|---|---|
| 79 | $^1$H NMR (CDCl$_3$): 7.62, d, 1 H; 7.34, d, 1 H; 7.26, s, 1 H; 6.15, dr d, 1 H; 5.94, s, 1 H; 4.52, q, 2 H; 4.19, d, 1 H; 4.18, d, 1 H; 3.97-4.10, m, 5 H; 3.72-3.87, m, 6 H; 3.64, ddd, 1 H; 3.50, dd, 1 H; 2.92, t, 2 H; 2.59, br d, 2 H; 2.29, s, 3 H. |
| 80 | $^1$H NMR (CDCl$_3$): 7.58, d, 1 H; 7.16, dd, 1 H; 7.08, d, 1 H; 5.88, s, 1 H; 4.29, s, 1 H; 3.97-4.07, m, 5 H; 3.80-3.87, m, 2 H; 3.73-3.78, m, 2 H; 3.71, s, 3 H; 3.63, ddd, 1 H; 3.50, dd, 1 H; 2.88, t, 2 H; 2.84-2.89, m, 1 H; 2.67-2.73, m, 1 H; 2.28, s, 3 H; 2.26-2.29, m, 2 H; 1.84-1.87, m, 2 H; 1.64, qd, 2 H. |
| 81 | $^1$H NMR (CDCl$_3$): 7.57, d, 1 H; 7.16, d,, 1 H; 7.08, d, 1 H; 5.88, s, 1 H; 4.29-4.32, m, 2 H; 4.14, q, 2 H; 3.97-4.08, m, 5 H; 3.73-3.86, m, 4 H; 3.63, ddd, 1 H; 3.49, dd, 1 H; 2.82-2.89, m, 4 HH; 2.66-2.74, m, 1 H; 2.28, s, 3 H; 1.84-1.87, m, 2 H; 1.63, qd, 2 H; 1.27, t, 3 H. |
| 82 | $^1$H NMR (CDCl$_3$): 7.58, d, 1 H; 7.16, dd, 1 H; 7.09, d, 1 H; 5.88, s, 1 H; 5.88, s, 1 H; 4.93, septet, 1 H; 4.29-4.31, m, 2 H; 3.97-4.09, m, 5 H; 3.73-3.87, m, 4 H; 3.64, ddd, 1 H; 3.50, dd, 1 H; 2.81-2.90, m, 4 H; 2.70, tt, 1 H; 2.28, s + m, 5 H; 1.83-1.87, m, 2 H; 1.64, qd, 2 H; 1.25, d, 6H. |
| 83 | $^1$H NMR (CDCl$_3$): 7.58, d, 1 H; 7.16, dd, 1 H; 7.09, d, 1 H; 5.88, s, 1 H; 4.50, q, 2 H; 4.25-4.35, m, 2 H; 3.98-4.09, m, 5 H; 3.73-3.87, m, 4 H; 3.63, ddd, 1 H; 3.50, dd, 1 H; 2.89-3.01, m, 4 H; 2.73, tt, 1 H; 2.28, s, 3 H; 1.88-1.91, m, 2 H; 1.66-1.69, m, 2 H. |
| 84 | $^1$H NMR (CDCl$_3$): 7.74, s, 1 H; 7.65, d, 2 H; 6.61, br s, 1 H; 5.90, s, 1 H; 3.99-4.07, m, 5 H; 3.74-3.83, m, 4 H; 3.64, ddd, 1 H; 3.51, dd, 1 H; 2.91-2.97, m, 3 H; 2.25, s, 3 H; 0.87-0.92, m, 2 H; 0.64-0.68, m, 2 H. |
| 86 | $^1$H NMR (CDCl$_3$): 7.56, d, 1 H; 6.45, dd, 1 H; 6.36, d, 1 H; 6.24, s, 1 H; 4.32, t, 4 H; 4.11-4.18, m, 2 H; 4.00-4.09, m, 3 H; 3.74-3.90, m, 4 H; 3.64, ddd, 1 H; 3.51, dd, 1 H; 2.91, t, 2 H; 2.31, s, 3 H. |
| 87 | $^1$H NMR (CDCl$_3$): 7.50, d, 1 H; 6.38, dd, 1 H; 6.26, d, 1 H; 6.09, s, 1 H; 4.86, s, 4 H; 4.12, s, 4 H; 4.06-4.11, m, 2 H; 3.99-4.06, m, 2 H; 3.81-3.88, m, 3 H; 3.74-3.79, m, 2 H; 3.65, ddd, 1 H; 3.51, dd, 1 H; 2.84, t, 2 H; 2.27, s, 3 H. |
| 88 | $^1$H NMR (CDCl$_3$): 7.66, d, 1 H; 7.50, dd, 1 H; 7.44, s, 1 H; 5.99, s, 1 H; 3.99-4.11, m, 5 H; 3.75-3.89, m, 4 H; 3.65, ddd, 1 H; 3.52, dd, 1 H; 3.11, br s, 3 H; 2.95, t, 2 H; 2.85, septet, 1 H; 2.31, s, 3 H; 0.64, br s, 2 H; 0.51, br s, 2 H. |
| 89 | $^1$H NMR (CDCl$_3$): 7.58, d, 1 H; 6.88, dd, 1 H; 6.80, d, 1 H; 6.22, s, 1 H; 3.98-4.13, m, 5 H; 3.86, s, 3 H; 3.80-3.88, m, 2 H; 3.73-3.78, m, 2 H; 3.64, ddd, 1 H; 3.51, dd, 1 H; 2.89, t, 2 H; 2.29, s, 3 H. |
| 91 | $^1$H NMR (CDCl$_3$): 7.50, d, 1 H; 6.39, dd, 1 H; 6.29, d, 1 H; 6.19, s, 1 H; 5.45, d x septet, 1 H; 4.22-4.31, m, 2 H; 3.99-4.12, m, 7 H; 3.73-3.88, m, 4 H; 3.64, ddd, 1 H; 3.51, dd, 1 H; 2.85, t, 2 H; 2.27, s, 3 H. |
| 92 | $^1$H NMR (CDCl$_3$): 7.44, d, 1 H; 6.33, dd, 1 H; 6.29, s, 1 H; 6.24, d, 1 H; 4.86, br s, 1 H; 4.07-4.10, m, 2 H; 3.92-4.02, m, 5 H; 3.73-3.89, m, 6 H; 3.63, ddd, 1 H; 3.50, dd, 1 H; 2.79-2.83, m, 3 H; 2.25, s, 3 H; 1.24, s, 6 H. |
| 93 | $^1$H NMR (CDCl$_3$): 7.48, d, 1 H; 6.34, dd, 1 H; 6.23, d, 1 H; 6.18, s, 1 H; 3.92-4.12, m, 9 H; 3.74-3.88, m, 4 H; 3.64, ddd, 1 H; 3.51, dd, 1 H; 2.84, t, 2 H; 2.42, pentet, 2 H; 2.28, s, 3 H. |
| 94 | $^1$H NMR (CDCl$_3$): 7.53, d, 1 H; 6.42, dd, 1 H; 6.32, d, 1 H; 6.10, s, 1 H; 4.27-4.32, m, 4 H; 4.00-4.16, m, 6 H; 3.74-3.89, m, 4 H; 3.65, ddd, 1 H; 3.51, dd, 1 H; 2.98, s, 3 H; 3.86, t, 2 H; 2.28, s, 3 H. |
| 95 | $^1$H NMR (CDCl$_3$): 7.59, d, 1 H; 7.57, dd, 1 H; 7.51, d, 1 H; 6.45, dd, 1 H; 6.35, d, 1 H; 6.32, t, 1 H; 6.24, s, 1 H; 5.27-5.32, m, 1 H; 4.45, t, 2 H; 4.37, d, 1 H; 4.34, d, 1 H; 3.98-4.13, m, 5 H; 3.73-3.88, m, 4 H; 3.64, ddd, 1 H; 3.51, dd, 1 H; 2.86, t, 2 H; 2.28, s, 3 H. |
| 96 | $^1$H NMR (CDCl$_3$): 7.47, d, 1 H; 6.36, s, 1 H; 6.33, dd, 1 H; 6.22, d, 1 H; 4.07-4.12, m, 2 H; 3.99-4.05, m, 3 H; 3.37-3.88, m, 4 H; 3.66, br s, 4 H; 3.64, ddd, 1 H; 3.51, dd, 1 H; 2.84, t, 2 H; 2.84, t, 2 H; 2.28, s, 3 H; 1.34, s, 6 H. |
| 97 | $^1$H NMR (CDCl$_3$): 7.50, d, 1 H; 6.40, s, 1 H; 6.39, dd, 1 H; 6.28, d, 1 H; 4.09-4.21, m, 6 H; 3.99-4.07, m, 3 H; 3.81-3.89, m, 3 H; 3.72-3.79, m, 1 H; 3.78, s, 3 H; 3.58-3.68, m, 2 H; 3.52, dd, 1 H; 2.86, t, 2 H; 2.30, s, 3 H. |
| 98 | $^1$H NMR (CDCl$_3$): 8.92, d, 1 H; 8.66, d, 1 H; 7.99, dt, 1 H; 7.79, d, 1 H; 7.62, dd, 1 H; 7.55, d, 1 H; 7.48, dd, 1 H; 6.62, s, 1 H; 4.19-4.25, m, 4 H; 4.04-4.08, m, 1 H; 3.73-3.91, m, 4 H; 3.64, ddd, 1 H; 3.53, dd, 1 H; 3.08, t, 2 H; 2.40, s, 3 H. |
| 99 | $^1$H NMR (CDCl$_3$): 7.73, d, 1 H; 7.57, dd, 1 H; 7.40-7.49, m, 3 H; 7.31-7.34, m, 1 H; 7.06-7.11, m, 1 H; 5.98, s, 1 H; 4.00-4.14, m, 5 H; 3.74-3.90, m, 4 H; 3.65, ddd, 1 H; 3.52, dd, 1 H; 3.00, t, 2 H; 2.35, s, 3 H. |
| 100 | $^1$H NMR (CDCl$_3$): 8.71, d, 2 H; 7.79, d, 1 H; 7.64, dd, 1 H; 7.55-7.56, m, 3 H; 6.08, s, 1 H; 4.02-4.14, m, 5 H; 3.75-3.90, m, 4 H; 3.65, ddd, 1 H; 3.53, dd, 1 H; 3.03, t, 2 H; 2.36, s, 3 H. |
| 101 | $^1$H NMR (CDCl$_3$): 8.72-8.74, m, 1 H; 8.00, d, 1 H; 7.93, dd, 1 H; 7.75-7.84, m, 3 H; 7.29-7.32, m, 1 H; 6.22, s, 1 H; 4.01-4.15, m, 5 H; 3.75-3.90, m, 4 H; 3.66, ddd, 1 H; 3.53, dd, 1 H; 3.03, t, 2 H; 2.36, s, 3 H. |
| 102 | $^1$H NMR (CDCl$_3$): 8.02, d, 1 H; 7.97, dd, 1 H; 7.76, d, 1 H; 7.71, t, 1 H; 7.60, d, 1 H; 7.18, d, 1 H; 6.73, s, 1 H; 4.22-4.29, m, 4 H; 4.05-4.08, m, 1 H; 3.73-3.91, m, 4 H; 3.64, ddd, 1 H; 3.53, dd, 1 H; 3.10, t, 2 H; 2.65, s, 3 H, 2.41, s, 3 H. |
| 103 | $^1$H NMR (CDCl$_3$): 8.57, d, 1 H; 7.97, d, 1 H; 7.90, dd, 1 H; 7.74, d, 1 H; 7.74, d, 1 H; 7.61, d, 1 H; 7.11, d, 1 H; 5.88, s, 1 H; 4.00-4.09, m, 5 H; 3.75-3.89, m, 5 H; 3.65, ddd, 1 H; 3.52, dd, 1 H; 3.01, t, 2 H; 2.45, s, 3 H; 2.34, s, 3 H. |
| 104 | $^1$H NMR (CDCl$_3$): 7.58, d, 1 H; 6.68, dd, 1 H; 6.65, d, 1 H; 5.87, s, 1 H; 4.90-4.94, m, 1 H; 4.34, d, 1 H; 4.31, d, 1 H; 3.98-4.06, m, 7 H; 3.74-3.85, m, 4 H; 3.64, ddd, 1 H; 3.50, dd, 1 H; 2.87, t, 2 H; 2.27, s, 3 H; 1.45, s, 9 H. |
| 105 | $^1$H NMR (CDCl$_3$): 7.62, d, 1 H; 6.99, dd, 1 H; 6.92, d, 1 H; 3.98-4.10, m, 5 H; 3.74-3.88, m, 4 H; 3.64, ddd, 1 H; 3.51, dd, 1 H, 2.90, t, 2 H; 2.27, s, 3 H. |
| 106 | $^1$H NMR (CDCl$_3$): 7.61, d, 1 H; 6.90, dd, 1 H; 6.86, d, 1 H; 5.84, s, 1 H; 3.98-4.07, m, 5 H; 3.74-3.89, m, 4 H; 3.64, ddd, 1 H; 3.51, dd, 1 H; 2.89, t, 2 H; 2.67, s, 3 H. |

TABLE IV-continued

NMR data of illustrative compounds of the invention

| Cpd # | NMR |
|---|---|
| 107 | $^1$H NMR (CDCl$_3$): 7.55, d, 1 H; 7.26-7.42, m, 5 H; 6.90, dd, 1 H; 6.83, d, 1 H; 5.84, s, 1 H; 5.12-5.14, m, 1 H; 5.08, s, 2H; 4.68-4.73, m 1 H; 4.57-4.63, m, 1 H; 4.19, dd, 1 H; 4.11, dd, 1 H; 3.99-4.04, m, 2 H; 2.84, t, 2 H; 2.76-2.81, m, 2 H; 2.57-2.62, m, 1 H; 2.25, s, 3 H. |
| 108 | $^1$H NMR (CDCl$_3$): 7.57, d, 1 H; 7.30-7.42, m, 5 H; 6.91, dd, 1 H; 6.84, d, 1 H; 5.83, s, 1 H; 5.09, s, 2 H; 4.28, ddd, 1 H; 3.92-4.06, m, 4 H; 3.79-3.86, m, 2 H; 2.84, t, 2 H; 2.26, s, 3 H; 2.03-2.12, m, 1 H; 1.90-1.97, m, 2 H; 1.63-1.71, m, 1 H. |
| 109 | $^1$H NMR (CDCl$_3$): 7.57, d, 1 H; 7.31-7.44, m, 5 H; 6.92, dd, 1 H; 6.85, d, 1 H; 5.83, s, 1 H; 5.10, s, 2 H; 3.96-4.04, m, 5 H; 3.68-3.74, m, 1 H; 3.44-3.50, m, 1 H; 2.85, t, 2 H; 2.28, s, 3 H; 1.89-1.92, m, 1 H; 1.51-1.64, m, 4 H; 1.37-1.46, m, 1 H. |
| 110 | $^1$H NMR (CDCl$_3$): 7.47, d, 1 H; 6.36, dd, 1 H; 6.26, d, 1 H; 6.16, s, 1 H; 4.35-4.38, m, 1 H; 4.14-4.18, m, 2 H; 3.98-4.11, m, 5 H; 3.73-3.87, m, 6 H; 3.63, ddd, 1 H; 3.50, dd, 1 H; 334, s, 3 H; 2.83, t, 2 H; 2.27, s, 3 H. |
| 111 | $^1$H NMR (CDCl$_3$): 7.49, d, 1 H; 6.82, dd, 1 H; 6.73, d, 1 H; 6.39, s, 1 H 3.95-4.15, m, 5 H; 3.72-3.89, m, 4 H; 3.59-3.66, m, 3 H; 3.50, dd, 1 H; 3.42, septet, 1 H; 3.37, s, 1 H; 3.08-3.14, m, 2 H; 2.86, t, 2 H; 2.28, s, 3 H; 1.95-2.02, m, 2 H; 1.64-1.73, m, 2 H. |
| 112 | $^1$H NMR (CDCl$_3$): 7.51, d, 1 H; 6.82, dd, 1 H; 6.73, d, 1 H; 6.27, s, 1 H 3.98-4.13, m, 5 H; 3.73-3.94, m, 6 H; 3.64, ddd, 1 H; 3.47-3.57, m, 5 H; 2.84-2.95, m, 4 H 2.68-2.75, m, 1 H; 2.29, s, 3 H; 1.97, dd, 1 H; 1.91, dd, 1 H; 1.79-1.82, m, 2 H; 1.54-1.68, m, 6 H. |
| 113 | $^1$H NMR (CDCl$_3$): 7.55, d, 1 H; 7.31-7.35, m, 2 H; 7.21-7.26, m, 3 H; 6.89, dd, 1 H; 6.78, d, 1 H; 5.89, s, 1 H; 3.96-4.09, m, 7 H; 3.74-3.89, m, 4 H; 3.65, ddd, 1 H; 3.51, dd, 1 H; 2.95, dt, 2 H; 2.87, t, 21 H; 2.73, tt, 1 H; 2.30, s, 3 H; 1.97-2.00, m, 2 H; 1.90, dd, 1; 1.84, dd, 1 H. |
| 114 | $^1$H NMR (CDCl$_3$): 7.53, d, 1 H; 6.85, dd, 1 H; 6.73, d, 1 H; 6.24, s, 1 H 3.99-4.13, m, 5 H; 3.74-3.91, m, 6 H; 3.71, s, 3 H; 3.64, ddd, 1 H; 3.51, dd, 1 H; 2.92-2.99, m, 2 H; 2.86, t, 2 H; 2.50-2.58, m, 1 H; 2.30, s, 3 H; 2.02-2.06, m, 2 H; 1.78-1.90, m, 2 H. |
| 114 | $^1$H NMR (CDCl$_3$): 7.50, d, 1 H; 6.83, dd, 1 H; 6.72, d, 1 H; 6.33, s, 1 H 3.98-4.44, m, 5 H; 3.72-3.88, m, 6 H; 3.64, ddd, 1 H; 3.51, dd, 1 H; 3.48, q, 2 H; 3.29-3.31, m, 2 H; 2.81-2.87, m, 4 H; 2.29, s, 3 H; 1.79-1.88, m, 3 H; 1.38, dd, 1 H; 1.32, dd, 1 H; 1.20, t, 3 H. |
| 115 | $^1$H NMR (CDCl$_3$): 7.52, d, 1 H; 6.83, dd, 1 H; 6.72, d, 1 H; 6.34, s, 1 H; 3.96-4.15, m, 5 H; 3.74-3.89, m, 4 H; 3.64, ddd, 1 H; 3.52, dd, 1 H; 3.31-3.34, m, 4 H; 2.86, t, 2 H; 2.31, s, 3 H; 1.65-1.71, m, 6 H. |
| 116 | $^1$H NMR (CDCl$_3$): 7.51, d, 1 H; 6.83, dd, 1 H; 6.72, d, 1 H; 6.49, s, 1 H; 3.98-4.17, m, 5 H; 3.68-3.89, m, 6 H; 3.64, ddd, 1 H; 3.52, dd, 1 H; 2.87, t, 2 H; 2.80, dt, 1 H; 2.49, dd, 1 H; 2.31, s, 3 H; 1.60-1.87, m, 4 H; 1.13, ddd, 1 H; 0.97, d, 3 H. |
| 117 | $^1$H NMR (CDCl$_3$): 7.54, d, 1 H; 7.17-7.21, m, 2 H; 6.98-7.02, m, 2 H; 6.88, dd, 1 H; 6.78, d, 1 H; 6.14, s, 1 H; 3.93-4.12, m, 7 H; 3.74-3.89, m, 4 H; 3.64, ddd, 1 H; 3.51, dd, 1 H; 2.95, dt, 2 H; 2.87, t, 2 H; 2.71, tt, 1 H; 2.30, s, 3 H; 1.95-1.98, m, 2 H; 1.84, dd, 1 H; 1.78, dd, 1 H. |
| 118 | $^1$H NMR (CDCl$_3$): 7.61, d, 1 H; 6.74, dd, 1 H; 6.71, d, 1 H; 6.44, s, 1 H; 5.03-5.06, m, 1 H; 4.68, t, 1 H; 4.34-4.45, m, 2 H; 3.99-4.17, m, 6 H; 3.74-3.89, m, 4 H; 3.64, ddd, 1 H; 3.52, dd, 1 H; 2.92, t, 2 H; 2.30, s, 3 H; 1.41-1.45, m, 1 H; 0.99-1.02, m, 2 H; 0.76-0.81, m, 2 H. |
| 119 | $^1$H NMR (CDCl$_3$): 7.62, d, 1 H; 6.72, dd, 1 H; 6.70, d, 1 H; 6.29, s, 1 H; 5.09-5.13, m, 1 H; 4.80-4.84, m, 1 H; 4.56-4.60, m, 1 H; 4.47-4.50, m, 1 H; 4.25, dd, 1 H; 3.99-4.16, m, 5 H; 3.74-3.89, m, 4 H; 3.64, ddd, 1 H; 3.52, dd, 1 H; 2.91, t, 2 H; 2.29, s, 3 H. |
| 120 | $^1$H NMR (CDCl$_3$): 7.59, d, 1 H; 6.68, dd, 1 H; 6.65, d, 1 H; 5.85, s, 1 H; 4.94-4.98, m, 1 H; 4.40, d, 1 H; 4.37, d, 1 H; 4.13, q, 2 H; 3.98-4.09, m, 7 H; 3.74-3.90, m, 4 H; 6.34, ddd, 1 H; 3.51, dd, 1 H; 2.87, t, 2 H; 2.27, s, 3 H; 1.25, t, 3 H. |
| 121 | $^1$H NMR (CDCl$_3$): 8.23, s, 1 H; 7.54, d, 1 H; 7.29-7.30, m, 3 H; 6.87, dd, 1 H; 6.71, d, 1 H; 6.49, s, 1 H; 4.61, septet, 1 H; 3.99-4.17, m, 5 H; 3.74-3.90, m, 4 H; 3.61-3.67, m, 3 H; 3.52, dd, 1 H; 3.30-3.36, m, 2 H; 2.89, t, 2 H; 2.31, s, 3 H; 2.09-2.16, m, 2 H; 1.92-2.00, m, 2 H. |
| 122 | $^1$H NMR (CDCl$_3$): 7.54, d, 1 H; 6.84, dd, 1 H; 6.74, d, 1 H; 6.20, s, 1 H; 3.93-4.12, m, 5 H; 3.73-3.88, m, 4 H; 3.64, ddd, 1 H; 3.48-3.58, m, 3 H; 3.25-3.31, m, 2 H; 2.84-2.90, m, 3 H; 2.28, s, 3 H; 1.95-2.11, m, 4 H. |
| 123 | $^1$H NMR (CDCl$_3$): 7.53, d, 1 H; 6.84, dd,, 1 H; 6.75, d, 1 H; 6.28, s, 1 H; 3.98-4.14, m, 5 H; 3.75-3.88, m, 4 H; 3.64, ddd, 1 H; 3.48-3.56, m, 3 H; 3.36, t, 2 H; 2.87, t, 2 H; 2.28, s, 3 H; 2.02-2.12, m, 2 H; 1.88-1.94, m, 2 H. |
| 124 | $^1$H NMR (CDCl$_3$): 7.59, d, 1 H; 7.24, dd, 1 H; 7.16, d, 1 H; 6.52, s, 1 H; 4.19, d, 2 H; 4.13, t, 2 H; 4.021-4.06, m, 1 H; 3.73-3.90, m, 4 H; 3.63, ddd, 1 H; 3.52, dd, 1 H; 2.92-2.99, m, 1 H; 2.95, t, 2 H; 2.35, s, 3 H, 1.29, d, 6 H. |
| 125 | $^1$H NMR (CDCl$_3$): 7.67, d, 1 H; 7.00-7.02, dd + d, 2 H; 4.48, q, 2 H; 4.35-4.41, m, 2 H; 4.29, t, 2 H; 4.06-4.08, m, 1 H; 3.89, dd, 1 H; 3.71-3.81, m, 3 H; 3.62, ddd, 1 H; 3.53, dd, 1 H; 3.08, t, 2 H; 2.35, s, 3 H. |
| 126 | $^1$H NMR (CDCl$_3$): 7.69, d, 1 H; 6.98, dd, 1 H; 6.95, d, 1 H; 4.30-4.38, m, 2 H; 4.20-4.24, t, 2 H; 4.03-1.09, m, 1 H; 3.74-3.91, m, 4 H; 3.64, ddd, 1 H; 3.54, dd, 1 H; 3.00, t, 2 H; 2.37, s, 3 H. |
| 127 | $^1$H NMR (CDCl$_3$): 7.57, d, 1 H; 6.83, dd, 1 H; 6.76, br s, 1 H; 6.18, s, 1 H; 4.94, s, 1 H; 4.78-4.80, m, 4 H; 3.98-4.12, m, 5 H; 3.73-3.86, m, 4 H; 3.60-3.65, m, 2 H; 3.51, dd + m, 2 H; 2.88, t, 2 H; 2.37, s, 3 H; 1.45, s, 9 H. |
| 128 | $^1$H NMR (CDCl$_3$): 7.58, d, 1 H; 6.88, dd, 1 H; 6.81, d, 1 H; 6.36, s, 1 H; 4.54-4.58, m, 1 H; 3.99-4.15, m, 6 H; 3.61-3.88, m, 6 H; 3.51, dd, 1 H; 3.35-3.41, m, 2 H; 2.90, t, 2 H; 2.30, s, 3 H; 1.92-1.99, m, 2 H; 1.75-1.82, m, 2 H; 1.47, s, 9 H. |
| 129 | $^1$H NMR (CDCl$_3$): 7.54, d, 1 H; 6.63, dd, 1 H; 6.50, d, 1 H; 6.35, s, 1 H; 4.01-4.13, m, 5 H; 3.64-3.89, m, 7 H; 3.52, dd, 1 H; 3.05, d, 3 H; 2.89, t, 2 H; 2.38-2.45, m, 2 H; 2.31, s, 3 H. |
| 130 | $^1$H NMR (CDCl$_3$): 7.50, d, 1 H; 6.50, dd, 1 H; 6.39, s, 1 H; 6.38, d, 1 H; 4.02-4.12, m, 5 H; 3.74-3.89, m, 4 H; 3.65, ddd, 1 H; 3.52, dd, 1 H; 3.36, t, 4 H; 2.87, t, 2 H; 2.31, s, 3 H; 2.03-2.06, m, 4 H. |

TABLE IV-continued

NMR data of illustrative compounds of the invention

| Cpd # | NMR |
|---|---|
| 131 | $^1$H NMR (CDCl$_3$): 7.54, d, 1 H; 6.50, dd, 1 H; 6.39, d, 1 H; 6.32, s, 1 H; 4.00-4.13, m, 5 H; 3.71-3.88, m, 6 H; 3.59-3.68, m, 3 H; 3.52, dd, 1 H; 2.89, t, 2 H; 2.51, heptet, 2 H; 2.29, s, 3 H. |
| 132 | $^1$H NMR (CDCl$_3$): 7.51, d, 1 H; 6.38, dd, 1 H; 6.28, d, 1 H; 6.18, s, 1 H; 4.14, t, 2 H; 3.99-4.10, m, 7 H; 3.74-3.88, m, 4 H; 3.64, ddd, 1 H; 3.51, dd, 1 H; 3.43-3.45, m, 1 H; 2.86, t, 2 H; 2.27, s, 3 H. |
| 133 | $^1$H NMR (CDCl$_3$): 7.56, d, 1 H; 6.83, dd, 1 H; 6.73, d, 1 H; 6.44-6.45, m, 1 H; 6.11, s, 1 H; 4.00-4.10, m, 5 H; 3.93-3.95, m, 2 H; 3.74-3.86, m, 4 H; 3.65, ddd, 1 H; 3.56, t, 2 H; 3.52, dd, 1 H; 2.89, t, 2 H; 2.45-2.46, m, 2 H; 2.29, s, 3 H. |
| 134 | $^1$H NMR (CDCl$_3$): 7.50, d, 1 H; 6.52, dd, 1 H; 6.42, s, 1 H; 6.39, d, 1 H; 3.96-4.13, m, 6 H; 3.74-3.89, m, 4 H; 3.65, ddd 1 H; 3.52, dd, 1 H; 3.46-3.48, m, 1 H; 3.24-3.26, m, 1 H; 2.87, t, 2 H; 2.31, s, 3 H; 2.044-2.10 m, 3 H; 1.75-1.78, m, 1 H; 1.21, d, 3 H. |
| 135 | $^1$H NMR (CDCl$_3$): 7.53, d, 1 H; 6.85, dd, 1 H; 6.75, d, 1 H; 6.35, s, 1 H; 4.78, d x heptet, 1 H; 3.96-4.15, m, 5 H; 3.74-3.89, m, 4 H; 3.65, ddd, 1 H; 3.43-3.57, m, 3 H; 3.27-3.37, m, 2 H; 2.87, t, 2 H; 2.30, s, 3 H; 1.89-2.02, m, 3 H; 1.65-1.73, m, 1 H. |
| 136 | $^1$H NMR (CDCl$_3$): 8.16, d, 2 H; 7.92, d, 1 H; 7.65, dd, 1 H; 7.58, d, 1 H; 7.52, d, 2 H; 7.45, td, 2 H; 7.32, td, 2 H; 6.47, s, 1 H; 4.24-4.25, m, 4 H; 4.04-4.09, m, 1 H; 3.75-3.93, m, 4 H; 3.66, ddd, 1 H; 3.55, dd, 1 H; 3.09, t, 2 H; 2.46, s, 3 H. |
| 137 | $^1$H NMR (CDCl$_3$): mixture of a major and minor isomers, major isomer: 7.50, d, 1 H; 6.82, dd, 1 H; 6.71, d, 1 H; 6.35, s, 1 H; 3.96-4.16, m, 5 H; 3.73-3.88, m, 6 H; 3.64, ddd, 1 H; 3.51, dd, 1 H; 2.87, t, 2 H; 2.35, t, 2 H; 2.30, s, 3 H; 1.71-1.86, m, 3 H; 0.95, d, 6 H; 0.77, s, 1 H. |
| 138 | $^1$H NMR (CDCl$_3$): 7.49, d, 1 H; 6.46, dd, 1 H; 6.42, s, 1 H; 6.34, d, 1 H; 4.05-4.13, m, 5 H; 3.74-3.89, m, 4 H; 3.65, ddd 1 H; 3.52, dd, 1 H; 3.44, t, 2 H; 3.44, t, 2 H; 3.12, s, 2 H; 2.87, t, 2 H; 2.31, s, 3 H; 1.83, t, 2 H; 1.16, s, 6 H. |
| 139 | $^1$H NMR (CDCl$_3$): 7.52, d, 1 H; 6.84, dd, 1 H; 6.73, d, 1 H; 6.30, s, 1 H; 3.99-4.15, m, 5 H; 3.74-3.89, m, 4 H; 3.65, ddd 1 H; 3.52, dd, 1 H; 3.32, t, 4 H; 2.87, t, 2 H; 2.31, s, 3 H; 1.52, t, 4 H; 1.01, s, 6 H. |
| 140 | $^1$H NMR (CDCl$_3$): 7.53, d, 1 H; 6.84, dd, 1 H; 6.75, d, 1 H; 6.15, s, 1 H; 3.98-4.11, m, 5 H; 3.91-3.94, m, 2 H; 3.81-3.88, m, 2 H; 3.74-3.79, m, 2 H; 3.64, ddd, 1 H; 3.51, dd, 1 H; 2.87, t, 2 H; 2.81, dd, 2 H; 2.29, s, 3 H; 2.21-2.27, m, 1 H; 1.99, br d, 2 H; 1.74, dd, 1 H; 1.68, dd, 1 H. |
| 141 | $^1$H NMR (CDCl$_3$): 7.52, d, 1 H; 6.83, dd, 1 H; 6.73, d, 1 H; 6.55, s, 1 H; 3.99-4.18, m, 5 H; 3.74-3.89, m, 6 H; 3.64, ddd, 1 H; 3.52, dd, 1 H; 2.82-2.89, m, 4 H; 2.32, s, 3 H; 1.76, br d, 2 H; 1.56-1.66, m, 1 H; 1.33, dd, 1 H; 1.26, dd, 1 H; 0.98, d, 3 H. |
| 142 | $^1$H NMR (CDCl$_3$): 7.49, d, 1 H; 6.65, dd, 1 H; 6.56, d, 1 H; 6.17, s, 1 H; 4.62, br s, 1 H; 3.98-4.12, m, 5 H; 3.74-3.88, m, 6 H; 3.64, ddd, 1 H; 3.51, dd, 1 H; 2.85, t, 2 H; 2.28, s, 3 H. |
| 143 | $^1$H NMR (CDCl$_3$): 7.51, d, 1 H; 6.79, dd, 1 H; 6.68, d, 1 H; 5.80, s, 1 H; 4.18-4.22, m, 1 H; 3.90-4.07, m, 5 H; 3.74-3.88, m, 4 H; 3.65, ddd, 1 H; 3.48-3.54, m, 2 H; 2.99, dt, 1 H; 2.83, t, 2 H; 2.29, s, 3 H; 1.78-1.91, m, 2 H; 1.58-1.66, m, 4 H; 1.11, d, 3 H. |
| 144 | $^1$H NMR (CDCl$_3$): Mixture of 2 isomers 7.59 + 7.61, d, 1 H; 6.87 + 6.84, dd, 1 H; 6.80 + 6.77, d, 1 H; 6.18 + 6.19, s, 1 H; 5.08-5.10 + 4.98-5.00, m, 1 H; 3.54-4.13, m, 15 H; 3.52, dd, 1 H; 2.90-2.87, t, 2 H; 2.13-2.42, m, 1 H; 2.30 + 2.29, s, 3 H; 1.54-1.61 + 1.65-1.69, m, 1 H; 0.98-1.07, m, 2 H; 0.77-0.82, m, 2 H. |
| 145 | $^1$H NMR (CDCl$_3$): 7.59, d, 1 H; 6.83, dd, 1 H; 6.77, d, 1 H; 6.17, s, 1 H; 4.97, br s, 1 H; 3.99-4.18, m, 7 H; 3.56-3.88, m, 9 H; 3.51, dd, 1 H; 2.89, t, 2 H; 2.29, s, 3 H; 2.13-2.25, m, 2 H; 1.26-1.29, m, 3 H. |
| 146 | $^1$H NMR (CDCl$_3$): 7.67, d, 1 H; 7.34, dd, 1 H; 7.31, d, 1 H; 6.36, s, 1 H; 4.72, t, 1 H; 4.46, t, 1 H; 4.31, t, 1 H; 4.20, d, 2 H; 4.03-4.13, m, 4 H; 3.74-3.92, m, 5 H; 3.65, ddd, 1 H; 3.53, dd, 1 H; 3.00, t, 2 H; 2.35, s, 3 H; 1.43-1.50, m, 1 H; 1.00-1.03, m, 2 H; 0.78-0.82, m, 2 H. |
| 147 | $^1$H NMR (CDCl$_3$): 7.65, d, 1 H; 7.30, dd, 1 H; 7.28, d, 1 H; 6.23, s, 1 H; 4.43, t, 2 H; 4.13-4.18, q + m, 4 H; 4.04-4.10, m, 4 H; 3.89, dd, 1 H; 3.74-3.85, m, 5 H; 3.64, ddd, 1 H; 3.52, dd, 1 H; 2.97, t, 2 H; 2.33, s, 3 H; 1.28, t, 3 H. |
| 148 | $^1$HNMR (CDCl$_3$): 7.65, d, 1 H; 7.34, dd, 1 H; 7.31, d, 1 H; 6.48, s, 1 H; 4.41, t, 2 H; 4.24, d, 2 H; 4.14, td, 2 H; 4.03-4.08, dd + m, 3 H; 3.92, dd, 1 H; 3.73-3.84, m, 4 H; 3.64, ddd, 1 H; 3.53, dd, 1 H; 3.00, t, 2 H; 2.90, s, 6 H; 2.35, s, 3 H. |
| 149 | $^1$H NMR (CDCl$_3$): 7.64, d, 1 H; 7.29-7.31, dd + d, 2 H; 6.11, s, 1 H; 4.35, t, 2 H; 3.96-4.13, m, 10 H; 3.74-3.90, m, 6 H; 3.65, ddd, 1 H; 3.52, dd, 1 H; 2.95, t, 2 H; 2.31, s, 3 H; 1.17, d, 3 H; 1.12, d, 3 H. |
| 150 | $^1$H NMR (CDCl$_3$): 7.61, d, 1 H; 6.74, dd, 1 H; 6.71, d, 1 H; 4.96-5.01, m, 1 H; 4.41, dd, 1 H; 4.39, dd, 1 H; 4.22-4.28, m, 2 H; 4.13-4.19, m, 2 H; 4.03-4.09, m, 3 H; 3.91, dd, 1 H; 3.73-3.85, m, 3 H; 3.63, ddd, 1 H; 3.53, dd, 1 H; 2.98, t, 2 H; 2.88, s, 6 H; 2.34, s, 3 H. |
| 151 | $^1$H NMR (CDCl$_3$): 7.58, d, 1 H; 6.68-6.72, m, 2 H; 6.20, s, 1 H; 5.53, br s, 1 H; 4.96-5.01, m, 1 H; 4.35, d, 1 H; 4.33, d, 1 H; 4.08-4.15, m, 2 H; 3.97-4.07, m, 5 H; 3.73-3.98, m, 5 H; 3.63, ddd, 1 H; 3.51, dd, 1 H; 2.92, t, 2 H; 2.29, s, 3 H; 1.14, d, 6 H. |
| 152 | $^1$H NMR (CDCl$_3$): 7.58, d, 1 H; 7.38-7.45, m, 4 H; 7.32-7.36, m, 1 H; 6.93, dd, 1 H; 6.86, d, 1 H; 5.86, 1 H, s; 5.11, s, 2 H; 4.95, ddd, 1 H; 4.18, dd, 1 H; 4.11, dd, 1 H; 4.07, td, 1 H; 3.99, td, 1 H; 2.85, t, 2 H; 2.49, 1 H, dd; 2.31, dd, 1 H; 2.28, s, 3 H; 1.52, s, 3 H; 1.44, s, 3 H. |
| 153 | $^1$H NMR (CDCl$_3$): 7.57, d, 1 H; 7.38-7.44, m, 4 H; 7.31-7.35, m, 1 H; 6.92, dd, 1 H; 6.86, d, 1 H; 5.83, s, 1 H; 5.11, s, 2 H; 4.01-4.06, m, 1 H; 3.96-4.00, m, 1 H; 3.90-3.95, m, 1 H; 3.88, br s, 2 H; 3.82-3.86, m, 1 H; 2.86, t, 2 H; 2.27, s, 3 H; 1.89-2.02, m, 3 H; 1.75-1.81, m, 1 H; 1.32, s, 3H. |
| 154 | $^1$H NMR (CDCl$_3$): 7.56, d, 1 H; 7.37-7.44, m, 4 H; 7.33-7.35, m, 1 H; 6.92, dd, H; 6.85, d, 1 H; 5.84, s, 1 H; 5.10, s, 2 H; 4.34-4.36, m, 1 H; 3.98-4.05, m, 4 H; 2.85, t, 2 H; 2.27, s, 3 H; 2.10-2.14, m, 1 H; 1.77-1.86, m, 3 H; 1.27, s, 3 H; 1.26, s, 3 H |
| 155 | $^1$H NMR (CDCl$_3$): 7.62, d, 1 H; 6.90, dd, 1 H; 6.86, d, 1 H; 5.84, s, 1 H; 4.48, dt, 2 H; 3.98-4.07, m, 5 H; 3.74-3.89, m, 4 H; 3.65, ddd, 1 H; 3.51, dd, 1 H; 2.90, t, 2 H; 2.27, s, 3 H. |

TABLE IV-continued

NMR data of illustrative compounds of the invention

| Cpd # | NMR |
|---|---|
| 156 | $^1$H NMR (CDCl$_3$): 7.63-7.65, m, 1 H; 7.32-7.37, m, 2 H; 7.25-7.27, m, 1 H; 5.81, s, 1 H; 3.98-4.09, m, 5 H; 3.73-3.89, m, 4 H; 3.64, ddd, 1 H; 3.51, dd, 1 H; 2.91, t, 2 H; 2.29, s, 3 H. |
| 157 | $^1$H NMR (CDCl$_3$): 7.85, d, 1 H; 7.65, d, 1 H; 7.39, dd, 1 H; 5.88, s, 1 H; 3.99-4.07, m, 5 H; 3.91, t, 2 H; 3.74-3.88, m, 4 H; 3.65, ddd, 1 H; 3.51, dd, 1 H; 2.93, t, 2 H; 2.65, t, 2 H; 2.29, s, 3 H, 2.20, tt, 2 H |
| 158 | $^1$H NMR (CDCl$_3$): 7.59, d, 1 H; 6.89, dd, 1 H; 6.83, d, 1 H; 3.98-4.07, m, 5 H; 3.75-3.89, m, 4 H; 3.66, ddd, 1 H; 3.52, dd, 1 H; 2.89, t, 2 H; 2.28, s, 3 H. |
| 159 | $^1$H NMR (CDCl$_3$): 7.59, d, 1 H; 6.88, dd, 1 H; 6.83, d, 1 H; 5.91, s, 1 H; 4.84-4.86, m, 1 H; 4.72-4.74, m, 1 H; 4.30-4.32, m, 1 H; 4.23-4.25, m, 1 H; 3.99-4.09, m, 5 H; 3.74-3.88, m, 4 H; 3.65, ddd, 1 H; 3.51, dd, 1 H; 2.89, br t, 2 H; 2.28, s, 3 H. |

Biological Examples

EXAMPLE 3

In Vitro Assays

3.1. Cell Based Assay: GTp-γS Binding Assay

The following assay can be used for determination of GPR84 activation. The [$^{35}$S]GTPγS binding assay measures the level of G protein activation following agonist occupation of a GPCR, by determining the binding of the non-hydrolysable analog [$^{35}$S]GTPγS to Gα subunits.

The assay is performed in a 96-well plate where the following reagents are added. First 50 μL compound is added into the assay plate, followed by addition of 20 μL 3,3'-diindolylmethane at EC80 concentration (concentration which gives 80% of the activity of GPR84). Then, 30 μL of a mixture consisting of membranes-GTPγS-SpA beads is added [mixture consists of 20 μg/well membranes derived from stable cell line over expressing GPR84 (membranes are pre-incubated with 0.1 μM GDP for 15 min at 4° C.), 0.1 nM [$^{35}$S]GTPγS (Perkin Elmer, NEG030) and 0.5 mg/well PVT-WGA SpA beads (Perkin Elmer, RPNQ0001)]. All components are diluted in assay buffer containing 20 mM Tris pH 7.5; 5 mM MgCl$_2$; 250 mM NaCl; 0.05% BSA; 75 μg/mL saponin. After an incubation of 90 min at room temperature, 20 μL CsCl$_2$ 0.8 M (MP Biomedicals, 02150589) is added, followed by centrifugation at 2000 rpm during 20 min. Plates are read on a topcount reader (perkin elmer) immediately after centrifugation (readout time, 1 min/well).

TABLE V

GPR84 GTPγS assay IC$_{50}$ of selected compounds of the invention.

| Cpd | IC$_{50}$ |
|---|---|
| 1 | *** |
| 2 | * |
| 3 | * |
| 4 | * |
| 5 | * |
| 6 | ** |
| 7 | **** |
| 8 | *** |
| 9 | *** |
| 10 | **** |
| 12 | *** |
| 13 | *** |
| 14 | **** |
| 16 | **** |
| 17 | **** |
| 18 | **** |
| 19 | ** |
| 20 | * |
| 21 | * |
| 22 | * |
| 23 | **** |
| 24 | **** |
| 25 | ** |
| 26 | ** |
| 27 | ** |
| 28 | **** |
| 29 | **** |
| 30 | **** |
| 31 | **** |
| 32 | **** |
| 33 | **** |
| 35 | *** |
| 36 | **** |
| 37 | **** |
| 38 | **** |
| 39 | *** |
| 40 | **** |
| 41 | **** |
| 42 | **** |
| 43 | **** |
| 44 | **** |
| 45 | **** |
| 46 | **** |
| 47 | **** |
| 48 | **** |
| 49 | **** |
| 50 | **** |
| 51 | **** |
| 53 | * |
| 54 | ** |
| 55 | ** |
| 56 | *** |
| 57 | **** |
| 58 | **** |
| 59 | **** |
| 61 | **** |
| 62 | **** |
| 63 | **** |
| 64 | **** |
| 65 | **** |
| 66 | * |
| 67 | *** |
| 68 | **** |
| 69 | **** |
| 70 | **** |
| 73 | *** |
| 74 | **** |
| 75 | **** |
| 76 | **** |
| 77 | **** |
| 78 | **** |
| 79 | **** |
| 80 | **** |

TABLE V-continued

GPR84 GTPγS assay $IC_{50}$ of selected compounds of the invention.

| Cpd | $IC_{50}$ |
|---|---|
| 81 | **** |
| 82 | **** |
| 83 | **** |
| 84 | * |
| 85 | *** |
| 86 | **** |
| 87 | ** |
| 88 | * |
| 89 | **** |
| 90 | N/A |
| 91 | **** |
| 92 | *** |
| 93 | **** |
| 94 | ** |
| 95 | **** |
| 96 | **** |
| 97 | *** |
| 98 | *** |
| 99 | **** |
| 100 | **** |
| 101 | **** |
| 102 | **** |
| 103 | **** |
| 104 | **** |
| 105 | **** |
| 106 | **** |
| 107 | *** |
| 108 | **** |
| 109 | **** |
| 110 | **** |
| 111 | **** |
| 112 | **** |
| 113 | **** |
| 114 | **** |
| 114 | **** |
| 115 | **** |
| 116 | **** |
| 117 | **** |
| 118 | *** |
| 119 | *** |
| 120 | **** |
| 121 | **** |
| 122 | **** |
| 123 | **** |
| 124 | **** |
| 125 | **** |
| 126 | **** |
| 127 | **** |
| 128 | **** |
| 129 | **** |
| 130 | **** |
| 131 | **** |
| 132 | **** |
| 133 | **** |
| 134 | **** |
| 135 | **** |
| 136 | **** |
| 137 | **** |
| 138 | **** |
| 139 | **** |
| 140 | **** |
| 141 | **** |
| 142 | **** |
| 143 | **** |
| 144 | *** |
| 145 | **** |
| 146 | ** |
| 147 | **** |
| 148 | ** |
| 149 | ** |
| 150 | ** |
| 151 | ** |
| 152 | *** |
| 153 | *** |
| 154 | **** |
| 155 | **** |
| 156 | *** |
| 157 | ** |
| 159 | **** |

N/A no activity measurable
* >1000 nM
** >500-1000 nM
*** >100-500 nM
**** 0.01-100 nM

3.2. Cellular Assays

3.2.1. Human Neutrophil Migration Assay

We have established that GPR84 agonists (medium chain free fatty acids such as sodium decanoate and sodium undecanoate, 3,3'-diindolylmethane and embelin) induce neutrophil chemotaxis and that GPR84 antagonists block GPR84 agonist-induced chemotaxis. GPR84 antagonists do not inhibit IL8- or fMLP-induced human neutrophil chemotaxis, indicating that GPR84 is an essential player in the process of neutrophil trafficking and recruitment.

The activity of GPR84 agonists and antagonists can therefore be assayed in a human neutrophil migration assay. The human neutrophil migration assay makes use of freshly isolated human neutrophils from buffy coats that are subsequently used in a functional chemotaxis assay setup. Freshly isolated human neutrophils from buffy coats obtained from healthy individuals are pre-treated with a compound for 30 min prior to the plating of neutrophils onto the upper chamber of the neutrophil chemotaxis assembly (Corning HTS 5-µm Transwell 96 permeable support system) in the presence of embelin (GPR84 agonist) at EC80 concentration (concentration for which 80% of activity is measured) in the lower chamber. After 1 h of incubation at 37° C. and 5% $CO_2$, the number of migrated neutrophils in the lower compartment can be quantified by measuring the ATP content using ATPlite™ Luminescence Assay System.

3.2.1.1. Isolation of Neutrophils from Human Buffy Coat

A human buffy coat suspension is diluted with an equal volume of ice cold DPBS. 20 mL of the diluted buffy coat suspension is gently mixed with 4 mL of ACD buffer (140 mM citric acid, 200 mM sodium citrate and 220 mM dextrose). Then, 12 mL of a 6% dextran/0.9% NaCl solution (15 g dextran T2000 and 2.25 g NaCl dissolved in 250 mL $H_2O$) is added to the mixture and the samples are inverted gently up to 20 times. The total volume is transferred to a new recipient and incubated at room temperature to allow sedimentation of red blood cells. The yellowish upper fraction is then transferred to a clean centrifugation tube and centrifuged for 12 min at 1300 rpm and 4° C. After centrifugation, the supernatant is discarded and the remaining cell pellet is rapidly resuspended in 12 mL of ice-cold $H_2O$ to perform a red blood cell lysis by osmotic burst. After 20 seconds, 4 mL of ice-cold 0.6 M KCl is added to restore salt concentration. Samples are mixed carefully and centrifuged for 6 min at 1300 rpm and 4° C. The supernatant is discarded and the red blood cell lysis procedure is repeated one more time. Subsequently, the cell pellet is resuspended in 4 mL of DPBS and layered over 5 mL of Lymphoprep™ (Axis Shield, prod. No. 1114545) in a 15 mL centrifuge tube. After a gradient centrifugation step (30 min at 1500 rpm, 4° C. and low brake), the supernatant is removed and the cell pellet, containing polymorphonuclear cells, is resuspended in 25 mL of chemotaxis buffer (RPMI 1640 medium, supplemented with 10 mM HEPES and 0.05% FFA-free BSA).

3.2.1.2. Migration Assay

A neutrophil cell suspension of $8.9 \times 10^6$ cells per mL is prepared in chemotaxis buffer and 180 µL per well is plated in a 96-well V-bottom plate. 20 µL of test compound solution in chemotaxis buffer is added to the 180 µL cell suspension. The mixture is incubated at room temperature for 30 min with intermediate gentle resuspension of the cells after 15 min. Following this, 75 µL of cell suspension is plated onto the upper compartment of a Transwell® permeable support system (Corning HTS Transwell 96 permeable support system with 5.0 µm pore size polycarbonate membrane, Corning, prod. No. 3387). The lower compartment (receiver well) is then filled with 200 µL chemotaxis buffer containing an equal concentration of test compound and a fixed concentration of chemotactic agent (embelin at EC80 concentration). After 1 h at 37° C., 5% $CO_2$ in a humidified incubator, the upper plate of the Transwell® system is gently removed. The number of migrated cells in the lower chamber is quantified by addition of 200 µL of ATPlite™ solution (ATPlite™ Luminescence Assay System, Perkin Elmer, Prod. No. 6016941) followed by incubation for 10 min in the dark with mild agitation. After incubation, 270 µL of cell lysate is then transferred onto a white 96-well plate for quantification by a luminescence plate reader. The relative luminescent signal measured is considered linearly related to the number of cells having migrated from the upper compartment into the receiver well.

TABLE VI

Human neutrophil migration $IC_{50}$ of selected compounds of the invention.

| Cpd | $IC_{50}$ |
|---|---|
| 1 | *** |
| 3 | N/A |
| 4 | * |
| 6 | * |
| 7 | *** |
| 8 | **** |
| 9 | *** |
| 10 | **** |
| 12 | *** |
| 13 | *** |
| 14 | **** |
| 16 | *** |
| 17 | *** |
| 18 | **** |
| 19 | * |
| 20 | * |
| 21 | * |
| 22 | * |
| 23 | **** |
| 24 | *** |
| 25 | * |
| 26 | ** |
| 27 | *** |
| 28 | **** |
| 29 | **** |
| 30 | **** |
| 31 | **** |
| 32 | **** |
| 33 | **** |
| 34 | **** |

TABLE VI-continued

Human neutrophil migration $IC_{50}$ of selected compounds of the invention.

| Cpd | $IC_{50}$ |
|---|---|
| 35 | **** |
| 36 | *** |
| 37 | **** |
| 38 | *** |
| 39 | **** |
| 40 | **** |
| 41 | **** |
| 42 | **** |
| 43 | **** |
| 44 | **** |
| 45 | *** |
| 46 | **** |
| 48 | **** |
| 49 | **** |
| 50 | **** |
| 51 | **** |
| 52 | **** |
| 58 | **** |
| 60 | **** |
| 61 | **** |
| 63 | *** |
| 65 | **** |
| 69 | **** |
| 70 | **** |
| 71 | **** |
| 72 | **** |
| 76 | **** |
| 77 | **** |
| 78 | **** |
| 79 | **** |
| 80 | **** |
| 81 | **** |
| 82 | **** |
| 83 | **** |
| 86 | **** |
| 90 | **** |
| 91 | *** |
| 93 | *** |
| 95 | *** |

N/A No measurable activity
\* >1000 nM
\*\* >500-1000 nM
\*\*\* >100-500 nM
\*\*\*\* 0.01-100 nM

3.2.2. Rat Neutrophil Migration Assay

We have established that GPR84 agonists (medium chain free fatty acids such as sodium decanoate and sodium undecanoate, 3,3'-diindolylmethane and embelin) induce neutrophil chemotaxis and that GPR84 antagonists could block GPR84 agonist-induced chemotaxis but not IL8-induced chemotaxis, indicating that G Protein-Coupled Receptor 84 (GPR84) is an essential player in the process of neutrophil recruitment.

The effect of agonists or antagonists for GPR84 can therefore be assayed in a neutrophil migration test. In the rat neutrophil migration assay, neutrophils, freshly isolated from rat after intraperitoneal injection of glycogen (0.1%, w/v), are treated with a compound for 30 min. Subsequently, the neutrophils are transferred to the upper wells of a Corning HTS transwell 96 permeable support system, of which the lower wells are filled with a embelin solution at EC80 (concentration which give 80% of the activity of the GPR84). After 1 h of incubation, migration of the neutrophils towards embelin in the lower compartment can be quantified by measuring the ATP-content of the lower wells using the Cell Titer Glow Substrate assay system (Promega, Cat.No.: G755B).

3.2.2.1. Isolation of Neutrophils from Rats 24 h after intraperitoneal injection of glycogen (0.1%, w/v), cells are harvested by peritoneal lavage with 25 mL HBSS then centrifuged for 12 min at 1300 rpm and 4° C. After centrifugation, the supernatant is discarded and the remaining cell pellet is rapidly resuspended in 12 mL of ice-cold $H_2O$ for red blood cell lysis to occur. After 20 seconds, 4 mL of ice-cold 0.6 M KCl is added. Samples are mixed carefully and centrifuged for 6 min at 1300 rpm, 4° C. The supernatant is discarded and the cell pellet is resuspended in 4 mL of DPBS and layered over 5 mL of Lymphoprep (Axis Shield, Cat. No.: 1114544) in a 15 mL centrifuge tube. After centrifugation for 30 min at 1500 rpm, 4° C., the supernatant is removed and the cell pellet, containing the neutrophils, is resuspended in 5 mL chemotaxis buffer (RPMI 1640 medium, supplemented with 10 mM HEPES; freshly made for each experiment).

3.2.2.2. Migration Assay

A cell suspension of $8.9 \times 10^6$ cells per milliliter is prepared. 10 μL of compound solution in chemotaxis buffer is added to 90 μL cell suspension. The mixture is incubated at 37° C. for 30 min with intermediate resuspension of the cells after 15 min. Following this, 75 μL cell suspension is transferred to the upper compartment of a Corning HTS transwell 96 permeable support system with 5.0 μm pore size polycarbonate membrane (Corning, Cat. No.: 3387). The receiver well of the transwell system is then filled with 200 μL chemotaxis buffer containing compound and chemotactic agent (embelin). After incubation at 37° C. in 5% $CO_2$ for 1 h, the upper plate of the transwell system is removed and 70 μL Cell Titer Glow Substrate (Promega, Cat. No.: G755B) are added in the receiver plate. The receiver plate is incubated for 10 min in the dark, while shaking. 180 μL of cell lysate is then transferred to a white 96-well plate and luminescence is measured. The detected luminescent signal is considered as linearly related to the number of cells having migrated from the upper well to the receiver well.

Example 4

ADME, PK and Safety Models

4.1. Aqueous Solubility

Starting from a 10 mM stock in DMSO, a serial dilution of the compound is prepared in DMSO. The dilution series is transferred to a 96 NUNC Maxisorb plate F-bottom and 0.1 M phosphate buffer pH 7.4 or 0.1 M citrate buffer pH 3.0 at room temperature is added.

The final concentrations range from 18.75 to 300 μM in 5 equal dilution steps. The final DMSO concentration does not exceed 3%.

200 μM Pyrene is added to the corner points of each 96-well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The first concentration at which the compound appears completely dissolved is the concentration reported, however the true concentration lies somewhere between this concentration and one dilution step higher.

Solubility values are reported in μM and in μg/mL.

4.2. Thermodynamic Solubility

Thermodynamic solubility of a compound is determined in water, phosphate or citrate buffer with pH of choice or biologically relevant gastrointestinal media (FaSSIF, FeSSIF, SGF). Dry matter of the compound is added to the medium of choice and incubated for 24 h at room temperature. The concentration of compound in the supernatant is analyzed by LC/MS-MS and the signal is plotted against the linear standard curve of that compound.

2.5-3 mg dry matter of test compound is dissolved in water, phosphate or citrate buffer with pH of choice or biologically relevant gastrointestinal media (FaSSIF, FeSSIF, SGF) in a glass vial. After addition of a magnetic stirrer, the samples are stirred for 24 h at room temperature. The vials are then centrifuged shortly and the supernatant is filtered. Each sample is diluted by a factor of 100 and a 10 in DMSO. A final 100 fold dilution in 70/30 water/acetonitrile is used for LCMS-MS analysis.

A standard curve is made starting from a 10 mM stock in DMSO, freshly prepared from dry matter. From this 10 mM DMSO stock solution, intermediate working solutions of 200, 50 and 10 μg/mL in DMSO are made and used to prepare 40, 20, 10, 5, 1, 0.2, 0.1 and 0.04 μg/mL solutions in DMSO. Two quality control samples are made: one of 15 μg/mL and one of 0.5 μg/mL in DMSO, also starting from the DMSO working stock solutions.

The standard curve and quality controls are diluted by a factor of 100 in 70/30 water/acetonitrile and analyzed on LC/MS-MS. The peak areas of the standard curve are plotted in a graph and a linear or polynomial of the second order equation is used to calculate the unknown concentrations of the test compound.

Solubility values are reported in μM or μg/mL.

4.3. Microsomal Stability

A 10 mM stock solution of compound in DMSO is 1,668 fold diluted in a 105 mM phosphate buffer pH 7.4. Of this compound dilution, 50 μL is transferred in two 96-well plates: one for time point 0 min (T0 plate) and one for time point 30 min (T30 plate) and pre-warmed at 37° C.

In the time zero reference sample (T0 plate), 100 μL MeOH (1:1) is added to the wells. In each assay plate (T0 and T30 min), 50 μL of microsomal mix is then added.

Final reaction concentrations are: 3 μM compound, 0.5 mg/mL microsomes, 0.4 U/mL GDPDH, 3.3 mM $MgCl_2$, 3.3 mM glucose-6-phosphate and 1.3 mM NADP+.

The T30 plate is incubated at 37° C., 300 rpm and after 30 min of incubation the reaction is stopped with MeOH (1:1). The samples are mixed, centrifuged and the supernatant is harvested for analysis on LC-MS/MS (API2000 from Applied Biosystems).

The samples are analyzed on LC-MS/MS with a flow rate of 0.5 mL/min. Solvent A is 0.1% Formic Acid in water and solvent B is 0.1% Formic Acid in methanol. The sample is run under positive ion spray on a Pursuit 5 C18 2.0 mm column (Varian). The solvent gradient has a total run time of 1.4 min and ranges from 10% B to 100% B. Peak area from the parent compound at time 0 is considered to be 100% remaining. The percentage remaining after 30 min incubation is calculated from time 0. The solubility of the compound in the final test concentration in buffer is inspected by microscope and results are also reported.

4.4. Hepatocyte Stability

Test compounds (1 μM initial concentration, n=2) are incubated in Williams' Medium E, containing 4 mM L-glutamine and 2 mM magnesium sulphate, with pooled cryopreserved hepatocytes (Celsis International) in suspension at cell densities of 0.25-0.5 million viable cells/mL. The incubations are performed at 37° C. in a shaking water bath with 100 μL samples taken from the incubation at 0, 10, 20, 45 and 90 min, and reactions terminated by addition of 100 μL of acetonitrile containing carbamazepine as analytical internal standard. Samples are centrifuged and the supernatant fractions analysed by LC-MS/MS. The instrument responses (i.e. peak heights) are referenced to the zero time-point samples (as 100%) in order to determine the percentage of compound remaining. Ln plots of the % remaining for each compound are used to determine the half-life for the hepatocyte incubations. Half-life values are calculated from the relationship: $T1/2$ (min)$=-0.693/\lambda$, where $\lambda$ is the slope of the Ln concentration vs time curve. Standard compounds testosterone, midazolam, and 4-methylumbelliferone are included in the assay design.

4.5. Plasma Protein Binding (Equilibrium Dialysis)

A 10 mM stock solution of the compound in DMSO is diluted with a factor 10 in DMSO. This solution is further diluted in freshly thawed human, rat, mouse or dog plasma (BioReclamation INC) with a final concentration of 5 μM and final DMSO concentration of 0.5%.

A Pierce Red Device plate with inserts (ThermoScientific) is prepared and filled with 450 μL PBS in the buffer chamber and 300 μL of the spiked plasma in the plasma chamber. The plate is incubated for 4 h at 37° C. while shaking at 100 rpm. After incubation, 120 μL of both chambers is transferred to 480 μL methanol in a 96-well round bottom, PP deep-well plates (Nunc) and sealed with an aluminum foil lid. The samples are mixed and immediately centrifuged 30 min at 1400 RCF at 4° C. and the supernatant is transferred to a 96 v-bottom PP plate (Greiner, 651201) for analysis on LC-MS/MS (API2000 from Applied Biosystems).

The samples are analyzed on LC-MS/MS with a flow rate of 0.5 mL/min. Solvent A is 0.1% formic acid in water and solvent B is 0.1% formic acid in methanol. The sample is run under positive ion spray on a Pursuit 5 C18 2.0 mm column (Varian). The solvent gradient has a total run time of 1.4 min and ranges from 10% B to 100% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

4.6. Caco-2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Corning, cell growth area: 0.33 cm², membrane pore size: 0.4 μM, membrane diameter: 6.5 mm).

$2 \times 10^5$ cells/well are seeded in plating medium consisting of DMEM+GlutaMAX™-I+1% NEAA+10% FBS (Fetal-Clone II)+1% Pen/Strep. The medium is changed every 2-3 days.

Test and reference compounds (propranolol and rhodamine123 or vinblastine, all purchased from Sigma) are prepared in Hanks' Balanced Salt Solution containing 25 mM HEPES (pH 7.4) and added to either the apical (125 μL) or basolateral (600 μL) chambers of the Transwell plate assembly at a concentration of 10 μM with a final DMSO concentration of 0.25%.

50 μM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 μL aliquots are taken from both apical (A) and basal (B) chambers and added to 100 μL 50:50 MeCN:water solution containing analytical internal standard (0.5 μM carbamazepine) in a 96-well plate.

Lucifer yellow is measured with a Spectramax Gemini XS (Ex 426 nm and Em 538 nm) in a clean 96-well plate containing 150 μL of liquid from basolateral and apical side.

Concentrations of compound in the samples are measured by high performance liquid-chromatography/mass spectroscopy (LC-MS/MS).

Apparent permeability (Papp) values are calculated from the relationship:

$$Papp=[\text{compound}]\text{acceptor final} \times V\text{acceptor}/([\text{compound}]\text{donor initial} \times V\text{donor})/T\text{inc} \times V\text{donor/surface area} \times 60 \times 10^{-6} \text{ cm/s}$$

V=chamber volume
Tinc=incubation time.
Surface area=0.33 cm²
The Efflux ratios, as an indication of active efflux from the apical cell surface, are calculated using the ratio of Papp B>A/Papp A>B.
The following assay acceptance criteria are used:
Propranolol: Papp (A>B) value $\geq 20(\times 10^{-6}$ cm/s)
Rhodamine 123 or Vinblastine: Papp (A>B) value <5 ($\times 10^{-6}$ cm/s) with Efflux ratio $\geq 5$.
Lucifer yellow permeability: $\leq 100$ nm/s

4.6.1. Liability for QT Prolongation

Potential for QT prolongation is assessed in the hERG manual patch clamp assay.

4.6.1.1. Conventional Whole-Cell Patch-Clamp

Whole-cell patch-clamp recordings are performed using an EPC10 amplifier controlled by Pulse v8.77 software (HEKA). Series resistance is typically less than 10 MΩ and compensated by greater than 60%, recordings are not leak subtracted. Electrodes are manufactured from GC150TF pipette glass (Harvard).

The external bathing solution contains: 135 mM NaCl, 5 mM KCl, 1.8 mM CaCl$_2$, 5 mM Glucose, 10 mM HEPES, pH 7.4.

The internal patch pipette solution contains: 100 mM K gluconate, 20 mM KCl, 1 mM CaCl$_2$, 1 mM MgCl$_2$, 5 mM Na$_2$ATP, 2 mM glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow).

hERG currents are evoked using an activating pulse to +40 mV for 1000 ms followed by a tail current pulse to −50 mV for 2000 ms, holding potential is −80 mV. Pulses are applied every 20 s and all experiments are performed at room temperature.

4.6.1.2. Data Analysis $IC_{50}$ values are calculated for each compound tested. The fold difference between the $IC_{50}$ in the manual hERG patch clamp and the unbound $IC_{50}$ in the whole blood assay is calculated.

For the concentration response curves, peak tail current amplitude is measured during the voltage step to −50 mV. Curve-fitting of concentration-response data is performed using the equation:

$$y=a+[(b-a)/(1+10^{((\log c-x)d)})]$$

where a is minimum response, b is maximum response and d is Hill slope, this equation can be used to calculate both $IC_{50}$ (where y=50 and c is the $IC_{50}$ value) and $IC_{20}$ (where y=20 and c is the $IC_{20}$ value). GraphPad® Prism® (Graphpad® Software Inc.) software is used for all curve fitting. A difference of 100 fold or greater indicates a low potential for QT prolongation.

4.6.2. Pharmacokinetic Study

4.6.2.1. Single Dose Pharmacokinetic Study in Rats

Compounds are formulated in PEG200/physiological saline mixtures for the intravenous route and in PEG400/0.5% methylcellulose (10/90 v/v) for the oral route. Test compounds are orally dosed as a single esophageal gavage at 5-10 mg/kg and intravenously dosed as a bolus via the caudal vein at 1 mg/kg to male Sprague-Dawley rats. Each group consists of 3 rats. Blood samples are collected either via the jugular vein using cannulated rats or at the retro-orbital sinus with lithium heparin as anti-coagulant at the time points in the following range: 0.05 to 8 h (intravenous route), and 0.25 to 6 or 24 h (oral route). Whole blood samples are centrifuged at 5000 rpm for 10 min and the resulting plasma samples are stored at −20° C. pending analysis.

4.6.2.2. Multiple Dose Pharmacokinetic Study in Rats

Compounds are formulated in PEG400/0.5% methylcellulose (10/90 v/v) for the oral route. Test compounds are orally dosed as an esophageal daily gavage at 30 or 300 mg/kg to male Sprague-Dawley rats for 14 days. Each group consists of 3 rats. Blood samples are collected via the tail vein with lithium heparin as anti-coagulant at the following time points on day 1, 7 and 14: 0.25, 1, 4, 8 and 24 h. In addition, on day 2 blood samples are taken at 0.25, 1 and 4 h and at day 4 and 11 at 0.25 h. Whole blood samples are centrifuged at 5000 rpm for 10 min and the resulting plasma samples are stored at −20° C. pending analysis.

4.6.2.3. Quantification of Compound Levels in Plasma

Plasma concentrations of each test compound are determined by an LC-MS/MS method in which the mass spectrometer is operated in positive or negative electrospray mode.

4.6.2.4. Determination of Pharmacokinetic Parameters

Pharmacokinetic parameters are calculated using Winnonlin® (Pharsight®, US)

4.6.3. Plasma Exposure and Brain Penetration

4.6.3.1. Animals

This study was performed with 12 naïve male Sprague Dawley rats obtained from Janvier, (France), 3 per sampling time, weighing (mean±SD) 266±12.2 g at the start of the oral treatment. The animals were kept in cages by groups of 3, at a temperature of 22±2° C., with a relative humidity of 30-70% and a 12 hour light/12 hour dark cycle (nightlight during the night period). Food (Pelleted diet for rodents UAR A04C-10) and water was provided ad libitum.

4.6.3.2. Study Protocol

Based on the individual body weights, each rat (n=12) received a single oral dose of test compound (250 mg/kg) formulated as a homogeneous suspension (10 mL/kg) in PEG 400/MC 0.5% (20/80; v/v).

Blood samples were collected into tubes containing lithium heparin as anticoagulant, at 1 h, 3 h, 6 h, and 24 h post dosing, and the samples were kept on ice. Within 1 h after sampling, blood was centrifuged at 4° C. and plasma was stored in polypropylene tubes at −20° C. until bioanalysis was done.

At sacrifice, the brain was collected, rapidly rinsed in saline, dried, weighed and stored in 50 mL polypropylene tubes at −20° C. until bioanalysis was done.

Plasma and brain samples were assayed by LC-MS/MS (Agilent 1200 Series HPLC pump (ref. G1312A, serial No. DE63062194), API5500 QTrap Mass Spectrometer (AB Sciex, serial No. AU21420911) equipped with a TurboIon-Spray probe)

The test compound concentrations in plasma and brain were calculated against a calibration curve consisting of eight levels with a 3 Log amplitude. Back-calculated values of the QCs (three levels prepared in duplicate) were used for accepting or rejecting the whole batch.

Plasma proteins were precipitated with an excess of acetonitrile containing the internal standard.

Brain samples were homogenized in acetonitrile containing the internal standard (10 mL per gram of tissue) with an Omni TissueMaster homogenizer (Omni, ref. TMIZ5-200).

For plasma and brain samples, the corresponding supernatants were injected on a $C_{18}$ column. Analytes were eluted out of the HPLC system by increasing the percentage of the organic mobile phase. An API5500 QTrap mass spectrometer (ABSciex™) was used for the detection and quantification.

4.6.3.3. Analysis

Plasma and brain levels of test compounds were compiled (average of the plasma or brain levels of the 3 rats at each sampling time) and the corresponding plasma and brain exposure-time profiles were plotted. SEM were tabulated only if more than two values were above the limit of quantification.

Pharmacokinetic parameters (maximum plasma or brain concentration, Cmax (ng/mL) with the corresponding time, Tmax (hours), area under the plasma or brain concentration versus time curve up to the last quantifiable concentration, AUC(0-last) (ng·h/mL) was calculated according to the linear up/log down trapezoidal method) were calculated from the mean plasma and brain levels by non-compartmental analysis using Phoenix® software (Certara, version 6.3.0.395):

From the area under the plasma or brain concentration, the following brain-to-plasma ratio was calculated:

$$\text{brain to plasma ratio} = \frac{AUC_{(0-last)} \text{ in brain}}{AUC_{(0-last)} \text{ in plasma}}$$

4.6.4. 7-Day Rat Toxicity Study

A 7-day oral toxicity study with test compounds is performed in Sprague-Dawley male rats to assess their toxic potential and toxicokinetics, at daily doses of 100, 300 and 1000 mg/kg/day, by gavage, at the constant dosage-volume of 10 mL/kg/day.

The test compounds are formulated in PEG400/0.5% methylcellulose (10/90, v/v). Each group includes 6 principal male rats as well as 3 satellite animals for toxicokinetics. A fourth group is given PEG400/0.5% methylcellulose (10/90, v/v) only, at the same frequency, dosage volume and by the same route of administration, and acts as the vehicle control group.

The goal of the study is to determine the lowest dose that results in no adverse events being identified (no observable adverse effect level—NOAEL).

4.6.5. Cytochrome P450 Inhibition

Reversible CYP inhibition and time-dependent CYP3A4 inhibition is determined in human liver microsomes and specific probe substrates.

4.6.5.1. P450 Inhibition in Human Liver Microsomes, Reversible Inhibition

The inhibitory potential of a test compound is assessed for human cytochrome P450 isoenzymes CYP1A2, 2C8, 2C9, 2C19, 2D6 and 3A4.

A 10 mM stock solution of the test compound is prepared in DMSO, serially diluted in Tris buffer (100 mM pH 7.4) and added to hepatic microsomes (Xenotech LLC) and NADPH at 37° C. in a shaking water bath. Seven different test compounds concentrations (0.05 to 100 µM), 1% DMSO and 1 mM NADPH are obtained to react.

After 15 or 30 min reactions are terminated by addition of 100 µL of acetonitrile containing carbamazepine as analytical internal standard. Samples are centrifuged and the supernatant fractions analysed by LC-MS/MS. For each isoform, the instrument responses (peak heights) are referenced to those for DMSO controls (considered as 100%) in order to determine the percentage reduction in probe metabolism, using midazolam and testosterone as probe substrate. Percentage inhibition of probe metabolism and Log [test compound concentration] are plotted using Graphpad Prism software. The sigmoidal dose response model is fitted to the data in order to determine the $IC_{50}$.

Inhibition of CYP3A4 using nifedipine and atorvastatin as probe substrate is carried out as follows.

A 1.67 mM stock solution of test compound is prepared in methanol, serially diluted 1:3 in 50 mM potassium phosphate buffer pH 7.4 and added to human hepatic microsomes (BD Gentest) and probe substrate. Seven different test compounds concentrations (0.045-33.3 µM), 2% methanol, 0.1 mg/mL microsomes, 10 µM atorvastatin or 5 µM nifedipine. After pre-warming 5 min at 37° C., the reaction is started by adding cofactor mix (7.65 mg/mL glucose-6-phosphate, 1.7 mg/mL NADP, 6 U/mL of glucose-6-phosphate dehydrogenase).

After 5 min (nifedipine) or 10 min (atorvastatin) at 37° C., the reaction (50 µL) is terminated with 150 µL acetonitrile:methanol (2:1) solution with internal standard (Warfarin). Samples are centrifuged and the supernatant fractions analyzed by LC-MS/MS. The instrument responses (ratio of test compound/internal standard peak areas) are referenced to those for solvent controls (assumed as 100%) in order to determine the percentage reduction in probe metabolism. Percent of control activity vs. concentration plots are generated and fitted using GraphPad Prism software to generate $IC_{50}$.

4.6.5.2. CYP3A4 Inhibition in Human Liver Microsomes, Time-Dependent

The time-dependent inhibitory potential of a test compound is assessed for human cytochrome P450 isoenzyme 3A4. The compound is pre-incubated with the human liver microsomes before addition of the probe substrates. The result is compared to the condition where the compound is not pre-incubated with the human liver microsomes to see if there is a shift in $IC_{50}$, indicating time-dependent inhibition.

A 10 mM stock solution of test compound is prepared in DMSO and diluted 1:20 with Tris buffer (100 mM pH 7.4) and further serially diluted in Tris buffer/5% DMSO.

The cofactor, NADPH, and each test compound dilution are mixed in two separate plates for 0 and 30 min pre-incubation. Human hepatic microsomes (Xenotech LLC) are added only to the "30 min pre-incubation" plate and both plates are then incubated for 30 min at 37° C. in a shaking water bath. Following the pre-incubation, microsomes are added to the "0 min" plate and appropriate probe substrates (in 0.5% DMSO) are added to both plates. Plates are then returned to the water bath for a further incubation.

In total, six different test compound concentrations (1.6 to 50 µM) are assessed. Reactions are terminated with 100 µL of acetonitrile containing carbamazepine as analytical internal standard. Samples are centrifuged and the supernatant fractions analysed by LC-MS/MS. For each isoform, the instrument responses (peak height ratio with internal standard) are referenced to those for DMSO controls (considered as 100%) in order to determine the percentage reduction in probe metabolism. Percentage inhibition of probe metabolism and Log [Test Compound concentration] are plotted using Graphpad Prism software. The sigmoidal dose response model is fitted to the data in order to determine the $IC_{50}$.

4.6.6. Chemical Stability

4.6.6.1. Protocol

This in vitro model is aimed at assessing the stability of a test compound in aqueous solutions with different pH. The decrease in parent compound is assessed by measuring the percentage parent remaining after 2 and 24 h incubation at 37° C.

A 2 mM DMSO stock is made for each test compound starting from dry matter. Then a 80 µM working solution of compound in DMSO is made by diluting the 2 mM DMSO.

The 80 µM working solution is diluted to a final concentration of 2 µM-2.5% DMSO in buffer with the desired pH (pH 1.2: hydrochloric acid buffer, pH 5.0: acetate buffer, pH 7.4: phosphate buffer, pH 9.0: Tris buffer) in 96-well plates with glass inserts (Cat no. 548-0201/548-0202, VWR-Thermo Scientific). Two replicates are run for each buffer solution and each time point.

One set of vials is incubated for 24 h at 200 rpm and another for 2 h at 200 rpm. To stop the reaction after the respective incubation times, 4 volumes of acetonitrile containing the internal standard (stop solution) are added to the reaction solution and the vials are vortexed briefly.

For the 0 h incubation, the stop solution with internal standard is first added to the buffer solution in glass vials and then the working solution of test compound (final concentration: 2 µM-2.5% DMSO) is added.

Propranolol is used as internal standard, but if the mass difference is too low with the test compound(s), another product is selected as internal standard. The concentration of the internal standard is chosen to obtain a peak area half of the average peak area of the test compounds and control at time point 0.

Analysis is performed on an LCMS-MS system (API2000 or API4000). The average of the peak areas of the two replicates from the parent compound at time 0 divided by the peak area of the internal standard is considered to be 100% remaining. The percentage remaining after 2 and 24 h of incubation is calculated for all other peaks and the percentage remaining after 2 and 24 h is reported.

TABLE VII

Chemical Stability Percentage remaining after 2 and 24 hours incubation.

| Cpd | pH 1.2 % rem. (2 h) | pH 1.2 % rem. (24 h) | pH 5.0 % rem. (2 h) | pH 5.0 % rem. (24 h) | pH 7.4 % rem. (2 h) | pH 7.4 % rem. (24 h) | pH 9.0 % rem. (2 h) | pH 9.0 % rem. (24 h) |
|---|---|---|---|---|---|---|---|---|
| 1 | *** | *** | *** | *** | *** | *** | *** | *** |
| 8 | *** | *** | *** | *** | *** | *** | *** | *** |
| 10 | *** | *** | *** | *** | *** | *** | *** | *** |
| 12 | *** | *** | *** | *** | *** | *** | *** | *** |
| 18 | *** | *** | *** | *** | *** | *** | *** | *** |

* 0-20%
** >20%-80%
*** >80%

4.6.6.2. Conclusion

As shown in Table VII above, the compounds of the invention, when tested in this protocol surprisingly exhibit a high chemical stability, in particular at acidic pH, more particularly between pH 1.0 and 6.0, and specifically at pH 1.2 and/or 5.0. Such property is particularly desirable for compounds administered orally, which need to transit through the acidic stomach environment.

4.6.7. Photostability

The aim of this assay is to determine the chemical stability of a test compound when exposed to light irradiation. The compound is tested in a PEG400/$H_2O$ formulation during 22 h of exposition to 250 W/$m^2$ of an ID65 irradiation at 15° C. in an Atlas SUNTEST® CPS+cabinet.

The test compound (typically 5 mg±0.1) is placed in a glass screw cap vial and an appropriate volume of PEG400/$H_2O$ (60/40 v/v) solution is added to a 1 mg/mL concentration. A control sample is prepared by wrapping the vial in aluminium foil and is simultaneously exposed to the same stress conditions as the test sample (22 h at 250 W/$m^2$, i.e. total visible exposure of approximately $1.2 \times 10^6$ lux·h and total UV exposure of approximately 505 W·h/$m^2$).

Prior to HPLC analysis, all suspensions are diluted with acetonitrile to yield a final test compound concentration of 0.5 mg/mL. A non-irradiated reference test compound solution is prepared at a concentration of 0.5 mg/mL of solid in acetonitrile.

Purity analysis is performed by an HPLC/DAD method on an Agilent HP1100 HPLC system. Chromatogram peak areas of control and test samples are compared using the reference test compound solution as internal standard.

4.7. In Vivo Studies

The in vivo activity of the compounds of the invention may be demonstrated in the following in vivo efficacy inflammation models.

4.7.1. Inflammatory Bowel Disease (Mice)

The mouse chronic DSS-induced inflammatory bowel disease model (IBD) is a well validated disease model for inflammatory bowel disease (Wirtz S. et al., 2007 Nature Protocols 2, 541-546; Sina et al., 2009 J. Immunol. 183 7514-7522).

To induce a chronic colitis, female BALB/c mice are fed with 4% dextran sodium sulfate (DSS) dissolved in drinking water for 4 days, followed by 3 days of regular drinking water. This cycle is repeated three times. This protocol allows inducing a strong colitis while avoiding high mortality rates. Animals are divided into several groups:
  intact water; vehicle alone, n=10),
  diseased (DSS; vehicle alone, n=10),
  sulfazalazine used as reference (DSS; 20 mg/kg/day, p.o., n=10) and
  the tested compound (DSS; 1, 3, 10, 30 mg/kg/day, p.o., n=10).
  Clinical parameters are measured every other day. The disease activity index (DAI) is a composite measure combining of the individual scores for weight loss, stool consistency and rectal bleeding. Mice are sacrificed at day 20 of the experiment according to the protocol introduced by Sina et al. (2009). At sacrifice time, the complete colon is removed and rinsed with sterile PBS. Segments of the distal colon are dissected for histological analysis, gene expression and protein level measurement.

4.7.2. Collagen-Induced Arthritis (Mice)

The mouse collagen-induced arthritis (CIA) is the gold standard rheumatoid arthritis model (Brand, et al., 2007 Nature Protocols 2, 1269-1275, Lin et al., 2007 Br J Pharmacol 1, 829-831). DBA 1//J male mice are injected with a collagen II solution (Completed Freund's adjuvant). Immune reaction is boosted by a second injection (incomplete Freund's adjuvant) 21 days later. At day 31, arthritis is scored according to the method of Khachigian et al. (Khachigian et al., 2006 Nature Protocols 1, 2512-2516) and animals are randomized to reach an average clinical score of 2 per group. Animals are divided into several groups: intact (no treatment, n=5), diseased (vehicle alone, n=10), Enbrel® as reference (10 mg/kg, 3× week, i.p., n=10), and the tested compound (3, 10 or 30 mg/kg/day, p.o., n=10). Therapeutic dosing lasted from day 31 to day 46 and the arthritis is scored every day. Mice are sacrificed at day 46, X-ray photos are taken of the hind paws of each individual animal and the severity of bone erosion is ranked with the radiological Larsen's score (Salvemini et al., 2001 Arthritis Rheum 44, 2909-2921).

4.7.3. Tabacco Smoke Model (Mice)

Daily exposures of female inbred C57BL/6J mice to tobacco smoke (TS) for 11 consecutive days result in pulmonary inflammation, as indicated by an increase in the total number of cells recovered in the bronchoalveolar lavage (BAL), when compared with a similarly treated air-exposed group, 24 h after the final exposure. The exposure period to TS is increased initially from 25 min at the start of the study (day 1) to a maximum of 45 min on day 3 until day 11. Animals are divided into several groups: intact (no treatment, n=5), diseased (vehicle alone, n=10), Roflumilast as reference (5 mg/kg/day p.o., n=10), and the tested compounds (10 or 30 mg/kg/bid, p.o., n=10). At the end of 11 days, the numbers of macrophages, epithelial cells, neutrophils and lymphocytes are counted in the BAL. BAL is further analysed for gene expression and protein level. Lung tissue is dissected for histological analysis, gene expression and protein level measurement.

It will be appreciated by those skilled in the art that the foregoing descriptions are exemplary and explanatory in nature, and intended to illustrate the invention and its preferred embodiments. Through routine experimentation, an artisan will recognise apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein are prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

REFERENCES

Abdel-Aziz H et al. 2015. GPR84 and TREM-1 signaling contribute to the pathogenesis of reflux esophagitis. Mol. Med. Camb. Mass.
Berry M P R et al. 2010. An Interferon-Inducible Neutrophil-Driven Blood Transcriptional Signature in Human Tuberculosis. Nature 466, 973-977.
Bois R M du. 2010. Strategies for treating idiopathic pulmonary fibrosis. Nat. Rev. Drug Discov. 9, 129-140.
Bouchard C et al. 2007. G protein-coupled receptor 84, a microglia-associated protein expressed in neuroinflammatory conditions. Glia 55, 790-800.
Bundgaard H. 1985. Design of prodrugs, Elsevier.
Hakak Y et al. 2007. Human G Protein-Coupled Receptor and Modulators Thereof for the Treatment of Atherosclerosis and Atherosclerotic Disease and for the Treatment of Conditions Related to Mcp-1 Expression. WO2007027661 (A2).
Kadl A et al. 2010. Identification of a Novel Macrophage Phenotype That Develops in Response to Atherogenic Phospholipids via Nrf2. Circ. Res. 107, 737-746.
Nagasaki H et al. 2012. Inflammatory changes in adipose tissue enhance expression of GPR84, a medium-chain fatty acid receptor: TNFα enhances GPR84 expression in adipocytes. FEBS Lett. 586, 368-372.
Nicol L S C et al. 2015. The Role of G-Protein Receptor 84 in Experimental Neuropathic Pain. J. Neurosci. 35, 8959-8969.
Roman S. 2010. Disruption of the GPR84 GPCR gene reduces inflammatory and abolishes neuropathic pain.
Suzuki M et al. 2013. Medium-chain Fatty Acid-sensing Receptor, GPR84, Is a Proinflammatory Receptor. J. Biol. Chem. 288, 10684-10691.
Venkataraman C, Kuo F. 2005. The G-protein coupled receptor, GPR84 regulates IL-4 production by T lymphocytes in response to CD3 crosslinking. Immunol. Lett. 101, 144-153.
Wang J et al. 2006. Medium-chain Fatty Acids as Ligands for Orphan G Protein-coupled Receptor GPR84. J. Biol. Chem. 281, 34457-34464.
Wittenberger T, Schaller H C, Hellebrand S. 2001. An expressed sequence tag (EST) data mining strategy succeeding in the discovery of new G-protein coupled receptors. J. Mol. Biol. 307, 799-813.
Wuts P G M, Greene T W. 2006. Greene's Protective Groups in Organic Synthesis 4th ed., Wiley-Interscience.
Yousefi S et al. 2001. Cloning and expression analysis of a novel G-protein-coupled receptor selectively expressed on granulocytes. J. Leukoc. Biol. 69, 1045-1052.

What is claimed:
1. A compound according to Formula Va:

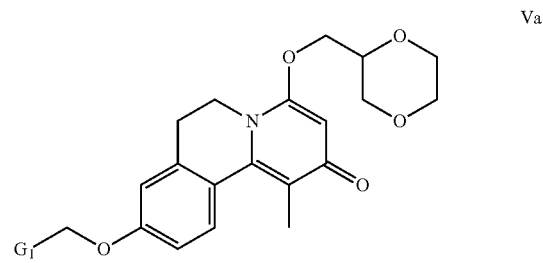

-continued

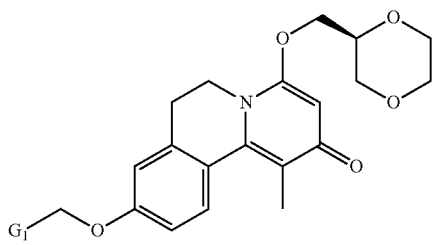

wherein
G₁ is
  C$_{3-6}$ cycloalkyl optionally substituted with one or more independently selected halo, or
  C$_{1-4}$ alkyl optionally substituted with one or more independently selected halo, —NR$^{7a}$R$^{7b}$, or C$_{1-4}$ alkoxy, which alkoxy is optionally substituted with one or more independently selected halo; and
each R$^{7a}$ and R$^{7b}$ is independently H or C$_{1-4}$ alkyl;
or a pharmaceutically acceptable salt, or a solvate, or a pharmaceutically acceptable salt of a solvate thereof.

2. A compound or pharmaceutically acceptable salt thereof according to claim 1, wherein G₁ is cyclopropyl, cyclobutyl, cyclopentyl or cyclohexyl, each of which is substituted with one or more F.

3. A compound or pharmaceutically acceptable salt thereof according to claim 1, wherein G₁ is —CF$_3$, —CHF$_2$, —CH$_2$—CHF$_2$, —CH$_2$—CF$_3$, —CH$_2$—CH$_2$—N(CH$_3$)$_2$, or —CH$_2$—CH$_2$—OCF$_3$.

4. A pharmaceutical composition comprising a compound or pharmaceutically acceptable salt thereof according to claim 1, and a pharmaceutically acceptable carrier.

5. A compound, or pharmaceutically acceptable salt thereof, wherein the compound is according to Formula Vb:

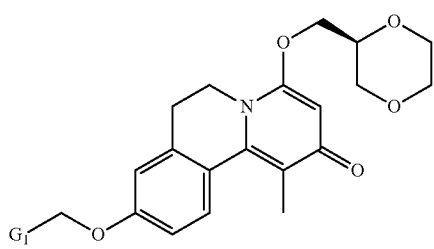

wherein
G₁ is
  C$_{3-6}$ cycloalkyl optionally substituted with one or more independently selected halo, or
  C$_{1-4}$ alkyl optionally substituted with one or more independently selected halo, —NR$^{7a}$R$^{7b}$, or C$_{1-4}$ alkoxy, which alkoxy is optionally substituted with one or more independently selected halo; and
each R$^{7a}$ and R$^{7b}$ is independently H or C$_{1-4}$ alkyl;
or a pharmaceutically acceptable salt, or a solvate, or a pharmaceutically acceptable salt of a solvate thereof.

6. A compound or pharmaceutically acceptable salt thereof according to claim 5, wherein G₁ is cyclopropyl, cyclobutyl, cyclopentyl or cyclohexyl, each of which is substituted with one or more F.

7. A compound or pharmaceutically acceptable salt thereof according to claim 5, wherein G₁ is —CF$_3$, —CHF$_2$, —CH$_2$—CHF$_2$, —CH$_2$—CF$_3$, —CH$_2$—CH$_2$—N(CH$_3$)$_2$, or —CH$_2$—CH$_2$—OCF$_3$.

8. A pharmaceutical composition comprising a compound or pharmaceutically acceptable salt thereof according to claim 5, and a pharmaceutically acceptable carrier.

9. A compound, or pharmaceutically acceptable salt thereof, according to claim 1, wherein the compound is
  4-[[(2S)-1,4-dioxan-2-yl]methoxy]-1-methyl-9-(2,2,2-trifluoroethoxy)-6,7-dihydrobenzo[a]quinolizin-2-one;
  9-(2-dimethylaminoethyloxy)-4-[[(2S)-1,4-dioxan-2-yl]methoxy]-1-methyl-6,7-dihydrobenzo[a]quinolizin-2-one;
  9-(2,2-difluoroethoxy)-4-[[(2S)-1,4-dioxan-2-yl]methoxy]-1-methyl-6,7-dihydrobenzo[a]quinolizin-2-one;
  4-[[(2S)-1,4-dioxan-2-yl]methoxy]-1-methyl-9-[2-(trifluoromethoxy)ethoxy]-6,7-dihydrobenzo[a]quinolizin-2-one;
  4-(1,4-dioxan-2-ylmethoxy)-1-methyl-9-(2,2,2-trifluoroethoxy)-6,7-dihydrobenzo[a]quinolizin-2-one;
  3-deuterio-4-[[(2S)-1,4-dioxan-2-yl]methoxy]-1-methyl-9-(1,1,2,2-tetradeuterio-2-fluoro-ethoxy)-6,7-dihydrobenzo[a]quinolizin-2-one; or
  4-[[(2S)-1,4-dioxan-2-yl]methoxy]-1-methyl-9-(2,2,3,3,3-pentafluoropropoxy)-6,7-dihydrobenzo[a]quinolizin-2-one.

10. A pharmaceutical composition comprising a compound or pharmaceutically acceptable salt thereof according to claim 9, and a pharmaceutically acceptable carrier.

* * * * *